(12) United States Patent
Tashiro et al.

(10) Patent No.: US 12,144,350 B2
(45) Date of Patent: Nov. 19, 2024

(54) HETEROCYCLIC COMPOUND AND HARMFUL ARTHROPOD CONTROL COMPOSITION CONTAINING SAME

(71) Applicant: SUMITOMO CHEMICAL COMPANY, LIMITED, Chuo-ku (JP)

(72) Inventors: Masayuki Tashiro, Takarazuka (JP); Ayaka Tanaka, Chuo-ku (JP); Shinichiro Murakami, Chuo-ku (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 763 days.

(21) Appl. No.: 17/426,938

(22) PCT Filed: Jan. 30, 2020

(86) PCT No.: PCT/JP2020/003521
§ 371 (c)(1),
(2) Date: Jul. 29, 2021

(87) PCT Pub. No.: WO2020/158889
PCT Pub. Date: Aug. 6, 2020

(65) Prior Publication Data
US 2022/0095620 A1    Mar. 31, 2022

(30) Foreign Application Priority Data
Jan. 31, 2019  (JP) .................. 2019-015345
Jun. 25, 2019  (JP) .................. 2019-117011
Dec. 10, 2019  (JP) .................. 2019-222703

(51) Int. Cl.
C07D 519/00    (2006.01)
A01N 43/90     (2006.01)
A01P 7/00      (2006.01)

(52) U.S. Cl.
CPC ............... *A01N 43/90* (2013.01); *A01P 7/00* (2021.08); *C07D 519/00* (2013.01)

(58) Field of Classification Search
CPC .......... C07D 519/00; A01N 43/90; A01P 7/00
See application file for complete search history.

(56) References Cited

U.S. PATENT DOCUMENTS

2018/0022760 A1  1/2018 Kudo et al.
2018/0116222 A1  5/2018 Fischer et al.
(Continued)

FOREIGN PATENT DOCUMENTS

WO      2016/129684     *  8/2016
WO   WO 2016/129684 A1    8/2016
(Continued)

OTHER PUBLICATIONS

Indian Office Action issued on Dec. 27, 2022 in Indian Patent Application No. 2021 47037599, 6 pages.
(Continued)

*Primary Examiner* — D Margaret M Seaman
(74) *Attorney, Agent, or Firm* — Oblon, McClelland, Maier & Neustadt, L.L.P.

(57) ABSTRACT

The present invention provides a compound having an excellent control effect on a harmful arthropod. A compound represented by formula (I)

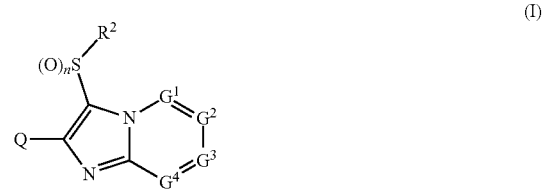

(I)

[wherein:
Q represents a group represented by Q1 or a group represented by Q2;

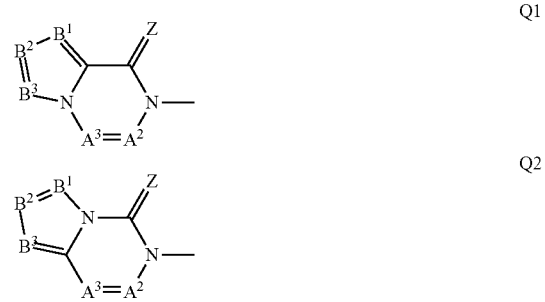

Z represents an oxygen atom or the like;
$A^2$ represents $CR^{4a}$ or the like;
$A^3$ represents a nitrogen atom, $CR^{4b}$, or the like;
$B^1$ represents $CR^1$ or the like;
$B^2$ represents a nitrogen atom, $CR^{6b}$, or the like;
$B^3$ represents a nitrogen atom, $CR^{6c}$, or the like;
$G^1$ represents a nitrogen atom or $CR^{3a}$;
$G^2$ represents a nitrogen atom or $CR^{3b}$;
$G^3$ represents a nitrogen atom or $CR^{3c}$;
$G^4$ represents a nitrogen atom or $CR^{3d}$;
$R^1$ represents a C1-C6 chain hydrocarbon group substituted with one or more substituent(s) selected from the group consisting of a cyano group and a halogen atom or the like;
$R^2$ represents a C1-C6 alkyl group or the like;
$R^{3a}$, $R^{3b}$, $R^{3c}$, and $R^{3d}$ are identical to or different from each other, and each represent a C1-C6 chain hydrocarbon group or the like;
$R^{4a}$, $R^{4b}$, $R^{6b}$, and $R^{6c}$ are identical to or different from each other, and each represent a hydrogen atom or the like; and
n represents 0, 1, or 2]
or an N-oxide thereof has an excellent control effect on a harmful arthropod.

15 Claims, No Drawings

(56) References Cited

U.S. PATENT DOCUMENTS

2020/0068893 A1 3/2020 Miyasaka et al.
2020/0181172 A1 6/2020 Hager et al.
2021/0084903 A1 3/2021 Orimoto et al.

FOREIGN PATENT DOCUMENTS

| WO | WO 2016/162318 A1 | | 10/2016 |
|----|----|----|----|
| WO | 2018/199210 | * | 1/2018 |
| WO | 2018/052136 | * | 3/2018 |
| WO | WO 2018/052136 A1 | | 3/2018 |
| WO | WO 2018/199210 A1 | | 11/2018 |
| WO | WO 2019/038195 A1 | | 2/2019 |
| WO | WO 2019/124548 A1 | | 6/2019 |

OTHER PUBLICATIONS

International Search Report issued Apr. 14, 2020 in PCT/JP2020/003521 filed Jan. 30, 2020, 3 pages.
International Preliminary Report on Patentability and Written Opinion issued Jul. 27, 2021 in PCT/JP2020/003521, 6 pages.
Japanese Office Action issued on Nov. 7, 2023 in Japanese Patent Application No. 2020-568609 (with unedited computer-generated English translation), 5 pages.
Extended European Search Report issued Aug. 25, 2022 in European Patent Application No. 20749233.1, 7 pages.
Combined Chinese Office Action and Search Report Issued Dec. 7, 2021 in Chinese Patent Application No. 202080011914.1 (with English translation), 15 pages.

* cited by examiner

HETEROCYCLIC COMPOUND AND HARMFUL ARTHROPOD CONTROL COMPOSITION CONTAINING SAME

TECHNICAL FIELD

This application claims the priorities to and the benefits of Japanese Patent Application No. 2019-015345 filed on Jan. 31, 2019, Japanese Patent Application No. 2019-117011 filed on Jun. 25, 2019, and Japanese Patent Application No. 2019-222703 filed on Dec. 10, 2019, the entire contents of which are incorporated herein by reference.

The present invention relates to heterocyclic compounds and compositions for controlling harmful arthropods comprising the same.

BACKGROUND ART

To date, various compounds have been studied in order to control harmful arthropods. For example, Patent Document 1 discloses that certain kinds of compounds have control effects on pests.

CITATION LIST

Patent Document

Patent Document 1: WO 2016/129684 pamphlet

SUMMARY OF THE INVENTION

Problems to be Solved by Invention

An object of the present invention is to provide compounds having excellent control efficacy against harmful arthropods.

Means to Solve Problems

The present invention provides the followings.
[1] A compound represented by formula (I)

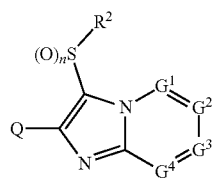

[wherein:
R$^2$ represents a C1-C6 alkyl group optionally substituted with one or more halogen atom(s), a cyclopropyl group, or a cyclopropylmethyl group;
n represents 0, 1, or 2;
G$^1$ represents a nitrogen atom or CR$^{3a}$;
G$^2$ represents a nitrogen atom or CR$^{3b}$;
G$^3$ represents a nitrogen atom or CR$^{3c}$;
G$^4$ represents a nitrogen atom or CR$^{3d}$;
R$^{3a}$, R$^{3b}$, R$^{3c}$, and R$^{3d}$ are identical to or different from each other, and each represent a C1-C6 chain hydrocarbon group optionally substituted with one or more substituent(s) selected from Group B, a C3-C7 cycloalkyl group optionally substituted with one or more substituent(s) selected from Group E, a phenyl group optionally substituted with one or more substituent(s) selected from Group H, a 5 or 6 membered aromatic heterocyclic group optionally substituted with one or more substituent(s) selected from Group H, OR$^{12}$, NR$^{11}$R$^{12}$, NR$^{11a}$R$^{12a}$, NR$^{24}$NR$^{11}$R$^{12}$, NR$^{24}$OR$^{11}$, NR$^{12}$C(O)R$^{13}$, NR$^{24}$NR$^{11}$C(O)R$^{13}$, NR$^{11}$C(O)OR$^{14}$, NR$^{24}$NR$^{11}$C(O)OR$^{14}$, NR$^{11}$C(O)NR$^{31}$R$^{32}$, NR$^{24}$NR$^{11}$C(O)NR$^{31}$R$^{32}$, N=CHNR$^{31}$R$^{32}$, N=S(O)$_p$R$^{15}$R$^{16}$, C(O)R$^{13}$, C(O)OR$^{17}$, C(O)NR$^{31}$R$^{32}$, C(O)NR$^{11}$S(O)$_2$R$^{23}$, CR$^{30}$=NOR$^{17}$, NR$^{11}$CR$^{24}$=NOR$^{17}$, S(O)$_m$R$^{23}$, a cyano group, a nitro group, a hydrogen atom, or a halogen atom;
p represents 0 or 1;
m represents 0, 1, or 2;
R$^{30}$ represents a C1-C6 chain hydrocarbon group optionally substituted with one or more halogen atom(s), a halogen atom, OR$^{35}$, NR$^{36}$R$^{37}$, or a hydrogen atom;
R$^{35}$ represents a C1-C6 chain hydrocarbon group optionally substituted with one or more halogen atom(s);
R$^{17}$ represents a C1-C6 chain hydrocarbon group optionally substituted with one or more halogen atom(s), a phenyl group optionally substituted with one or more substituent(s) selected from Group D, or a hydrogen atom;
R$^{11}$, R$^{24}$, R$^{36}$, and R$^{37}$ are identical to or different from each other, and each represent a C1-C6 chain hydrocarbon group optionally substituted with one or more halogen atom(s), or a hydrogen atom;
R$^{12}$ represents a C1-C6 chain hydrocarbon group optionally substituted with one or more substituent(s) selected from Group F, a C3-C7 cycloalkyl group optionally substituted with one or more substituent(s) selected from Group J, a C3-C7 cycloalkenyl group optionally substituted with one or more substituent(s) selected from Group J, a phenyl group optionally substituted with one or more substituent(s) selected from Group D, a 6 membered aromatic heterocyclic group optionally substituted with one or more substituent(s) selected from Group D, a hydrogen atom, or S(O)$_2$R$^{23}$;
R$^{23}$ represents a C1-C6 chain hydrocarbon group optionally substituted with one or more halogen atom(s), or a phenyl group optionally substituted with one or more substituent(s) selected from Group D;
R$^{11a}$ and R$^{12a}$ are combined with the nitrogen atom to which they are attached to form a 3-7 membered nonaromatic heterocyclic group optionally substituted with one or more substituent(s) selected from Group E;
R$^{13}$ represents a C1-C6 chain hydrocarbon group optionally substituted with one or more halogen atom(s), a C3-C7 cycloalkyl group optionally substituted with one or more halogen atom(s), a (C3-C6 cycloalkyl) C1-C3 alkyl group optionally substituted with one or more halogen atom(s), a phenyl group optionally substituted with one or more substituent(s) selected from Group D, a 5 or 6 membered aromatic heterocyclic group optionally substituted with one or more substituent(s) selected from Group D, or a hydrogen atom;
R$^{14}$ represents a C1-C6 chain hydrocarbon group optionally substituted with one or more halogen atom(s), a C3-C7 cycloalkyl group optionally substituted with one or more halogen atom(s), a (C3-C6 cycloalkyl) C1-C3 alkyl group optionally substituted with one or more halogen atom(s), or a phenyl C1-C3 alkyl group {wherein the phenyl moiety in said phenyl C1-C3 alkyl group is optionally substituted with one or more substituent(s) selected from Group D};

$R^{15}$ and $R^{16}$ are identical to or different from each other, and each represent a C1-C6 alkyl group optionally substituted with one or more halogen atom(s);

$R^{31}$ represents a C1-C6 alkyl group optionally substituted with one or more halogen atom(s), or a hydrogen atom;

$R^{32}$ represents a C1-C6 chain hydrocarbon group optionally substituted with one or more substituent(s) selected from Group F, a C3-C7 cycloalkyl group optionally substituted with one or more substituent(s) selected from Group J, $S(O)_2R^{23}$, or a hydrogen atom;

Q represents a group represented by Q1 or a group represented by Q2;

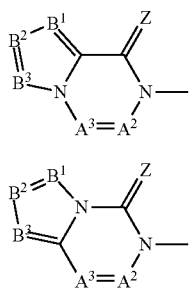

Z represents an oxygen atom or a sulfur atom;

the combination of $A^2$ and $A^3$ represents:
a combination wherein $A^2$ represents $CR^{4a}$, and $A^3$ represents a nitrogen atom or $CR^{4b}$; or
a combination wherein $A^2$ represents a nitrogen atom, and $A^3$ represents $CR^{4b}$;

the combination of $B^1$, $B^2$, and $B^3$ represents:
a combination wherein $B^1$ represents $CR^1$, $B^2$ represents a nitrogen atom or $CR^{6b}$, and $B^3$ represents a nitrogen atom or $CR^{6c}$;
a combination wherein $B^1$ represents a nitrogen atom or $CR^{6a}$, $B^2$ represents $CR^1$, and $B^3$ represents a nitrogen atom or $CR^{6c}$; or
a combination wherein $B^1$ represents a nitrogen atom or $CR^{6a}$, $B^2$ represents a nitrogen atom or $CR^{61a}$, and $B^3$ represents $CR^1$;

$R^1$ represents a C1-C6 chain hydrocarbon group substituted with one or more substituent(s) selected from the group consisting of a cyano group and a halogen atom, a C3-C4 cycloalkyl group optionally substituted with one or more substituent(s) selected from the group consisting of a cyano group and a halogen atom, $SR^8$, $S(O)R^8$, $S(O)_2R^8$, $OR^8$, or $OS(O)_2R^8$;

$R^8$ represents a C1-C6 chain hydrocarbon group substituted with one or more substituent(s) selected from the group consisting of a cyano group and a halogen atom, or a C3-C4 cycloalkyl group optionally substituted with one or more substituent(s) selected from the group consisting of a cyano group and a halogen atom;

$R^{4a}$, $R^{4b}$, $R^{6a}$, $R^{61a}$, and $R^{6c}$ are identical to or different from each other, and each represent a C1-C6 chain hydrocarbon group optionally substituted with one or more halogen atom(s), a C3-C7 cycloalkyl group optionally substituted with one or more halogen atom(s), a C1-C6 alkoxy group optionally substituted with one or more halogen atom(s), $NR^{25}R^{26}$, $C(O)R^7$, $C(O)OR^7$, $C(O)NR^{19}R^{20}$, $NR^{25}C(O)R^{18}$, $NR^{25}C(O)OR^{18}$, $NR^{25}C(O)NR^{19}R^{20}$, a cyano group, a halogen atom, or a hydrogen atom;

$R^{19}$ and $R^{25}$ are identical to or different from each other, and each represent a C1-C6 chain hydrocarbon group optionally substituted with one or more halogen atom(s), or a hydrogen atom;

$R^{26}$ represents a C1-C6 chain hydrocarbon group optionally substituted with one or more substituent(s) selected from Group L, a C3-C7 cycloalkyl group optionally substituted with one or more substituent(s) selected from Group M, a C3-C7 cycloalkenyl group optionally substituted with one or more substituent(s) selected from Group M, a phenyl group optionally substituted with one or more substituent(s) selected from Group K, a 6 membered aromatic heterocyclic group optionally substituted with one or more substituent(s) selected from Group K, a hydrogen atom, or $S(O)_2R^{27}$;

$R^{27}$ represents a C1-C6 chain hydrocarbon group optionally substituted with one or more halogen atom(s), a C3-C7 cycloalkyl group optionally substituted with one or more halogen atom(s), or a phenyl group optionally substituted with one or more substituent(s) selected from Group K; and $R^7$, $R^{18}$, and $R^{20}$ are identical to or different from each other, and each represent a C1-C6 chain hydrocarbon group optionally substituted with one or more substituent(s) selected from Group L, a C3-C7 cycloalkyl group optionally substituted with one or more substituent(s) selected from Group M, or a hydrogen atom;

Group B: a group consisting of a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C3-C6 cycloalkyl group optionally substituted with one or more halogen atom(s), a cyano group, a hydroxy group, and a halogen atom;

Group C: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), and a halogen atom;

Group D: a group consisting of a C1-C6 chain hydrocarbon group optionally substituted with one or more halogen atom(s), a hydroxy group, a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a sulfanyl group, a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), an amino group, $NHR^{21}$, $NR^{21}R^{22}$, $C(O)R^{21}$, $OC(O)R^{21}$, $C(O)OR^{21}$, a cyano group, a nitro group, and a halogen atom;

$R^{21}$ and $R^{22}$ are identical to or different from each other, and each represent a C1-C6 alkyl group optionally substituted with one or more halogen atom(s);

Group E: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a halogen atom, an oxo group, a hydroxy group, a cyano group, and a nitro group;

Group F: a group consisting of a C1-C6 alkoxy group optionally substituted with one or more halogen atom(s), a phenyl group optionally substituted with one or more substituent(s) selected from Group D, a 5 or 6 membered aromatic heterocyclic group optionally substituted with one or more substituent(s) selected from Group D, a C3-C7 cycloalkyl group optionally substituted with one or more halogen atom(s), a 3-7 membered nonaromatic heterocyclic group optionally substituted with one or more substituent(s) selected from Group C, an amino group, $NHR^{21}$, $NR^{21}R^{22}$, a halogen atom, and a cyano group;

Group H: a group consisting of a C1-C6 alkyl group optionally substituted with one or more halogen atom(s), a or 6 membered aromatic heterocyclic group optionally substituted with one or more substituent(s) selected from Group D, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a halogen atom, a nitro group, a cyano group, and an amino group;

$R^9$ represents a C1-C6 alkyl group optionally substituted with one or more halogen atom(s), or a C3-C6 cycloalkyl group optionally substituted with one or more halogen atom(s);

$R^{10}$ represents a C1-C6 alkyl group optionally substituted with one or more halogen atom(s), a C3-C6 cycloalkyl group optionally substituted with one or more halogen atom(s), or a hydrogen atom;

Group J: a group consisting of a C1-C6 alkyl group optionally substituted with one or more halogen atom(s), a halogen atom, and a cyano group;

Group K: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C3-C6 cycloalkyl group optionally substituted with one or more halogen atom(s), a (C1-C6 alkyl optionally substituted with one or more halogen atom(s))amino group, a di(C1-C4 alkyl)amino group optionally substituted with one or more halogen atom(s), a C2-C6 alkylcarbonyl group optionally substituted with one or more halogen atom(s), a C2-C6 alkoxycarbonyl group optionally substituted with one or more halogen atom(s), a C2-C6 alkoxycarbonyloxy group optionally substituted with one or more halogen atom(s), an aminocarbonyl group, a (C1-C6 alkyl optionally substituted with one or more halogen atom(s))aminocarbonyl group, a [di(C1-C4 alkyl) amino optionally substituted with one or more halogen atom(s)]carbonyl group, a (C2-C6 alkoxycarbonyl optionally substituted with one or more halogen atom(s))amino group, a (C2-C6 alkoxycarbonyl)(C1-C6 alkyl)amino group optionally substituted with one or more halogen atom(s), a cyano group, an amino group, a nitro group, a hydroxy group, and a halogen atom;

Group L: a group consisting of a C3-C6 cycloalkyl group optionally substituted with one or more halogen atom(s), a phenyl group optionally substituted with one or more substituent(s) selected from Group K, a 5 or 6 membered aromatic heterocyclic group optionally substituted with one or more substituent(s) selected from Group K, a C1-C6 alkoxy group optionally substituted with one or more halogen atom(s), a (C1-C6 alkyl optionally substituted with one or more halogen atom(s))amino group, a di(C1-C4 alkyl)amino group optionally substituted with one or more halogen atom(s), a cyano group, an amino group, a nitro group, a hydroxy group, and a halogen atom;

Group M: a group consisting of a C1-C6 alkyl group optionally substituted with one or more halogen atom(s), a C1-C6 alkoxy group optionally substituted with one or more halogen atom(s), a C2-C6 alkoxycarbonyl group optionally substituted with one or more halogen atom(s), an amino group, a cyano group, and a halogen atom](hereinafter referred to as "Present compound N" or "Compound N of the present invention") or an N-oxide thereof (hereinafter the compound represented by formula (I) or an N-oxide thereof is referred to as "Present compound" or "Compound of the present invention").

[2] The compound or an N-oxide thereof according to [1], wherein Q represents the group represented by Q1.

[3] The compound or an N-oxide thereof according to [1], wherein Q represents the group represented by Q2.

[4] The compound or an N-oxide thereof according to any one of [1] to [3], wherein $R^{3a}$, $R^{3b}$, $R^{3c}$, and $R^{3d}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group {wherein said phenyl group, said pyridyl group, and said pyrimidinyl group are optionally substituted with one or more substituent(s) selected from Group J}, $OR^{12}$, $CR^{30}$=$NOR^{17}$, a hydrogen atom, or a halogen atom.

[5] The compound or an N-oxide thereof according to any one of [1] to [4], wherein $G^1$ represents a nitrogen atom or CH;

$G^2$ represents $CR^{3b}$;

$G^3$ represents $CR^{3c}$;

$G^4$ represents a nitrogen atom or CH; and $R^{3b}$ and $R^{3c}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more substituent(s) selected from the group consisting of a halogen atom and a cyano group}, $OR^{12}$, a hydrogen atom, or a halogen atom.

[5] The compound or an N-oxide thereof according to any one of [1] to [5], wherein $G^1$ represents CH;

$G^2$ represents $CR^{3b}$;

G³ represents CR³ᶜ;

G⁴ represents CH; and

R³ᵇ and R³ᶜ are identical to or different from each other, and each represent a C1-C6 alkyl group optionally substituted with one or more halogen atom(s), or a hydrogen atom.

[7] The compound or an N-oxide thereof according to any one of [1] to [6], wherein R¹ represents a C1-C6 alkyl group substituted with one or more substituent(s) selected from the group consisting of a halogen atom and a cyano group; or a cyclopropyl group optionally substituted with one or more substituent(s) selected from the group consisting of a cyano group and a halogen atom.

[8] The compound or an N-oxide thereof according to any one of [1] to [7], wherein R² represents an ethyl group.

[9] The compound or an N-oxide thereof according to any one of [1] to [8], wherein Z represents an oxygen atom.

[10] A composition for controlling a harmful arthropod comprising the compound or an N-oxide thereof according to any one of [1] to [9].

[11] A composition comprising one or more ingredient(s) selected from the group consisting of Group (a), Group (b), Group (c), and Group (d), and the compound or an N-oxide thereof according to any one of [1] to [9]:

Group (a): a group consisting of insecticidal active ingredients, miticidal active ingredients, and nematicidal active ingredients;

Group (b): fungicidal active ingredients;

Group (c): plant growth regulatory ingredients;

Group (d): repellent ingredients.

[12] A method for controlling a harmful arthropod which comprises applying an effective amount of the compound or an N-oxide thereof according to any one of [1] to [9] or an effective amount of the composition according to [11] to a harmful arthropod or a habitat where a harmful arthropod lives.

[13] A seed or a vegetative reproduction organ holding an effective amount of the compound or an N-oxide thereof according to any one of [1] to [9] or an effective amount of the composition according to [11].

Effect of Invention

According to the present invention, harmful arthropods can be controlled.

MODE FOR CARRYING OUT THE INVENTION

The substituents in the present invention are explained as follows.

The term of "halogen atom" represents a fluorine atom, a chlorine atom, a bromine atom, or an iodine atom.

When a substituent is substituted with two or more halogen atoms or substituents, these halogen atoms or substituents may be identical to or different from each other.

The expression of "CX-CY" as described herein means that the number of carbon atom is X to Y. For example, the expression of "C1-C6" means that the number of carbon atom is 1 to 6.

The term of "chain hydrocarbon group" represents an alkyl group, an alkenyl group, or an alkynyl group.

Examples of the term of "alkyl group" include a methyl group, an ethyl group, a propyl group, an isopropyl group, a 1,1-dimethylpropyl group, a 1,2-dimethylpropyl group, a 1-ethylpropyl group, a butyl group, a sec-butyl group, a tert-butyl group, a pentyl group, and a hexyl group.

Examples of the term of "alkenyl group" include a vinyl group, a 1-propenyl group, a 2-propenyl group, a 1-methyl-1-propenyl group, a 1-methyl-2-propenyl group, a 1,2-dimethyl-1-propenyl group, a 1-ethyl-2-propenyl group, a 3-butenyl group, a 4-pentenyl group, and a 5-hexenyl group.

Examples of the term of "alkynyl group" include an ethynyl group, a 1-propynyl group, a 2-propynyl group, a 1-methyl-2-propynyl group, a 1,1-dimethyl-2-propynyl group, a 1-ethyl-2-propynyl group, a 2-butynyl group, a 4-pentynyl group, and a 5-hexynyl group.

Examples of the term of "alkoxy group" include a methoxy group, an ethoxy group, a propoxy group, an isopropoxy group, a butoxy group, a tert-butoxy group, a pentyloxy group, and a hexyloxy group.

Examples of the term of "alkenyloxy group" include a 2-propenyloxy group, a 2-butenyloxy group, and a 5-hexenyloxy group.

Examples of the term of "alkynyloxy group" include a 2-propynyloxy group, a 2-butynyloxy group, and a 5-hexynyloxy group.

Examples of the term of "fluoroalkyl group" include a trifluoromethyl group, a 2,2,2-trifluoroethyl group, a pentafluoroethyl group, a 2,2,3,3,3-pentafluoropropyl group, a 1,1,1-trifluoropropan-2-yl group, and a heptafluoropropyl group.

Examples of the term of "cycloalkyl group" include a cyclopropyl group, a cyclobutyl group, a cyclopentyl group, a cyclohexyl group, and a cycloheptyl group.

Examples of the term of "cycloalkenyl group" include a cyclopropenyl group, a cyclobutenyl group, a cyclopentenyl group, a cyclohexenyl group, and a cycloheptenyl group.

The term of "3-7 membered nonaromatic heterocyclic group" represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiazinane ring, a thiomorpholine ring, or a 1,4-thiazepane ring.

Examples of the term of "3-7 membered nonaromatic heterocyclic group optionally substituted with one or more substituent(s) selected from Group E" include the following groups.

-continued

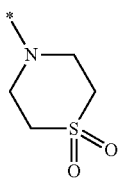

The term of "5 or 6 membered aromatic heterocyclic group" represents a 5 membered aromatic heterocyclic group or a 6 membered aromatic heterocyclic group. The term of "5 membered aromatic heterocyclic group" represents a pyrrolyl group, a furyl group, a thienyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, or a thiadiazolyl group. The term of "6 membered aromatic heterocyclic group" represents a pyridyl group, a pyridazinyl group, a pyrimidinyl group, a pyrazinyl group, a triazinyl group, or a tetrazinyl group.

Examples of the term of "(C3-C6 cycloalkyl) C1-C3 alkyl group optionally substituted with one or more halogen atom(s)" include a cyclopropylmethyl group, a (2-fluorocyclopropyl)methyl group, a cyclopropyl(fluoro)methyl group, and a (2-fluorocyclopropyl)(fluoro)methyl group.

Examples of the term of "phenyl C1-C3 alkyl group {wherein the phenyl moiety in said phenyl C1-C3 alkyl group is optionally substituted with one or more substituent(s) selected from Group D}" include a benzyl group, a 2-fluorobenzyl group, a 4-chlorobenzyl group, a 4-(trifluoromethyl)benzyl group, and a 2-[4-(trifluoromethyl)phenyl]ethyl group.

Examples of the term of "alkylsulfanyl group" include a methylsulfanyl group, an ethylsulfanyl group, a propylsulfanyl group, and an isopropylsulfanyl group.

Examples of the term of "alkylsulfinyl group" include a methylsulfinyl group, an ethylsulfinyl group, a propylsulfinyl group, and an isopropylsulfinyl group.

Examples of the term of "alkylsulfonyl group" include a methylsulfonyl group, an ethylsulfonyl group, a propylsulfonyl group, and an isopropylsulfonyl group.

Examples of the term of "(C1-C6 alkyl)amino group" include a methylamino group, an ethylamino group, a propylamino group, and an isopropylamino group.

Examples of the term of "di(C1-C4 alkyl)amino group" include a dimethylamino group and a diethylamino group.

Examples of the term of "alkylcarbonyl group" include a methylcarbonyl group and an ethylcarbonyl group.

Examples of the term of "alkoxycarbonyl group" include a methoxycarbonyl group and an ethoxycarbonyl group.

Examples of the term of "alkoxycarbonyloxy group" include a methoxycarbonyloxy group and an ethoxycarbonyloxy group.

Examples of the term of "(C1-C6 alkyl)aminocarbonyl" group include a methylaminocarbonyl group and an ethylaminocarbonyl group.

Examples of the term of "[di(C1-C4 alkyl)amino]carbonyl group" include a dimethylaminocarbonyl group and a diethylaminocarbonyl group.

Examples of the term of "(C2-C6 alkoxycarbonyl)amino group" include a methoxycarbonylamino group and an ethoxycarbonylamino group.

Examples of the term of "(C2-C6 alkoxycarbonyl)(C1-C6 alkyl)amino group" include a methoxycarbonylmethylamino group and an ethoxycarbonylmethylamino group.

Examples of N-oxide of the compound represented by formula (I) include the compounds represented by the following formulae.

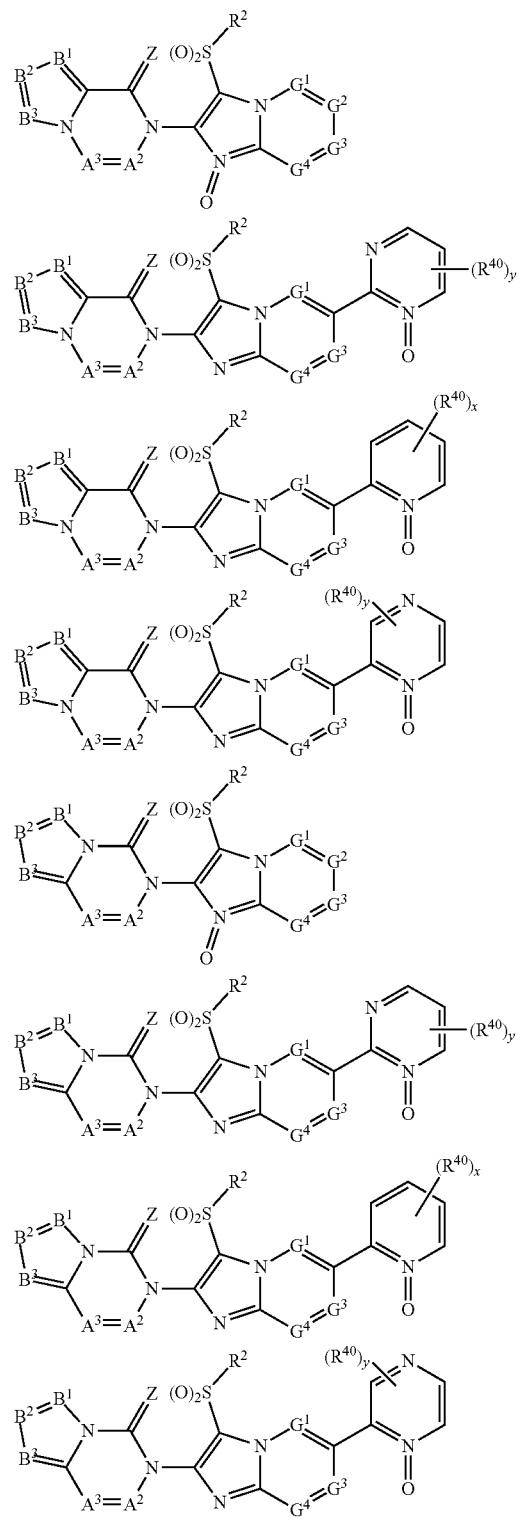

[wherein $R^{40}$ represents any one substituent selected from Group H; x represents 0, 1, 2, 3, or 4; y represents 0, 1, 2, or 3; and the other symbols are the same as defined above.]

The Present compound may optionally have one or more stereoisomer(s). Examples of the stereoisomer(s) include enantiomers, diastereomers, and geometric isomers. The Present compound encompasses each stereoisomer and mixtures of stereoisomers at any ratio.

The Present compound may optionally form an acid addition salt. Examples of the acid to form the acid addition salt include inorganic acids such as hydrogen chloride, phosphoric acid, and sulfuric acid; and organic acids such as acetic acid, trifluoroacetic acid, benzoic acid, and p-toluenesulfonic acid. Such acid addition salt may be prepared by mixing the Present compound with an acid.

Aspects of the Present compound N include the following compounds.

[Aspect 1] The Present compound N, wherein
$R^1$ represents a C1-C6 alkyl group substituted with one or more substituent(s) selected from the group consisting of a halogen atom and a cyano group; or a cyclopropyl group optionally substituted with one or more substituent(s) selected from the group consisting of a cyano group and a halogen atom;
$B^1$ represents a nitrogen atom or $CR^{6a}$;
$B^2$ represents $CR^1$; and
$B^3$ represents a nitrogen atom or $CR^{6c}$.

[Aspect 2] The compound according to the Aspect 1, wherein
$R^{4a}$, $R^{4b}$, $R^{6a}$, and $R^{6c}$ are identical to or different from each other, and each represent a halogen atom or a hydrogen atom.

[Aspect 3] The compound according to the Aspect 2, wherein
$A^2$ represents $CR^{4a}$; and
$A^3$ represents $CR^{4b}$.

[Aspect 4] The compound according to the Aspect 3, wherein
$R^{6c}$ represents a hydrogen atom.

[Aspect 5] The compound according to the Aspect 1, wherein
$R^{4a}$, $R^{4b}$, $R^{6a}$, and $R^{6c}$ are identical to or different from each other, and each represent a C1-C6 alkyl group optionally substituted with one or more halogen atom(s), a C1-C6 alkoxy group optionally substituted with one or more halogen atom(s), a halogen atom, or a hydrogen atom.

[Aspect 6] The compound according to the Aspect 5, wherein
$R^1$ represents a C1-C3 fluoroalkyl group.

[Aspect 7] The Present compound N, wherein
$R^1$ represents a C1-C3 fluoroalkyl group;
$B^1$ represents a nitrogen atom or $CR^{6a}$;
$B^2$ represents $CR^1$;
$B^3$ represents a nitrogen atom or $CR^{6c}$; and
$R^{4a}$, $R^{4b}$, $R^{6a}$, and $R^{6c}$ are identical to or different from each other, and each represent a halogen atom or a hydrogen atom.

[Aspect 8] The compound according to the Aspect 7, wherein
$A^2$ represents $CR^{4a}$; and
$A^3$ represents $CR^{4b}$.

[Aspect 9] The compound according to the Aspect 8, wherein
$R^{6c}$ represents a hydrogen atom.

[Aspect 10] The compound according to the Aspect 8, wherein
$B^1$ represents a nitrogen atom or $CR^{6a}$;
$B^2$ represents $CR^1$; and
$B^3$ represents a nitrogen atom.

[Aspect 11] The compound according to the Aspect 8, wherein
$B^1$ represents $CR^{6a}$;
$B^2$ represents $CR^1$; and
$B^3$ represents a nitrogen atom.

[Aspect 12] The compound according to the Aspect 11, wherein
$R^{4a}$, $R^{4b}$, and $R^{6a}$ each represent a hydrogen atom.

[Aspect 13] The Present compound N, wherein
$R^2$ represents a C1-C6 alkyl group.

[Aspect 14] The Present compound N, wherein
$R^2$ represents an ethyl group.

[Aspect 15] The compound according to the Aspect 1, wherein
$R^2$ represents a C1-C6 alkyl group.

[Aspect 16] The compound according to the Aspect 2, wherein
$R^2$ represents a C1-C6 alkyl group.

[Aspect 17] The compound according to the Aspect 3, wherein
$R^2$ represents a C1-C6 alkyl group.

[Aspect 18] The compound according to the Aspect 4, wherein
$R^2$ represents a C1-C6 alkyl group.

[Aspect 19] The compound according to the Aspect 5, wherein
$R^2$ represents a C1-C6 alkyl group.

[Aspect 20] The compound according to the Aspect 6, wherein
$R^2$ represents a C1-C6 alkyl group.

[Aspect 21] The compound according to the Aspect 7, wherein
$R^2$ represents a C1-C6 alkyl group.

[Aspect 22] The compound according to the Aspect 8, wherein
$R^2$ represents a C1-C6 alkyl group.

[Aspect 23] The compound according to the Aspect 9, wherein
$R^2$ represents a C1-C6 alkyl group.

[Aspect 24] The compound according to the Aspect 10, wherein
$R^2$ represents a C1-C6 alkyl group.

[Aspect 25] The compound according to the Aspect 11, wherein
$R^2$ represents a C1-C6 alkyl group.

[Aspect 26] The compound according to the Aspect 12, wherein
$R^2$ represents a C1-C6 alkyl group.

[Aspect 27] The compound according to the Aspect 1, wherein
$R^2$ represents an ethyl group.

[Aspect 28] The compound according to the Aspect 2, wherein
$R^2$ represents an ethyl group.

[Aspect 29] The compound according to the Aspect 3, wherein
$R^2$ represents an ethyl group.

[Aspect 30] The compound according to the Aspect 4, wherein
$R^2$ represents an ethyl group.

[Aspect 31] The compound according to the Aspect 5, wherein
$R^2$ represents an ethyl group.

[Aspect 32] The compound according to the Aspect 6, wherein
$R^2$ represents an ethyl group.

[Aspect 33] The compound according to the Aspect 7, wherein
R² represents an ethyl group.
[Aspect 34] The compound according to the Aspect 8, wherein
R² represents an ethyl group.
[Aspect 35] The compound according to the Aspect 9, wherein
R² represents an ethyl group.
[Aspect 36] The compound according to the Aspect 10, wherein
R² represents an ethyl group.
[Aspect 37] The compound according to the Aspect 11, wherein
R² represents an ethyl group.
[Aspect 38] The compound according to the Aspect 12, wherein
R² represents an ethyl group.
[Aspect 39] The Present compound N, wherein
Z represents an oxygen atom.
[Aspect 40] The compound according to the Aspect 1, wherein
Z represents an oxygen atom.
[Aspect 41] The compound according to the Aspect 2, wherein
Z represents an oxygen atom.
[Aspect 42] The compound according to the Aspect 3, wherein
Z represents an oxygen atom.
[Aspect 43] The compound according to the Aspect 4, wherein
Z represents an oxygen atom.
[Aspect 44] The compound according to the Aspect 5, wherein
Z represents an oxygen atom.
[Aspect 45] The compound according to the Aspect 6, wherein
Z represents an oxygen atom.
[Aspect 46] The compound according to the Aspect 7, wherein
Z represents an oxygen atom.
[Aspect 47] The compound according to the Aspect 8, wherein
Z represents an oxygen atom.
[Aspect 48] The compound according to the Aspect 9, wherein
Z represents an oxygen atom.
[Aspect 49] The compound according to the Aspect 10, wherein
Z represents an oxygen atom.
[Aspect 50] The compound according to the Aspect 11, wherein
Z represents an oxygen atom.
[Aspect 51] The compound according to the Aspect 12, wherein
Z represents an oxygen atom.
[Aspect 52] The compound according to the Aspect 13, wherein
Z represents an oxygen atom.
[Aspect 53] The compound according to the Aspect 14, wherein
Z represents an oxygen atom.
[Aspect 54] The compound according to the Aspect 15, wherein
Z represents an oxygen atom.
[Aspect 55] The compound according to the Aspect 16, wherein
Z represents an oxygen atom.
[Aspect 56] The compound according to the Aspect 17, wherein
Z represents an oxygen atom.
[Aspect 57] The compound according to the Aspect 18, wherein
Z represents an oxygen atom.
[Aspect 58] The compound according to the Aspect 19, wherein
Z represents an oxygen atom.
[Aspect 59] The compound according to the Aspect 20, wherein
Z represents an oxygen atom.
[Aspect 60] The compound according to the Aspect 21, wherein
Z represents an oxygen atom.
[Aspect 61] The compound according to the Aspect 22, wherein
Z represents an oxygen atom.
[Aspect 62] The compound according to the Aspect 23, wherein
Z represents an oxygen atom.
[Aspect 63] The compound according to the Aspect 24, wherein
Z represents an oxygen atom.
[Aspect 64] The compound according to the Aspect 25, wherein
Z represents an oxygen atom.
[Aspect 65] The compound according to the Aspect 26, wherein
Z represents an oxygen atom.
[Aspect 66] The compound according to the Aspect 27, wherein
Z represents an oxygen atom.
[Aspect 67] The compound according to the Aspect 28, wherein
Z represents an oxygen atom.
[Aspect 68] The compound according to the Aspect 29, wherein
Z represents an oxygen atom.
[Aspect 69] The compound according to the Aspect 30, wherein
Z represents an oxygen atom.
[Aspect 70] The compound according to the Aspect 31, wherein
Z represents an oxygen atom.
[Aspect 71] The compound according to the Aspect 32, wherein
Z represents an oxygen atom.
[Aspect 72] The compound according to the Aspect 33, wherein
Z represents an oxygen atom.
[Aspect 73] The compound according to the Aspect 34, wherein
Z represents an oxygen atom.
[Aspect 74] The compound according to the Aspect 35, wherein
Z represents an oxygen atom.
[Aspect 75] The compound according to the Aspect 36, wherein
Z represents an oxygen atom.
[Aspect 76] The compound according to the Aspect 37, wherein
Z represents an oxygen atom.
[Aspect 77] The compound according to the Aspect 38, wherein
Z represents an oxygen atom.

[Aspect 78] The Present compound N, wherein
Q represents the group represented by Q1.
[Aspect 79] The compound according to the Aspect 1, wherein
Q represents the group represented by Q1.
[Aspect 80] The compound according to the Aspect 2, wherein
Q represents the group represented by Q1.
[Aspect 81] The compound according to the Aspect 3, wherein
Q represents the group represented by Q1.
[Aspect 82] The compound according to the Aspect 4, wherein
Q represents the group represented by Q1.
[Aspect 83] The compound according to the Aspect 5, wherein
Q represents the group represented by Q1.
[Aspect 84] The compound according to the Aspect 6, wherein
Q represents the group represented by Q1.
[Aspect 85] The compound according to the Aspect 7, wherein
Q represents the group represented by Q1.
[Aspect 86] The compound according to the Aspect 8, wherein
Q represents the group represented by Q1.
[Aspect 87] The compound according to the Aspect 9, wherein
Q represents the group represented by Q1.
[Aspect 88] The compound according to the Aspect 10, wherein
Q represents the group represented by Q1.
[Aspect 89] The compound according to the Aspect 11, wherein
Q represents the group represented by Q1.
[Aspect 90] The compound according to the Aspect 12, wherein
Q represents the group represented by Q1.
[Aspect 91] The compound according to the Aspect 13, wherein
Q represents the group represented by Q1.
[Aspect 92] The compound according to the Aspect 14, wherein
Q represents the group represented by Q1.
[Aspect 93] The compound according to the Aspect 15, wherein
Q represents the group represented by Q1.
[Aspect 94] The compound according to the Aspect 16, wherein
Q represents the group represented by Q1.
[Aspect 95] The compound according to the Aspect 17, wherein
Q represents the group represented by Q1.
[Aspect 96] The compound according to the Aspect 18, wherein
Q represents the group represented by Q1.
[Aspect 97] The compound according to the Aspect 19, wherein
Q represents the group represented by Q1.
[Aspect 98] The compound according to the Aspect 20, wherein
Q represents the group represented by Q1.
[Aspect 99] The compound according to the Aspect 21, wherein
Q represents the group represented by Q1.
[Aspect 100] The compound according to the Aspect 22, wherein
Q represents the group represented by Q1.
[Aspect 101] The compound according to the Aspect 23, wherein
Q represents the group represented by Q1.
[Aspect 102] The compound according to the Aspect 24, wherein
Q represents the group represented by Q1.
[Aspect 103] The compound according to the Aspect 25, wherein
Q represents the group represented by Q1.
[Aspect 104] The compound according to the Aspect 26, wherein
Q represents the group represented by Q1.
[Aspect 105] The compound according to the Aspect 27, wherein
Q represents the group represented by Q1.
[Aspect 106] The compound according to the Aspect 28, wherein
Q represents the group represented by Q1.
[Aspect 107] The compound according to the Aspect 29, wherein
Q represents the group represented by Q1.
[Aspect 108] The compound according to the Aspect 30, wherein
Q represents the group represented by Q1.
[Aspect 109] The compound according to the Aspect 31, wherein
Q represents the group represented by Q1.
[Aspect 110] The compound according to the Aspect 32, wherein
Q represents the group represented by Q1.
[Aspect 111] The compound according to the Aspect 33, wherein
Q represents the group represented by Q1.
[Aspect 112] The compound according to the Aspect 34, wherein
Q represents the group represented by Q1.
[Aspect 113] The compound according to the Aspect 35, wherein
Q represents the group represented by Q1.
[Aspect 114] The compound according to the Aspect 36, wherein
Q represents the group represented by Q1.
[Aspect 115] The compound according to the Aspect 37, wherein
Q represents the group represented by Q1.
[Aspect 116] The compound according to the Aspect 38, wherein
Q represents the group represented by Q1.
[Aspect 117] The compound according to the Aspect 39, wherein
Q represents the group represented by Q1.
[Aspect 118] The compound according to the Aspect 40, wherein
Q represents the group represented by Q1.
[Aspect 119] The compound according to the Aspect 41, wherein
Q represents the group represented by Q1.
[Aspect 120] The compound according to the Aspect 42, wherein
Q represents the group represented by Q1.
[Aspect 121] The compound according to the Aspect 43, wherein
Q represents the group represented by Q1.
[Aspect 122] The compound according to the Aspect 44, wherein
Q represents the group represented by Q1.

[Aspect 123] The compound according to the Aspect 45, wherein
Q represents the group represented by Q1.
[Aspect 124] The compound according to the Aspect 46, wherein
Q represents the group represented by Q1.
[Aspect 125] The compound according to the Aspect 47, wherein
Q represents the group represented by Q1.
[Aspect 126] The compound according to the Aspect 48, wherein
Q represents the group represented by Q1.
[Aspect 127] The compound according to the Aspect 49, wherein
Q represents the group represented by Q1.
[Aspect 128] The compound according to the Aspect 50, wherein
Q represents the group represented by Q1.
[Aspect 129] The compound according to the Aspect 51, wherein
Q represents the group represented by Q1.
[Aspect 130] The compound according to the Aspect 52, wherein
Q represents the group represented by Q1.
[Aspect 131] The compound according to the Aspect 53, wherein
Q represents the group represented by Q1.
[Aspect 132] The compound according to the Aspect 54, wherein
Q represents the group represented by Q1.
[Aspect 133] The compound according to the Aspect 55, wherein
Q represents the group represented by Q1.
[Aspect 134] The compound according to the Aspect 56, wherein
Q represents the group represented by Q1.
[Aspect 135] The compound according to the Aspect 57, wherein
Q represents the group represented by Q1.
[Aspect 136] The compound according to the Aspect 58, wherein
Q represents the group represented by Q1.
[Aspect 137] The compound according to the Aspect 59, wherein
Q represents the group represented by Q1.
[Aspect 138] The compound according to the Aspect 60, wherein
Q represents the group represented by Q1.
[Aspect 139] The compound according to the Aspect 61, wherein
Q represents the group represented by Q1.
[Aspect 140] The compound according to the Aspect 62, wherein
Q represents the group represented by Q1.
[Aspect 141] The compound according to the Aspect 63, wherein
Q represents the group represented by Q1.
[Aspect 142] The compound according to the Aspect 64, wherein
Q represents the group represented by Q1.
[Aspect 143] The compound according to the Aspect 65, wherein
Q represents the group represented by Q1.
[Aspect 144] The compound according to the Aspect 66, wherein
Q represents the group represented by Q1.
[Aspect 145] The compound according to the Aspect 67, wherein
Q represents the group represented by Q1.
[Aspect 146] The compound according to the Aspect 68, wherein
Q represents the group represented by Q1.
[Aspect 147] The compound according to the Aspect 69, wherein
Q represents the group represented by Q1.
[Aspect 148] The compound according to the Aspect 70, wherein
Q represents the group represented by Q1.
[Aspect 149] The compound according to the Aspect 71, wherein
Q represents the group represented by Q1.
[Aspect 150] The compound according to the Aspect 72, wherein
Q represents the group represented by Q1.
[Aspect 151] The compound according to the Aspect 73, wherein
Q represents the group represented by Q1.
[Aspect 152] The compound according to the Aspect 74, wherein
Q represents the group represented by Q1.
[Aspect 153] The compound according to the Aspect 75, wherein
Q represents the group represented by Q1.
[Aspect 154] The compound according to the Aspect 76, wherein
Q represents the group represented by Q1.
[Aspect 155] The compound according to the Aspect 77, wherein
Q represents the group represented by Q1.
[Aspect 156] The Present compound N, wherein
Q represents the group represented by Q2.
[Aspect 157] The compound according to the Aspect 1, wherein
Q represents the group represented by Q2.
[Aspect 158] The compound according to the Aspect 2, wherein
Q represents the group represented by Q2.
[Aspect 159] The compound according to the Aspect 3, wherein
Q represents the group represented by Q2.
[Aspect 160] The compound according to the Aspect 4, wherein
Q represents the group represented by Q2.
[Aspect 161] The compound according to the Aspect 5, wherein
Q represents the group represented by Q2.
[Aspect 162] The compound according to the Aspect 6, wherein
Q represents the group represented by Q2.
[Aspect 163] The compound according to the Aspect 7, wherein
Q represents the group represented by Q2.
[Aspect 164] The compound according to the Aspect 8, wherein
Q represents the group represented by Q2.
[Aspect 165] The compound according to the Aspect 9, wherein
Q represents the group represented by Q2.
[Aspect 166] The compound according to the Aspect 10, wherein
Q represents the group represented by Q2.
[Aspect 167] The compound according to the Aspect 11, wherein
Q represents the group represented by Q2.

[Aspect 168] The compound according to the Aspect 12, wherein
Q represents the group represented by Q2.
[Aspect 169] The compound according to the Aspect 13, wherein
Q represents the group represented by Q2.
[Aspect 170] The compound according to the Aspect 14, wherein
Q represents the group represented by Q2.
[Aspect 171] The compound according to the Aspect 15, wherein
Q represents the group represented by Q2.
[Aspect 172] The compound according to the Aspect 16, wherein
Q represents the group represented by Q2.
[Aspect 173] The compound according to the Aspect 17, wherein
Q represents the group represented by Q2.
[Aspect 174] The compound according to the Aspect 18, wherein
Q represents the group represented by Q2.
[Aspect 175] The compound according to the Aspect 19, wherein
Q represents the group represented by Q2.
[Aspect 176] The compound according to the Aspect 20, wherein
Q represents the group represented by Q2.
[Aspect 177] The compound according to the Aspect 21, wherein
Q represents the group represented by Q2.
[Aspect 178] The compound according to the Aspect 22, wherein
Q represents the group represented by Q2.
[Aspect 179] The compound according to the Aspect 23, wherein
Q represents the group represented by Q2.
[Aspect 180] The compound according to the Aspect 24, wherein
Q represents the group represented by Q2.
[Aspect 181] The compound according to the Aspect 25, wherein
Q represents the group represented by Q2.
[Aspect 182] The compound according to the Aspect 26, wherein
Q represents the group represented by Q2.
[Aspect 183] The compound according to the Aspect 27, wherein
Q represents the group represented by Q2.
[Aspect 184] The compound according to the Aspect 28, wherein
Q represents the group represented by Q2.
[Aspect 185] The compound according to the Aspect 29, wherein
Q represents the group represented by Q2.
[Aspect 186] The compound according to the Aspect 30, wherein
Q represents the group represented by Q2.
[Aspect 187] The compound according to the Aspect 31, wherein
Q represents the group represented by Q2.
[Aspect 188] The compound according to the Aspect 32, wherein
Q represents the group represented by Q2.
[Aspect 189] The compound according to the Aspect 33, wherein
Q represents the group represented by Q2.
[Aspect 190] The compound according to the Aspect 34, wherein
Q represents the group represented by Q2.
[Aspect 191] The compound according to the Aspect 35, wherein
Q represents the group represented by Q2.
[Aspect 192] The compound according to the Aspect 36, wherein
Q represents the group represented by Q2.
[Aspect 193] The compound according to the Aspect 37, wherein
Q represents the group represented by Q2.
[Aspect 194] The compound according to the Aspect 38, wherein
Q represents the group represented by Q2.
[Aspect 195] The compound according to the Aspect 39, wherein
Q represents the group represented by Q2.
[Aspect 196] The compound according to the Aspect 40, wherein
Q represents the group represented by Q2.
[Aspect 197] The compound according to the Aspect 41, wherein
Q represents the group represented by Q2.
[Aspect 198] The compound according to the Aspect 42, wherein
Q represents the group represented by Q2.
[Aspect 199] The compound according to the Aspect 43, wherein
Q represents the group represented by Q2.
[Aspect 200] The compound according to the Aspect 44, wherein
Q represents the group represented by Q2.
[Aspect 201] The compound according to the Aspect 45, wherein
Q represents the group represented by Q2.
[Aspect 202] The compound according to the Aspect 46, wherein
Q represents the group represented by Q2.
[Aspect 203] The compound according to the Aspect 47, wherein
Q represents the group represented by Q2.
[Aspect 204] The compound according to the Aspect 48, wherein
Q represents the group represented by Q2.
[Aspect 205] The compound according to the Aspect 49, wherein
Q represents the group represented by Q2.
[Aspect 206] The compound according to the Aspect 50, wherein
Q represents the group represented by Q2.
[Aspect 207] The compound according to the Aspect 51, wherein
Q represents the group represented by Q2.
[Aspect 208] The compound according to the Aspect 52, wherein
Q represents the group represented by Q2.
[Aspect 209] The compound according to the Aspect 53, wherein
Q represents the group represented by Q2.
[Aspect 210] The compound according to the Aspect 54, wherein
Q represents the group represented by Q2.
[Aspect 211] The compound according to the Aspect 55, wherein
Q represents the group represented by Q2.

[Aspect 212] The compound according to the Aspect 56, wherein
Q represents the group represented by Q2.
[Aspect 213] The compound according to the Aspect 57, wherein
Q represents the group represented by Q2.
[Aspect 214] The compound according to the Aspect 58, wherein
Q represents the group represented by Q2.
[Aspect 215] The compound according to the Aspect 59, wherein
Q represents the group represented by Q2.
[Aspect 216] The compound according to the Aspect 60, wherein
Q represents the group represented by Q2.
[Aspect 217] The compound according to the Aspect 61, wherein
Q represents the group represented by Q2.
[Aspect 218] The compound according to the Aspect 62, wherein
Q represents the group represented by Q2.
[Aspect 219] The compound according to the Aspect 63, wherein
Q represents the group represented by Q2.
[Aspect 220] The compound according to the Aspect 64, wherein
Q represents the group represented by Q2.
[Aspect 221] The compound according to the Aspect 65, wherein
Q represents the group represented by Q2.
[Aspect 222] The compound according to the Aspect 66, wherein
Q represents the group represented by Q2.
[Aspect 223] The compound according to the Aspect 67, wherein
Q represents the group represented by Q2.
[Aspect 224] The compound according to the Aspect 68, wherein
Q represents the group represented by Q2.
[Aspect 225] The compound according to the Aspect 69, wherein
Q represents the group represented by Q2.
[Aspect 226] The compound according to the Aspect 70, wherein
Q represents the group represented by Q2.
[Aspect 227] The compound according to the Aspect 71, wherein
Q represents the group represented by Q2.
[Aspect 228] The compound according to the Aspect 72, wherein
Q represents the group represented by Q2.
[Aspect 229] The compound according to the Aspect 73, wherein
Q represents the group represented by Q2.
[Aspect 230] The compound according to the Aspect 74, wherein
Q represents the group represented by Q2.
[Aspect 231] The compound according to the Aspect 75, wherein
Q represents the group represented by Q2.
[Aspect 232] The compound according to the Aspect 76, wherein
Q represents the group represented by Q2.
[Aspect 233] The compound according to the Aspect 77, wherein
Q represents the group represented by Q2.

[Aspect 234] The Present compound N, wherein
$R^{3a}$, $R^{3b}$, $R^{3c}$, and $R^{3d}$ are identical to or different from each other, and each represent a C1-C6 alkyl group, a C2-C6 alkenyl group, a C3-C7 cycloalkyl group [wherein said C1-C6 alkyl group, said C2-C6 alkenyl group, and said C3-C7 cycloalkyl group are optionally substituted with one or more substituent(s) selected from the group consisting of a halogen atom and a cyano group], a phenyl group, a pyridyl group, a pyrimidinyl group {wherein said phenyl group, said pyridyl group, and said pyrimidinyl group are optionally substituted with one or more substituent(s) selected from Group J}, $OR^{12}$, $CR^{30}$=$NOR^{27}$, a hydrogen atom, or a halogen atom.
[Aspect 235] The Present compound N, wherein
$R^{3a}$, $R^{3b}$, $R^{3c}$, and $R^{3d}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more halogen atom(s)}, a hydrogen atom, or a halogen atom.
[Aspect 236] The Present compound N, wherein
$G^1$ represents a nitrogen atom or CH;
$G^2$ represents $CR^{3b}$;
$G^3$ represents $CR^{3c}$;
$G^4$ represents a nitrogen atom or CH; and
$R^{3b}$ and $R^{3c}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more halogen atom(s)}, a hydrogen atom, or a halogen atom.
[Aspect 237] The Present compound N, wherein
$G^1$ represents CH;
$G^2$ represents $CR^{3b}$;
$G^3$ represents $CR^{3c}$;
$G^4$ represents CH; and
$R^{3b}$ and $R^{3c}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more halogen atom(s)}, a hydrogen atom, or a halogen atom.
[Aspect 238] The Present compound N, wherein
$G^1$ represents CH;
$G^2$ represents $CR^{3b}$;
$G^3$ represents $CR^{3c}$;
$G^4$ represents CH; and
$R^{3b}$ and $R^{3c}$ are identical to or different from each other, and each represent a C1-C6 alkyl group optionally substituted with one or more halogen atom(s), or a hydrogen atom.
[Aspect 239] The Present compound N, wherein
$G^1$, $G^3$, and $G^4$ each represent CH; and
$G^2$ represents $CCF_3$.
[Aspect 240] The Present compound N, wherein
$G^1$ represents a nitrogen atom;
$G^2$ represents $CR^{3b}$;
$G^3$ represents $CR^{3c}$;
$G^4$ represents CH; and
$R^{3b}$ and $R^{3c}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more halogen atom(s)}, a hydrogen atom, or a halogen atom.

[Aspect 241] The Present compound N, wherein
$G^1$ represents CH;
$G^2$ represents $CR^{3b}$;
$G^3$ represents $CR^{3c}$;
$G^4$ represents a nitrogen atom; and
$R^{3b}$ and $R^{3c}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more halogen atom(s)}, a hydrogen atom, or a halogen atom.

[Aspect 242] The compound according to any one of the Aspects 1 to 233, wherein
$R^{3a}$, $R^{3b}$, $R^{3c}$, and $R^{3d}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group {wherein said phenyl group, said pyridyl group, and said pyrimidinyl group are optionally substituted with one or more substituent(s) selected from Group J}, $OR^{12}$, $CR^{30}=NOR^{17}$, a hydrogen atom, or a halogen atom.

[Aspect 243] The compound according to any one of the Aspects 1 to 233, wherein
$R^{3a}$, $R^{3b}$, $R^{3c}$, and $R^{3d}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more halogen atom(s)}, a hydrogen atom, or a halogen atom.

[Aspect 244] The compound according to any one of the Aspects 1 to 233, wherein
$G^1$ represents a nitrogen atom or CH;
$G^2$ represents $CR^{3b}$;
$G^3$ represents $CR^{3c}$;
$G^4$ represents a nitrogen atom or CH; and
$R^{3b}$ and $R^{3c}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more halogen atom(s)}, a hydrogen atom, or a halogen atom.

[Aspect 245] The compound according to any one of the Aspects 1 to 233, wherein
$G^1$ represents CH;
$G^2$ represents $CR^{3b}$;
$G^3$ represents $CR^{3c}$;
$G^4$ represents CH; and
$R^{3b}$ and $R^{3c}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more halogen atom(s)}, a hydrogen atom, or a halogen atom.

[Aspect 246] The compound according to any one of the Aspects 1 to 233, wherein
$G^1$ represents CH;
$G^2$ represents $CR^{3b}$;
$G^3$ represents $CR^{3c}$;
$G^4$ represents CH; and
$R^{3b}$ and $R^{3c}$ are identical to or different from each other, and each represent a C1-C6 alkyl group optionally substituted with one or more halogen atom(s), or a hydrogen atom.

[Aspect 247] The compound according to any one of the Aspects 1 to 233, wherein
$G^1$, $G^3$, and $G^4$ each represent CH; and
$G^2$ represents $CCF_3$.

[Aspect 248] The compound according to any one of the Aspects 1 to 233, wherein
$G^1$ represents a nitrogen atom;
$G^2$ represents $CR^{3b}$;
$G^3$ represents $CR^{3c}$;
$G^4$ represents CH; and
$R^{3b}$ and $R^{3c}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more halogen atom(s)}, a hydrogen atom, or a halogen atom.

[Aspect 249] The compound according to any one of the Aspects 1 to 233, wherein
$G^1$ represents CH;
$G^2$ represents $CR^{3b}$;
$G^3$ represents $CR^{3c}$;
$G^4$ represents a nitrogen atom; and
$R^{3b}$ and $R^{3c}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more halogen atom(s)}, a hydrogen atom, or a halogen atom.

[Aspect A1] The Present compound N, wherein
$R^2$ represents an ethyl group;
$G^1$ and $G^4$ each represent CH;
$G^2$ represents $CR^{3b}$;
$G^3$ represents $CR^{3c}$;
$R^{3b}$ and $R^{3c}$ are identical to or different from each other, and each represent a C1-C3 chain hydrocarbon group optionally substituted with one or more halogen atom(s), a cyclopropyl group, a phenyl group optionally substituted with one or more halogen atom(s), $OR^{12}$, a halogen atom, or a hydrogen atom;
$R^{12}$ represents a C1-C3 alkyl group optionally substituted with one or more halogen atom(s), or a hydrogen atom;
Z represents an oxygen atom;
$A^2$ and $A^3$ each represent CH;
$B^1$ represents a nitrogen atom or CH;
$B^2$ represents $CR^1$;
$B^3$ represents a nitrogen atom or CH; and
$R^1$ represents a C1-C3 fluoroalkyl group.

[Aspect A2] The compound according to the Aspect A1, wherein
Q represents the group represented by Q1.

[Aspect A3] The compound according to the Aspect A1, wherein
Q represents the group represented by Q2.

[Aspect A4] The compound according to the Aspect A2, wherein
$R^1$ represents a trifluoromethyl group; and $R^{3c}$ represents a trifluoromethyl group, a halogen atom, a cyclopropyl group, or a hydrogen atom.

[Aspect A5] The compound according to the Aspect A4, wherein $B^1$ represents CH; and
$B^3$ represents a nitrogen atom.

[Aspect A6] The compound according to any one of the Aspects A1 to A4, wherein $R^{3b}$ and $R^{3c}$ are identical to or different from each other, and each represent a C1-C3 alkyl group optionally substituted with one or more halogen atom(s), a cyclopropyl group, a phenyl group optionally substituted with one or more halogen atom(s), $OR^{12}$, a halogen atom, or a hydrogen atom; and $R^{12}$ represents a C1-C3 alkyl group optionally substituted with one or more halogen atom(s).

[Aspect A7] The compound according to any one of the Aspects A1 to A4, wherein $R^{3b}$ represents a C1-C3 alkyl group optionally substituted with one or more halogen atom(s), a cyclopropyl group, a phenyl group optionally substituted with one or more halogen atom(s), $OR^{12}$, a halogen atom, or a hydrogen atom;

$R^{12}$ represents a C1-C3 alkyl group; and $R^{3c}$ represents a C1-C3 alkyl group optionally substituted with one or more halogen atom(s), a cyclopropyl group, or a halogen atom.

[Aspect A8] The compound according to the Aspect A3, wherein $R^1$ represents a C1-C2 fluoroalkyl group;
$R^{3b}$ represents a trifluoromethyl group or a halogen atom;
$R^{3c}$ represents a hydrogen atom;
$B^1$ represents CH; and
$B^3$ represents a nitrogen atom.

[Aspect A9] The compound according to the Aspect A1, wherein $R^1$ represents a C1-C2 fluoroalkyl group.

[Aspect A10] The compound according to the Aspect A2, wherein $R^1$ represents a C1-C2 fluoroalkyl group.

[Aspect A11] The compound according to the Aspect A3, wherein $R^1$ represents a C1-C2 fluoroalkyl group.

[Aspect A12] The compound according to the Aspect A10, wherein $B^1$ represents CH; and
$B^3$ represents a nitrogen atom.

[Aspect A13] The compound according to any one of the Aspects A9 to A12, wherein $R^{3b}$ and $R^{3c}$ are identical to or different from each other, and each represent a C1-C3 alkyl group optionally substituted with one or more halogen atom(s), a cyclopropyl group, a phenyl group optionally substituted with one or more halogen atom(s), $OR^{12}$, a halogen atom, or a hydrogen atom; and $R^{12}$ represents a C1-C3 alkyl group optionally substituted with one or more halogen atom(s).

[Aspect A14] The compound according to any one of the Aspects A9 to A12, wherein $R^{3b}$ represents a C1-C3 alkyl group optionally substituted with one or more halogen atom(s), a cyclopropyl group, a phenyl group optionally substituted with one or more halogen atom(s), $OR^{12}$, a halogen atom, or a hydrogen atom;

$R^{12}$ represents a C1-C3 alkyl group; and $R^{3c}$ represents a C1-C3 alkyl group optionally substituted with one or more halogen atom(s), a cyclopropyl group, or a halogen atom.

[Aspect A15] The compound according to any one of the Aspects A9 to A12, wherein $R^{3b}$ represents a trifluoromethyl group, a halogen atom, a cyclopropyl group, or a hydrogen atom; and $R^{3c}$ represents a hydrogen atom.

Next, production methods for the Present compounds are described.

Production Method 1

A compound represented by formula (I-b) (hereinafter referred to as "Compound (I-b)") or a compound represented by formula (I-c) (hereinafter referred to as "Compound (I-c)") may be prepared by reacting a compound represented by formula (I-a) (hereinafter referred to as "Compound (I-a)") with an oxidizing agent.

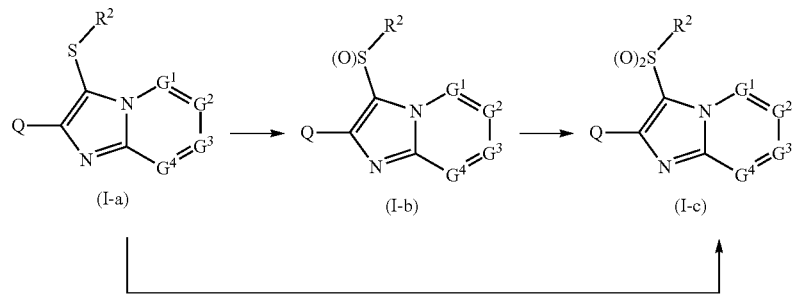

[wherein the symbols are the same as defined above.]

First, a method for producing the Compound (I-b) from the Compound (I-a) is described.

The reaction is usually carried out in a solvent. Examples of the solvent include halogenated hydrocarbons such as dichloromethane and chloroform (hereinafter collectively referred to as "halogenated hydrocarbons"); nitriles such as acetonitrile (hereinafter collectively referred to as "nitriles"); alcohols such as methanol and ethanol (hereinafter collectively referred to as "alcohols"); acetic acid; water; and mixtures of two or more of them.

Examples of the oxidizing agent include sodium periodate, m-chloroperbenzoic acid (hereinafter referred to as "mCPBA"), and hydrogen peroxide.

When hydrogen peroxide is used as the oxidizing agent, a base or a catalyst may be used as needed.

Examples of the base include sodium carbonate. When a base is used in the reaction, the base is usually used at a ratio of 0.01 to 1 mol relative to 1 mol of the Compound (I-a).

Examples of the catalyst include tungstic acid and sodium tungstate. When a catalyst is used in the reaction, the catalyst is usually used at a ratio of 0.01 to 0.5 mol relative to 1 mol of the Compound (I-a).

In the reaction, the oxidizing agent is usually used at a ratio of 1 to 1.2 mol relative to 1 mol of the Compound (I-a).

The reaction temperature is usually within the range of −20 to 80° C. The reaction time is usually within the range of 0.1 to 12 hour(s).

When the reaction is completed, to the reaction mixture is added water, the resulting mixture is extracted with organic solvent(s), and the resulting organic layer is washed with an aqueous solution of a reducing agent (for example, sodium sulfite or sodium thiosulfate) and an aqueous solution of a base (for example, sodium hydrogen carbonate) as needed. The resulting organic layer may be dried or concentrated to give the Compound (I-b).

Next, a method for producing the Compound (I-c) from the Compound (I-b) is described.

The reaction is usually carried out in a solvent. Examples of the solvent include halogenated hydrocarbons, nitriles, alcohols, acetic acid, water, and mixtures of two or more of them.

Examples of the oxidizing agent include mCPBA and hydrogen peroxide.

When hydrogen peroxide is used as the oxidizing agent, a base or a catalyst may be used as needed.

Examples of the base include sodium carbonate. When a base is used in the reaction, the base is usually used at a ratio of 0.01 to 1 mol relative to 1 mol of the Compound (I-b).

Examples of the catalyst include sodium tungstate. When a catalyst is used in the reaction, the catalyst is usually used at a ratio of 0.01 to 0.5 mol relative to 1 mol of the Compound (I-b).

In the reaction, the oxidizing agent is usually used at a ratio of 1 to 2 mol relative to 1 mol of the Compound (I-b).

The reaction temperature is usually within the range of −20 to 120° C. The reaction time is usually within the range of 0.1 to 12 hour(s).

When the reaction is completed, to the reaction mixture is added water, the resulting mixture is extracted with organic solvent(s), and the resulting organic layer is washed with an aqueous solution of a reducing agent (for example, sodium sulfite or sodium thiosulfate) and an aqueous solution of a base (for example, sodium hydrogen carbonate) as needed. The resulting organic layer may be dried or concentrated to give the Compound (I-c).

Also, the Compound (I-c) may be prepared in one step reaction (one-pot) by reacting the Compound (I-a) with an oxidizing agent.

The reaction may be carried out according to the method for producing the Compound (I-c) from the Compound (I-b) by usually using the oxidizing agent at a ratio of 2 to 5 mol relative to 1 mol of the Compound (I-a).

Production Method 2

A compound represented by formula (II-1S) (hereinafter referred to as "Compound (II-1S)") may be prepared by reacting a compound represented by formula (II-1O) (hereinafter referred to as "Compound (II-1O)") with a sulfating agent.

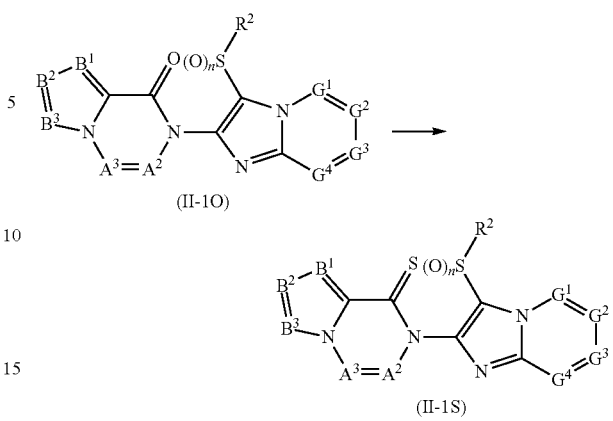

[wherein the symbols are the same as defined above.]

The reaction is carried out in a solvent or in the absence of a solvent. Examples of the solvent include ethers such as tetrahydrofuran and methyl tert-butyl ether (hereinafter collectively referred to as "ethers"); halogenated hydrocarbons; aromatic hydrocarbons such as toluene and xylene (hereinafter collectively referred to as "aromatic hydrocarbons"); nitriles; nitrogen-containing aromatic compounds such as pyridine, picoline, lutidine, and quinoline; and mixtures of two or more of them.

Examples of the sulfating agent include phosphorus pentasulfide and Lawesson's reagent (2,4-bis(4-methoxyphenyl)-1,3-dithia-2,4-diphosphetane-2,4-disulfide).

In the reaction, the sulfating agent is usually used at a ratio of 1 mol to 3 mol relative to 1 mol of the Compound (II-1O).

The reaction temperature is usually within the range of 0° C. to 200° C. The reaction time is usually within the range of 1 to 24 hour(s).

When the reaction is completed, the reaction mixture may be subjected to a work-up such as adding water to the reaction mixture, extracting the resulting reaction mixture with organic solvent(s), and drying and/or concentrating the resulting organic layer to give the Compound (II-1S).

Production Method 3

A compound represented by formula (II-2S) (hereinafter referred to as "Compound (II-2S)") may be prepared by reacting a compound represented by formula (II-2O) (hereinafter referred to as "Compound (II-2O)") with a sulfating agent.

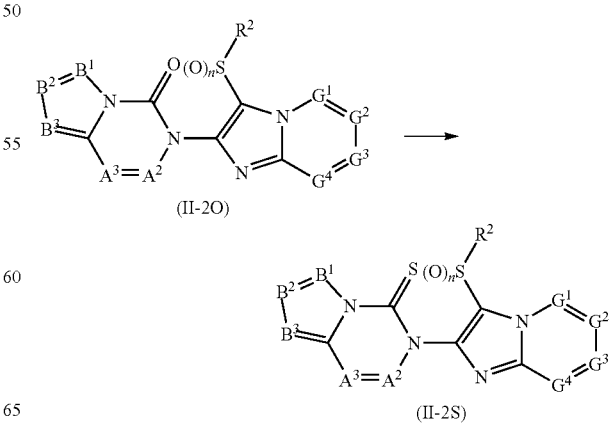

[wherein the symbols are the same as defined above.]

The reaction may be carried out according to the Production method 2.

Production Method 4

The Compound (II-1O) may be prepared by reacting a compound represented by formula (M-1) (hereinafter referred to as "Compound (M-1)") with a compound represented by formula (M-2) (hereinafter referred to as "Compound (M-2)") in the presence of a base.

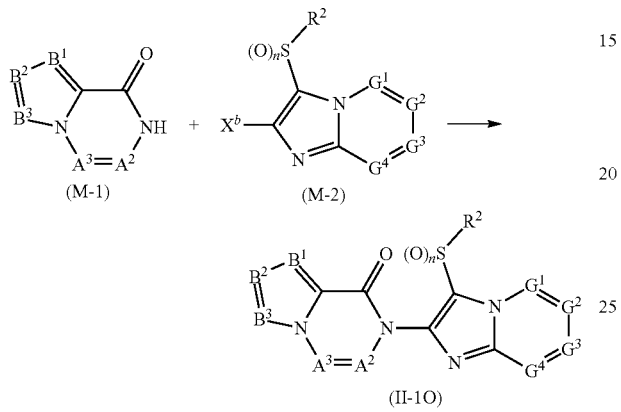

[wherein $X^b$ represents a leaving group such as a fluorine atom, a chlorine atom, a bromine atom, and an iodine atom; and the other symbols are the same as defined above.]

The reaction is usually carried out in a solvent. Examples of the solvent include ethers; aromatic hydrocarbons; nitriles; aprotic polar solvents such as dimethylformamide (hereinafter referred to as "DMF"), N-methylpyrrolidone (hereinafter referred to as "NMP"), and dimethyl sulfoxide (hereinafter referred to as "DMSO") (hereinafter collectively referred to as "aprotic polar solvents"); and mixtures of two or more of them.

Examples of the base include organic bases such as triethylamine, diisopropylethylamine, pyridine, and 4-(dimethylamino)pyridine (hereinafter collectively referred to as "organic bases"); alkali metal carbonates such as sodium carbonate and potassium carbonate (hereinafter referred to as "alkali metal carbonates"); and alkali metal hydrides such as sodium hydride (hereinafter collectively referred to as "alkali metal hydrides").

The reaction may also be carried out by using a metal catalyst as needed. Examples of the metal catalyst include copper catalysts such as copper(I) iodide, copper(I) bromide, copper(I) chloride, copper(I) oxide, copper(I) trifluoromethanesulfonate benzene complex, tetrakis(acetonitrile)copper(I) hexafluorophosphate, and copper(I) 2-thiophenecarboxylate; nickel catalysts such as bis(cyclooctadiene)nickel(0) and nickel(II) chloride; and palladium catalysts such as palladium(II) acetate, tetrakis(triphenylphosphine)palladium(0), and tris(dibenzylideneacetone)dipalladium(II). When a metal catalyst is used in the reaction, the metal catalyst is usually used at a ratio of 0.01 to 0.5 mol relative to 1 mol of the Compound (M-1).

The reaction may also be carried out by using a ligand as needed. Examples of the ligand include triphenylphosphine, 4,5-bis(diphenylphosphino)-9,9-dimethylxanthene (hereinafter referred to as "Xantphos"), 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, 1,10-phenanthroline, trans-1,2-cyclohexanediamine, trans-N,N'-dimethylcyclohexane-1,2-diamine, and N,N'-dimethylethylenediamine. When a ligand is used in the reaction, the ligand is usually used at a ratio of 0.01 to 0.5 mol, relative to 1 mol of the Compound (M-1).

In the reaction, the Compound (M-2) is usually used at a ratio of 0.8 to 1.2 mol, and the base is usually used at a ratio of 1 to 3 mol, relative to 1 mol of the Compound (M-1).

The reaction temperature is usually within the range of −20° C. to 150° C. The reaction time is usually within the range of 0.5 to 24 hour(s).

When the reaction is completed, the reaction mixture may be subjected to a work-up such as adding water to the reaction mixture, extracting the resulting reaction mixture with organic solvent(s), and drying and/or concentrating the resulting organic layer to give the Compound (11-1O).

Production Method 5

The Compound (II-2O) may be prepared by reacting a compound represented by formula (M-3) (hereinafter referred to as "Compound (M-3)") with the Compound (M-2) in the presence of a base.

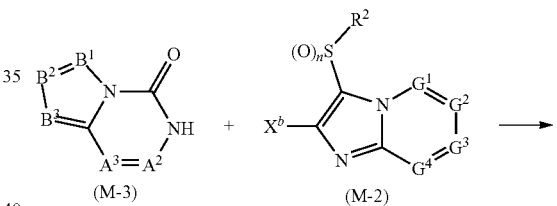

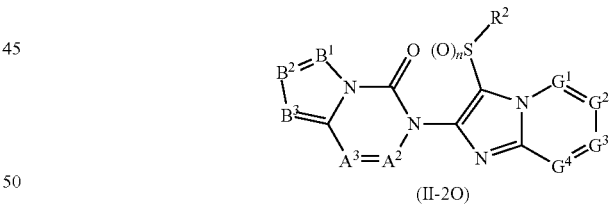

[wherein the symbols are the same as defined above.]

The reaction may be carried out according to the Production method 4 by using the Compound (M-3) instead of the Compound (M-1).

Production Method 6

A compound represented by formula (II-1A) (hereinafter referred to as "Compound (II-1A)") may be prepared by reacting a compound represented by formula (M-4) (hereinafter referred to as "Compound (M-4)") with a compound represented by formula (R-1) (hereinafter referred to as "Compound (R-1)").

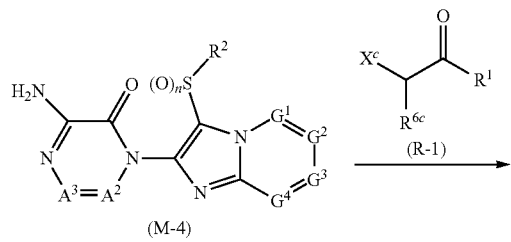

(M-4)

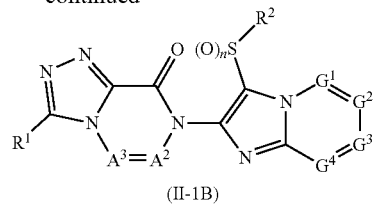

(II-1B)

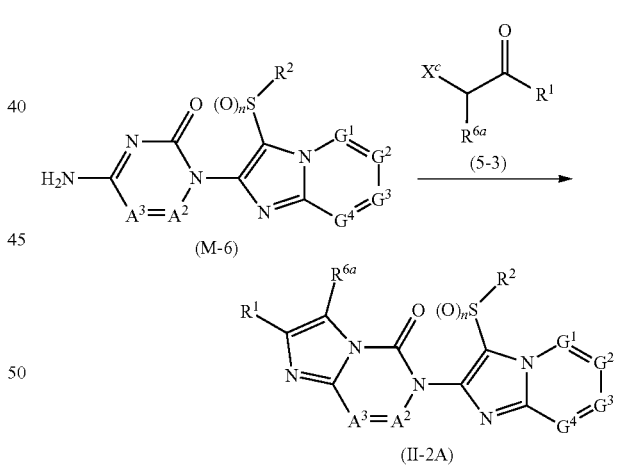

(II-1A)

[wherein $X^c$ represents a chlorine atom or a bromine atom; and the other symbols are the same as defined above.]

The reaction is carried out in a solvent or in the absence of a solvent. Examples of the solvent include ethers; aromatic hydrocarbons; halogenated hydrocarbons; esters such as ethyl acetate (hereinafter collectively referred to as "esters"); nitriles; aprotic polar solvents; and mixtures of two or more of them.

The reaction may also be carried out by using a base as needed. Examples of the base include alkali metal carbonates; and alkali metal hydrogen carbonates such as sodium hydrogen carbonate. When a base is used in the reaction, the base is usually used at a ratio of 1 to 3 mol relative to 1 mol of the Compound (M-4).

In the reaction, the Compound (R-1) is usually used at a ratio of 1 to 3 mol relative to 1 mol of the Compound (M-4).

The reaction temperature is usually within the range of 20 to 200° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying and/or concentrating the resulting organic layer to give the Compound (II-1A).

The Compound (R-1) is a commercially available compound or may be prepared by using known method(s).

Production Method 7

A compound represented by formula (II-1B) (hereinafter referred to as "Compound (II-1B)") may be prepared by reacting a compound represented by formula (M-5) (hereinafter referred to as "Compound (M-5)") with a compound represented by formula (R-2) (hereinafter referred to as "Compound (R-2)").

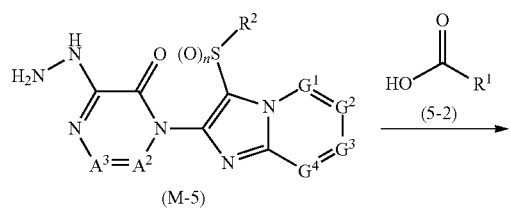

(M-5)

[wherein the symbols are the same as defined above.]

The reaction is carried out in a solvent or in the absence of a solvent. Examples of the solvent include ethers, aromatic hydrocarbons, halogenated hydrocarbons, esters, nitriles, aprotic polar solvents, and mixtures of two or more of them.

In the reaction, the Compound (R-2) is usually used at a ratio of 1 to 3 mol relative to 1 mol of the Compound (M-5).

The reaction temperature is usually within the range of 20 to 200° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying and/or concentrating the resulting organic layer to give the Compound (II-1B).

The Compound (R-2) is a commercially available compound or may be prepared by using known method(s).

Production Method 8

A compound represented by formula (II-2A) may be prepared by reacting a compound represented by formula (M-6) (hereinafter referred to as "Compound (M-6)") with a compound represented by formula (R-3) (hereinafter referred to as "Compound (R-3)").

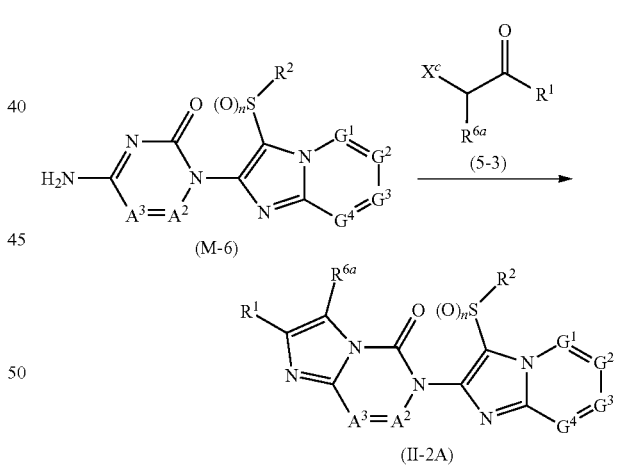

[wherein the symbols are the same as defined above.]

The reaction may be carried out according to the Production method 6 by using the Compound (M-6) instead of the Compound (M-4), and using the Compound (R-3) instead of the Compound (R-1).

The Compound (R-3) is a commercially available compound or may be prepared by using known method(s).

Production Method 9

A compound represented by formula (II-1n0) (hereinafter referred to as "Compound (II-1n0)") may be prepared according to the following scheme.

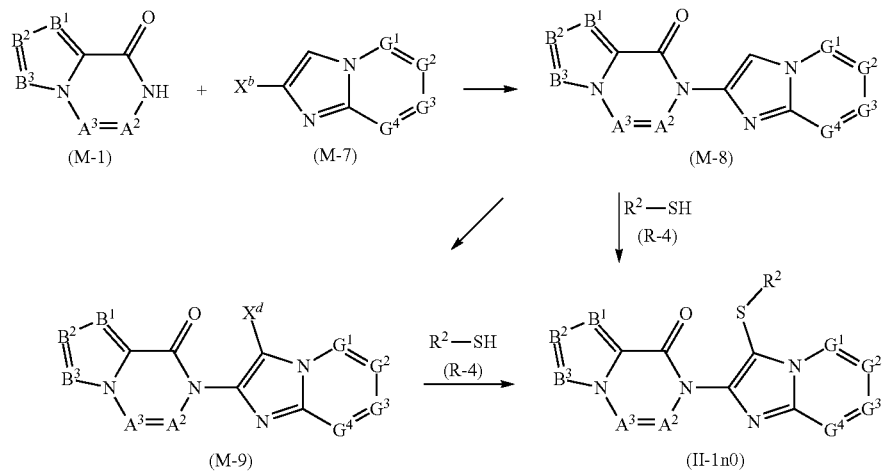

[wherein $X^d$ represents a chlorine atom, a bromine atom, or an iodine atom; and the other symbols are the same as defined above.]

First, a method for producing a compound represented by formula (M-8) (hereinafter referred to as "Compound (M-8)") is described.

The Compound (M-8) may be prepared according to the Production method 4 by using a compound represented by formula (M-7) (hereinafter referred to as "Compound (M-7)") instead of the Compound (M-2).

Next, a method for producing a compound represented by formula (M-9) (hereinafter referred to as "Compound (M-9)") is described.

The Compound (M-9) may be prepared by reacting the Compound (M-8) with a halogenating agent.

The reaction is usually carried out in a solvent. Examples of the solvent include alcohols, nitriles, ethers, aromatic hydrocarbons, aprotic polar solvents, halogenated hydrocarbons, water, and mixtures of two or more of them.

Examples of the halogenating agent include chlorine, bromine, iodine, N-chlorosuccinimide, N-bromosuccinimide, and N-iodosuccinimide.

In the reaction, the halogenating agent is usually used at a ratio of 1 to 20 mol relative to 1 mol of the Compound (M-8).

The reaction temperature is usually within the range of −20° C. to 200° C. The reaction time is usually within the range of 0.1 to 72 hour(s).

When the reaction is completed, the reaction mixture may be subjected to a work-up such as adding water to the reaction mixture, extracting the resulting reaction mixture with organic solvent(s), and drying and/or concentrating the resulting organic layer to give the Compound (M-9).

Next, a method for producing the Compound (II-1n0) from the Compound (M-8) is described.

The Compound (II-1n0) may be prepared by reacting the Compound (M-8), a compound represented by formula (R-4) (hereinafter referred to as "Compound (R-4)"), and a halogenating agent.

The reaction is usually carried out in a solvent. Examples of the solvent include alcohols, nitriles, ethers, aromatic hydrocarbons, aprotic polar solvents, halogenated hydrocarbons, water, and mixtures of two or more of them.

Examples of the halogenating agent include chlorine, bromine, iodine, N-chlorosuccinimide, N-bromosuccinimide, and N-iodosuccinimide.

In the reaction, the Compound (R-4) is usually used at a ratio of 1 to 20 mol, and the halogenating agent is usually used at a ratio of 1 to 20 mol, relative to 1 mol of the Compound (M-8).

The reaction temperature is usually within the range of −20° C. to 200° C. The reaction time is usually within the range of 0.1 to 72 hour(s).

When the reaction is completed, the reaction mixture may be subjected to a work-up such as adding water to the reaction mixture, extracting the resulting reaction mixture with organic solvent(s), and drying and/or concentrating the resulting organic layer to give the Compound (II-1n0).

The Compound (R-4) is a commercially available compound or may be prepared by using known method(s).

Next, a method for producing the Compound (II-1n0) from the Compound (M-9) is described.

The Compound (II-1n0) may also be prepared by reacting the Compound (M-9) with the Compound (R-4) in the presence of a metal catalyst and a base.

The reaction is usually carried out in a solvent. Examples of the solvent include alcohols, nitriles, ethers, aromatic hydrocarbons, aprotic polar solvents, water, and mixtures of two or more of them.

Examples of the metal catalyst include palladium catalysts such as tetrakis(triphenylphosphine)palladium(0), [1,1'-bis(diphenylphosphino)ferrocene]palladium(II) dichloride, tris(dibenzylideneacetone)dipalladium(0), and palladium(II) acetate; nickel catalysts such as bis(cyclooctadiene)nickel(0) and nickel(II) chloride; and copper catalysts such as copper(I) iodide and copper(I) chloride.

Examples of the base include alkali metal hydrides, alkali metal carbonates, and organic bases.

In the reaction, a ligand may also be used. Examples of the ligand include triphenylphosphine, Xantphos, 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline. When a ligand is used in the reaction, the ligand is usually used at a ratio of 0.01 to 1 mol relative to 1 mol of the Compound (M-9).

In the reaction, the Compound (R-4) is usually used at a ratio of 1 to 20 mol, the metal catalyst is usually used at a ratio of 0.01 to 0.5 mol, and the base is usually used at a ratio of 0.1 to 5 mol, relative to 1 mol of the Compound (M-9).

The reaction temperature is usually within the range of −20° C. to 200° C. The reaction time is usually within the range of 0.1 to 72 hour(s).

When the reaction is completed, the reaction mixture may be subjected to a work-up such as adding water to the reaction mixture, extracting the resulting reaction mixture with organic solvent(s), and drying and/or concentrating the resulting organic layer to give the Compound (II-1n0).

Production Method 10

A compound represented by formula (II-2n0) (hereinafter referred to as "Compound (II-2n0)") may be prepared according to the following scheme.

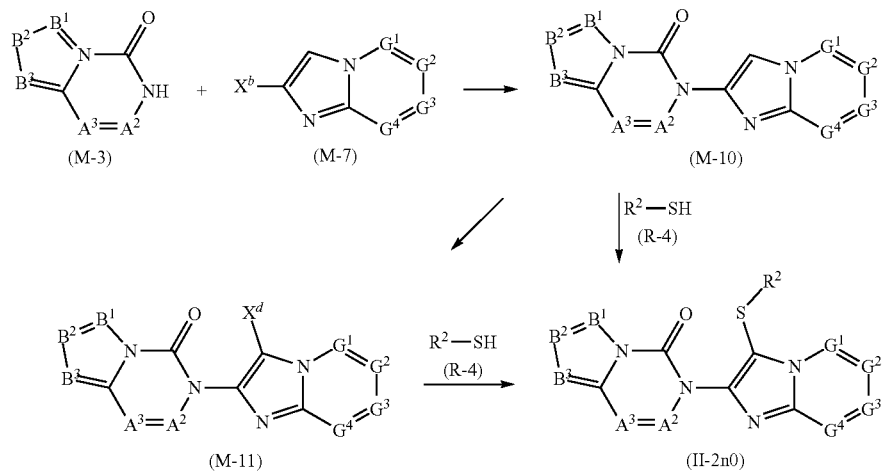

[wherein the symbols are the same as defined above.]

A compound represented by formula (M-10) (hereinafter referred to as "Compound (M-10)") may be prepared according to the Production method 4 by using the Compound (M-3) instead of the Compound (M-1), and using the Compound (M-7) instead of the Compound (M-2).

A compound represented by formula (M-11) (hereinafter referred to as "Compound (M-11)") may be prepared according to the method for producing the Compound (M-9) from the Compound (M-8) in the Production method 9 by using the Compound (M-10) instead of the Compound (M-8).

The Compound (II-2n0) may also be prepared according to the method for producing the Compound (II-1n0) from the Compound (M-8) in the Production method 9 by using the Compound (M-10) instead of the Compound (M-8).

Also, the Compound (II-2n0) may also be prepared according to the method for producing the Compound (II-1n0) from the Compound (M-9) in the Production method 9 by using the Compound (M-11) instead of the Compound (M-9).

Production Method 11

An N-oxide of the compound represented by formula (I) may be prepared by reacting the compound represented by formula (I) with an oxidizing agent. The reaction may be carried out according to the method described in, for example, the Production method 1, US Patent Application Publication No. 2018/0009778, or WO 2016/121970 pamphlet.

Hereinafter, production methods for the production intermediate compounds are described.

Reference Production Method 1

A compound represented by formula (M-1A) (hereinafter referred to as "Compound (M-1A)") may be prepared according to the following scheme.

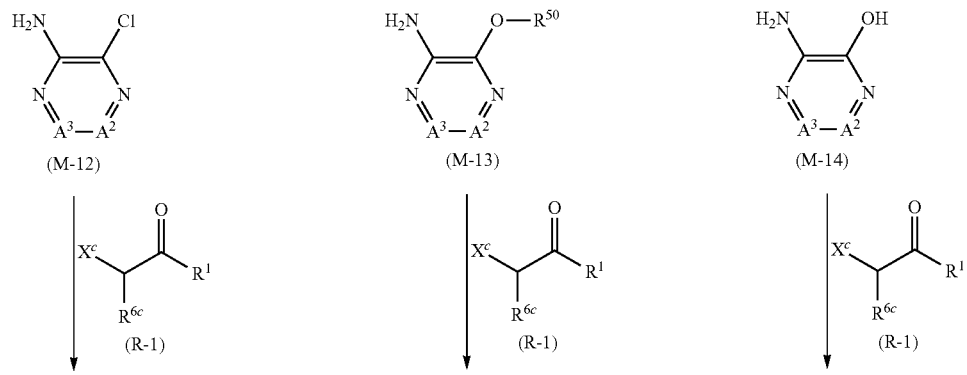

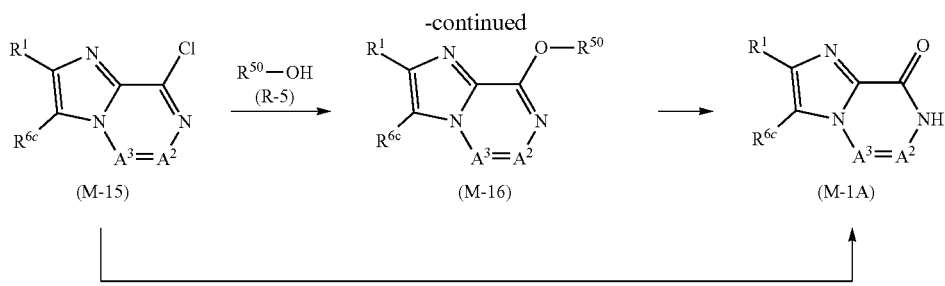

[wherein $R^{50}$ represents a benzyl group or a C1-C3 alkyl group; and the other symbols are the same as defined above.]

A compound represented by formula (M-15) (hereinafter referred to as "Compound (M-15)") may be prepared according to the Production method 6 by using a compound represented by formula (M-12) (hereinafter referred to as "Compound (M-12)") instead of the Compound (M-4).

A compound represented by formula (M-16) (hereinafter referred to as "Compound (M-16)") may be prepared according to the Production method 6 by using a compound represented by formula (M-13) (hereinafter referred to as "Compound (M-13)") instead of the Compound (M-4).

Further, the Compound (M-16) may also be prepared by reacting the Compound (M-15) with a compound represented by formula (R-5) (hereinafter referred to as "Compound (R-5)") in the presence of a base.

The reaction is usually carried out in a solvent. Examples of the solvent include ethers; aromatic hydrocarbons; nitriles; aprotic polar solvents; water; and mixtures of two or more of them.

Examples of the base include alkali metal carbonates; alkali metal hydrides; and organic bases.

In the reaction, the Compound (R-5) is usually used at a ratio of 1 to 3 mol, and the base is usually used at a ratio of 1 to 3 mol, relative to 1 mol of the Compound (M-15).

The reaction temperature is usually within the range of −20° C. to 150° C. The reaction time is usually within the range of 0.5 to 24 hour(s).

When the reaction is completed, the reaction mixture may be subjected to a work-up such as adding water to the reaction mixture, extracting the resulting reaction mixture with organic solvent(s), and drying and/or concentrating the resulting organic layer to give the Compound (M-16).

The Compound (R-5) is a commercially available compound or may be prepared by using known method(s).

The Compound (M-1A) may be prepared according to the Production method 6 by using a compound represented by formula (M-14) (hereinafter referred to as "Compound (M-14)") instead of the Compound (M-4).

Further, the Compound (M-1A) may also be prepared by reacting the Compound (M-16) wherein $R^{50}$ represents a benzyl group (hereinafter referred to as "Compound (M-16A)") with hydrogen in the presence of a catalyst.

The reaction is carried out usually under hydrogen atmosphere of 1 to 100 atm and usually in a solvent. Examples of the solvent include ethers, esters, alcohols, water, and mixtures of two or more of them.

Examples of the catalyst include transition metal compounds such as palladium carbon, palladium(II) hydroxide, Raney nickel, and platinum oxide.

In the reaction, the catalyst is usually used at a ratio of 0.001 to 0.5 mol relative to 1 mol of the Compound (M-16A).

The reaction may also be carried out by using an acid, a base, or the like as needed.

Examples of the acid include acetic acid and hydrochloric acid, and examples of the base include tertiary amines such as triethylamine. When an acid is used in the reaction, the acid is usually used at a ratio of 0.001 to 0.5 mol relative to 1 mol of the Compound (M-16A). When a base is used in the reaction, the base is usually used at a ratio of 0.1 to 5 mol relative to 1 mol of the Compound (M-16A).

The reaction temperature is usually within the range of −20 to 100° C. The reaction time is usually within the range of 0.1 to 24 hour(s).

When the reaction is completed, the reaction mixture may be subjected to a work-up such as filtering the reaction mixture, and as needed, extracting the resulting reaction mixture with organic solvent(s), and drying and/or concentrating the resulting organic layer to give the Compound (M-1A).

Further, the Compound (M-1A) may also be prepared by reacting the Compound (M-16) with an acid.

The reaction is usually carried out in a solvent. Examples of the solvent include halogenated hydrocarbons, water, and mixtures of two or more of them.

Examples of the acid include mineral acids such as hydrochloric acid and sulfuric acid.

In the reaction, the acid is usually used at a ratio of 1 to 100 mol relative to 1 mol of the Compound (M-16).

The reaction temperature is usually within the range of 50 to 150° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying and/or concentrating the resulting organic layer to give the Compound (M-1A).

Further, the Compound (M-1A) may also be prepared by hydrolyzing the Compound (M-15) in the presence of an acid or a base.

When the Compound (M-15) is hydrolyzed in the presence of an acid, the reaction is usually carried out in water. Further, ethers, alcohols, or the like may also be added thereto as a solvent.

Examples of the acid include mineral acids such as hydrochloric acid and sulfuric acid.

In the reaction, the acid is usually used at a ratio of 1 to 100 mol relative to 1 mol of the Compound (M-15).

The reaction temperature is usually within the range of 50 to 100° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying and/or concentrating the resulting organic layer to give the Compound (M-1A).

When the Compound (M-15) is hydrolyzed in the presence of a base, the reaction is usually carried out in water. Further, ethers, alcohols, or the like may also be added thereto as a solvent.

Examples of the base include alkali metal hydroxides such as sodium hydroxide and potassium hydroxide.

In the reaction, the base is usually used at a ratio of 1 to 10 mol relative to 1 mol of the Compound (M-15).

The reaction temperature is usually within the range of 50 to 120° C. The reaction time is usually within the range of 0.1 to 24 hour(s).

When the reaction is completed, the reaction mixture may be subjected to a work-up such as adding an acid to the reaction mixture to acidify it, then extracting the resulting reaction mixture with organic solvent(s), and drying and/or concentrating the resulting organic layer to give the Compound (M-1A).

The Compound (M-12), the Compound (M-13), and the Compound (M-14) are commercially available compounds or may be prepared by using known methods.

Reference Production Method 2

A compound represented by formula (M-1B) (hereinafter referred to as "Compound (M-1B)") may be prepared according to the following scheme.

A compound represented by formula (M-20) (hereinafter referred to as "Compound (M-20)") may be prepared according to the Production method 7 by using a compound represented by formula (M-17) (hereinafter referred to as "Compound (M-17)") instead of the Compound (M-5).

A compound represented by formula (M-21) (hereinafter referred to as "Compound (M-21)") may be prepared according to the Production method 7 by using a compound represented by formula (M-18) (hereinafter referred to as "Compound (M-18)") instead of the Compound (M-5).

Further, the Compound (M-21) may also be prepared according to the method for producing the Compound (M-16) from the Compound (M-15) in the Reference production method 1 by using the Compound (M-20) instead of the Compound (M-15).

The Compound (M-1B) may be prepared according to the Production method 7 by using a compound represented by formula (M-19) (hereinafter referred to as "Compound (M-19)") instead of the Compound (M-5).

Further, the Compound (M-1B) may also be prepared according to the method for producing the Compound (M-1A) from the Compound (M-16) in the Reference production method 1 by using the Compound (M-21) instead of the Compound (M-16).

Further, the Compound (M-1B) may also be prepared according to the method for producing the Compound (M-1A) from the Compound (M-15) in the Reference production method 1 by using the Compound (M-20) instead of the Compound (M-15).

The Compound (M-17), the Compound (M-18), and the Compound (M-19) are commercially available compounds or may be prepared by using known methods.

Reference Production Method 3

A compound represented by formula (M-3A) (hereinafter referred to as "Compound (M-3A)") may be prepared according to the following scheme.

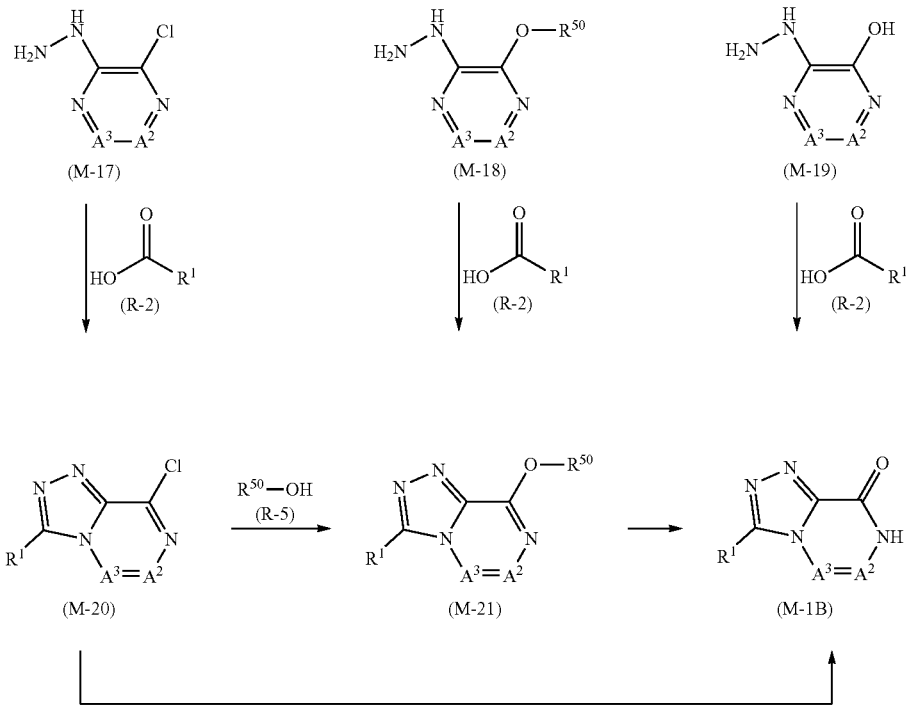

[wherein the symbols are the same as defined above.]

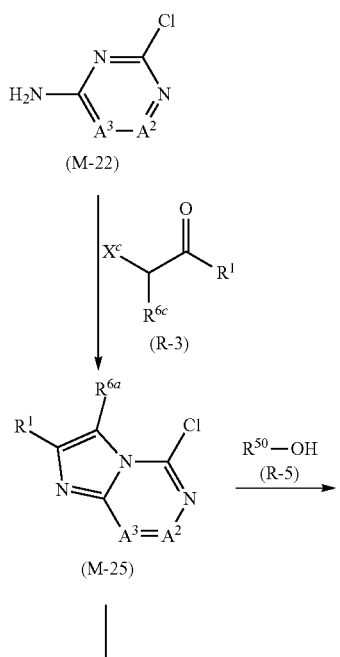
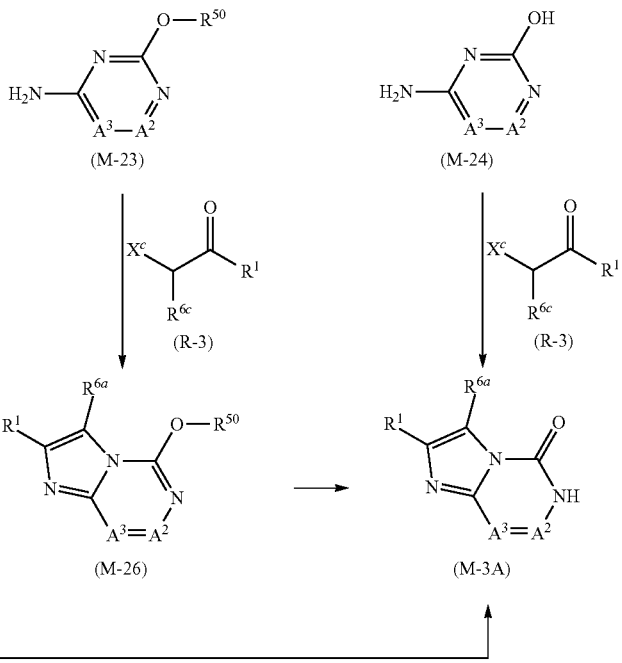

[wherein the symbols are the same as defined above.]

A compound represented by formula (M-25) (hereinafter referred to as "Compound (M-25)") may be prepared according to the Production method 8 by using a compound represented by formula (M-22) (hereinafter referred to as "Compound (M-22)") instead of the Compound (M-6).

A compound represented by formula (M-26) (hereinafter referred to as "Compound (M-26)") may be prepared according to the Production method 8 by using a compound represented by formula (M-23) (hereinafter referred to as "Compound (M-23)") instead of the Compound (M-6).

Further, the Compound (M-26) may also be prepared according to the method for producing the Compound (M-16) from the Compound (M-15) in the Reference production method 1 by using the Compound (M-25) instead of the Compound (14-15).

The Compound (M-3A) may be prepared according to the Production method 8 by using a compound represented by formula (M-24) (hereinafter referred to as "Compound (M-24)") instead of the Compound (M-6).

Further, the Compound (M-3A) may also be prepared according to the method for producing the Compound (M-1A) from the Compound (M-16) in the Reference production method 1 by using the Compound (M-26) instead of the Compound (14-16).

Further, the Compound (M-3A) may also be prepared according to the method for producing the Compound (M-1A) from the Compound (M-15) in the Reference production method 1 by using the Compound (M-25) instead of the Compound (14-15).

The Compound (M-22), the Compound (M-23), and the Compound (M-24) are commercially available compounds or may be prepared by using known methods.

Reference Production Method 4

A compound represented by formula (M-31) (hereinafter referred to as "Compound (M-31)") may be prepared according to the following scheme.

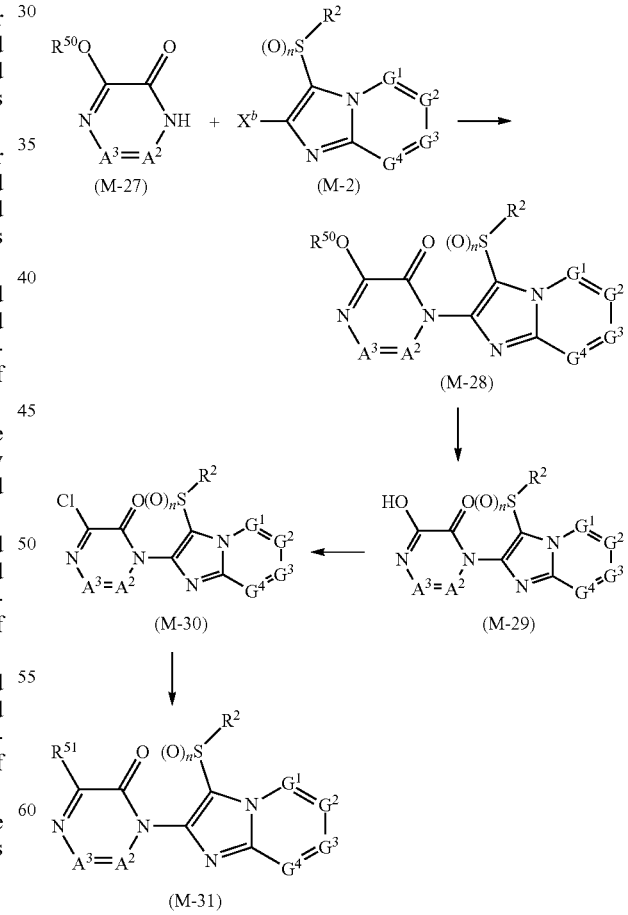

[wherein $R^{51}$ represents an amino group or a hydrazinyl group; and the other symbols are the same as defined above.]

A compound represented by formula (M-28) (hereinafter referred to as "Compound (M-28)") may be prepared according to the Production method 4 by using a compound represented by formula (M-27) (hereinafter referred to as "Compound (M-27)") instead of the Compound (M-1).

The Compound (M-27) is a commercially available compound or may be prepared by using known method(s).

A compound represented by formula (M-29) (hereinafter referred to as "Compound (M-29)") may be prepared according to the method for producing the Compound (M-1A) from the Compound (M-16) in the Reference production method 1 by using the Compound (M-28) instead of the Compound (M-16).

A compound represented by formula (M-30) (hereinafter referred to as "Compound (M-30)") may be prepared by reacting the Compound (M-29) with a chlorinating agent.

The reaction is usually carried out in a solvent. Examples of the solvent include ethers, aromatic hydrocarbons, halogenated hydrocarbons, and mixtures of two or more of them.

Examples of the chlorinating agent include thionyl chloride, oxalyl chloride, phosphorus oxychloride, and phosphorus pentachloride.

In the reaction, the chlorinating agent is usually used at a ratio of 1 to 5 mol relative to 1 mol of the Compound (M-29).

The reaction temperature is usually within the range of 0 to 100° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying and/or concentrating the resulting organic layer to give the Compound (M-30).

The Compound (M-31) may be prepared by reacting the Compound (M-30) with ammonia or hydrazine.

The reaction is usually carried out in a solvent. Examples of the solvent include ethers, aromatic hydrocarbons, nitriles, aprotic polar solvents, water, and mixtures of two or more of them.

The reaction may also be carried out by using a base as needed. Examples of the base include alkali metal hydrides, alkali metal carbonates, and organic bases. When a base is used in the reaction, the base is usually used at a ratio of 1 to 10 mol relative to 1 mol of the Compound (M-30).

In the reaction, ammonia or hydrazine is usually used at a ratio of 1 to 10 mol relative to 1 mol of the Compound (M-30).

The reaction temperature is usually within the range of 0 to 150° C. The reaction time is usually within the range of 0.5 to 24 hour(s).

When the reaction is completed, the reaction mixture may be subjected to a work-up such as adding water to the reaction mixture, extracting the resulting reaction mixture with organic solvent(s), and drying and/or concentrating the resulting organic layer to give the Compound (M-31).

Reference Production Method 5

The Compound (M-6) may be prepared according to the following scheme.

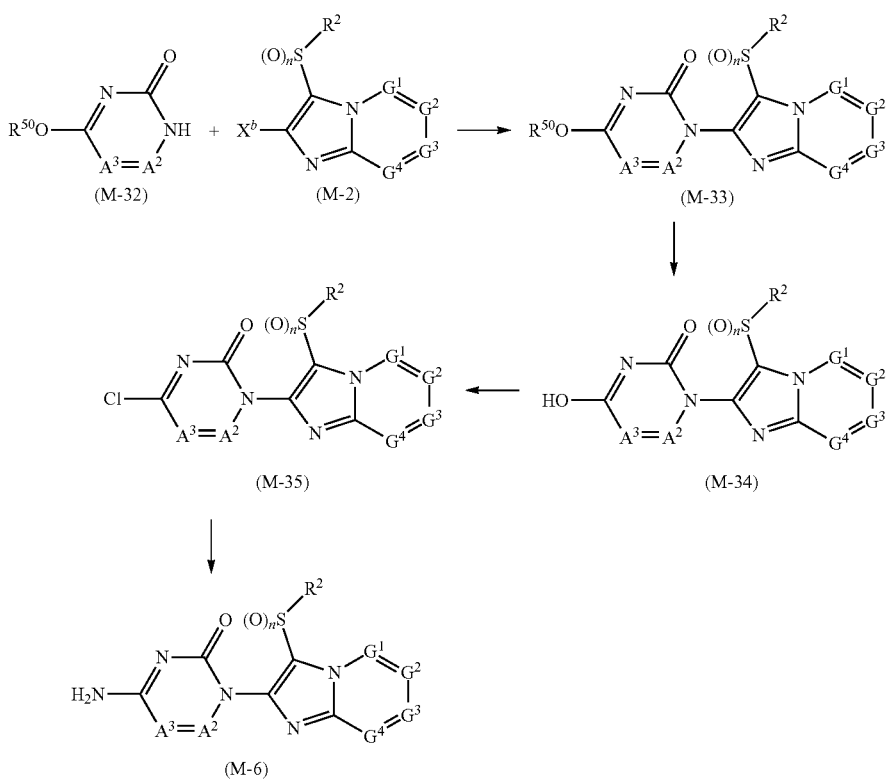

[wherein the symbols are the same as defined above.]

A compound represented by formula (M-33) (hereinafter referred to as "Compound (M-33)") may be prepared according to the Production method 4 by using a compound represented by formula (M-32) (hereinafter referred to as "Compound (M-32)") instead of the Compound (M-1).

The Compound (M-32) is a commercially available compound or may be prepared by using known method(s).

A compound represented by formula (M-34) (hereinafter referred to as "Compound (M-34)") may be prepared according to the method for producing the Compound (M-1A) from the Compound (M-16) in the Reference production method 1 by using the Compound (M-33) instead of the Compound (M-16).

A compound represented by formula (M-35) (hereinafter referred to as "Compound (M-35)") may be prepared according to the method for producing the Compound (M-30) from the Compound (M-29) in the Reference production method 4 by using the Compound (M-34) instead of the Compound (M-29).

The Compound (M-6) may be prepared by reacting the Compound (M-35) with ammonia. The reaction may be carried out according to the method for producing the Compound (M-31) from the Compound (M-30) in the Reference production method 4 by using the Compound (M-35) instead of the Compound (M-30).

Reference Production Method 6

A compound represented by formula (M-2-b) and a compound represented by formula (M-2-c) may be prepared by reacting a compound represented by formula (M-2-a) with an oxidizing agent.

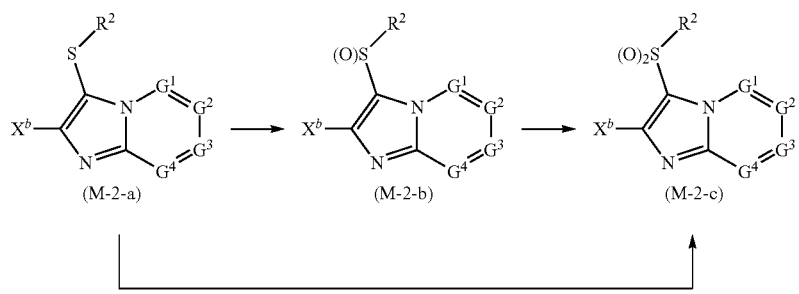

[wherein the symbols are the same as defined above.]

These reactions may be carried out according to the Production method 1.

Reference Production Method 7

A compound represented by formula (M-2-d) (hereinafter referred to as "Compound (M-2-d)") may be prepared according to the following scheme.

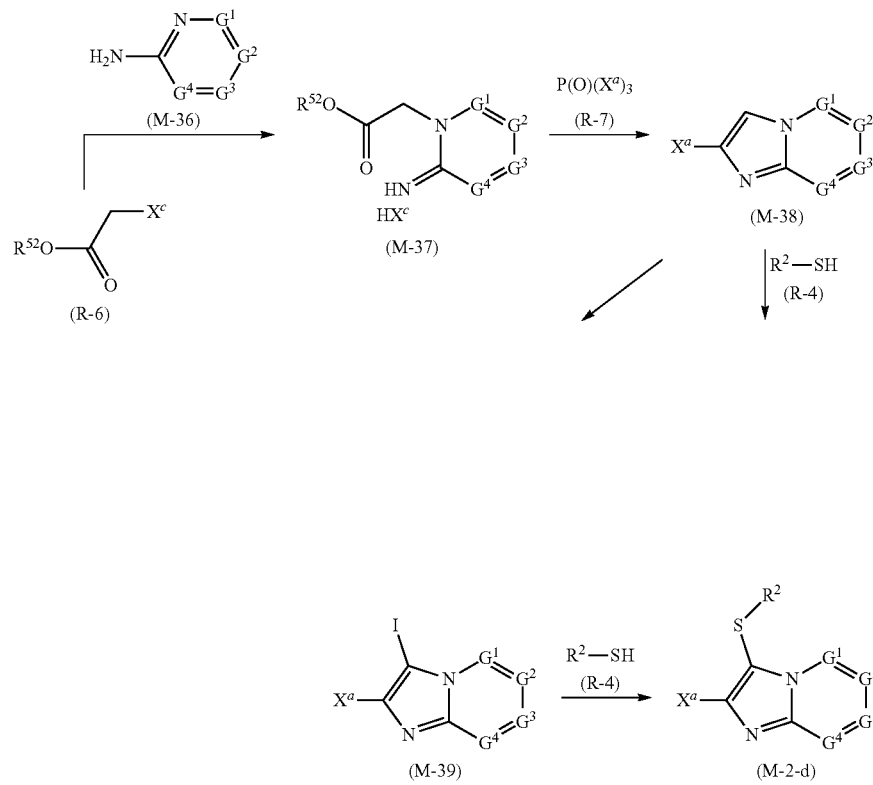

[wherein R$^{52}$ represents a hydrogen atom, a methyl group, or an ethyl group; X$^a$ represents a chlorine atom or a bromine atom; and the other symbols are the same as defined above.]

A compound represented by formula (M-37) (hereinafter referred to as "Compound (M-37)") may be prepared by reacting a compound represented by formula (M-36) (hereinafter referred to as "Compound (M-36)") with a compound represented by formula (R-6) (hereinafter referred to as "Compound (R-6)").

The reaction is usually carried out in a solvent. Examples of the solvent include aromatic hydrocarbons, alcohols, nitriles, and mixtures of two or more of them.

In the reaction, the Compound (M-36) is usually used at a ratio of 1 to 10 mol relative to 1 mol of the Compound (R-6).

The reaction temperature is usually within the range of 0° C. to 200° C. The reaction time is usually within the range of 0.1 to 48 hour(s).

When the reaction is completed, the reaction mixture may be subjected to a conventional work-up to give the Compound (M-37).

The Compound (R-6) and the Compound (M-36) are commercially available compounds or may be prepared by using known method(s).

A compound represented by formula (M-38) (hereinafter referred to as "Compound (M-38)") may be prepared by reacting the Compound (M-37) with a compound represented by formula (R-7) (hereinafter referred to as "Compound (R-7)").

The reaction is usually carried out in a solvent. Examples of the solvent include aromatic hydrocarbons, nitriles, and mixtures of two or more of them.

In the reaction, the Compound (R-7) is usually used at a ratio of 1 to 10 mol relative to 1 mol of the Compound (M-37).

The reaction temperature is usually within the range of 60° C. to 120° C. The reaction time is usually within the range of 0.1 to 48 hour(s).

When the reaction is completed, the reaction mixture may be subjected to a conventional work-up to give the Compound (M-38).

The Compound (R-7) is a commercially available compound or may be prepared by using known method(s).

A compound represented by formula (M-39) (hereinafter referred to as "Compound (M-39)") may be prepared by reacting the Compound (M-38) with N-iodosuccinimide. The reaction may be carried out according to the method for producing the Compound (M-9) from the Compound (M-8) in the Production method 9.

The Compound (M-2-d) may be prepared by reacting the Compound (M-38) or the Compound (M-39) with the Compound (R-4). These reactions may be carried out according to the method for producing the Compound (II-1n0) from the Compound (M-8) or the Compound (M-9) in the Production method 9.

Reference Production Method 8

A compound represented by formula (M-2-f) may be prepared by reacting a compound represented by formula (M-2-e) (hereinafter referred to as "Compound (M-2-e)") with silver fluoride in the presence of a metal catalyst.

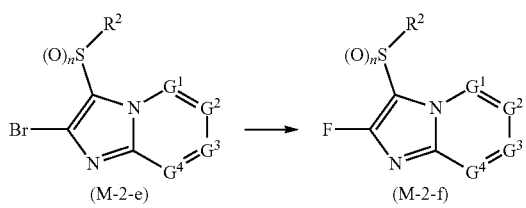

(M-2-e)   (M-2-f)

[wherein the symbols are the same as defined above.]

The reaction may be carried out according to the method described in, for example, Journal of the American Chemical Society, 2014, 136, 3792.

Reference Production Method 9

A compound represented by formula (M-2-g) may be prepared by reacting the Compound (M-2-e) with sodium iodide in the presence of a metal catalyst.

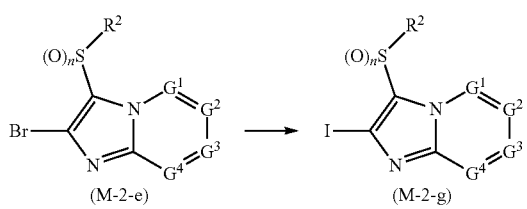

(M-2-e)   (M-2-g)

[wherein the symbols are the same as defined above.]

The reaction may be carried out according to the method described in, for example, Journal of the American Chemical Society, 2002, 124, 14844.

The Present compound may be mixed with or used in combination with one or more ingredient(s) selected from the group consisting of the following Group (a), Group (b), Group (c), and Group (d) (hereinafter referred to as "Present ingredient").

When the Present compound is mixed with or used in combination with the Present ingredient, they are used simultaneously, separately, or at time intervals with each other.

When the Present compound is used simultaneously with the Present ingredient, the Present compound and the Present ingredient may be contained in separate formulations with each other or contained in one formulation.

One aspect of the present invention provides a composition comprising one or more ingredient(s) selected from the group consisting of Group (a), Group (b), Group (c), and Group (d), and the Present compound (hereinafter referred to as "Composition A").

Group (a) is a group consisting of acetyicholinesterase inhibitors (for example, carbamate insecticides and organophosphate insecticides), GABA-gated chloride channel blockers (for example, phenylpyrazole insecticides), sodium channel modulators (for example, pyrethroid insecticides), nicotinic acetylcholine receptor competitive modulators (for example, neonicotinoid insecticides), nicotinic acetylcholine receptor allosteric modulators, glutamate-gated chloride channel allosteric modulators (for example, macrolide insecticides), juvenile hormone mimics, multisite inhibitors, chordotonal organ TRPV channel modulators, mite growth inhibitors, microbial disruptors of insect midgut membranes, inhibitors of mitochondrial ATP synthase, uncouplers of oxidative phosphorylation, nicotinic acetylcholine receptor channel blockers (for example, nereistoxin insecticides), inhibitors of chitin biosynthesis, moulting disruptors, ecdysone receptor agonists, octopamine receptor agonists, mitochondrial complexes I, II, III, and IV electron transport inhibitors, voltage-dependent sodium channel blockers, inhibitors of acetyl CoA carboxylase, ryanodine receptor modulators (for example, diamide insecticides), chordotonal organ modulators, and microbial insecticides, and other insecticidal active ingredients, miticidal active ingredients, and nematicidal active ingredients. These ingredients are described in the classification on the basis of action mechanism by IRAC.

Group (b) is a group consisting of nucleic acids synthesis inhibitors (for example, phenylamide fungicides and acylamino acid fungicides), cell division and cytoskeleton inhibitors (for example, MBC fungicides), respiration inhibitors (for example, QoI fungicides and QiI fungicides), amino acids synthesis and protein synthesis inhibitors (for example, anilino-pyridine fungicides), signal transduction inhibitors, lipid synthesis and membrane synthesis inhibitors, sterol biosynthesis inhibitors (for example, DMI fungicides such as triazole fungicides), cell wall biosynthesis inhibitors, melanin synthesis inhibitors, plant defense inducers, fungicides with multi-site contact activity, microbial fungicides, and other fungicidal active ingredients. These ingredients are described in the classification on the basis of action mechanism by FRAC.

Group (c) is a group of plant growth regulatory ingredients (including mycorrhizal fungi and root nodule bacteria).

Group (d) is a group of repellent ingredients.

Hereinafter, examples of the combination of the Present ingredient and the Present compound are described. For example, "alanycarb+SX" indicates a combination of alanycarb and SX.

The abbreviation of "SX" indicates any one of the Present compound selected from the Compound groups SX1 to SX633 described in Examples. Also, all of the following Present ingredient are known ingredients, and may be obtained from commercially available formulations, or may be prepared by known methods. When the Present ingredient is a microorganism, it may also be available from a bacterial authority depository. Further, the number in parentheses represents the CAS RN (registered trademark).

Combinations of the Present ingredient in the above Group (a) and the Present compound:

abamectin+SX, acephate+SX, acequinocyl+SX, acetamiprid+SX, acetoprole+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, bark of *Celastrus angulatus*+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, concanamycin A+SX, coumaphos+SX, cryolite+SX, cyanophos+SX, cyantraniliprole+SX, cycloniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dimpropyridaz+SX, dinotefuran+SX, disodium octaborate+SX, disulfoton+SX, DNOC (2-methyl-4,6-dinitrophenol)+SX, doramectin+SX, dried leaves of *Dryopteris filix-mas*+SX, emamectin-benzoate+SX, empenthrin+SX, endosulfan+SX, EPN (O-ethyl O-(4-nitrophenyl) phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*+SX, extract of *Cassia nigricans*+SX, extract of *Clitoria ternatea*+SX, extract of *Symphytum officinale*+SX, extracts or simulated blend of *Chenopodium ambrosioides*+SX, extract of *Tanacetum vulgare*+SX, extract of *Urtica dioica*+SX, extract of *Viscum album*+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX-Hvla peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid+SX, imidaclothiz+SX, imiprothrin+SX, indoxacarb+SX, isocycloseram+SX, isofenphos+SX, isoprocarb+SX, isopropyl-O-(methoxyaminothiophosphoryl) salicylate+SX, isoxathion+SX, ivermectin+SX, kadethrin+SX, kappa-tefluthrin+SX, kappa-bifenthrin+SX, kinoprene+SX, lambda-cyhalothrin+SX, lenoremycin+SX, lepimectin+SX, lime sulfur+SX, lotilaner+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, neem oil+SX, nicotine+SX, nicotine-sulfate+SX, nitenpyram+SX, novaluron+SX, noviflumuron+SX, oil of the seeds of *Chenopodium anthelminticum*+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, prallethrin+SX, profenofos+SX, profluthrin+SX, propargite+SX, propetamphos+SX, propoxur+SX, propylene glycol alginate+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, sarolaner+SX, selamectin+SX, sigma-cypermethrin+SX, silafluofen+SX, sodium borate+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of Chenopodium ambrosioides near ambrosioides+SX, tetrachlorantraniliprole+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, wood extract of Quassia amara+SX, XMC (3,5-dimethylphenyl N-methylcarbamate)+SX, xylylcarb+SX, zeta-cypermethrin+SX, zinc phosphide+SX, N-[3-chloro-1-(pyridin-3-yl)-1H-pyrazol-4-yl]-N-ethyl-3-(3,3,3-trifluoropropanesulfinyl)propanamide (1477923-37-7)+SX, 4-[5-(3,5-dichlorophenyl)-5-(trifluoromethyl)-4,5-dihydro-1,2-oxazol-3-yl]-2-methyl-N-(1-oxothietan-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propanamide (1118626-57-5)+SX, N-[2-bromo-6-chloro-4-(1,1,1,2,3,3,3-heptafluoropropan-2-yl)phenyl]-3-{ethyl[(pyridin-4-yl)carbonyl]amino}-2-methoxybenzamide (1429513-53-0)+SX, N-[2-bromo-6-chloro-4-(1,1,1,2,3,3,3-heptafluoropropan-2-yl)phenyl]-3-[ethyl(4-cyanobenzoyl)amino]-2-methoxybenzamide (1609007-65-9)+SX, N-[2-bromo-6-(difluoromethoxy)-4-(1,1,1,2,3,3,3-heptafluoropropan-2-yl)phenyl]-3-{methyl[(pyridin-4-yl)carbonyl]amino}-2-methoxybenzamide (1630969-78-6)+SX, 1-{2-fluoro-4-methyl-5-[(2,2,2-trifluoroethyl)sulfanyl]phenyl}-3-(trifluoromethyl)-1H-1,2,4-triazol-5-amine (885026-50-6)+SX, BT crop protein Cry1Ab+SX, BT crop protein Cry1Ac+SX, BT crop protein Cry1Fa+SX, BT crop protein Cry1A.105+SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34Ab1/Cry35Ab1+SX, Adoxophyes orana granulosis virus strain BV-0001+SX, Anticarsia gemmatalis mNPV+SX, Autographa californica mNPV+SX, Cydia pomonella GV strain V15+SX, Cydia pomonella GV strain V22+SX, Cryptophlebia leucotreta GV+SX, Dendrolimus punctatus cypovirus+SX, Helicoverpa armigera NPV strain BV-0003+SX, Helicoverpa zea NPV+SX, Lymantria dispar NPV+SX, Mamestra brassicae NPV+SX, Mamestra configurata NPV+SX, Neodiprion abietis NPV+SX, Neodiprion lecontei NPV+SX, Neodiprion sertifer NPV+SX, Nosema locustae+SX, Orgyia pseudotsugata NPV+SX, Pieris rapae GV+SX, Plodia interpunctella GV+SX, Spodoptera exigua mNPV+SX, Spodoptera littoralis mNPV+SX, Spodoptera litura NPV+SX, Arthrobotrys dactyloides+SX, Bacillus firmus strain GB-126+SX, Bacillus firmus strain I-1582+SX, Bacillus megaterium+SX, Bacillus sp. strain AQ175+SX, Bacillus sp. strain AQ177+SX, Bacillus sp. strain AQ178+SX, Bacillus sphaericus strain 2362+SX, Bacillus sphaericus strain ABTS1743+SX, Bacillus sphaericus Serotype strain H5a5b+SX, Bacillus thuringiensis strain AQ52+SX, Bacillus thuringiensis strain BD #32+SX, Bacillus thuringiensis strain CR-371+SX, Bacillus thuringiensis subsp. aizawai strain ABTS-1857+SX, Bacillus thuringiensis subsp. aizawai strain AM65-52+SX, Bacillus thuringiensis subsp. aizawai strain GC-91+SX, Bacillus thuringiensis subsp. aizawai Serotype strain H-7+SX, Bacillus thuringiensis subsp. Kurstaki strain ABTS351+SX, Bacillus thuringiensis subsp. Kurstaki strain BMP123+SX, Bacillus thuringiensis subsp. Kurstaki strain EG234+SX, Bacillus thuringiensis subsp. Kurstaki strain EG7841+SX, Bacillus thuringiensis subsp. Kurstaki strain EVB113-19+SX, Bacillus thuringiensis subsp. Kurstaki strain F810+SX, Bacillus thuringiensis subsp. Kurstaki strain HD-1+SX, Bacillus thuringiensis subsp. Kurstaki strain PB54+SX, Bacillus thuringiensis subsp. Kurstaki strain SA-11+SX, Bacillus thuringiensis subsp. Kurstaki strain SA-12+SX, Bacillus thuringiensis subsp. Tenebriosis strain NB176+SX, Bacillus thuringiensis subsp. thuringiensis strain MPPL002+SX, Bacillus thuringiensis subsp. morrisoni+SX, Bacillus thuringiensis var. colmeri+SX, Bacillus thuringiensis var. darmstadiensis strain 24-91+SX, Bacillus thuringiensis var. dendrolimus+SX, Bacillus thuringiensis var. galleriae+SX, Bacillus thuringiensis var. israelensis strain BMP144+SX, Bacillus thuringiensis var. israelensis serotype strain H-14+SX, Bacillus thuringiensis var. japonensis strain buibui+SX, Bacillus thuringiensis var. san diego strain M-7+SX, Bacillus thuringiensis var. 7216+SX, Bacillus thuringiensis var. aegypti+SX, Bacillus thuringiensis var. T36+SX, Beauveria bassiana strain ANT-03+SX, Beauveria bassiana strain ATCC74040+SX, Beauveria bassiana strain GHA+SX, Beauveria brongniartii+SX, Burkholderia rinojensis strain A396+SX, Chromobacterium subtsugae strain PPAA4-1T+SX, Dactyllela ellipsospora+SX, Dectylaria thaumasia+SX, Hirsutella minnesotensis+SX, Hirsutella rhossiliensis+SX, Hirsutella thompsonii+SX, Lagenidium giganteum+SX, Lecanicillium lecanii strain KV01+SX, Lecanicillium lecanii conidia of strain DAOM198499+SX, Lecanicillium lecanii conidia of strain DAOM216596+SX, Lecanicillium muscarium strain Ve6+SX, Metarhizium anisopliae strain F52+SX, Metarhizium anisopliae var. acridum+SX, Metarhizium anisopliae var. anisopliae BIPESCO 5/F52+SX, Metarhizium flavoviride+SX, Monacrosporium phymatopagum+SX, Paecilomyces fumosoroseus Apopka strain 97+SX, Paecilomyces lilacinus strain 251+SX, Paecilomyces tenuipes strain T1+SX, Paenibacillus popilliae+SX, Pasteuria nishizawae strain Pn1+SX, Pasteuria penetrans+SX, Pasteuria usgae+SX, Pasteuria thoynei+SX, Serratia entomophila+SX, Verticillium chlamydosporium+SX, Verticillium lecani strain NCIM1312+SX, 2-chloro-4-fluoro-5-{[5-(trifluoromethylthio)pentyl]oxy}phenyl 2,2,2-trifluoroethyl sulfoxide (1472050-04-6)+SX, 4-chloro-5-[2,2-difluoro-2-(3,4,5-trifluorophenyl)ethoxy]-2-methylphenyl 2,2,2-trifluoroethyl sulfoxide (1632218-00-8)+SX, 4-fluoro-5-[2,2-difluoro-2-(3,4,5-trifluorophenyl) ethoxy]-2-methylphenyl 2,2,2-trifluoroethyl sulfoxide (1632217-98-1)+SX, 2-({2-fluoro-4-methyl-5-[(2,2,2-trifluoroethyl)sulfinyl]phenyl}imino)-3-(2,2,2-trifluoroethyl)-1,3-thiazolidin-4-one (1445683-71-5)+SX, (1Z)-2-(4-tert-butylphenyl)-2-cyano-1-(1-ethyl-3-methyl-1H-pyrazol-5-yl)ethenyl 2,2-dimethylpropanoate (1253429-01-4)+SX, N-[(1S,2S)-2-(2,4-dichlorophenyl)cyclobutyl]-2-(trifluoromethyl)pyridine-3-carboxamide (1644251-74-0)+SX, (3R)-3-(2-chlorothiazol-5-yl)-8-methyl-7-oxo-6-phenyl-2,3-dihydrothiazolo[3,2-a]pyrimidin-4-ium-5-olate (2249718-27-0)+SX.

Combinations of the Present ingredient in the above Group (b) and the Present compound:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthiavalicarb-isopropyl+SX, benzovindiflupyr+SX, binapacryl+SX, biphenyl+SX, bitertanol+SX, bixafen+SX, blasticidin-S+SX, Bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroneb+SX, chlorothalonil+SX, chlozolinate+SX, colletochlorin B+SX, copper(II) acetate+SX, copper(II) hydroxide+SX, copper oxychloride+SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, dimethachlone+SX, dimethirimol+SX, dimethomorph+SX, dimoxystrobin+SX, diniconazole+SX, diniconazole-M+SX, dinocap+SX, dipotassium hydrogenphosphite+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract from *Melaleuca alternifolia*+SX, extract from *Reynoutria sachalinensis*+SX, extract from the cotyledons of lupine plantlets ("BLAD")+SX, extract of *Allium sativum*+SX, extract of *Equisetum arvense*+SX, extract of *Tropaeolum majus*+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, fludioxonil+SX, flufenoxystrobin+SX, fluindapyr+SX, flumorph+SX, fluopicolide+SX, fluopyram+SX, fluopimomide+SX, fluoroimide+SX, fluoxapiprolin+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of *Quercus*+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazole+SX, methasulfocarb+SX, metiram+SX, metominostrobin+SX, metrafenone+SX, metyltetraprole+SX, mineral oils+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph+SX, pyriofenone+SX, pyrisoxazole+SX, pyroquilon+SX, Quillaja extract+SX, quinconazole+SX, quinofumelin+SX, quinoxyfen+SX, quintozene+SX, Saponins of *Chenopodium quinoa*+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, N'-[4-({3-[(4-chlorophenyl) methyl]-1,2,4-thiadiazol-5-yl}oxy)-2,5-dimethylphenyl]-N-ethyl-N-methylmethanimidamide (1202781-91-6)+SX, 4-(2-bromo-4-fluorophenyl)-N-(2-chloro-6-fluorophenyl)-1,3-dimethyl-1H-pyrazol-5-amine (1362477-26-6)+SX, 2-[6-(3-fluoro-4-methoxyphenyl)-5-methylpyridin-2-yl]quinazoline (1257056-97-5)+SX, 5-fluoro-2-[(4-methylphenyl)methoxy]pyrimidin-4-amine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridin-2-amine (1446247-98-8)+SX, 5-(4-chlorobenzyl)-2-(chloromethyl)-2-methyl-1-(1H-1,2,4-triazol-1- ylmethyl)cyclopentan-1-ol (1394057-11-4)+SX, (1R, 2S, 5S)-5-(4-chlorobenzyl)-2-(chloromethyl)-2-methyl-1-(1H-1,2,4-triazol-1-ylmethyl)cyclopentan-1-ol (1801930-06-2)+SX, (1S, 2R, 5R)-5-(4-chlorobenzyl)-2-(chloromethyl)-2-methyl-1-(1H-1,2,4-triazol-1-ylmethyl)cyclopentan-1-ol (1801930-07-3)+SX, 2-(chloromethyl)-5-(4-fluorobenzyl)-2-methyl-1-(1H-1,2,4-triazol-1-ylmethyl)cyclopentan-1-ol (1394057-13-6)+SX, (1R, 2S, 5S)-2-(chloromethyl)-5-(4-fluorobenzyl)-2-methyl-1-(1H-1,2,4-triazol-1-ylmethyl) cyclopentan-1-ol (1801930-08-4)+SX, (1S, 2R, 5R)-2-(chloromethyl)-5-(4-fluorobenzyl)-2-methyl-1-(1H-1,2,4-triazol-1-ylmethyl)cyclopentan-1-ol (1801930-09-5)+SX, methyl 3-[(4-chlorophenyl)methyl]-2-hydroxy-1-methyl-2-(1H-1,2,4-triazol-1-ylmethyl)cyclopentan-1-carboxylate (1791398-02-1)+SX, methyl ({2-methyl-5-[1-(4-methoxy-2-methylphenyl)-1H-pyrazol-3-yl]phenyl}methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+SX, 2-(difluoromethyl)-N-[3-propyl-1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-(methoxyimino)-N,3-dimethylpent-3-enamide (1445331-27-0)+SX, Agrobacterium radiobactor strain K1026+SX, Agrobacterium radiobactor strain K84+SX, Bacillus amyloliquefaciens (Aveo (trademark) EZ Nematicide)+SX, Bacillus amyloliquefaciens strain AT332+SX, Bacillus amyloliquefaciens strain B3+SX, Bacillus amyloliquefaciens strain D747+SX, Bacillus amyloliquefaciens strain DB101+SX, Bacillus amyloliquefaciens strain DB102+SX, Bacillus amyloliquefaciens strain GB03+SX, Bacillus amyloliquefaciens strain FZB24+SX, Bacillus amyloliquefaciens strain FZB42+SX, Bacillus amyloliquefaciens strain IN937a+SX, Bacillus amyloliquefaciens strain MBI600+SX, Bacillus amyloliquefaciens strain QST713+SX, Bacillus amyloliquefaciens isolate strain B246+SX, Bacillus amyloliquefaciens strain F727+SX, Bacillus amyloliquefaciens subsp. plantarum strain D747+SX, Bacillus licheniformis strain HB-2+SX, Bacillus licheniformis strain SB3086+SX, Bacillus pumilus strain AQ717+SX, Bacillus pumilus strain BUF-33+SX, Bacillus pumilus strain GB34+SX, Bacillus pumilus strain QST2808+SX, Bacillus simplex strain CGF2856+SX, Bacillus subtilis strain AQ153+SX, Bacillus subtilis strain AQ743+SX, Bacillus subtilis strain BU1814+SX, Bacillus subtilis strain D747+SX, Bacillus subtilis strain DB101+SX, Bacillus subtilis strain FZB24+SX, Bacillus subtilis strain GB03+SX, Bacillus subtilis strain HAI0404+SX, Bacillus subtilis strain IAB/BS03+SX, Bacillus subtilis strain MB1600+SX, Bacillus subtilis strain QST30002/AQ30002+SX, Bacillus subtilis strain QST30004/AQ30004+SX, Bacillus subtilis strain QST713+SX, Bacillus subtilis strain QST714+SX, Bacillus subtilis var. Amyloliquefaciens strain FZB24+SX, Bacillus subtilis strain Y1336+SX, Burkholderia cepacia+SX, Burkholderia cepacia type Wisconsin strain J82+SX, Burkholderia cepacia type Wisconsin strain M54+SX, Candida oleophila strain O+SX, Candida saitoana+SX, Chaetomium cupreum+SX, Clonostachys rosea+SX, Coniothyrium minitans strain CGMCC8325+SX, Coniothyrium minitans strain CON/M/91-8+SX, Cryptococcus albidus+SX, Erwinia carotovora subsp. carotovora strain CGE234M403+SX, Fusarium oxysporum strain Fo47+SX, Gliocladium catenulatum strain J1446+SX, Paenibacillus polymyxa strain AC-1+SX, Paenibacillus polymyxa strain BS-0105+SX, Pantoea agglomerans strain E325+SX, Phlebiopsis gigantea strain VRA1992+SX, Pseudomonas aureofaciens strain TX-1+SX, Pseudomonas chlororaphis strain 63-28+SX, Pseudomonas chlororaphis strain AFS009+SX, Pseudomonas chlororaphis strain MA342+SX, Pseudomonas fluorescens strain 1629RS+SX, Pseudomonas fluorescens strain A506+SX, Pseudomonas fluorescens strain CL145A+SX, Pseudomonas fluorescens strain G7090+SX, Pseudomonas sp. strain CAB-02+SX, Pseudomonas syringae strain 742RS+SX, Pseudomonas syringae strain MA-4+SX, Pseudozyma flocculosa strain PF-A22UL+SX, Pseudomonas rhodesiae strain HAI-0804+SX, Pythium oligandrum strain DV74+SX, Pythium oligandrum strain M1+SX, Streptomyces griseoviridis strain K61+SX, Streptomyces lydicus strain WYCD108US+SX, Streptomyces lydicus strain WYEC108+SX, Talaromyces flavus strain SAY-Y-94-01+SX, Talaromyces flavus strain V117b+SX, Trichoderma asperellum strain ICC012+SX, Trichoderma asperellum SKT-1+SX, Trichoderma asperellum strain T25+SX, Trichoderma asperellum strain T34+SX, Trichoderma asperellum strain TVi+SX, Trichoderma atroviride strain CNCM 1-1237+SX, Trichoderma atroviride strain LC52+SX, Trichoderma atroviride strain IMI 206040+SX, Trichoderma atroviride strain SCi+SX, Trichoderma atroviride strain SKT-1+SX, Trichoderma atroviride strain T11+SX, Trichoderma gamsii strain ICC080+SX, Trichoderma harzianum strain 21+SX, Trichoderma harzianum strain DB104+SX, Trichoderma harzianum strain DSM 14944+SX, Trichoderma harzianum strain ESALQ-1303+SX, Trichoderma harzianum strain ESALQ-1306+SX, Trichoderma harzianum strain IIHR-Th-2+SX, Trichoderma harzianum strain ITEM908+SX, Trichoderma harzianum strain kd+SX, Trichoderma harzianum strain MO1+SX, Trichoderma harzianum strain SF+SX, Trichoderma harzianum strain T22+SX, Trichoderma harzianum strain T39+SX, Trichoderma harzianum strain T78+SX, Trichoderma harzianum strain TH35+SX, Trichoderma polysporum strain IMI206039+SX, Trichoderma stromaticum+SX, Trichoderma virens strain G-41+SX, Trichoderma virens strain GL-21+SX, Trichoderma viride+SX, Variovorax paradoxus strain CGF4526+SX, Harpin protein+SX, N'-[5-choro-4-(2-fluorophenoxy)-2-methylphenyl)-N-ethyl-N-methylmethanimidamide (2055589-28-9)+SX, N'-[2-choro-4-(2-fluorophenoxy)-5-methylphenyl)-N-ethyl-N-methylmethanimidamide (2055756-21-1)+SX, N'-[4-(1-hydroxy-1-phenyl-2,2,2-trifluoroethyl)-2-methyl-5-methoxyphenyl)-N-isopropyl-N-methylmethanimidamide (2101814-55-3)+SX, N'-[5-bromo-6-(1-methyl-2-propoxyethoxy)-2-methylpyridin-3-yl)-N-ethyl-N-methylmethanimidamide (1817828-69-5)+SX, 1-(2,4-difluorophenyl)-2-(1H-1,2,4-triazol-1-yl)-1-[1-(4-bromo-2,6-difluorophenoxy)cyclopropyl]ethanol (2019215-86-0)+SX, 1-(2,4-difluorophenyl)-2-(1H-1,2,4-triazol-1-yl)-1-[1-(4-chloro-2,6-difluorophenoxy)cyclopropyl]ethanol (2019215-84-8)+SX, 1-[2-(1-chlorocyclopropyl)-3-(2-fluorophenyl)-2-hydroxypropyl]-1H-imidazole-5-carbonitrile (2018316-13-5)+SX, 1-[2-(1-chlorocyclopropyl)-3-(2,3-difluorophenyl)-2-hydroxypropyl]-1H-imidazole-5-carbonitrile (2018317-25-2)+SX, 4-({6-[2-(2,4-difluorophenyl)-1,1-difluoro-2-hydroxy-3-(1H-1,2,4-triazol-1-yl)propyl]pyridin-3-yl}oxy)benzonitrile (2046300-61-0)+SX, 2-[6-(4-bromophenoxy)-2-(trifluoromethyl)pyridin-3-yl]-1-(1H-1,2,4-triazol-1-yl)propan-2-ol (2082661-43-4)+SX, 2-[6-(4-chlorophenoxy)-2-(trifluoromethyl)pyridin-3-yl]-1-(1H-1,2,4-triazol-1-yl)propan-2-ol (2082660-27-1)+SX, (2E,3Z)-5-{[1-(2,4-dichlorophenyl)-1H-pyrazol-3-yl]oxy}-2-(methoxyimino)-N,3-dimethylpent-3-enamide (1445331-54-3)+SX, 5-chloro-4-({2-[6-(4-chlorophenoxy)pyridin-3-yl]ethyl}amino)-6-methylpyrimidine (1605340-92-8)+SX, N-(1-benzyl-1,3-dimethylbutyl)-8-fluoroquinoline-3-carboxamide (2132414-04-9)+SX, N-(1-benzyl-3,3,3-trifluoro-1-methylpropyl)-8-fluoroquinoline-3-carboxamide (2132414-00-5)+SX, 4,4-dimethyl-2-({4-[5-(trifluoromethyl)-1,2,4-oxadiazol-3-yl]phenyl}methyl)isoxazolidin-3-one (2098918-25-1)+SX, 5,5-dimethyl-2-({4-[5-(trifluoromethyl)-1,2,4-oxadiazol-3-yl]phenyl}methyl)isoxazolidin-3-one (2098918-26-2)+SX.

Combinations of the Present ingredient in the above Group (c) and the Present compound:

1-methylcyclopropene+SX, 1,3-diphenylurea+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, formononetin+SX, Gibberellin A+SX, Gibberellin A3+SX, inabenfide+SX, Kinetin+SX, lipochitooligosaccharide SP104+SX, maleic hydrazide+SX, mefluidide+SX, mepiquat-chloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalen-1-yl)acetamide+SX, [4-oxo-4-(2-phenylethyl)amino]butyric acid+SX, methyl 5-(trifluoromethyl)benzo[b]thiophene-2-carboxylate+SX, 3-[(6-chloro-4-phenylquinazolin-2-yl)amino]-1-propanol+SX, *Claroideoglomus etunicatum*+SX, *Claroideoglomus claroideum*+SX, *Funneliformis mosseae*+SX, *Gigaspora margarita*+SX, *Gigaspora rosea*+SX, *Glomus aggregatum*+SX, *Glomus deserticola*+SX, *Glomus monosporum*+SX, *Paraglomus brasillianum*+SX, *Rhizophagus clarus*+SX, *Rhizophagus intraradices* RTI-801+SX, *Rhizophagus irregularis* DAOM 197198+SX, *Azorhizobium caulinodans*+SX, *Azospirillum amazonense*+SX, *Azospirillum brasilense* XOH+SX, *Azospirillum brasilense* Ab-V5+SX, *Azospirillum brasilense* Ab-V6+SX, *Azospirillum caulinodans*+SX, *Azospirillum halopraeferens*+SX, *Azospirillum irakense*+SX, *Azospirillum lipoferum*+SX, *Bradyrhizobium elkanii* SEMIA 587+SX, *Bradyrhizobium elkanii* SEMIA 5019+SX, *Bradyrhizobium japonicum* TA-11+SX, *Bradyrhizobium japonicum* USDA 110+SX, *Bradyrhizobium liaoningense*+SX, *Bradyrhizobium lupini*+SX, *Delftia acidovorans* RAY209+SX, *Mesorhizobium ciceri*+SX, *Mesorhizobium huakii*+SX, *Mesorhizobium loti*+SX, *Rhizobium etli*+SX, *Rhizobium galegae*+SX, *Rhizobium leguminosarum* bv. *Phaseoli*+SX, *Rhizobium leguminosarum* bv. *Trifolii*+SX, *Rhizobium leguminosarum* bv. *Viciae*+SX, *Rhizobium trifolii*+SX, *Rhizobium tropici*+SX, *Sinorhizobium fredii*+SX, *Sinorhizobium meliloti*+SX, Zucchini Yellow Mosaik Virus weak strain+SX.

Combinations of the Present ingredient in the above Group (d) and the Present compound:

anthraquinone+SX, deet+SX, icaridin+SX.

Examples of the ratio of the Present compound and the Present ingredient include, but are not limited to, 1000:1 to 1:1000, 500:1 to 1:500, 100:1 to 1:100, 50:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, and 1:50, in the ratio by weight (Present compound:Present ingredient).

The Present compound has control effects on harmful arthropods such as harmful insects and harmful mites, harmful nematodes, and harmful mollusks. Examples of the harmful arthropods, harmful nematodes, and harmful mollusks include the followings.

Hemiptera:

from the family Delphacidae, small brown planthopper (*Laodelphax striatellus*), brown planthopper (*Nilaparvata lugens*), white-backed planthopper (*Sogatella furcifera*), corn planthopper (*Peregrinus maidis*), cereal leafhopper (*Javesella pellucida*), sugarcane leafhopper (*Perkinsiella saccharicida*), *Tagosodes orizicolus*, and the like;

from the family Cicadellidae, green rice leafhopper (*Nephotettix cincticeps*), green paddy leafhopper (*Nephotettix virescens*), rice leafhopper (*Nephotettix nigropictus*), zigzag-striped leafhopper (*Recilia dorsalis*), tea green leafhopper (*Empoasca onukii*), potato leafhopper (*Empoasca fabae*), corn leafhopper (*Dalbulus maidis*), rice leafhopper (*Cofana spectra*), and the like;

from the family Cercopidae, *Mahanarva posticata, Mahanarva fimbriolata*, and the like;

from the family Aphididae, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), rosy apple aphid (*Dysaphis plantaginea*), false cabbage aphid (*Lipaphis erysimi*), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (*Tetraneura nigriabdominalis*), sugarcane cottony aphid (*Ceratovacuna lanigera*), apple woolly aphid (*Eriosoma lanigerum*), and the like;

from the family Phylloxeridae, grapevine *phylloxera* (*Daktulosphaira vitifoliae*), Pecan *phylloxera* (*Phyllox-*

*era devastatrix*), Pecan leaf *phylloxera* (*Phylloxera notabilis*), Southern pecan leaf *phylloxera* (*Phylloxera russellae*), and the like;

from the family Adelgidae, hemlock woolly aphid (*Adelges tsugae*), *Adelges piceae, Aphrastasia pectinatae,* and the like;

from the family Pentatomidae, black rice bug (*Scotinophara lurida*), Malayan rice black bug (*Scotinophara coarctata*), common green stink bug (*Nezara antennata*), white-spotted spined bug (*Eysarcoris aeneus*), lewis spined bug (*Eysarcoris lewisi*), white-spotted bug (*Eysarcoris ventralis*), *Eysarcoris* annamita, brown marmorated stink bug (*Halyomorpha halys*), green plant bug (*Nezara viridula*), Brown stink bug (*Euschistus heros*), Red banded stink bug (*Piezodorus guildinii*), *Oebalus pugnax, Dichelops melacanthus,* and the like;

from the family Cydnidae, Burrower brown bug (*Scaptocoris castanea*), and the like;

from the family Alydidae, bean bug (*Riptortus pedestris*), corbett rice bug (*Leptocorisa chinensis*), rice bug (*Leptocorisa acuta*), and the like;

from the family Coreidae, *Cletus punctiger*, Australian leaf-footed bug (*Leptoglossus australis*), and the like;

from the family Lygaeidae, oriental chinch bug (*Caverelius saccharivorus*), seed bug (*Togo hemipterus*), chinch bug (*Blissus leucopterus*), and the like;

from the family Miridae, rice leaf bug (*Trigonotylus caelestialium*), sorghum plant bug (*Stenotus rubrovittatus*), wheat leaf bug (*Stenodema calcarata*), American tarnished plant bug (*Lygus lineolaris*), and the like;

from the family Aleyrodidae, greenhouse whitefly (*Trialeurodes vaporariorum*), tobacco whitefly (*Bemisia tabaci*), citrus whitefly (*Dialeurodes citri*), citrus spiny whitefly (*Aleurocanthus spiniferus*), tea spiny whitefly (*Aleurocanthus camelliae*), *Pealius euryae,* and the like;

from the family Diaspididae, *Abgrallaspis cyanophylli,* red scale (*Aonidiella aurantii*), San José scale (*Diaspidiotus perniciosus*), white peach scale (*Pseudaulacaspis pentagona*), arrowhead scale (*Unaspis yanonensis*), citrus snow scale (*Unaspis citri*), and the like;

from the family Coccidae, pink wax scale (*Ceroplastes rubens*), and the like;

from the family Margarodidae, fluted scale (*Icerya purchasi*), seychelles fluted scale (*Icerya seychellarum*), and the like;

from the family Pseudococcidae, solanum mealybug (*Phenacoccus solani*), cotton mealybug (*Phenacoccus solenopsis*), Japanese mealybug (*Planococcus kraunhiae*), white peach scale (*Pseudococcus comstocki*), citrus mealybug (*Planococcus citri*), currant mealybug (*Pseudococcus calceolariae*), long-tailed mealybug (*Pseudococcus longispinus*), tuttle mealybug (*Brevennia rehi*), and the like;

from the family Psyllidae, citrus *psylla* (*Diaphorina citri*), two-spotted citrus psyllid (*Trioza erytreae*), pear sucker (*Cacopsylla* pyrisuga), *Cacopsylla chinensis*, potato psyllid (*Bactericera cockerelli*), Pear *psylla* (*Cacopsylla pyricola*), and the like;

from the family Tingidae, sycamore lace bug (*Corythucha ciliata*), aster tingid (*Corythucha marmorata*), Japanese pear lace bug (*Stephanitis nashi*), azalea lace bug (*Stephanitis pyrioides*), and the like;

from the family Cimicidae, common bed bug (*Cimex lectularius*), tropical bed bug (*Cimex lectularius*), and the like;

from the family Cicadidae, Giant Cicada (*Quesada gigas*), and the like;

from the family Reduviidae, *Triatoma infestans, Rhodnius prolixus,* and the like, *Triatoma* spp.; and the others.

Lepidoptera:

from the family Crambidae, rice stem borer (*Chilo suppressalis*), Dark-headed stem borer (*Chilo polychrysus*), white stem borer (*Scirpophaga innotata*), yellow paddy borer (*Scirpophaga incertulas*), *Rupela albina*, rice leaf roller (*Cnaphalocrocis medinalis*), *Marasmia patnalis*, rice leaf roller (*Marasmia exigua*), cotton leaf roller (*Notarcha derogata*), corn borer (*Ostrinia furnacalis*), European corn borer (*Ostrinia nubilalis*), cabbage webworm (*Hellula undalis*), grape leafroller (*Herpetogramma luctuosale*), bluegrass webworm (*Pediasia teterrellus*), rice case-worm (*Nymphula depunctalis*), Sugarcane borer (*Diatraea saccharalis*), and the like;

from the family Pyralidae, lesser cornstalk borer (*Elasmopalpus lignosellus*), mealworm moth (*Plodia interpunctella*), persimmon bark borer (*Euzophera batangensis*), fig moth (*Cadra cautella*), and the like;

from the family Noctuidae, cotton worm (*Spodoptera litura*), beet armyworm (*Spodoptera exigua*), rice armyworm (*Mythimna separata*), cabbage moth (*Mamestra brassicae*), pink borer (*Sesamia inferens*), grass armyworm (*Spodoptera mauritia*), green rice caterpillar (*Naranga aenescens*), *Spodoptera frugiperda*, true armyworm (*Spodoptera exempta*), black cutworm (*Agrotis ipsilon*), beet worm (*Autographa nigrisigna*), rice looper (*Plusia festucae*), soybean looper (*Chrysodeixis includens*), *Trichoplusia* spp., *Heliothis* spp. (such as tobacco budworm (*Heliothis virescens*)), *Helicoverpa* spp. (such as tobacco budworm (*Helicoverpa armigera*) and corn earworm (*Helicoverpa zea*)), Velvetbean caterpillar (*Anticarsia gemmatalis*), Cotton leafworm (*Alabama argillacea*), Hop vine borer (*Hydraecia immanis*), and the like;

from the family Pieridae, common cabbage worm (*Pieris rapae*), and the like;

from the family Tortricidae, oriental fruit moth (*Grapholita molesta*), *Grapholita* dimorpha, soybean moth (*Leguminivora glycinivorella*), *Matsumuraeses azukivora*, summer fruit *tortrix* (*Adoxophyes orana fasciata*), smaller tea *tortrix* (*Adoxophyes honmai*), Japanese tea *tortrix* (*Homona magnanima*), apple *tortrix* (*Archips fuscocupreanus*), codling moth (*Cydia pomonella*), sugarcane shoot borer (*Tetramoera schistaceana*), Bean Shoot Borer (*Epinotia aporema*), Citrus fruit borer (*Ecdytolopha aurantiana*), and the like;

from the family Gracillariidae, tea leaf roller (*Caloptilia theivora*), Asiatic apple leaf miner (*Phyllonorycter ringoniella*), and the like;

from the family Carposinidae, peach fruit moth (*Carposina sasakii*), and the like;

from the family Lyonetiidae, Coffee Leaf miner (*Leucoptera coffeella*), peach leaf miner (*Lyonetia clerkella*), *Lyonetia* prunifoliella, and the like;

from the family Lymantriidae, *Lymantria* spp. (such as gypsy moth (*Lymantria dispar*)), *Euproctis* spp. (such as tea lymantriid (*Euproctis pseudoconspersa*)), and the like;

from the family Plutellidae, diamondback moth (*Plutella xylostella*), and the like;

from the family Gelechiidae, peach worm (*Anarsia lineatella*), sweetpotato leaf folder (*Helcystogramma tri-* annulella), pink bollworm (*Pectinophora gossypiella*), potato moth (*Phthorimaea operculella*), *Tuta absoluta*, and the like;

from the family Arctiidae, American white moth (*Hyphantria cunea*), and the like;

from the family Castniidae, Giant Sugarcane borer (*Telchin licus*), and the like;

from the family Cossidae, *Cossus insularis*, and the like;

from the family Geometridae, *Ascotis selenaria*, and the like;

from the family Limacodidae, blue-striped nettle grub (*Parasa lepida*), and the like;

from the family Stathmopodidae, persimmon fruit moth (*Stathmopoda masinissa*), and the like;

from the family Sphingidae, tobacco hornworm (*Acherontia lachesis*), and the like;

from the family Sesiidae, *Nokona feralis*, cherry borer (*Synanthedon hector*), *Synanthedon tenuis*, and the like:

from the family Hesperiidae, rice skipper (*Parnara guttata*), and the like;

from the family Tineidae, casemaking clothes moth (*Tinea translucens*), common clothes moth (*Tineola bisselliella*), and the like;

and the others.

Thysanoptera:

from the family Thripidae, western flower thrips (*Frankliniella occidentalis*), oriental thrips (*Thrips palmi*) yellow tea thrips (*Scirtothrips dorsalis*), onion thrips (*Thrips tabaci*), eastern flower thrips (*Frankliniella intonsa*), rice thrips (*Stenchaetothrips biformis*), Echinothrips americanus, and the like;

from the family Phlaeothripidae, aculeated rice thrips (*Haplothrips aculeatus*), and the like;

and the others.

Diptera:

from the family Anthomyiidae, seedcorn maggot (*Delia platura*), onion maggot (*Delia antiqua*), beet leaf miner (*Pegomya cunicularia*), and the like;

from the family Ulidiidae, sugarbeet root maggot (*Tetanops myopaeformis*), and the like;

from the family Agromyzidae, rice leaf miner (*Agromyza oryzae*), tomato leaf miner (*Liriomyza sativae*), chrysanthemum leaf miner (*Liriomyza trifolii*), pea leafminer (*Chromatomyia horticola*), and the like;

from the family Chloropidae, rice stem maggot (*Chlorops oryzae*), and the like;

from the family Tephritidae, melon fly (*Bactrocera cucurbitae*), oriental fruit fly (*Bactrocera dorsalis*), Malaysian fruit fly (*Bactrocera latifrons*), olive fruit fly (*Bactrocera oleae*), Queensland fruit fly (*Bactrocera tryoni*) Mediterranean fruit fly (*Ceratitis capitata*), apple maggot (*Rhagoletis pomonella*), Japanese cherry fruit fly (*Rhacochlaena japonica*), and the like;

from the family Ephydridae, smaller rice leaf miner (*Hydrellia griseola*), whorl maggot (*Hydrellia philippina*), paddy stem maggot (*Hydrellia sasakii*), and the like; from the family Drosophilidae, cherry *drosophila* (*Drosophila suzukii*), and the like;

from the family Phoridae, *Megaselia spiracularis*, and the like;

from the family Psychodidae, *Clogmia albipunctata*, and the like;

from the family Sciaridae, *Bradysia difformis*, and the like;

from the family Cecidomyiidae, Hessian fly (*Mayetiola destructor*), paddy gall fly (*Orseolia oryzae*), and the like;

from the family Diopsidae, *Diopsis macrophthalma*, and the like;

from the family Tipulidae, rice crane fly (*Tipula aino*), Common cranefly (*Tipula oleracea*), European cranefly (*Tipula paludosa*), and the like;

from the family Culicidae, southern house mosquito (*Culex pipiens pallens*), *Culex tritaeniorhynchus*, *Culex pipiens* f. *molestus*, brown house mosquito (*Culex quinquefasciatus*), northern house mosquito (*Culex pipiens pipiens*), *Culex vishnui*, Asian tiger mosquito (*Aedes albopictus*), dengue mosquito (*Aedes aegypti*), Chinese malaria mosquito (*Anopheles sinensis*), *Anopheles gambiae*, *Anopheles stephensi*, *Anopheles coluzzii*, *Anopheles albimanus*, *Anopheles sundaicus*, *Anopheles arabiensis*, *Anopheles funestus*, *Anopheles darlingi*, *Anopheles farauti*, *Anopheles minimus*, and the like;

from the family Simulidae, *Prosimulium yezoensis*, *Simulium ornatum*, and the like;

from the family Tabanidae, *Tabanus trigonus*, and the like;

from the family Muscidae, house fly (*Musca domestica*), false stable fly (*Muscina stabulans*), biting house fly (*Stomoxys calcitrans*), buffalo fly (*Haematobia irritans*), and the like;

from the family Calliphoridae;

from the family Sarcophagidae;

from the family Chironomidae, *Chironomus plumosus*, *Chironomus yoshimatsui*, *Glyptotendipes tokunagai*, and the like;

from the family Fannidae;

and the others.

Coleoptera:

from the family Chrysomelidae, western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata*), Cucurbit Beetle (*Diabrotica speciosa*), bean leaf beetle (*Cerotoma trifurcata*), barley leaf beetle (*Oulema melanopus*), cucurbit leaf beetle (*Aulacophora femoralis*), striped flea beetle (*Phyllotreta striolata*), Cabbage flea beetle (*Phyllotreta cruciferae*), Western black flea beetle (*Phyllotreta pusilla*), Cabbage stem flea beetle (*Psylliodes chrysocephala*), Colorado potato beetle (*Leptinotarsa decemlineata*), rice leaf beetle (*Oulema oryzae*), grape *colaspis* (*Colaspis brunnea*), corn flea beetle (*Chaetocnema pulicaria*), sweet-potato flea beetle (*Chaetocnema confinis*), potato flea beetle (*Epitrix cucumeris*), rice leaf beetle (*Dicladispa armigera*), southern corn leaf beetle (*Myochrous denticollis*), *Laccoptera quadrimaculata*, tobacco flea beetle (*Epitrix hirtipennis*), and the like;

from the family Carabidae, Seedcorn beetle (*Stenolophus lecontei*), Slender seedcorn beetle (*Clivina impressifrons*), and the like;

from the family Scarabaeidae, cupreus chafer (*Anomala cuprea*), soybean beetle (*Anomala rufocuprea*), *Anomala albopilosa*, Japanese beetle (*Popillia japonica*), yellowish elongate chafer (*Heptophylla picea*), European Chafer (*Rhizotrogus majalis*), *Tomarus gibbosus*, *Holotrichia* spp., *Phyllophaga* spp.

(such as June beetle (*Phyllophaga crinita*)), *Diloboderus* spp. (such as *Diloboderus abderus*), and the like;

from the family Curculionidae, coffee bean weevil (*Araecerus coffeae*), sweet-potato weevil (*Cylas formicarius*), West Indian sweet-potato weevil (*Euscepes postfasciatus*), alfalfa weevil (*Hypera postica*), maize wevil (*Sitophilus zeamais*), rice weevil (*Sitophilus oryzae*), grain weevil (*Sitophilus granarius*), rice plant weevil (*Echinocnemus squameus*), rice water weevil (*Lissorhoptrus oryzophilus*), *Rhabdoscelus lineatocollis*, boll weevil (*Anthonomus grandis*), nunting billbug (*Sphenophorus venatus*), Southern Corn Billbug (*Sphenophorus callosus*), Soybean stalk weevil (*Sternechus subsignatus*), Sugarcane weevil (*Sphenophorus levis*), rusty gourd-shaped weevil (*Scepticus griseus*), brown gourd-shaped weevil (*Scepticus uniformis*), Mexican bean weevil (*Zabrotes subfasciatus*), pine beetle (*Tomicus piniperda*), Coffee Berry Borer (*Hypothenemus hampei*), *Aracanthus* spp. (such as *Aracanthus mourei*), and cotton root borer (*Eutinobothrus brasiliensis*), and the like;

from the family Tenebrionidae, red meal beetle (*Tribolium castaneum*), mason beetle (*Tribolium confusum*), lesser mealworm (*Alphitobius diaperinus*), and the like;

from the family Coccinellidae, twenty-eight-spotted ladybird (*Epilachna vigintioctopunctata*), and the like;

from the family Bostrychidae, common powder-post beetle (*Lyctus brunneus*), lesser grain borer (*Rhyzopertha dominica*) and the like;

from the family Ptinidae;

from the family Cerambycidae, citrus long-horned beetle (*Anoplophora malasiaca*), *Migdolus fryanus*, and the like;

from the family Elateridae, *Melanotus okinawensis*, barley wireworm (*Agriotes fuscicollis*), *Melanotus legatus, Anchastus* spp., *Conoderus* spp., *Ctenicera* spp., *Limonius* spp., *Aeolus* spp., and the like;

from the family Staphylinidae, *Paederus fuscipes*, and the like;

from the family Dermestidae, varied carpet beetle (*Anthrenus verbasci*), hide beetle (*Dermestes maculates*), khapra beetle (*Trogoderma granarium*), and the like;

from the family Anobiidae, tobacco beetle (*Lasioderma serricorne*), biscuit beetle (*Stegobium paniceum*), and the like from the family Laemophloeidae, flat grain beetle (*Cryptolestes ferrugineus*), and the like;

from the family Silvanidae, saw-toothed grain beetle (*Oryzaephilus surinamensis*), and the like;

and the others.

Orthoptera:

from the family Acrididae, oriental migratory locust (*Locusta migratoria*), Moroccan locust (*Dociostaurus maroccanus*), Australian plague locust (*Chortoicetes terminifera*), red locust (*Nomadacris septemfasciata*), Brown Locust (*Locustana pardalina*), Tree Locust (*Anacridium melanorhodon*), Italian Locust (*Callipatamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (*Camnula pellucida*), desert locust (*Schistocerca gregaria*), Yellow-winged locust (*Gastrimargus musicus*), Spur-throated locust (*Austracris guttulosa*), Japanese grasshopper (*Oxya yezoensis*), rice grasshopper (*Oxya japonica*), Bombay locust (*Patanga succincta*), and the like;

from the family Gryllotalpidae, oriental mole cricket (*Gryllotalpa orientalis*), and the like;

from the family Gryllidae, house cricket (*Acheta domestica*), emma field cricket (*Teleogryllus emma*), and the like;

from the family Tettigoniidae, Mormon cricket (*Anabrus simplex*), and the like;

and the others.

Hymenoptera:

from the family Tenthredinidae, beet sawfly (*Athalia rosae*), nippon cabbage sawfly (*Athalia japonica*), and the like;

from the family Formicidae, *Solenopsis* spp. (such as red imported fire ant (*Solenopsis invicta*) and tropical fire ant (*Solenopsis geminata*)), *Atta* spp. (such as Brown leaf-cutting ant (*Atta capiguara*)), *Acromyrmex* spp., *Paraponera clavata*, black house ant (*Ochetellus glaber*), little red ant (*Monomorium pharaonis*), Argentine ant (*Linepithema humile*), *Formica fusca japonica, Pristomyrmex punctutus, Pheidole noda*, big-headed ant (*Pheidole megacephala*), *Camponotus* spp. (such as *Camponotus japonicus* and *Camponotus obscuripes*), *Pogonomyrmex* spp. (such as western harvester ant (*Pogonomyrmex occidentalis*)), *Wasmania* spp. (such as *Wasmania auropunctata*), long-legged ant (*Anoplolepis gracilipes*), and the like;

from the family Vespidae, Asian giant hornet (*Vespa mandarinia japonica*), *Vespa simillima, Vespa analis Fabriciusi*, Asian hornet (*Vespa velutina*), *Polistes jokahamae*, and the like;

from the family Siricidae, pine wood wasp (*Urocerus gigas*), and the like;

from the family Bethylidae;

and the others.

Blattodea:

from the family Blattellidae, German cockroach (*Blattella germanica*), and the like;

from the family Blattidae, smoky-brown cockroach (*Periplaneta fuliginosa*), American cockroach (*Periplaneta americana*), brown cockroach (*Periplaneta brunnea*), black cockroach (*Blatta orientalis*), and the like;

from the family Termitidae, Japanese termite (*Reticulitermes speratus*), Formosan termite (*Coptotermes formosanus*), western drywood termite (*Incisitermes minor*), *Cryptotermes domesticus, Odontotermes formosanus, Neotermes koshunensis, Glyptotermes satsumensis, Glyptotermes nakajimai, Glyptotermes fuscus, Hodotermopsis sjostedti, Coptotermes guangzhouensis, Reticulitermes amamianus, Reticulitermes miyatakei, Reticulitermes kanmonensis, Nasutitermes takasagoensis, Pericapritermes nitobei, Sinocapritermes mushae, Cornitermes cumulans*, and the like;

and the others.

Siphonaptera:

*Pulex* spp. (such as human flea (*Pulex irritans*) *Ctenocephalides* spp. (such as cat flea (*Ctenocephalides felis*) and dog flea (*Ctenocephalides canis*)), *Xenopsylla* spp. (such as oriental rat flea (*Xenopsylla cheopis*)), *Tunga* spp. (such as chigoe flea (*Tunga penetrans*)), *Echidnophaga* spp. (such as chicken flea (*Echidnophaga gallinacea*)), *Nosopsyllus* spp. (such as European rat flea (*Nosopsyllus fasciatus*)), and the like.

Psocodea:
- Pediculus spp. (such as head louse (Pediculus humanus capitis)); Pthirus spp. (such as crab louse (Pthirus pubis)); Haematopinus spp. (such as short-nosed cattle louse (Haematopinus eurysternus) and pig louse (Haematopinus suis)); Damalinia spp. (such as Dalmalinia ovis and Damalinia bovis); Linognathus spp. (such as blue cattle louse (Linognathus vituli) and sheep face louse (Linognathus ovillus)); Solenopotes spp. (such as capillate louse (Solenopotes capillatus)); Menopon spp. (such as common chicken louse (Menopon gallinae)); Trimenopon spp.; Trinoton spp.; Trichodectes spp. (such as dog biting louse (Trichodectes canis)); Felicola spp. (such as cat louse (Felicola subrostratus)); Bovicola spp. (such as cattle biting louse (Bovicola bovis)); Menacanthus spp. (such as chicken body louse (Menacanthus stramineus)); Werneckiella spp.; Lepikentron spp.;
- from the family Liposcelididae, book louse (Liposcelis subfuscas), Liposcelis bostrychophilus, Liposcelis simulans, Liposcelis divinatorius, Liposcelis entomophila, and the like;

and the others.

Thysanura:
- from the family Lepismatidae, oriental silverfish (Ctenolepisma villosa), moth fish (Lepisma saccharina), and the like.

Acari:
- from the family Tetranychidae, common red spider mite (Tetranychus urticae), kanzawa spider mite (Tetranychus kanzawai), red spider mite (Tetranychus evansi), citrus red mite (Panonychus citri), fruit-tree red spider mite (Panonychus ulmi), Oligonychus spp., and the like;
- from the family Eriophyidae, Japanese citrus rust mite (Aculops pelekassi), Phyllocoptruta citri, tomato mite (Aculops lycopersici), purple mite (Calacarus carinatus), tea rust mite (Acaphylla theavagrans), Eriophyes chibaensis, apple bud mite (Aculus schlechtendali), Aceria diospyri, Aceria tosichella, Shevtchenkella sp., and the like;
- from the family Tarsonemidae, broad mite (Polyphagotarsonemus latus), and the like;
- from the family Tenuipalpidae, Brevipalpus phoenicis, and the like;
- from the family Tuckerellidae;
- from the family Ixodidae, Haemaphysalis spp. (such as Haemaphysalis longicornis, Haemaphysalis flava, and Haemaphysalis campanulata), Dermacentor spp. (such as American dog tick (Dermacentor variabilis), Dermacentor taiwanicus, and Rocky Mountain wood tick (Dermacentor andersoni)), Ixodes spp. (such as Ixodes ovatus, Ixodes persulcatus, black-legged tick (Ixodes scapularis), Ixodes pacificus, and Ixodes holocyclus), Amblyomma spp. (such as lone star tick (Amblyomma americanum) and gulf coast tick (Amblyomma maculatum)), Boophilus spp. (such as Rhipicephalus (Boophilus) microplus and Boophilus annulatus) and Rhipicephalus spp. (such as brown dog tick (Rhipicephalus sanguineus) and Rhipicephalus appendiculatus);
- from the family Acaridae, cereal mite (Tyrophagus putrescentiae), grassland mite (Tyrophagus similis), and the like;
- from the family Pyroglyphidae, American house dust mite (Dermatophagoides farinae), European house dust mite (Dermatophagoides pteronyssinus), and the like;
- from the family Cheyletidae, Cheyletus eruditus, Cheyletus malaccensis, Chelacaropsis moorei, Cheyletiella yasguri, and the like;
- Argas spp. (such as fowl tick (Argas persicus)), Ornithodorus spp. (such as Ornithodorus hermsi and Ornithodorus turicata), Psoroptes spp. (such as sheep scab mite (Psoroptes ovis) and horse psoroptic mange mite (Psoroptes equi)), Knemidocoptes spp. (such as Knemidocoptes mutans), Notoedres spp. (such as Notoedres cati and Notoedres muris), Sarcoptes spp. (such as itch mite (Sarcoptes scabiei)), Otodectes spp. (such as ear mange mite (Otodectes cynotis)), Listrophorus spp. (such as Listrophorus gibbus), Chorioptes spp., Hypodectes spp., Pterolichus spp., Cytodites spp., Laminosioptes spp., Dermanyssus spp. (such as bird mite (Dermanyssus gallinae)), Ornithonyssus spp. (such as feather mite (Ornithonyssus sylviarum) and tropical rat mite (Ornithonyssus bacoti)), Varroa spp. (such as Varroa jacobsoni), Cheyletiella spp. (such as Cheyletiella yasguri and Cheyletiella blakei), Ornithocheyletia spp., Demodex spp. (such as dog follicle mite (Demodex canis) and cat follicle mite (Demodex cati)), Myobia spp., Psorergates spp., and Trombicula spp. (such as Trombicula akamushi, Trombicula pallida, and Trombicula scutellaris);

and the others.

Araneae:
- from the family Eutichuridae, Cheiracanthium japonicum, and the like;
- from the family Theridiidae, red-back spider (Latrodectus hasseltii), and the like;

and the others.

Polydesmida:
- from the family Paradoxosomatidae, flat-backed millipede (Oxidus gracilis), Nedyopus tambanus, and the like;

and the others.

Isopoda:
- from the family Armadillidiidae, common pill bug (Armadillidium vulgare), and the like;

and the others.

Chilopoda:
- from the family Scutigeridae, Thereuonema hilgendorfi, and the like;
- from the family Scolopendridae, giant tropical centipede (Scolopendra subspinipes), and the like;
- from the family Ethopolyidae, Bothropolys rugosus, and the like;

and the others.

Gastropoda:
- from the family Limacidae, tree slug (Limax marginatus), garden tawny slug (Limax flavus), and the like;
- from the family Philomycidae, Meghimatium bilineatum, and the like;
- from the family Ampullariidae, golden apple snail (Pomacea canaliculata), and the like;
- from the family Lymnaeidae, Austropeplea ollula, and the like;

and the others.

Nematoda:
- from the family Aphelenchoididae, rice white-tip nematode (Aphelenchoides besseyi), and the like;
- from the family Pratylenchidae, root lesion nematode (Pratylenchus coffeae), Pratylenchus brachyurus, California meadow nematode (Pratylenchus neglectus), Radopholus similis, and the like;
- from the family Heteroderidae, javanese root-knot nematode (Meloidogyne javanica), southern root-knot nematode (Meloidogyne incognita), northern root-knot nematode (*Meloidogyne hapla*), soybean cyst nematode (*Heterodera glycines*), potato cyst nematode (*Globodera rostochiensis*), white potato cyst nematode (*Globodera pallida*), and the like; from the family Hoplolaimidae, *Rotylenchulus reniformis*, and the like;

from the family Anguinidae, strawberry bud nematode (*Nothotylenchus acris*), stem nematode (*Ditylenchus dipsaci*), and the like;

from the family Tylenchulidae, citrus nematode (*Tylenchulus semipenetrans*), and the like;

from the family Longidoridae, dagger nematode (*Xiphinema index*), and the like;

from the family Trichodoridae;

from the family Parasitaphelenchidae, pine wilt disease (*Bursaphelenchus xylophilus*), and the like;

and the others.

The target harmful arthropods such as harmful insects and harmful mites, harmful mollusks, and harmful nematodes may have a reduced agent-sensitivity to or a developed agent-resistance to an insecticide, a miticide, a molluscicide or a nematicide. However, when the agent-sensitivity is greatly reduced or the agent-resistance is greatly developed, a composition comprising an insecticide, a miticide, a molluscicide, and a nematicide other than the intended insecticide, miticide, molluscicide, and nematicide is preferably used.

The method for controlling harmful arthropods of the present invention is carried out by applying an effective amount of the Present compound or the Composition A to harmful arthropods directly and/or habitats where harmful arthropods live (for example, plant bodies, soil, interiors of houses, and animal bodies). Examples of the method for controlling harmful arthropods of the present invention include foliage treatment, soil treatment, root treatment, shower treatment, smoking treatment, water surface treatment, and seed treatment.

The Present compound or the Composition A is usually mixed with inert carrier(s) such as solid carrier(s), liquid carrier(s), and gaseous carrier(s), and as needed, surfactant(s) and other auxiliary agent(s) for formulation is/are added thereto, to formulate into an emulsifiable concentrate, an oil solution, a dust formulation, a granule, a wettable powder, a granular wettable powder, a flowable, a dry flowable, a microcapsule, an aerosol, a poison bait, a resin formulation, a shampoo formulation, a paste-like formulation, a foam, a carbon dioxide formulation, a tablet, or the like to be used. Such formulation may be processed into and used as a mosquito repellent coil, an electric mosquito repellent mat, a liquid mosquito repellent formulation, a smoking agent, a fumigant, a sheet formulation, a spot-on formulation, or a formulation for oral treatment. These formulations usually comprise 0.0001 to 95% by weight of the Present compound or the Composition A.

Examples of the solid carrier(s) to be used in the formulation include fine powders and granules of clays (for example, kaolin clay, diatomaceous earth, bentonite, and acid white clay), dry silica, wet silica, talc, ceramic, other inorganic minerals (for example, sericite, quartz, sulfur, active carbon, and calcium carbonate), chemical fertilizers (for example, ammonium sulfate, ammonium phosphate, ammonium nitrate, urea, and ammonium chloride), and the others; as well as synthetic resins (for example, polyester resins such as polypropylene, polyacrylonitrile, polymethylmethacrylate, and polyethylene terephthalate; nylon resins such as nylon-6, nylon-11, and nylon-66; polyamide resins; polyvinyl chloride, polyvinylidene chloride, vinyl chloride-propylene copolymers, and the others).

Examples of the liquid carrier(s) include water; alcohols (for example, methanol, ethanol, isopropyl alcohol, butanol, hexanol, benzyl alcohol, ethylene glycol, propylene glycol, and phenoxy ethanol); ketones (for example, acetone, methyl ethyl ketone, and cyclohexanone); aromatic hydrocarbons (for example, toluene, xylene, ethyl benzene, dodecyl benzene, phenyl xylyl ethane, and methylnaphthalene); aliphatic hydrocarbons (for example, hexane, cyclohexane, kerosene, and light oil); esters (for example, ethyl acetate, butyl acetate, isopropyl myristate, ethyl oleate, diisopropyl adipate, diisobutyl adipate, and propylene glycol monomethyl ether acetate); nitriles (for example, acetonitrile and isobutyronitrile); ethers (for example, diisopropyl ether, 1,4-dioxane, 1,2-dimethoxyethane, diethylene glycol dimethyl ether, diethylene glycol monomethyl ether, propylene glycol monomethyl ether, dipropylene glycol monomethyl ether, and 3-methoxy-3-methyl-1-butanol); amides (for example, DMF and N,N-dimethylacetamide); sulfoxides (for example, DMSO); propylene carbonate; and vegetable oils (for example, soybean oil and cottonseed oil).

Examples of the gaseous carrier(s) include fluorocarbon, butane gas, LPG (liquefied petroleum gas), dimethyl ether, and carbon dioxide.

Examples of the surfactant(s) include nonionic surfactants such as polyoxyethylene alkyl ethers, polyoxyethylene alkyl aryl ethers, and polyethylene glycol fatty acid esters; and anionic surfactants such as alkyl sulfonates, alkylbenzene sulfonates, and alkyl sulfates.

Examples of the other auxiliary agent(s) for formulation include binders, dispersants, colorants, and stabilizers. Specific examples thereof include casein, gelatin, saccharides (for example, starch, gum arabic, cellulose derivatives, and alginic acid), lignin derivatives, bentonite, water-soluble synthetic polymers (for example, polyvinyl alcohol, polyvinyl pyrrolidone, and polyacrylic acids), acidic isopropyl phosphate, 2,6-di-tert-butyl-4-methylphenol, and BHA (a mixture of 2-tert-butyl-4-methoxyphenol and 3-tert-butyl-4-methoxyphenol).

Examples of the base material of the resin formulation include vinyl chloride polymers, polyurethane, and the others, and plasticizer(s) such as phthalic acid esters (for example, dimethyl phthalate and dioctyl phthalate), adipic acid esters, and stearic acid may also be added to these base materials, as needed. The resin formulation may be prepared by mixing a compound with the above-mentioned base material, kneading the mixture in a conventional kneading apparatus, followed by molding it by injection molding, extrusion molding, pressure molding, or the like. The resultant resin formulation may be subjected to further molding, cutting procedure, or the like, as needed, to be processed into a shape such as plate, film, tape, net, and string shapes. These resin formulations may be processed into an animal collar, an animal ear tag, a sheet formulation, a trap string, a gardening support, or other products.

Examples of the base material for the poison bait include grain powders, vegetable oils, saccharides, crystalline celluloses, and the others, and further, antioxidant(s) such as dibutylhydroxytoluene and nordihydroguaiaretic acid, preservative(s) such as dehydroacetic acid, accidental ingestion inhibitor(s) for children and pets such as chili powder, insect attraction fragrance(s) such as cheese flavor, onion flavor, and peanut oil, or the other ingredient(s) may be added thereto as needed.

In the present invention, examples of the plants include whole plants, foliages, flowers, ears, fruits, tree stems, branches, tree crowns, seeds, vegetative reproduction organs, and seedlings.

A vegetative reproduction organ means a part of plant such as root, stem, and leaf which has a growth capability even when said part is separated from the plant body and placed into soil. Examples of the vegetative reproduction organ include tuberous root, creeping root, bulb, corm or solid bulb, tuber, rhizome, stolon, rhizophore, cane cuttings, propagule, and vine cutting. Stolon is also referred to as "runner", and propagule is also referred to as "propagulum" and categorized into broad bud and bulbil. Vine cutting means a shoot (collective term of leaf and stem) of sweet potato, glutinous yam, or the like. Bulb, corm or solid bulb, tuber, rhizome, cane cuttings, rhizophore, and tuberous root are also collectively referred to as "bulb". For example, cultivation of potato starts with planting a tuber into soil, and the tuber to be used is generally referred to as "seed potato".

Examples of the method for controlling harmful arthropods by applying an effective amount of the Present compound or the Composition A to soil include a method for applying an effective amount of the Present compound or the Composition A to soil before or after planting plants, a method for applying an effective amount of the Present compound or the Composition A to rhizosphere of crops to be protected from harm such as eating by harmful arthropods, and, a method for controlling plant-eating harmful arthropods by impregnating an effective amount of the Present compound or the Composition A from roots or the like and migrating it to inside plant bodies. More specific examples thereof include planting hole treatments (for example, planting hole application and planting hole soil incorporation), plant foot treatments (for example, plant foot application, plant foot soil incorporation, plant foot irrigation, and plant foot treatment at latter half of raising of seedling period), planting trench treatments (for example, planting trench application and planting trench soil incorporation), row treatments (for example, row application, row soil incorporation, and row application at growing season), row treatments at seeding (for example, row application at seeding and row soil incorporation at seeding), overall treatments (for example, overall soil application and overall soil incorporation), side row treatments, water surface treatments (for example, water surface application and water surface application after flooding), other soil application treatments (for example, foliar application of granule at growing season, application under tree crown or around trunk, soil surface application, soil surface incorporation, seeding hole application, ridge area surface application, and intrarow spacing application), other irrigation treatments (for example, soil irrigation, irrigation at raising of seedling period, chemical injection treatment, ground area irrigation, chemical drip irrigation, and chemigation), raising seedling box treatments (for example, raising seedling box application, raising seedling box irrigation, raising seedling box chemical flooding), raising seedling tray treatments (for example, raising seedling tray application, raising seedling tray irrigation, and raising seedling tray chemical flooding), nursery treatments (for example, nursery application, nursery irrigation, flooded nursery application, and seedling soaking), bed soil incorporation treatments (for example, bed soil incorporation, bed soil incorporation before seeding, application at seeding before soil covering, application at seeding after soil covering, and soil covering incorporation), and other treatments (for example, culture soil incorporation, plowing, surface soil incorporation, rain dropping point soil incorporation, planting position treatment, flower cluster application of granule, and paste fertilizer incorporation).

Examples of the seed treatment include application of the Present compound or the Composition A to seeds or vegetative reproduction organs. Specific examples thereof include spray treatment wherein mist of a suspension of the Present compound or the Composition A is sprayed to seed surfaces or vegetative reproduction organ surfaces; smear treatment wherein the Present compound or the Composition A is smeared to seeds or vegetative reproduction organs; immersion treatment wherein seeds are immersed in a drug solution of the Present compound or the Composition A for a period of time; and methods for coating seeds or vegetative reproduction organs by a carrier comprising the Present compound or the Composition A (for example, film coat treatment and pellet coat treatment). Examples of the above vegetative reproduction organ include seed potato.

When the Composition A is applied to seeds or vegetative reproduction organs, a formulation of the Composition A may be applied to seeds or vegetative reproduction organs, or a plurality of different formulations of the Composition A may be applied separately in a plurality of times to seeds or vegetative reproduction organs. Examples of the method for applying a plurality of different formulations of the Composition A separately in a plurality of times include a method wherein a formulation comprising the Present compound only as an active ingredient is applied seeds or vegetative reproduction organs, said seeds or vegetative reproduction organs are air-dried, and a formulation comprising the Present ingredient(s) is applied thereto; and a method wherein a formulation comprising the Present compound and the Present ingredient(s) as active ingredients is applied to seeds or vegetative reproduction organs, said seeds or vegetative reproduction organs are air-dried, and then a formulation comprising the Present ingredient(s) other than the applied Present ingredient(s) is applied.

In the present invention, the seed or the vegetative reproduction organ holding the Present compound or the Composition A means a seed or a vegetative reproduction organ in which the Present compound or the Composition A is attached to the surface of the seed or the vegetative reproduction organ. A material other than the Present compound or the Composition A may be attached to the above seed or vegetative reproduction organ holding the Present compound or the Composition A before or after the Present compound or the Composition A is attached to the seed or the vegetative reproduction organ.

Also, when the Composition A is attached to surfaces of seeds or vegetative reproduction organs to form layer(s), said layer(s) consist(s) of a layer or a plurality of layers. When said layer(s) consist(s) of a plurality of layers, each layer consists of a layer comprising one or more active ingredient(s), or consists of a layer comprising one or more active ingredient(s) and a layer comprising no active ingredient.

The seeds or the vegetative reproduction organs holding the Present compound or the Composition A may be prepared by, for example, applying a formulation comprising the Present compound or the Composition A to seeds or vegetative reproduction organs by the above seed treatment method.

When the Present compound or the Composition A is used for controlling harmful arthropods in the agricultural field, the application dose as an amount of the Present compound is usually within the range from 1 to 10,000 g per 10,000 $m^2$. When the Present compound or the Composition A is applied to seeds or vegetative reproduction organs, the application dose as an amount of the Present compound is usually within the range from 0.001 to 100 g per 1 Kg of the seeds or vegetative reproduction organs. An emulsifiable concentrate, a wettable powder, a flowable, or the like of the Present compound or the Composition A is usually applied by diluting it with water in such a way that a concentration of the active ingredient is within the range from 0.01 to 10,000 ppm. A granule, a dust formulation, or the like is usually applied as itself without diluting it.

Also, a resin formulation of the Present compound or the Composition A processed into a sheet shape or a string shape may be wrapped around crops, stretched near crops, spread on plant foot soil, or the like.

When the Present compound or the Composition A is used to control harmful arthropods that live inside a house, the application dose as an amount of the Present compound is usually within the range from 0.01 to 1,000 mg per 1 m$^2$ of an area to be treated in the case of using it on a planar area. In the case of using it spatially, the application dose as an amount of the Present compound is usually within the range from 0.01 to 500 mg per 1 m$^3$ of the space to be treated. When the Present compound or the Composition A is formulated into an emulsifiable concentrate, a wettable powder, a flowable, or the like, such formulation is usually applied after diluting it with water in such a way that a concentration of the active ingredient is within the range from 0.1 to 10,000 ppm, and then sparging it. In the case of being formulated into an oil solution, an aerosol, a smoking agent, a poison bait, or the like, such formulation is used as itself without diluting it.

When the Present compound or the Composition A is used for controlling external parasites of livestock such as cows, horses, pigs, sheep, goats, and chickens, and small animals such as dogs, cats, rats, and mice, the Present compound or the Composition A may be applied to the animals by a known method in the veterinary field. Examples of the specific method for using the Present compound or the Composition A include administration by a tablet, a mixture with feed, a suppository, or an injection (for example, intramuscular, subcutaneous, intravenous, or intraperitoneal injection) when systemic control is intended, and include spraying of an oil solution or an aqueous liquid, pour-on treatment or spot-on treatment, washing of animals with a shampoo formulation, or application of a resin formulation in the form of a collar, an ear tag, or the like to animals when non-systemic control is intended. In case of administered to animals, the dose of the Present compound is usually within the range from 0.1 to 1,000 mg per 1 kg of animal body weight.

Also, the Present compound or the Composition A may be used as an agent for controlling harmful arthropods in croplands such as fields, paddy fields, grasses, and orchards. Examples of the plants include the followings.

corn, rice, wheat, barley, rye, oat, sorghum, cotton, soybean, peanut, buckwheat, beet, rapeseed, sunflower, sugar cane, tobacco, solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, welsh onion, onion, garlic, and asparagus), ammiaceous vegetables (for example, carrot, parsley, celery, and parsnip), chenopodiaceous vegetables (for example, spinach and Swiss chard), lamiaceous vegetables (for example, perilla, mint, and basil), strawberry, sweet potato, glutinous yam, eddoe, pomaceous fruits (for example, apple, pear, Japanese pear, Chinese quince, and quince), stone fleshy fruits (for example, peach, plum, nectarine, Japanese apricot (*Prunus mume*), cherry fruit, apricot, and prune), citrus fruits (for example, Citrus unshiu, orange, lemon, lime, and grapefruit), nuts (for example, chestnuts, walnuts, hazelnuts, almond, pistachio, cashew nuts, and macadamia nuts), berry fruits (for example, blueberry, cranberry, blackberry, and raspberry), grapes, Japanese persimmon, olive, Japanese plum, banana, coffee, date palm, coconuts, tea, mulberry, ornamental plants, forest plants, turfs, grasses, and the others.

The above plants also include plants which may be produced by natural breeding, plants which may be generated by mutation, F1 hybrid plants, and genetically modified crops. Examples of the genetically modified crops include plants which have resistance to HPPD (4-hydroxyphenylpyruvate dioxygenase enzyme) inhibitors such as isoxaflutole, ALS (acetolactate synthase) inhibitors such as imazethapyr and thifensulfuron-methyl, EPSP (5-enolpyruvylshikimate-3-phosphate synthase) inhibitors, glutamine synthetase inhibitors, PPO (protoporphyrinogen oxidase) inhibitors, or herbicide such as bromoxynil and dicamba; plants which can synthesize a selective toxin known in *Bacillus* such as *Bacillus thuringiensis* or the like; and plants which can synthesize a gene fragment or the like which is partially identical to an endogenous gene derived from a harmful insect, and induce a gene silencing (RNAi; RNA interference) in the target harmful insect to achieve a specific insecticidal activity.

The above plants are not specifically limited as long as they are generally cultivated cultivars.

EXAMPLES

Hereinafter, the present invention is illustrated more in detail by Preparation Examples, Formulation Examples, Test Examples, and the like, but the present invention is not limited to these Examples only.

In the present description, Me represents a methyl group, Et represents an ethyl group, Pr represents a propyl group, i-Pr represents an isopropyl group, c-Pr represents a cyclopropyl group, c-Bu represents a cyclobutyl group, c-Pen represents a cyclopentyl group, c-Hex represents a cyclohexyl group, Ph represents a phenyl group, Py2 represents a 2-pyridyl group, Py3 represents a 3-pyridyl group, Py4 represents a 4-pyridyl group, and Bn represents a benzyl group. When c-Pr, c-Bu, c-Pen, c-Hex, Ph, Py2, Py3, and Py4 have substituent(s), the substituent(s) is/are indicated before the symbols with the substitution position(s). For example, 1-CN-c-Pr represents a 1-cyanocyclopropyl group, 3,4-F$_2$-Ph represents a 3,4-difluorophenyl group, 4-CF$_3$-Py2 represents a 4-(trifluoromethyl)-2-pyridyl group, and 5-OCH$_2$CF$_2$CF$_3$-Py2 represents a 5-(2,2,3,3,3-pentafluoropropoxy)-2-pyridyl group.

First, Preparation Examples of the Present compounds are shown below.

When a physical property of a compound is measured by liquid chromatography/mass spectrometry (hereinafter referred to as "LCMS"), the measured molecular ion value [M+H]$^+$ or [M−H]$^−$, and retention time (hereinafter referred to as "RT") are described. The conditions of liquid chromatography (hereinafter referred to as "LC") and mass spectrometry (hereinafter referred to as "MS") are as follows.

[LC Conditions]

Column: L-column2 ODS, inner diameter: 4.6 mm, length: 30 mm, particle size: 3 μm (Chemicals Evaluation and Research Institute, Japan)
UV measurement wavelength: 254 nm
Mobile phase: Solution A: 0.1% formic acid in water, Solution B: 0.1% formic acid in acetonitrile
Flow rate: 2.0 mL/min
Pump: two LC-20AD (manufactured by Shimadzu Corporation) (high pressure gradient)
Gradient conditions: sending a solution with the concentration gradient described in Table LC1.

TABLE LC1

| Time (min) | Solution A (%) | Solution B (%) |
|---|---|---|
| 0.01 | 90 | 10 |
| 2.00 | 0 | 100 |
| 4.00 | 0 | 100 |
| 4.01 | 90 | 10 |

[MS Conditions]
Detector: LCMS-2020 (manufactured by Shimadzu Corporation) Ionization method: DUIS Reference Preparation Example 1

To a mixture of chloroacetic acid (9.49 g) and water (15 mL) was added triethylamine (16.7 mL) at 0° C. over 30 min. To the resulting mixture was added 2-amino-5-(trifluoromethyl)pyridine (16.1 g), and the resulting mixture was stirred under reflux for 2 hours. The resulting mixture was filtered, and the filtered residue was washed with water. The resulting solids were dried to give a crude product of the Intermediate compound 1 represented by the following formula (11.0 g).

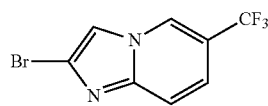

Intermediate compound 1: LCMS: 219 [M−H]⁻, RT=0.42 min

Reference Preparation Example 2

A mixture of the crude product of the Intermediate compound 1 obtained in the Reference Preparation Example 1 (4.40 g), phosphorus oxybromide (22.37 g), and toluene (50 mL) was stirred under reflux for 5 hours. The resulting mixture was added dropwise to an aqueous solution of sodium hydroxide, and the resulting mixture was extracted with toluene. The resulting organic layer was dried over anhydrous sodium sulfate, and concentrated under reduced pressure to give the Intermediate compound 2 represented by the following formula (4.7 g).

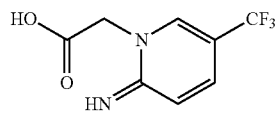

Intermediate compound 2: $^1$H-NMR (CDCl$_3$) δ: 8.45 (1H, d), 7.69 (1H, s), 7.67 (1H, dd), 7.36 (1H, d).

Reference Preparation Example 3

A mixture of the Intermediate compound 2 (481 mg), 2-(trifluoromethyl)-pyrazo[1,5-a]pyrazin-4(5H)-one (369 mg), pyridine-2-carboxylic acid (90 mg), copper(I) iodide (139 mg), cesium carbonate (889 mg), and NMP (5 mL) was stirred at 120° C. for 9 hours. To the resulting mixture was added water, and the resulting mixture was extracted with chloroform. The resulting organic layer was dried over anhydrous sodium sulfate, and concentrated under reduced pressure. The resulting residue was subjected to silica gel column chromatography to give the Intermediate compound 3 represented by the following formula (135 mg).

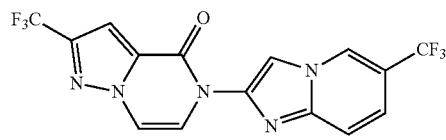 [SMILES: O=c1c2cc(C(F)(F)F)nn2ccn1-c1cn2cc(C(F)(F)F)ccc2n1]

Intermediate compound 3: $^1$H-NMR (CDCl$_3$) δ: 8.66 (1H, s), 8.57 (1H, s), 8.39 (1H, d), 7.69 (1H, d), 7.65 (1H, d), 7.44 (1H, s), 7.44 (1H, d).

Reference Preparation Example 4

To a mixture of the Intermediate compound 3 (135 mg) and DMF (3 mL) was added N-iodosuccinimide (86 mg) under ice-cooling, and the resulting mixture was stirred at room temperature for 5 hours. To the resulting mixture was added an aqueous solution of sodium thiosulfate, and the resulting mixture was extracted with chloroform. The resulting organic layer was dried over anhydrous sodium sulfate, and concentrated under reduced pressure. The resulting residue was subjected to silica gel column chromatography to give the Intermediate compound 4 represented by the following formula (137 mg).

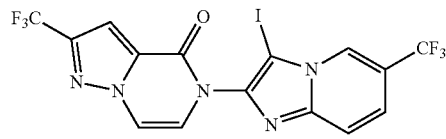 [SMILES: O=c1c2cc(C(F)(F)F)nn2ccn1-c1nc2ccc(C(F)(F)F)cn2c1I]

Intermediate compound 4: $^1$H-NMR (CDCl$_3$) δ: 8.56 (1H, s), 7.75 (1H, d), 7.60 (1H, d), 7.53 (1H, d), 7.45 (1H, s), 7.08 (1H, d).

Reference Preparation Example 5

The compounds prepared according to the Reference Preparation Example 1 and physical properties thereof are shown below.
A compound represented by formula (B-1)

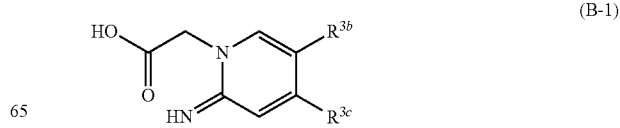

wherein the combination of $R^{3b}$ and $R^{3c}$ represents any one combination indicated in Table B-1.

TABLE B-1

| Intermediate compound | $R^{3b}$ | $R^{3c}$ |
| --- | --- | --- |
| 5 | Br | H |
| 6 | Cl | H |
| 7 | H | $CF_3$ |
| 55 | H | Br |
| 56 | H | Cl |

Intermediate compound 5: LCMS: 229 [M−H]⁻, RT=0.34 min

Intermediate compound 6: LCMS: 187 [M+H]⁺, RT=0.34 min

Intermediate compound 7: LCMS: 219 [M−H]⁻, RT=1.18 min

Intermediate compound 55: LCMS: 231 [M+H]⁺, RT=0.40 min

Intermediate compound 56: LCMS: 187 [M+H]⁺, RT=0.35 min

Reference Preparation Example 6

A mixture of the crude product of the Intermediate compound 1 prepared according to the Reference Preparation Example 1 (13.21 g), phosphorus oxychloride (18 mL), and toluene (150 mL) was stirred under reflux for 6 hours. The resulting mixture was added dropwise to an aqueous solution of sodium hydroxide, and the resulting mixture was extracted with toluene. The resulting organic layer was dried over anhydrous sodium sulfate, and concentrated under reduced pressure to give the Intermediate compound 8 represented by the following formula (13.2 g).

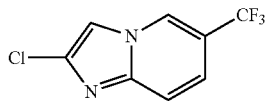 [SMILES: FC(F)(F)c1ccc2nc(Cl)cn2c1]

Intermediate compound 8: ¹H-NMR (CDCl₃) δ: 8.44 (1H, s), 7.65 (1H, d), 7.62 (1H, s), 7.38 (1H, d).

Reference Preparation Example 7

The compounds prepared according to the Reference Preparation Example 6 and physical properties thereof are shown below.

A compound represented by formula (B-2)

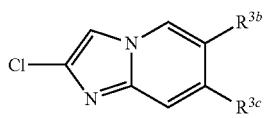

wherein the combination of $R^{3b}$ and $R^{3c}$ represents any one combination indicated in Table B-2.

TABLE B-2

| Intermediate compound | $R^{3b}$ | $R^{3c}$ |
| --- | --- | --- |
| 9 | Br | H |
| 10 | Cl | H |
| 11 | H | $CF_3$ |
| 12 | H | Br |
| 13 | H | Cl |

Intermediate compound 9: ¹H-NMR (CDCl₃) δ: 8.21 (1H, s), 7.48 (1H, s), 7.44 (1H, d), 7.28 (1H, d).

Intermediate compound 10: ¹H-NMR (CDCl₃) δ: 8.11 (1H, s), 7.48-7.50 (2H, m), 7.19 (1H, d).

Intermediate compound 11: ¹H-NMR (CDCl₃) δ: 8.17 (1H, d), 7.86 (1H, s), 7.64 (1H, s), 7.04 (1H, d).

Intermediate compound 12: ¹H-NMR (CDCl₃) δ: 7.91 (1H, d), 7.72 (1H, s), 7.51 (1H, s), 6.96 (1H, d).

Intermediate compound 13: ¹H-NMR (CDCl₃) δ: 7.97 (1H, d), 7.54 (1H, s), 7.49 (1H, s), 6.85 (1H, d).

Reference Preparation Example 8

To a mixture of the Intermediate compound 8 prepared according to the Reference Preparation Example 6 (15.44 g) and DMF (75 mL) was added N-iodosuccinimide (17.32 g) under ice-cooling, and the resulting mixture was stirred at 70° C. for 5 hours. To the resulting mixture was added an aqueous solution of sodium thiosulfate, and the precipitated solids were collected by filtration. The resulting solids were washed with water, and dried under reduced pressure to give the Intermediate compound 14 represented by the following formula (18.0 g).

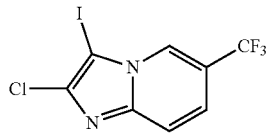 [SMILES: FC(F)(F)c1ccc2nc(Cl)c(I)n2c1]

Intermediate compound 14: ¹H-NMR (CDCl₃) δ: 8.41 (1H, s), 7.65 (1H, d), 7.44 (1H, d).

Reference Preparation Example 9

The compounds prepared according to the Reference Preparation Example 8 and physical properties thereof are shown below.

A compound represented by formula (B-3)

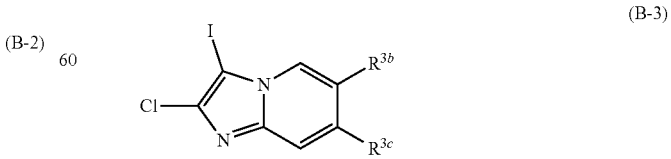

wherein the combination of $R^{3b}$ and $R^{3c}$ represents any one combination indicated in Table B-3.

TABLE B-3

| Intermediate compound | $R^{3b}$ | $R^{3c}$ |
|---|---|---|
| 15 | Br | H |
| 16 | Cl | H |
| 17 | H | $CF_3$ |
| 18 | H | Br |
| 19 | H | Cl |

Intermediate compound 15: $^1$H-NMR (CDCl$_3$) δ: 8.20 (1H, s), 7.43 (1H, d), 7.35 (1H, d).

Intermediate compound 16: $^1$H-NMR (CDCl$_3$) δ: 8.46 (1H, s), 7.64 (1H, d), 7.47 (1H, d).

Intermediate compound 17: $^1$H-NMR (CDCl$_3$) δ: 8.18 (1H, d), 7.84 (1H, s), 7.15 (1H, d).

Intermediate compound 18: $^1$H-NMR (CDCl$_3$) δ: 7.93 (1H, d), 7.72 (1H, s), 7.06 (1H, d).

Intermediate compound 19: $^1$H-NMR (CDCl$_3$) δ: 7.98 (1H, d), 7.55 (1H, s), 6.96 (1H, d).

Reference Preparation Example 10

A mixture of the Intermediate compound 14 (18.0 g), 1,4-dioxane (140 mL), tris(dibenzylideneacetone)dipalladium(0) (2.38 g), Xantphos (3.01 g), diisopropylethylamine (27.2 mL), and ethanethiol (3.75 mL) was stirred under reflux for 3 hours. The resulting mixture was cooled to room temperature, and concentrated under reduced pressure. The resulting residue was subjected to silica gel column chromatography to give the Intermediate compound 20 represented by the following formula (13.39 g).

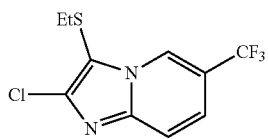

Intermediate compound 20: $^1$H-NMR (CDCl$_3$) δ: 8.74 (1H, s), 7.67 (1H, d), 7.48 (1H, d), 2.78 (2H, d), 1.24 (3H, t).

Reference Preparation Example 11

The compounds prepared according to the Reference Preparation Example 10 and physical properties thereof are shown below.

A compound represented by formula (B-4)

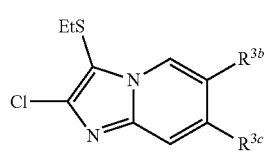

(B-4)

wherein the combination of $R^{3b}$ and $R^{3c}$ represents any one combination indicated in Table B-4.

TABLE B-4

| Intermediate compound | $R^{3b}$ | $R^{3c}$ |
|---|---|---|
| 21 | Br | H |
| 22 | Cl | H |
| 23 | H | $CF_3$ |
| 24 | H | Br |
| 25 | H | Cl |

Intermediate compound 21: $^1$H-NMR (CDCl$_3$) δ: 8.51 (1H, s), 7.46 (1H, d), 7.38 (1H, d), 2.73 (2H, d), 1.23 (3H, t).

Intermediate compound 22: $^1$H-NMR (CDCl$_3$) δ: 8.42 (1H, s), 7.51 (1H, d), 7.28 (1H, d), 2.75 (2H, d), 1.23 (3H, t).

Intermediate compound 23: LCMS: 281 [M+H]$^+$, RT=2.11 min Intermediate compound 24: $^1$H-NMR (CDCl$_3$) δ: 8.25 (1H, d), 7.74 (1H, s), 7.07 (1H, d), 2.73 (2H, q), 1.21 (3H, t).

Intermediate compound 25: $^1$H-NMR (CDCl$_3$) δ: 8.31 (1H, d), 7.57 (1H, s), 6.96 (1H, d), 2.73 (2H, q), 1.21 (3H, t).

Reference Preparation Example 12

To a mixture of the Intermediate compound 21 (2.66 g) and chloroform (10 mL) was added mCPBA (purity: 70%, comprising 30% of water) (5.16 g) under ice-cooling, and the resulting mixture was stirred at room temperature for 2 hours. To the resulting mixture were sequentially added a saturated aqueous solution of sodium hydrogen carbonate and an aqueous solution of sodium thiosulfate, and the resulting mixture was extracted with chloroform. The resulting organic layer was dried over anhydrous sodium sulfate, and concentrated under reduced pressure. The resulting residue was subjected to silica gel column chromatography to give the Intermediate compound 26 represented by the following formula (1.79 g).

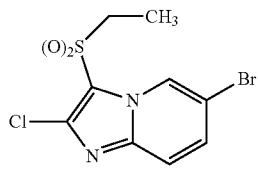

Intermediate compound 26: $^1$H-NMR (CDCl$_3$) δ: 9.15 (1H, s), 7.60 (1H, d), 7.57 (1H, d), 3.36 (2H, q), 1.36 (3H, t).

Reference Preparation Example 13

The compounds prepared according to the Reference Preparation Example 12 and physical properties thereof are shown below.

A compound represented by formula (B-5)

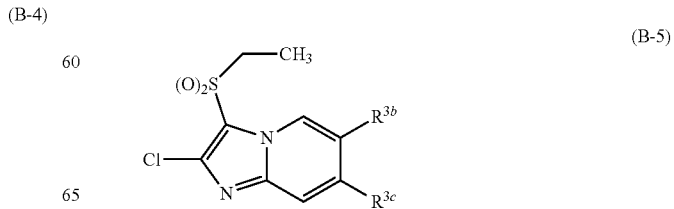

(B-5)

wherein the combination of $R^{3b}$ and $R^{3c}$ represents any one combination indicated in Table B-5.

TABLE B-5

| Intermediate compound | $R^{3b}$ | $R^{3c}$ |
|---|---|---|
| 27 | CF₃ | H |
| 28 | Cl | H |
| 29 | H | CF₃ |
| 30 | H | Br |
| 31 | H | Cl |

Intermediate compound 27: ¹H-NMR (CDCl₃) δ: 9.39 (1H, s), 7.81 (1H, d), 7.67 (1H, d), 3.39 (2H, q), 1.37 (3H, t).

Intermediate compound 28: ¹H-NMR (CDCl₃) δ: 9.07 (1H, s), 7.63 (1H, d), 7.49 (1H, d), 3.37 (2H, q), 1.36 (3H, t).

Intermediate compound 29: ¹H-NMR (CDCl₃) δ: 9.16 (1H, d), 7.98 (1H, s), 7.27 (1H, d), 3.38 (2H, q), 1.35 (3H, t).

Intermediate compound 30: ¹H-NMR (CDCl₃) δ: 8.87 (1H, d), 7.86 (1H, s), 7.20 (1H, d), 3.34 (2H, q), 1.33 (3H, t).

Intermediate compound 31: ¹H-NMR (CDCl₃) δ: 8.93 (1H, d), 7.68 (1H, s), 7.08 (1H, d), 3.34 (2H, q), 1.33 (3H, t).

Reference Preparation Example 14

A mixture of the Intermediate compound 26 (324 mg), trans-N,N'-dimethylcyclohexane-1,2-diamine (0.32 mL), sodium iodide (225 mg), copper(I) iodide (190 mg), and toluene (4 mL) was stirred at 120° C. for 21 hours. The resulting mixture was cooled to room temperature, and then filtered. To the resulting filtrate was added water, and the resulting mixture was extracted twice with chloroform. The resulting organic layer was dried over anhydrous sodium sulfate, and concentrated under reduced pressure. The resulting residue was subjected to silica gel chromatography to give the Intermediate compound 32 represented by the following formula (70 mg).

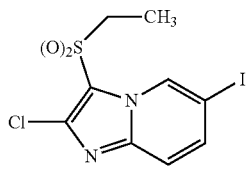

Intermediate compound 32: ¹H-NMR (CDCl₃) δ: 9.23 (1H, s), 7.70 (1H, d), 7.46 (1H, d), 3.35 (2H, ddd), 1.35 (3H, t).

Reference Preparation Example 15

The Intermediate compound 27 (936 mg), cesium fluoride (4.56 g), and DMSO (10 mL) were stirred at 95° C. The resulting mixture was cooled to room temperature, then ethyl acetate and water were sequentially added thereto, and the resulting mixture was filtered through Celite (registered trademark). The resulting filtrate was separated, the resulting organic layer was dried over anhydrous sodium sulfate, and concentrated under reduced pressure. The resulting residue was subjected to silica gel column chromatography to give a crude product of the Intermediate compound 33 represented by the following formula (comprising 22% of the Intermediate compound 27) (330 mg).

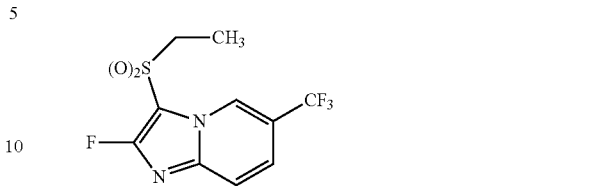

Intermediate compound 33: LCMS: 297 [M+H]⁺, RT=1.76 min

Reference Preparation Example 16

The compounds prepared according to the Reference Preparation Example 15 and physical properties thereof are shown below.

A compound represented by formula (B-6)

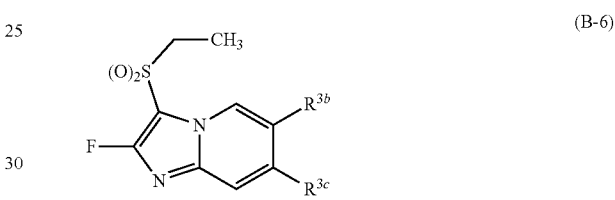

(B-6)

wherein the combination of $R^{3b}$ and $R^{3c}$ represents any one combination indicated in Table B-6.

TABLE B-6

| Intermediate compound | $R^{3b}$ | $R^{3c}$ |
|---|---|---|
| 34 | Br | H |
| 35 | Cl | H |
| 36 | H | CF₃ |
| 37 | H | Br |
| 38 | I | H |

Intermediate compound 34: LCMS: 307 [M+H]⁺, RT=1.64 min

Intermediate compound 35: LCMS: 263 [M+H]⁺, RT=1.61 min

Intermediate compound 36: LCMS: 297 [M+H]⁺, RT=1.78 min

Intermediate compound 37: LCMS: 307 [M+H]⁺, RT=1.69 min

Intermediate compound 38: LCMS: 355 [M+H]⁺, RT=1.72 min

Reference Preparation Example 17

A vial comprising a mixture of 4-amino-2-oxo-1,2-dihydropyrimidine (2.0 g), 1-bromo-3,3,3-trifluoro-2-propanone (1.9 mL), and methanol (20 mL) was covered, and the mixture was stirred under microwave at 120° C. for 3 hours. The mixture was cooled to room temperature, water was added thereto, and the resulting mixture was extracted with ethyl acetate. The resulting organic layer was dried over anhydrous sodium sulfate, and concentrated under reduced pressure. The resulting residue was subjected to silica gel chromatography to give the Intermediate compound 39 represented by the following formula (0.5 g).

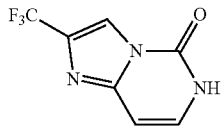

Intermediate compound 39: $^1$H-NMR (DMSO-$d_6$) δ: 11.89 (1H, s), 8.38 (1H, s), 7.41 (1H, d), 6.64 (1H, d).

Reference Preparation Example 18

The following Intermediate compound 40 was prepared according to the Reference Preparation Example 17 by using 1-bromo-3,3,4,4,4-pentafluoro-2-butanone instead of 1-bromo-3,3,3-trifluoro-2-propanone.

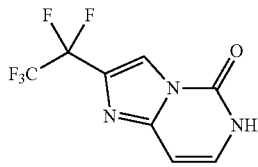 [SMILES: O=c1[nH]ccc2nc(C(F)(F)C(F)(F)F)cn12]

Intermediate compound 40: $^1$H-NMR (CDCl$_3$) δ: 9.19 (1H, s), 8.11 (1H, s), 7.16 (1H, dd), 6.76 (1H, d).

Reference Preparation Example 19

A mixture of 3-chloro-2-aminopyrazine (1.0 g) and 1-bromo-3,3,3-trifluoro-2-propanone (4.0 mL) in a closed container was stirred at 100° C. for 10.5 hours. The resulting mixture was cooled to room temperature, and filtered. The resulting solids were washed with hexane to give the Intermediate compound 41 represented by the following formula (2.45 g)

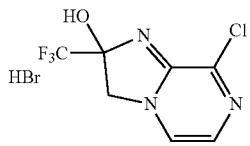 [SMILES: Br ; OC1(C(F)(F)F)CN2C=CN=C(Cl)C2=N1]

Intermediate compound 41: $^1$H-NMR (DMSO-$d_6$) δ: 8.36 (1H, s), 7.99 (1H, s), 5.05 (1H, d), 4.89 (1H, d).

Reference Preparation Example 20

A mixture of the Intermediate compound 41 (2.16 g) and propionitrile (10 mL) was stirred under reflux for 2 hours. The resulting mixture was cooled to room temperature, 2N hydrochloric acid was added thereto to make the mixture weakly acidic, and the resulting mixture was extracted with ethyl acetate. The resulting organic layer was dried over anhydrous sodium sulfate, and concentrated under reduced pressure to give the Intermediate compound 42 represented by the following formula (1.32 g).

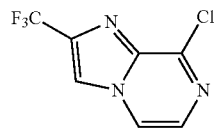

Intermediate compound 42: $^1$H-NMR (CDCl$_3$) δ: 8.10-8.09 (2H, m), 7.82 (1H, t).

Reference Preparation Example 21

A mixture of the Intermediate compound 42 (1.32 g), concentrated hydrochloric acid (3 mL), and water (1 mL) was stirred at 100° C. for 4 hours. The resulting mixture was cooled to room temperature, the precipitated solids were collected by filtration, and washed sequentially with water and chloroform to give the Intermediate compound 43 represented by the following formula (0.92 g).

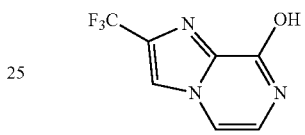

Intermediate compound 43: $^1$H-NMR (DMSO-$d_6$) δ: 11.45 (1H, s), 8.42 (1H, d), 7.50 (1H, d), 6.99 (1H, d).

Reference Preparation Example 22

Under nitrogen atmosphere, to a mixture of 2-(trifluoromethyl)pyrazolo[1,5-a]pyrazin-4(5H)-one (which was prepared according to the method described in WO 2006/023750 pamphlet) (0.20 g) and DMF (5 mL) was added N-chlorosuccinimide (0.15 g) at room temperature, and the resulting mixture was stirred at room temperature for 2.5 hours, then stirred at 80° C. for 1.5 hours. The resulting mixture was allowed to cool to room temperature, a saturated aqueous solution of sodium hydrogen carbonate was added thereto, and the resulting mixture was extracted with ethyl acetate. The resulting organic layer was dried over anhydrous magnesium sulfate, and then concentrated under reduced pressure. The resulting residue was subjected to silica gel column chromatography to give the Intermediate compound 44 represented by the following formula (0.18 g).

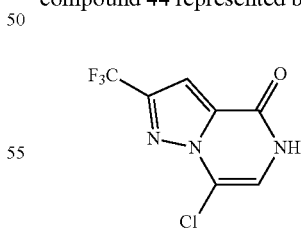

Intermediate compound 44: $^1$H-NMR (CDCl$_3$) δ: 9.81 (1H, br s), 7.46 (1H, s), 6.94 (1H, s).

Reference Preparation Example 23

The following Intermediate compound 45 was prepared according to the Reference Preparation Example 22.

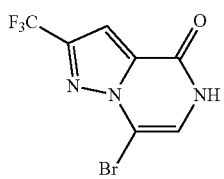 [SMILES: O=c1[nH]cc(Br)n2nc(C(F)(F)F)cc12]

Intermediate compound 45: $^1$H-NMR (CDCl$_3$) δ: 10.15 (1H, br s), 7.49 (1H, s), 7.03 (1H, s).

Reference Preparation Example 24

Under nitrogen atmosphere, to a mixture of 3-trifluoromethyl-1H-pyrazole-5-carboxylic acid methyl ester (0.58 g) and DMF (10 mL) was added N-bromosuccinimide (0.59 g), and the resulting mixture was stirred at 60° C. for one day. To the resulting mixture were added a 1 M aqueous solution of sodium thiosulfate and a saturated aqueous solution of sodium hydrogen carbonate, and the resulting mixture was extracted with methyl tert-butyl ether. The resulting organic layer was dried over anhydrous magnesium sulfate, and then concentrated under reduced pressure. The resulting residue was subjected to silica gel column chromatography to give the Intermediate compound 46 represented by the following formula (0.53 g).

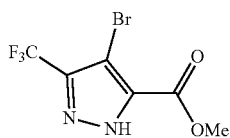 [SMILES: COC(=O)c1[nH]nc(C(F)(F)F)c1Br]

Intermediate compound 46: $^1$H-NMR (CDCl$_3$) δ: 11.35 (1H, br s), 4.02 (3H, s).

Reference Preparation Example 25

The following Intermediate compound 47 was prepared according to the Reference Preparation Example 24.

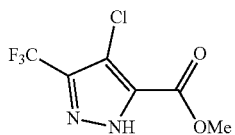 [SMILES: COC(=O)c1[nH]nc(C(F)(F)F)c1Cl]

Intermediate compound 47: $^1$H-NMR (CDCl$_3$) δ: 11.46 (1H, br s), 4.02 (3H, s).

Reference Preparation Example 26

Under nitrogen atmosphere, to a mixture of the Intermediate compound 46 (0.53 g), THF (2 mL), water (2 mL), and methanol (2 mL) was added lithium hydroxide monohydrate (0.21 g) at room temperature, and the resulting mixture was stirred at room temperature for 1 hour. To the resulting mixture was added sodium hydroxide (0.21 g), and the resulting mixture was stirred at room temperature for one day. To the resulting mixture was added a saturated aqueous solution of sodium hydrogen carbonate, and the resulting mixture was extracted with ethyl acetate. To the resulting aqueous layer was added 1N hydrochloric acid, and the resulting mixture was extracted with ethyl acetate. The resulting organic layer was dried over anhydrous magnesium sulfate, and then concentrated under reduced pressure to give the Intermediate compound 48 represented by the following formula (0.37 g).

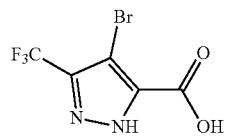

Intermediate compound 48: $^1$H-NMR (DMSO-d$_6$) δ: 8.28 (1H, s)

Reference Preparation Example 27

The following Intermediate compound 49 was prepared according to the Reference Preparation Example 26.

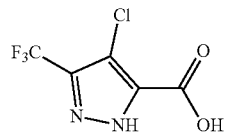 [SMILES: O=C(O)c1[nH]nc(C(F)(F)F)c1Br]

Intermediate compound 49: $^1$H-NMR (DMSO-d$_6$) δ: 7.21 (1H, s)

Reference Preparation Example 28

The following compounds were synthesized according to the methods described in WO 2006/023750 pamphlet.

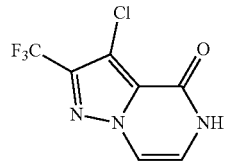 [SMILES: O=c1[nH]ccn2nc(C(F)(F)F)c(Br)c12]

Intermediate compound 50: $^1$H-NMR (DMSO-d$_6$) δ: 10.98 (1H, s), 7.77 (1H, d), 7.10 (1H, d).

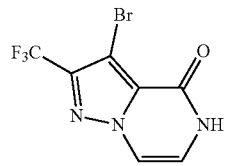

Intermediate compound 51: $^1$H-NMR (DMSO-d$_6$) δ: 7.79 (1H, d), 7.10 (1H, d).

Reference Preparation Example 29

The compound prepared according to the Reference Preparation Example 3 and physical property thereof are shown below.

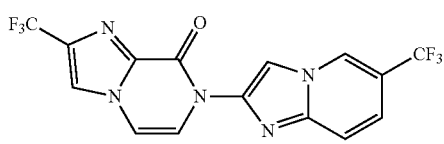 [SMILES: O=c1c2nc(C(F)(F)F)cn2ccn1-c1cn2cc(C(F)(F)F)ccc2n1]

Intermediate compound 52: $^1$H-NMR (CDCl$_3$) δ: 9.42 (1H, s), 8.86 (1H, s), 8.54 (1H, s), 8.31 (1H, d), 7.83 (1H, d), 7.78 (1H, d), 7.62 (1H, d).

Reference Preparation Example 30

The compound prepared according to the Reference Preparation Example 4 and physical property thereof are shown below.

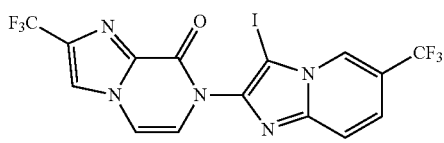 [SMILES: O=c1c2nc(C(F)(F)F)cn2ccn1-c1nc2ccc(C(F)(F)F)cn2c1I]

Intermediate compound 53: LCMS: 514 [M+H]$^+$, RT=1.77 min

Reference Preparation Example 31

The compound prepared according to the method described in WO 2006/023750 pamphlet and physical property thereof are shown below.

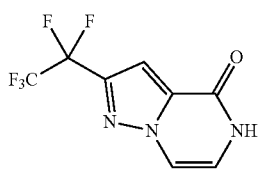 [SMILES: O=c1[nH]ccn2nc(C(F)(F)C(F)(F)F)cc12]

Intermediate compound 54: $^1$H-NMR (CDCl$_3$) δ: 8.56 (1H, s), 7.53 (1H, d), 7.38 (1H, s), 6.79 (1H, d).

Preparation Example 1

A mixture of the Intermediate compound 4 (137 mg), 1,4-dioxane (2 mL), tris(dibenzylideneacetone)dipalladium (0) (24 mg), Xantphos (31 mg), diisopropylethylamine (0.047 mL), and ethanethiol (0.038 mL) was stirred under reflux for 4.5 hours. To the resulting mixture was added water, and the resulting mixture was extracted with chloroform. The resulting organic layer was dried over anhydrous sodium sulfate, and concentrated under reduced pressure to give a crude product of the Present compound 1 represented by the following formula (190 mg).

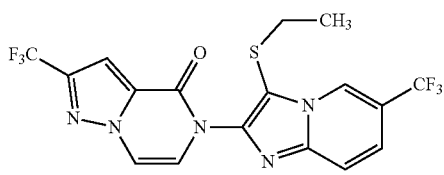 [SMILES: CCSc1c(-n2ccn3nc(C(F)(F)F)cc3c2=O)nc2ccc(C(F)(F)F)cn12]

Present compound 1: LCMS: 448 [M+H]$^+$, RT=2.2 min

Preparation Example 2

To a mixture of the crude product of the Present compound 1 prepared in the Preparation Example 1 (190 mg) and chloroform (3 mL) was added mCPBA (purity: 70%, comprising 30% of water) (320 mg) under ice-cooling, and the resulting mixture was stirred at room temperature for 4 hours. To the resulting mixture were sequentially added a saturated aqueous solution of sodium hydrogen carbonate and an aqueous solution of sodium thiosulfate, and the resulting mixture was extracted with chloroform. The resulting organic layer was dried over anhydrous sodium sulfate, and concentrated under reduced pressure. The resulting residue was subjected to silica gel column chromatography (chloroform:methanol=96:4) to give the Present compound 2 represented by the following formula (90 mg).

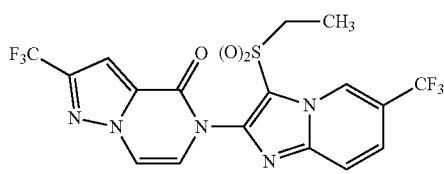

Present compound 2: $^1$H-NMR (CDCl$_3$) δ: 9.25 (1H, s), 7.91 (1H, d), 7.74 (1H, d), 7.61 (1H, d), 7.42 (1H, s), 7.09 (1H, d), 3.67 (2H, q), 1.50 (3H, t).

Preparation Example 3

The compound prepared according to the Preparation Example 1 and physical property thereof are shown below.

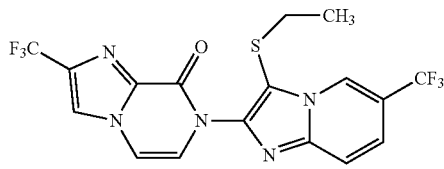 [SMILES: CCSc1c(-n2ccn3cc(C(F)(F)F)nc3c2=O)nc2ccc(C(F)(F)F)cn12]

Present compound 3: $^1$H-NMR (CDCl$_3$) δ: 8.86 (1H, s), 7.77-7.76 (2H, m), 7.55 (1H, d), 7.22 (1H, d), 7.04 (1H, d), 2.93 (2H, q), 1.24 (3H, t).

Preparation Example 4

The compound prepared according to the Preparation Example 2 and physical property thereof are shown below.

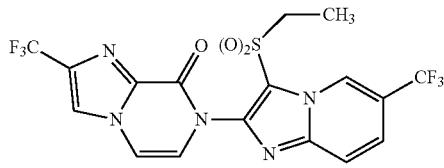

Present compound 4: $^1$H-NMR (Acetone-d$_6$) δ:9.33 (1H, s), 8.39 (1H, s), 8.09 (1H, d), 7.97 (1H, d), 7.78 (1H, d), 7.39 (1H, d), 3.77 (2H, q), 1.42 (3H, t).

Preparation Example 5

To a mixture of 2-(trifluoromethyl)pyrazo[1,5-a]pyrazin-4(5H)-one (4.06 g), the Intermediate compound 34 (comprising 30% of the Intermediate compound 26) (7.68 g), and DMF (30 mL) was added cesium carbonate (9.77 g) at room temperature, and the resulting mixture was stirred at 70° C. for 2 hours. To the resulting mixture was added water, and the resulting mixture was extracted with ethyl acetate. The resulting organic layer was dried over anhydrous sodium sulfate, and concentrated under reduced pressure. The resulting residue was subjected to silica gel chromatography (ethyl acetate:hexane=40:60) to give the Present compound 5 represented by the following formula (6.58 g).

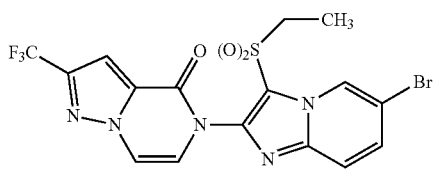

Present compound 5: $^1$H-NMR (CDCl$_3$) δ: 9.02 (1H, s), 7.68-7.67 (2H, m), 7.59 (1H, d), 7.41 (1H, s), 7.06 (1H, d), 3.62 (2H, q), 1.48 (3H, t).

Preparation Example 6

The compounds prepared according to the Preparation Example 5 and physical properties thereof are shown below. A compound represented by formula (A-1)

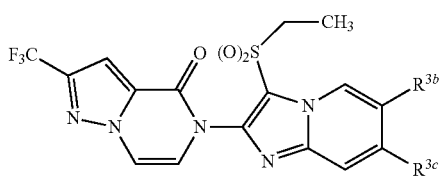

wherein the combination of R$^{3b}$ and R$^{3c}$ represents any one combination indicated in Table A-1.

TABLE A-1

| Present compound | R$^{3b}$ | R$^{3c}$ |
|---|---|---|
| 6 | Cl | H |
| 7 | H | CF$_3$ |
| 8 | H | Br |

Present compound 6: $^1$H-NMR (CDCl$_3$) δ: 8.93 (1H, s), 7.74 (1H, d), 7.58-7.56 (2H, m), 7.41 (1H, s), 7.06 (1H, d), 3.62 (2H, q), 1.48 (3H, t).

Present compound 7: $^1$H-NMR (CDCl$_3$) δ: 9.04 (1H, d), 8.09 (1H, s), 7.61 (1H, d), 7.42 (1H, s), 7.36 (1H, d), 7.08 (1H, d), 3.66 (2H, q), 1.49 (3H, t).

Present compound 8: $^1$H-NMR (CDCl$_3$) δ: 8.75 (1H, d), 7.97 (1H, s), 7.59 (1H, d), 7.41 (1H, d), 7.29 (1H, d), 7.06 (1H, d), 3.61 (2H, q), 1.46 (3H, t).

Preparation Example 7

The compounds prepared according to the Preparation Example 5 and physical properties thereof are shown below. A compound represented by formula (A-2)

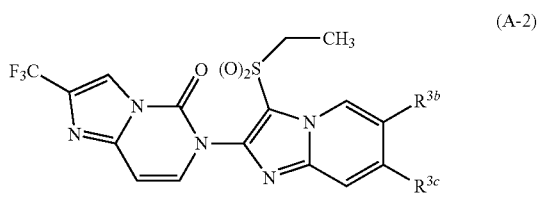

wherein the combination of R$^1$, R$^{3b}$, and R$^{3c}$ represents any one combination indicated in Table A-2.

TABLE A-2

| Present compound | R$^1$ | R$^{3b}$ | R$^{3c}$ |
|---|---|---|---|
| 9 | CF$_3$ | Br | H |
| 10 | CF$_3$ | CF$_3$ | H |
| 11 | C$_2$F$_5$ | Cl | H |
| 12 | CF$_3$ | Cl | H |
| 24 | C$_2$F$_5$ | Br | H |
| 25 | C$_2$F$_5$ | I | H |
| 26 | C$_2$F$_5$ | H | H |
| 27 | C$_2$F$_5$ | CF$_3$ | H |
| 31 | CF$_3$ | I | H |

Present compound 9: $^1$H-NMR (CDCl$_3$) δ: 9.00 (1H, s), 8.10 (1H, s), 7.69 (2H, m), 7.36 (1H, d), 6.80 (1H, d), 3.58 (2H, q), 1.49 (3H, t).

Present compound 10: $^1$H-NMR (CDCl$_3$) δ: 9.23 (1H, s), 8.11 (1H, s), 7.93 (1H, d), 7.76 (1H, d), 7.39 (1H, d), 6.83 (1H, d), 3.63 (2H, q), 1.50 (3H, t).

Present compound 11: $^1$H-NMR (CDCl$_3$) δ: 8.92 (1H, s), 8.13 (1H, s), 7.76 (1H, d), 7.59 (1H, d), 7.37 (1H, d), 6.83 (1H, d), 3.59 (2H, q), 1.49 (3H, t).

Present compound 12: $^1$H-NMR (CDCl$_3$) δ: 8.91 (1H, d), 8.10 (1H, s), 7.76 (1H, d), 7.59 (1H, d), 7.37 (1H, d), 6.81 (1H, d), 3.58 (2H, q), 1.49 (3H, t).

Present compound 24: $^1$H-NMR (CDCl$_3$) δ: 9.00 (1H, s), 8.13 (1H, s), 7.70-7.68 (2H, m), 7.37 (1H, d), 6.83 (1H, d), 3.59 (2H, q), 1.49 (3H, t).

Present compound 25: $^1$H-NMR (CDCl$_3$) δ: 9.09 (1H, s), 8.13 (1H, s), 7.80 (1H, d), 7.58 (1H, d), 7.36 (1H, d), 6.82 (1H, d), 3.58 (2H, q), 1.49 (3H, t).

Present compound 26: $^1$H-NMR (CDCl$_3$) δ: 8.88 (1H, d), 8.14 (1H, s), 7.81 (1H, d), 7.62 (1H, dd), 7.39 (1H, d), 7.23 (1H, dd), 6.82 (1H, d), 3.57 (2H, q), 1.47 (3H, t).

Present compound 27: $^1$H-NMR (CDCl$_3$) δ: 9.23 (1H, s), 8.14 (1H, s), 7.93 (1H, d), 7.76 (1H, d), 7.39 (1H, d), 6.85 (1H, d), 3.64 (2H, q), 1.51 (3H, t).

Present compound 31: $^1$H-NMR (CDCl$_3$) δ: 9.09 (1H, s), 8.09 (1H, s), 7.79 (1H, d), 7.58 (1H, d), 7.36 (1H, d), 6.80 (1H, d), 3.57 (2H, q), 1.48 (3H, t).

Preparation Example 8

A mixture of the Present compound 5 (490 mg), bis(pinacolato)diboron (508 mg), potassium acetate (294 mg), 1,1'-bis(diphenylphosphino)ferrocene (37 mg), and toluene (10 mL) was stirred at 110° C. for 3 hours. To the resulting mixture was added water, and the resulting mixture was extracted with ethyl acetate. The resulting organic layer was dried over anhydrous sodium sulfate, and concentrated under reduced pressure. To the resulting mixture were added sodium acetate (615 mg), water (5 mL), and THF (5 mL). The resulting mixture was cooled to 0° C., 30% hydrogen peroxide water (0.18 mL) was added thereto, and the resulting mixture was stirred at room temperature for 5 hours. To the resulting mixture was added an aqueous solution of sodium thiosulfate, and the resulting mixture was extracted with chloroform. The resulting organic layer was dried over anhydrous sodium sulfate, and concentrated under reduced pressure to give a crude product of the Present compound 13 represented by the following formula (500 mg).

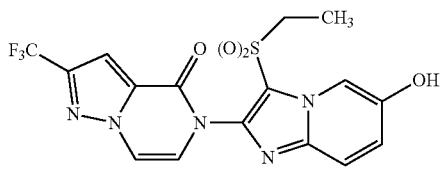

Present compound 13: LCMS: 426 [M−H]⁻, RT=1.66 min

Preparation Example 9

A mixture of the crude product of the Present compound 13 prepared in the Preparation Example 8 (500 mg), cesium carbonate (391 mg), DMF (4 mL), and iodoethane (0.100 mL) was stirred at room temperature for 4 hours. To the resulting mixture was added water, and the resulting mixture was extracted with chloroform. The resulting organic layer was dried over anhydrous sodium sulfate, and concentrated under reduced pressure. The resulting residue was subjected to silica gel chromatography (ethyl acetate:hexane=40:60) to give the Present compound 14 represented by the following formula (169 mg).

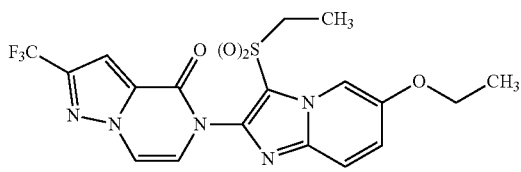

Present compound 14: ¹H-NMR (CDCl$_3$) δ: 8.40 (1H, s), 7.65 (1H, d), 7.57 (1H, d), 7.40 (1H, s), 7.34 (1H, d), 7.03 (1H, d), 4.09 (2H, q), 3.56 (2H, q), 1.49 (3H, t), 1.45 (3H, t).

Preparation Example 10

A mixture of the Present compound 5 (490 mg), 2-isopropenyl-4,4,5,5-tetramethyl-1,3,2-dioxaborolane (252 mg), tripotassium phosphate (637 mg), 1,1'-bis(diphenylphosphino)ferrocene (29 mg), 1,2-dimethoxyethane (8 mL), and water (0.8 mL) was stirred at 80° C. for 4 hours. To the resulting mixture was added water, and the resulting mixture was extracted with ethyl acetate. The resulting organic layer was dried over anhydrous sodium sulfate, and concentrated under reduced pressure. The resulting residue was subjected to silica gel chromatography (ethyl acetate:hexane=40:60) to give the Present compound 15 represented by the following formula (300 mg).

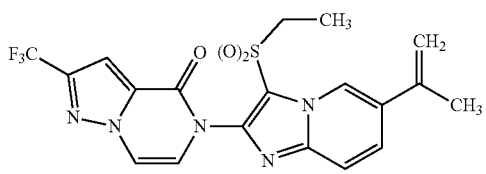

Present compound 15: ¹H-NMR (CDCl$_3$) δ: 8.87 (1H, s), 7.77 (1H, d), 7.71 (1H, d), 7.60 (1H, t), 7.41 (1H, s), 7.07 (1H, d), 5.53 (1H, s), 5.33 (1H, s), 3.60 (2H, q), 2.23 (3H, s), 1.47 (3H, t).

Preparation Example 11

The compounds prepared according to the Preparation Example 10 and physical properties thereof are shown below. A compound represented by formula (A-3)

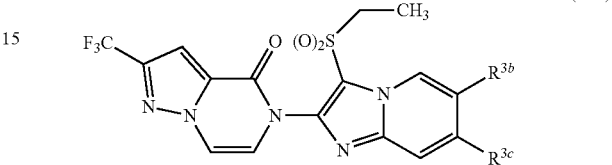

wherein the combination of R$^{3b}$ and R$^{3c}$ represents any one combination indicated in Table A-3.

TABLE A-3

| Present compound | R$^{3b}$ | R$^{3c}$ |
|---|---|---|
| 16 | c-Pr | H |
| 17 | 4-F—Ph | H |
| 18 | •CH$_3$ (CH=CH—CH$_3$) | H |
| 19 | CH=CH$_2$ | H |
| 20 | H | c-Pr |

Present compound 16: ¹H-NMR (DMSO-d$_6$) δ: 8.64 (1H, s), 8.07 (1H, d), 7.85 (1H, d), 7.79 (1H, s), 7.54 (1H, d), 7.43 (1H, d), 3.49 (2H, q), 2.33-2.32 (1H, m), 1.25 (3H, t), 1.07-1.05 (2H, m), 0.83-0.81 (2H, m).

Present compound 17: ¹H-NMR (CDCl$_3$) δ: 8.99 (1H, s), 7.85 (1H, d), 7.78 (1H, d), 7.61-7.55 (3H, m), 7.42 (1H, s), 7.27-7.25 (2H, m), 7.10 (1H, m), 3.63 (2H, q), 1.49 (3H, t).

Present compound 18: ¹H-NMR (CDCl$_3$) δ: 8.68 (1H, s), 7.69-7.69 (2H, m), 7.57 (1H, d), 7.40 (1H, s), 7.05 (1H, d), 6.45-6.39 (2H, m), 3.58 (2H, q), 1.97 (3H, d), 1.46 (3H, t).

Present compound 19: ¹H-NMR (CDCl$_3$) δ: 8.77 (1H, s), 7.76-7.75 (2H, m), 7.59 (1H, s), 7.41 (1H, s), 7.07 (1H, s), 6.75 (1H, dd), 5.89 (1H, d), 5.52 (1H, d), 3.60 (2H, q), 1.47 (3H, t).

Present compound 20: ¹H-NMR (CDCl$_3$) δ: 8.72 (1H, d), 7.57 (1H, d), 7.40 (2H, d), 7.06 (1H, d), 6.86 (1H, d), 3.57 (2H, q), 2.08-2.01 (1H, m), 1.44 (3H, t), 1.22-1.20 (2H, m), 0.88-0.87 (2H, m).

Preparation Example 12

A mixture of the Present compound 6 (446 mg), formic acid (0.06 mL), triethylamine (0.22 mL), tetrakis(triphenylphosphine)palladium(0) (280 mg), and N,N-dimethylacetamide (10 mL) was stirred at 105° C. for 14 hours. To the resulting mixture was added water, and the resulting mixture was extracted with ethyl acetate. The resulting organic layer was dried over anhydrous sodium sulfate, and concentrated under reduced pressure. The resulting residue was subjected to silica gel chromatography (ethyl acetate:

hexane=40:60) to give the Present compound 21 represented by the following formula (132 mg).

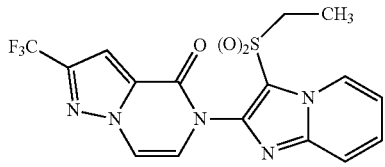

Present compound 21: $^1$H-NMR (DMSO-$d_6$) δ: 8.88 (1H, d), 8.09 (1H, d), 7.96 (1H, d), 7.80 (1H, s), 7.78-7.76 (1H, m), 7.56 (1H, d), 7.42 (1H, m), 3.34 (2H, q), 1.25 (3H, t).

Preparation Example 13

Under hydrogen atmosphere, a mixture of the Present compound 15 (120 mg), ethanol (5 mL), and palladium carbon (10 mg) was stirred at room temperature for 4 hours. The resulting mixture was filtered, and the resulting filtrate was concentrated under reduced pressure to give the Present compound 22 represented by the following formula (103 mg).

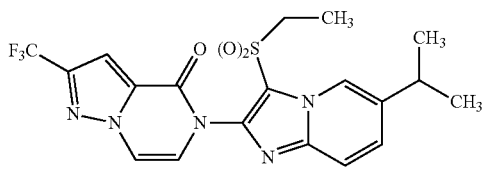

Present compound 22: $^1$H-NMR (CDCl$_3$) δ: 8.68 (1H, s), 7.72 (1H, d), 7.57 (1H, d), 7.52 (1H, d), 7.40 (1H, s), 7.05 (1H, d), 3.58 (2H, q), 3.06 (1H, m), 1.46 (3H, t), 1.35 (6H, d).

Preparation Example 14

A mixture of the Present compound 5 (490 mg), trans-N,N'-dimethylcyclohexane-1,2-diamine (0.24 mL), sodium iodide (150 mg), copper(I) iodide (114 mg), and toluene (4 mL) was stirred at 120° C. for 21 hours. The resulting mixture was cooled to room temperature, and then filtered. To the resulting filtrate was added water, and the resulting mixture was extracted twice with chloroform. The resulting organic layer was dried over anhydrous sodium sulfate, and concentrated under reduced pressure. The resulting residue was subjected to silica gel chromatography (ethyl acetate:hexane=57:43) to give the Present compound 23 represented by the following formula (50 mg).

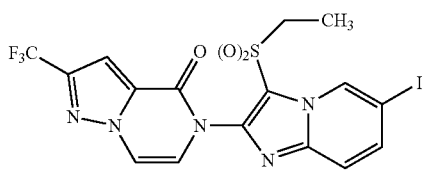

Present compound 23: $^1$H-NMR (CDCl$_3$) δ: 9.11 (1H, s), 7.77 (1H, d), 7.59-7.56 (2H, m), 7.41 (1H, s), 7.05 (1H, d), 3.61 (2H, q), 1.48 (3H, t).

Preparation Example 15

The compounds prepared according to the Preparation Example 5 and physical properties thereof are shown below. A compound represented by formula (A-4)

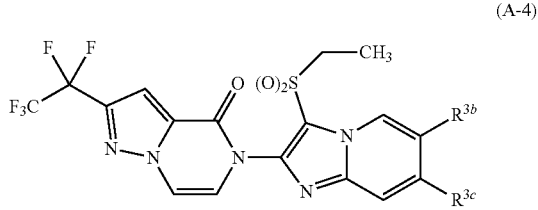

wherein the combination of $R^{3b}$ and $R^{3c}$ represents any one combination indicated in Table A-4.

TABLE A-4

| Present compound | $R^{3b}$ | $R^{3c}$ |
|---|---|---|
| 28 | Cl | H |
| 29 | Br | H |
| 30 | I | H |

Present compound 28: $^1$H-NMR (CDCl$_3$) δ: 8.93 (1H, s), 7.74 (1H, d), 7.61 (1H, d), 7.56 (1H, d), 7.44 (1H, s), 7.07 (1H, d), 3.63 (2H, q), 1.49 (3H, t).

Present compound 29: $^1$H-NMR (CDCl$_3$) δ: 9.02 (1H, s), 7.67 (1H, d), 7.66 (1H, d), 7.61 (1H, d), 7.44 (1H, s), 7.06 (1H, d), 3.62 (2H, q), 1.48 (3H, t).

Present compound 30: $^1$H-NMR (CDCl$_3$) δ: 9.11 (1H, s), 7.77 (1H, d), 7.60 (1H, d), 7.56 (1H, d), 7.44 (1H, s), 7.06 (1H, d), 3.62 (2H, q), 1.48 (3H, t).

Next, examples of the Present compound prepared according to any one of the Preparation Examples described in the EXAMPLES and the Production methods described in the present description are shown below. Here, Q11 to Q21 represent the following groups.

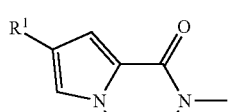

Q11

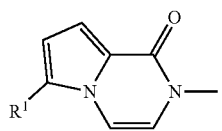

Q12

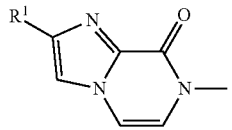

Q13

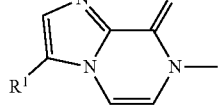

Q14

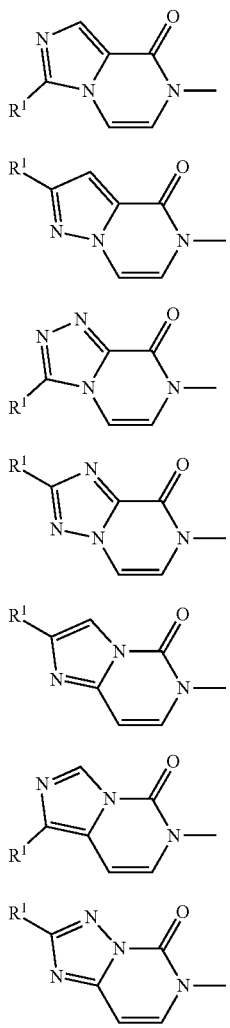

A compound represented by formula (L-1)

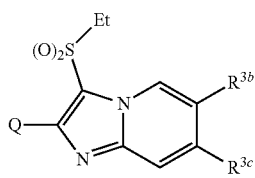

(hereinafter referred to as "Compound (L-1)"), wherein Q represents the group represented by Q11; $R^{3b}$ and $R^{3c}$ each represent a hydrogen atom; and $R^1$ represents any one substituent described in Table A1 or Table A2 (hereinafter referred to as "Compound group SX1").

TABLE A1

CF₃
CHF₂
CH₂CF₃
CF₂CF₃
CH₂CF₂CF₃
CF₂CF₂CF₃

TABLE A1-continued

CF₂CF₂CF₂CF₃
CF₂CF₂CF₂CF₂CF₃
C(CF₃)₃
C(CH₃)₂CN
OCF₃
OCHF₂
OCH₂CF₃
OCH₂CHF₂
OCF₂CF₃
OCH(CH₃)CF₃
OCH₂CF₂CHF₂
OCH₂CF₂CF₃
OCF₂CF₂CF₃
OCH₂CF₂CHFCF₃
OCH₂CF₂CF₂CF₃
OCF₂CF₂CF₂CF₃
OCH₂CF₂CF₂CF₂CF₃
OS(O)₂CF₃
OS(O)₂CF₂CF₃
OS(O)₂CF₂CF₂CF₃

TABLE A2

SCF₃
SCH₂CF₃
SCF₂CF₃
SCH₂CF₂CF₃
SCF₂CF₂CF₃
SCH₂CF₂CF₂CF₃
SCF₂CF₂CF₂CF₃
S(O)CF₃
S(O)CH₂CF₃
S(O)CF₂CF₃
S(O)CH₂CF₂CF₃
S(O)CF₂CF₂CF₃
S(O)CH₂CF₂CF₂CF₃
S(O)CF₂CF₂CF₂CF₃
S(O)₂CF₃
S(O)₂CH₂CF₃
S(O)₂CF₂CF₃
S(O)₂CH₂CF₂CF₃
S(O)₂CF₂CF₂CF₃
S(O)₂CH₂CF₂CF₂CF₃
S(O)₂CF₂CF₂CF₂CF₃
c-Pr
1-CN—c-Pr
2-CN—c-Pr
1-CN—c-Bu
CF(CF₃)₂

The Compound (L-1), wherein Q represents the group represented by Q12; $R^{3b}$ and $R^{3c}$ each represent a hydrogen atom; and $R^1$ represents any one substituent described in Table A1 or Table A2 (hereinafter referred to as "Compound group SX2").

The Compound (L-1), wherein Q represents the group represented by Q13; $R^{3b}$ and $R^{3c}$ each represent a hydrogen atom; and $R^1$ represents any one substituent described in Table A1 or Table A2 (hereinafter referred to as "Compound group SX3").

The Compound (L-1), wherein Q represents the group represented by Q14; $R^{3b}$ and $R^{3c}$ each represent a hydrogen atom; and $R^1$ represents any one substituent described in Table A1 or Table A2 (hereinafter referred to as "Compound group SX4").

The Compound (L-1), wherein Q represents the group represented by Q15; $R^{3b}$ and $R^{3c}$ each represent a hydrogen atom; and $R^1$ represents any one substituent described in Table A1 or Table A2 (hereinafter referred to as "Compound group SX5").

The Compound (L-1), wherein Q represents the group represented by Q16; $R^{3b}$ and $R^{3c}$ each represent a hydrogen atom; and R¹ represents any one substituent described in Table A1 or Table A2 (hereinafter referred to as "Compound group SX6").

The Compound (L-1), wherein Q represents the group represented by Q17; $R^{3b}$ and $R^{3c}$ each represent a hydrogen atom; and R¹ represents any one substituent described in Table A1 or Table A2 (hereinafter referred to as "Compound group SX7").

The Compound (L-1), wherein Q represents the group represented by Q18; $R^{3b}$ and $R^{3c}$ each represent a hydrogen atom; and R¹ represents any one substituent described in Table A1 or Table A2 (hereinafter referred to as "Compound group SX8").

The Compound (L-1), wherein Q represents the group represented by Q19; $R^{3b}$ and $R^{3c}$ each represent a hydrogen atom; and R¹ represents any one substituent described in Table A1 or Table A2 (hereinafter referred to as "Compound group SX9").

The Compound (L-1), wherein Q represents the group represented by Q20; $R^{3b}$ and $R^{3c}$ each represent a hydrogen atom; and R¹ represents any one substituent described in Table A1 or Table A2 (hereinafter referred to as "Compound group SX10").

The Compound (L-1), wherein Q represents the group represented by Q21; $R^{3b}$ and $R^{3c}$ each represent a hydrogen atom; and R¹ represents any one substituent described in Table A1 or Table A2 (hereinafter referred to as "Compound group SX11").

The Compound (L-1), wherein Q represents the group represented by Q11; $R^{3b}$ represents a chlorine atom; $R^{3c}$ represents a hydrogen atom; and R¹ represents any one substituent described in Table A1 or Table A2 (hereinafter referred to as "Compound group SX12").

The Compound (L-1), wherein Q represents the group represented by Q12; $R^{3b}$ represents a chlorine atom; $R^{3c}$ represents a hydrogen atom; and R¹ represents any one substituent described in Table A1 or Table A2 (hereinafter referred to as "Compound group SX13").

The Compound (L-1), wherein Q represents the group represented by Q13; $R^{3b}$ represents a chlorine atom; $R^{3c}$ represents a hydrogen atom; and R¹ represents any one substituent described in Table A1 or Table A2 (hereinafter referred to as "Compound group SX14").

The Compound (L-1), wherein Q represents the group represented by Q14; $R^{31}$ represents a chlorine atom; $R^{3c}$ represents a hydrogen atom; and R¹ represents any one substituent described in Table A1 or Table A2 (hereinafter referred to as "Compound group SX15").

The Compound (L-1), wherein Q represents the group represented by Q15; $R^{3b}$ represents a chlorine atom; $R^{3c}$ represents a hydrogen atom; and R¹ represents any one substituent described in Table A1 or Table A2 (hereinafter referred to as "Compound group SX16").

The Compound (L-1), wherein Q represents the group represented by Q16; $R^{3b}$ represents a chlorine atom; $R^{3c}$ represents a hydrogen atom; and R¹ represents any one substituent described in Table A1 or Table A2 (hereinafter referred to as "Compound group SX17").

The Compound (L-1), wherein Q represents the group represented by Q17; $R^{3b}$ represents a chlorine atom; $R^{3c}$ represents a hydrogen atom; and R¹ represents any one substituent described in Table A1 or Table A2 (hereinafter referred to as "Compound group SX18").

The Compound (L-1), wherein Q represents the group represented by Q18; $R^{3b}$ represents a chlorine atom; $R^{3c}$ represents a hydrogen atom; and R¹ represents any one substituent described in Table A1 or Table A2 (hereinafter referred to as "Compound group SX19").

The Compound (L-1), wherein Q represents the group represented by Q19; $R^{31}$ represents a chlorine atom; $R^{3c}$ represents a hydrogen atom; and R¹ represents any one substituent described in Table A1 or Table A2 (hereinafter referred to as "Compound group SX20").

The Compound (L-1), wherein Q represents the group represented by Q20; $R^{3b}$ represents a chlorine atom; $R^{3c}$ represents a hydrogen atom; and R¹ represents any one substituent described in Table A1 or Table A2 (hereinafter referred to as "Compound group SX21").

The Compound (L-1), wherein Q represents the group represented by Q21; $R^{3b}$ represents a chlorine atom; $R^{3c}$ represents a hydrogen atom; and R¹ represents any one substituent described in Table A1 or Table A2 (hereinafter referred to as "Compound group SX22").

The Compound (L-1), wherein Q represents the group represented by Q11; $R^{3b}$ represents a bromine atom; $R^{3c}$ represents a hydrogen atom; and R¹ represents any one substituent described in Table A1 or Table A2 (hereinafter referred to as "Compound group SX23").

The Compound (L-1), wherein Q represents the group represented by Q12; $R^{3b}$ represents a bromine atom; $R^{3c}$ represents a hydrogen atom; and R¹ represents any one substituent described in Table A1 or Table A2 (hereinafter referred to as "Compound group SX24").

The Compound (L-1), wherein Q represents the group represented by Q13; $R^{3b}$ represents a bromine atom; $R^{3c}$ represents a hydrogen atom; and R¹ represents any one substituent described in Table A1 or Table A2 (hereinafter referred to as "Compound group SX25").

The Compound (L-1), wherein Q represents the group represented by Q14; $R^{3b}$ represents a bromine atom; $R^{3c}$ represents a hydrogen atom; and R¹ represents any one substituent described in Table A1 or Table A2 (hereinafter referred to as "Compound group SX26").

The Compound (L-1), wherein Q represents the group represented by Q15; $R^{3b}$ represents a bromine atom; $R^{3c}$ represents a hydrogen atom; and R¹ represents any one substituent described in Table A1 or Table A2 (hereinafter referred to as "Compound group SX27").

The Compound (L-1), wherein Q represents the group represented by Q16; $R^{3b}$ represents a bromine atom; $R^{3c}$ represents a hydrogen atom; and R¹ represents any one substituent described in Table A1 or Table A2 (hereinafter referred to as "Compound group SX28").

The Compound (L-1), wherein Q represents the group represented by Q17; $R^{3b}$ represents a bromine atom; $R^{3c}$ represents a hydrogen atom; and R¹ represents any one substituent described in Table A1 or Table A2 (hereinafter referred to as "Compound group SX29").

The Compound (L-1), wherein Q represents the group represented by Q18; $R^{31}$ represents a bromine atom; $R^{3c}$ represents a hydrogen atom; and R¹ represents any one substituent described in Table A1 or Table A2 (hereinafter referred to as "Compound group SX30").

The Compound (L-1), wherein Q represents the group represented by Q19; $R^{3b}$ represents a bromine atom; $R^{3c}$ represents a hydrogen atom; and R¹ represents any one substituent described in Table A1 or Table A2 (hereinafter referred to as "Compound group SX31").

The Compound (L-1), wherein Q represents the group represented by Q20; $R^{3b}$ represents a bromine atom; $R^{3c}$ represents a hydrogen atom; and R¹ represents any one substituent described in Table A1 or Table A2 (hereinafter referred to as "Compound group SX32").

The Compound (L-1), wherein Q represents the group represented by Q21; $R^{3b}$ represents a bromine atom; $R^{3c}$ represents a hydrogen atom; and $R^1$ represents any one substituent described in Table A1 or Table A2 (hereinafter referred to as "Compound group SX33").

The Compound (L-1), wherein Q represents the group represented by Q11; $R^{3b}$ represents an iodine atom; $R^{3c}$ represents a hydrogen atom; and $R^1$ represents any one substituent described in Table A1 or Table A2 (hereinafter referred to as "Compound group SX34").

The Compound (L-1), wherein Q represents the group represented by Q12; $R^{3b}$ represents an iodine atom; $R^{3c}$ represents a hydrogen atom; and $R^1$ represents any one substituent described in Table A1 or Table A2 (hereinafter referred to as "Compound group SX35").

The Compound (L-1), wherein Q represents the group represented by Q13; $R^{3b}$ represents an iodine atom; $R^{3c}$ represents a hydrogen atom; and $R^1$ represents any one substituent described in Table A1 or Table A2 (hereinafter referred to as "Compound group SX36").

The Compound (L-1), wherein Q represents the group represented by Q14; $R^{3b}$ represents an iodine atom; $R^{3c}$ represents a hydrogen atom; and $R^1$ represents any one substituent described in Table A1 or Table A2 (hereinafter referred to as "Compound group SX37").

The Compound (L-1), wherein Q represents the group represented by Q15; $R^{3b}$ represents an iodine atom; $R^{3c}$ represents a hydrogen atom; and $R^1$ represents any one substituent described in Table A1 or Table A2 (hereinafter referred to as "Compound group SX38").

The Compound (L-1), wherein Q represents the group represented by Q16; $R^{3b}$ represents an iodine atom; $R^{3c}$ represents a hydrogen atom; and $R^1$ represents any one substituent described in Table A1 or Table A2 (hereinafter referred to as "Compound group SX39").

The Compound (L-1), wherein Q represents the group represented by Q17; $R^{3b}$ represents an iodine atom; $R^{3c}$ represents a hydrogen atom; and $R^1$ represents any one substituent described in Table A1 or Table A2 (hereinafter referred to as "Compound group SX40").

The Compound (L-1), wherein Q represents the group represented by Q18; $R^{3b}$ represents an iodine atom; $R^{3c}$ represents a hydrogen atom; and $R^1$ represents any one substituent described in Table A1 or Table A2 (hereinafter referred to as "Compound group SX41").

The Compound (L-1), wherein Q represents the group represented by Q19; $R^{3b}$ represents an iodine atom; $R^{3c}$ represents a hydrogen atom; and $R^1$ represents any one substituent described in Table A1 or Table A2 (hereinafter referred to as "Compound group SX42").

The Compound (L-1), wherein Q represents the group represented by Q20; $R^{3b}$ represents an iodine atom; $R^{3c}$ represents a hydrogen atom; and $R^1$ represents any one substituent described in Table A1 or Table A2 (hereinafter referred to as "Compound group SX43").

The Compound (L-1), wherein Q represents the group represented by Q21; $R^{3b}$ represents an iodine atom; $R^{3c}$ represents a hydrogen atom; and $R^1$ represents any one substituent described in Table A1 or Table A2 (hereinafter referred to as "Compound group SX44").

The Compound (L-1), wherein Q represents the group represented by Q11; $R^{3b}$ represents a trifluoromethyl group; $R^{3c}$ represents a hydrogen atom; and $R^1$ represents any one substituent described in Table A1 or Table A2 (hereinafter referred to as "Compound group SX45").

The Compound (L-1), wherein Q represents the group represented by Q12; $R^{3b}$ represents a trifluoromethyl group; $R^{3c}$ represents a hydrogen atom; and $R^1$ represents any one substituent described in Table A1 or Table A2 (hereinafter referred to as "Compound group SX46").

The Compound (L-1), wherein Q represents the group represented by Q13; $R^{3b}$ represents a trifluoromethyl group; $R^{3c}$ represents a hydrogen atom; and $R^1$ represents any one substituent described in Table A1 or Table A2 (hereinafter referred to as "Compound group SX47").

The Compound (L-1), wherein Q represents the group represented by Q14; $R^{3b}$ represents a trifluoromethyl group; $R^{3c}$ represents a hydrogen atom; and $R^1$ represents any one substituent described in Table A1 or Table A2 (hereinafter referred to as "Compound group SX48").

The Compound (L-1), wherein Q represents the group represented by Q15; $R^{3b}$ represents a trifluoromethyl group; $R^{3c}$ represents a hydrogen atom; and $R^1$ represents any one substituent described in Table A1 or Table A2 (hereinafter referred to as "Compound group SX49").

The Compound (L-1), wherein Q represents the group represented by Q16; $R^{3b}$ represents a trifluoromethyl group; $R^{3c}$ represents a hydrogen atom; and $R^1$ represents any one substituent described in Table A1 or Table A2 (hereinafter referred to as "Compound group SX50").

The Compound (L-1), wherein Q represents the group represented by Q17; $R^{3b}$ represents a trifluoromethyl group; $R^{3c}$ represents a hydrogen atom; and $R^1$ represents any one substituent described in Table A1 or Table A2 (hereinafter referred to as "Compound group SX51").

The Compound (L-1), wherein Q represents the group represented by Q18; $R^{3b}$ represents a trifluoromethyl group; $R^{3c}$ represents a hydrogen atom; and $R^1$ represents any one substituent described in Table A1 or Table A2 (hereinafter referred to as "Compound group SX52").

The Compound (L-1), wherein Q represents the group represented by Q19; $R^{3b}$ represents a trifluoromethyl group; $R^{3c}$ represents a hydrogen atom; and $R^1$ represents any one substituent described in Table A1 or Table A2 (hereinafter referred to as "Compound group SX53").

The Compound (L-1), wherein Q represents the group represented by Q20; $R^{3b}$ represents a trifluoromethyl group; $R^{3c}$ represents a hydrogen atom; and $R^1$ represents any one substituent described in Table A1 or Table A2 (hereinafter referred to as "Compound group SX54").

The Compound (L-1), wherein Q represents the group represented by Q21; $R^{3b}$ represents a trifluoromethyl group; $R^{3c}$ represents a hydrogen atom; and $R^1$ represents any one substituent described in Table A1 or Table A2 (hereinafter referred to as "Compound group SX55").

The Compound (L-1), wherein Q represents the group represented by Q11; $R^{3b}$ represents a hydrogen atom; $R^{3c}$ represents a chlorine atom; and $R^1$ represents any one substituent described in Table A1 or Table A2 (hereinafter referred to as "Compound group SX56").

The Compound (L-1), wherein Q represents the group represented by Q12; $R^{3b}$ represents a hydrogen atom; $R^{3c}$ represents a chlorine atom; and $R^1$ represents any one substituent described in Table A1 or Table A2 (hereinafter referred to as "Compound group SX57").

The Compound (L-1), wherein Q represents the group represented by Q13; $R^{3b}$ represents a hydrogen atom; $R^{3c}$ represents a chlorine atom; and $R^1$ represents any one substituent described in Table A1 or Table A2 (hereinafter referred to as "Compound group SX58").

The Compound (L-1), wherein Q represents the group represented by Q14; $R^{3b}$ represents a hydrogen atom; $R^{3c}$ represents a chlorine atom; and $R^1$ represents any one substituent described in Table A1 or Table A2 (hereinafter referred to as "Compound group SX59").

The Compound (L-1), wherein Q represents the group represented by Q15; $R^{3b}$ represents a hydrogen atom; $R^{3c}$ represents a chlorine atom; and $R^1$ represents any one substituent described in Table A1 or Table A2 (hereinafter referred to as "Compound group SX60").

The Compound (L-1), wherein Q represents the group represented by Q16; $R^{3b}$ represents a hydrogen atom; $R^{3c}$ represents a chlorine atom; and $R^1$ represents any one substituent described in Table A1 or Table A2 (hereinafter referred to as "Compound group SX61").

The Compound (L-1), wherein Q represents the group represented by Q17; $R^{3b}$ represents a hydrogen atom; $R^{3c}$ represents a chlorine atom; and $R^1$ represents any one substituent described in Table A1 or Table A2 (hereinafter referred to as "Compound group SX62").

The Compound (L-1), wherein Q represents the group represented by Q18; $R^{3b}$ represents a hydrogen atom; $R^{3c}$ represents a chlorine atom; and $R^1$ represents any one substituent described in Table A1 or Table A2 (hereinafter referred to as "Compound group SX63").

The Compound (L-1), wherein Q represents the group represented by Q19; $R^{3b}$ represents a hydrogen atom; $R^{3c}$ represents a chlorine atom; and $R^1$ represents any one substituent described in Table A1 or Table A2 (hereinafter referred to as "Compound group SX64").

The Compound (L-1), wherein Q represents the group represented by Q20; $R^{3b}$ represents a hydrogen atom; $R^{3c}$ represents a chlorine atom; and $R^1$ represents any one substituent described in Table A1 or Table A2 (hereinafter referred to as "Compound group SX65").

The Compound (L-1), wherein Q represents the group represented by Q21; $R^{3b}$ represents a hydrogen atom; $R^{3c}$ represents a chlorine atom; and $R^1$ represents any one substituent described in Table A1 or Table A2 (hereinafter referred to as "Compound group SX66").

The Compound (L-1), wherein Q represents the group represented by Q11; $R^{3b}$ represents a hydrogen atom; $R^{3c}$ represents a bromine atom; and $R^1$ represents any one substituent described in Table A1 or Table A2 (hereinafter referred to as "Compound group SX67").

The Compound (L-1), wherein Q represents the group represented by Q12; $R^{3b}$ represents a hydrogen atom; $R^{3c}$ represents a bromine atom; and $R^1$ represents any one substituent described in Table A1 or Table A2 (hereinafter referred to as "Compound group SX68").

The Compound (L-1), wherein Q represents the group represented by Q13; $R^{3b}$ represents a hydrogen atom; $R^{3c}$ represents a bromine atom; and $R^1$ represents any one substituent described in Table A1 or Table A2 (hereinafter referred to as "Compound group SX69").

The Compound (L-1), wherein Q represents the group represented by Q14; $R^{3b}$ represents a hydrogen atom; $R^{3c}$ represents a bromine atom; and $R^1$ represents any one substituent described in Table A1 or Table A2 (hereinafter referred to as "Compound group SX70").

The Compound (L-1), wherein Q represents the group represented by Q15; $R^{3b}$ represents a hydrogen atom; $R^{3c}$ represents a bromine atom; and $R^1$ represents any one substituent described in Table A1 or Table A2 (hereinafter referred to as "Compound group SX71").

The Compound (L-1), wherein Q represents the group represented by Q16; $R^{3b}$ represents a hydrogen atom; $R^{3c}$ represents a bromine atom; and $R^1$ represents any one substituent described in Table A1 or Table A2 (hereinafter referred to as "Compound group SX72").

The Compound (L-1), wherein Q represents the group represented by Q17; $R^{3b}$ represents a hydrogen atom; $R^{3c}$ represents a bromine atom; and $R^1$ represents any one substituent described in Table A1 or Table A2 (hereinafter referred to as "Compound group SX73").

The Compound (L-1), wherein Q represents the group represented by Q18; $R^{3b}$ represents a hydrogen atom; $R^{3c}$ represents a bromine atom; and $R^1$ represents any one substituent described in Table A1 or Table A2 (hereinafter referred to as "Compound group SX74").

The Compound (L-1), wherein Q represents the group represented by Q19; $R^{3b}$ represents a hydrogen atom; $R^{3c}$ represents a bromine atom; and $R^1$ represents any one substituent described in Table A1 or Table A2 (hereinafter referred to as "Compound group SX75").

The Compound (L-1), wherein Q represents the group represented by Q20; $R^{3b}$ represents a hydrogen atom; $R^{3c}$ represents a bromine atom; and $R^1$ represents any one substituent described in Table A1 or Table A2 (hereinafter referred to as "Compound group SX76").

The Compound (L-1), wherein Q represents the group represented by Q21; $R^{3b}$ represents a hydrogen atom; $R^{3c}$ represents a bromine atom; and $R^1$ represents any one substituent described in Table A1 or Table A2 (hereinafter referred to as "Compound group SX77").

The Compound (L-1), wherein Q represents the group represented by Q11; $R^{3b}$ represents a hydrogen atom; $R^{3c}$ represents an iodine atom; and $R^1$ represents any one substituent described in Table A1 or Table A2 (hereinafter referred to as "Compound group SX78").

The Compound (L-1), wherein Q represents the group represented by Q12; $R^{3b}$ represents a hydrogen atom; $R^{3c}$ represents an iodine atom; and $R^1$ represents any one substituent described in Table A1 or Table A2 (hereinafter referred to as "Compound group SX79").

The Compound (L-1), wherein Q represents the group represented by Q13; $R^{3b}$ represents a hydrogen atom; $R^{3c}$ represents an iodine atom; and $R^1$ represents any one substituent described in Table A1 or Table A2 (hereinafter referred to as "Compound group SX80").

The Compound (L-1), wherein Q represents the group represented by Q14; $R^{3b}$ represents a hydrogen atom; $R^{3c}$ represents an iodine atom; and $R^1$ represents any one substituent described in Table A1 or Table A2 (hereinafter referred to as "Compound group SX81").

The Compound (L-1), wherein Q represents the group represented by Q15; $R^{3b}$ represents a hydrogen atom; $R^{3c}$ represents an iodine atom; and $R^1$ represents any one substituent described in Table A1 or Table A2 (hereinafter referred to as "Compound group SX82").

The Compound (L-1), wherein Q represents the group represented by Q16; $R^{3b}$ represents a hydrogen atom; $R^{3c}$ represents an iodine atom; and $R^1$ represents any one substituent described in Table A1 or Table A2 (hereinafter referred to as "Compound group SX83").

The Compound (L-1), wherein Q represents the group represented by Q17; $R^{3b}$ represents a hydrogen atom; $R^{3c}$ represents an iodine atom; and $R^1$ represents any one substituent described in Table A1 or Table A2 (hereinafter referred to as "Compound group SX84").

The Compound (L-1), wherein Q represents the group represented by Q18; $R^{3b}$ represents a hydrogen atom; $R^{3c}$ represents an iodine atom; and $R^1$ represents any one substituent described in Table A1 or Table A2 (hereinafter referred to as "Compound group SX85").

The Compound (L-1), wherein Q represents the group represented by Q19; $R^{3b}$ represents a hydrogen atom; $R^{3c}$ represents an iodine atom; and $R^1$ represents any one substituent described in Table A1 or Table A2 (hereinafter referred to as "Compound group SX86").

The Compound (L-1), wherein Q represents the group represented by Q20; $R^{3b}$ represents a hydrogen atom; $R^{3c}$ represents an iodine atom; and $R^1$ represents any one substituent described in Table A1 or Table A2 (hereinafter referred to as "Compound group SX87").

The Compound (L-1), wherein Q represents the group represented by Q21; $R^{3b}$ represents a hydrogen atom; $R^{3c}$ represents an iodine atom; and $R^1$ represents any one substituent described in Table A1 or Table A2 (hereinafter referred to as "Compound group SX88").

The Compound (L-1), wherein Q represents the group represented by Q11; $R^{3b}$ represents a hydrogen atom; $R^{3c}$ represents a trifluoromethyl group; and $R^1$ represents any one substituent described in Table A1 or Table A2 (hereinafter referred to as "Compound group SX89").

The Compound (L-1), wherein Q represents the group represented by Q12; $R^{3b}$ represents a hydrogen atom; $R^{3c}$ represents a trifluoromethyl group; and $R^1$ represents any one substituent described in Table A1 or Table A2 (hereinafter referred to as "Compound group SX90").

The Compound (L-1), wherein Q represents the group represented by Q13; $R^{3b}$ represents a hydrogen atom; $R^{3c}$ represents a trifluoromethyl group; and $R^1$ represents any one substituent described in Table A1 or Table A2 (hereinafter referred to as "Compound group SX91").

The Compound (L-1), wherein Q represents the group represented by Q14; $R^{3b}$ represents a hydrogen atom; $R^{3c}$ represents a trifluoromethyl group; and $R^1$ represents any one substituent described in Table A1 or Table A2 (hereinafter referred to as "Compound group SX92").

The Compound (L-1), wherein Q represents the group represented by Q15; $R^{3b}$ represents a hydrogen atom; $R^{3c}$ represents a trifluoromethyl group; and $R^1$ represents any one substituent described in Table A1 or Table A2 (hereinafter referred to as "Compound group SX93").

The Compound (L-1), wherein Q represents the group represented by Q16; $R^{3b}$ represents a hydrogen atom; $R^{3c}$ represents a trifluoromethyl group; and $R^1$ represents any one substituent described in Table A1 or Table A2 (hereinafter referred to as "Compound group SX94").

The Compound (L-1), wherein Q represents the group represented by Q17; $R^{3b}$ represents a hydrogen atom; $R^{3c}$ represents a trifluoromethyl group; and $R^1$ represents any one substituent described in Table A1 or Table A2 (hereinafter referred to as "Compound group SX95").

The Compound (L-1), wherein Q represents the group represented by Q18; $R^{3b}$ represents a hydrogen atom; $R^{3c}$ represents a trifluoromethyl group; and $R^1$ represents any one substituent described in Table A1 or Table A2 (hereinafter referred to as "Compound group SX96").

The Compound (L-1), wherein Q represents the group represented by Q19; $R^{3b}$ represents a hydrogen atom; $R^{3c}$ represents a trifluoromethyl group; and $R^1$ represents any one substituent described in Table A1 or Table A2 (hereinafter referred to as "Compound group SX97").

The Compound (L-1), wherein Q represents the group represented by Q20; $R^{3b}$ represents a hydrogen atom; $R^{3c}$ represents a trifluoromethyl group; and $R^1$ represents any one substituent described in Table A1 or Table A2 (hereinafter referred to as "Compound group SX98").

The Compound (L-1), wherein Q represents the group represented by Q21; $R^{3b}$ represents a hydrogen atom; $R^{3c}$ represents a trifluoromethyl group; and $R^1$ represents any one substituent described in Table A1 or Table A2 (hereinafter referred to as "Compound group SX99").

A compound represented by formula (L-2)

$$\text{(L-2)}$$

(hereinafter referred to as "Compound (L-2)"), wherein Q represents the group represented by Q11; $R^{3b}$ and $R^{3c}$ each represent a hydrogen atom; and $R^1$ represents any one substituent described in Table A1 or Table A2 (hereinafter referred to as "Compound group SX100").

The Compound (L-2), wherein Q represents the group represented by Q12; $R^{3b}$ and $R^{3c}$ each represent a hydrogen atom; and $R^1$ represents any one substituent described in Table A1 or Table A2 (hereinafter referred to as "Compound group SX101").

The Compound (L-2), wherein Q represents the group represented by Q13; $R^{3b}$ and $R^{3c}$ each represent a hydrogen atom; and $R^1$ represents any one substituent described in Table A1 or Table A2 (hereinafter referred to as "Compound group SX102").

The Compound (L-2), wherein Q represents the group represented by Q14; $R^{3b}$ and $R^{3c}$ each represent a hydrogen atom; and $R^1$ represents any one substituent described in Table A1 or Table A2 (hereinafter referred to as "Compound group SX103").

The Compound (L-2), wherein Q represents the group represented by Q15; $R^{3b}$ and $R^{3c}$ each represent a hydrogen atom; and $R^1$ represents any one substituent described in Table A1 or Table A2 (hereinafter referred to as "Compound group SX104").

The Compound (L-2), wherein Q represents the group represented by Q16; $R^{3b}$ and $R^{3c}$ each represent a hydrogen atom; and $R^1$ represents any one substituent described in Table A1 or Table A2 (hereinafter referred to as "Compound group SX105").

The Compound (L-2), wherein Q represents the group represented by Q17; $R^{3b}$ and $R^{3c}$ each represent a hydrogen atom; and $R^1$ represents any one substituent described in Table A1 or Table A2 (hereinafter referred to as "Compound group SX106").

The Compound (L-2), wherein Q represents the group represented by Q18; $R^{3b}$ and $R^{3c}$ each represent a hydrogen atom; and $R^1$ represents any one substituent described in Table A1 or Table A2 (hereinafter referred to as "Compound group SX107").

The Compound (L-2), wherein Q represents the group represented by Q19; $R^{3b}$ and $R^{3c}$ each represent a hydrogen atom; and $R^1$ represents any one substituent described in Table A1 or Table A2 (hereinafter referred to as "Compound group SX108").

The Compound (L-2), wherein Q represents the group represented by Q20; $R^{3b}$ and $R^{3c}$ each represent a hydrogen atom; and $R^1$ represents any one substituent described in Table A1 or Table A2 (hereinafter referred to as "Compound group SX109").

The Compound (L-2), wherein Q represents the group represented by Q21; $R^{3b}$ and $R^{3c}$ each represent a hydrogen atom; and $R^1$ represents any one substituent described in Table A1 or Table A2 (hereinafter referred to as "Compound group SX110").

The Compound (L-2), wherein Q represents the group represented by Q11; $R^{3b}$ represents a chlorine atom; $R^{3c}$ represents a hydrogen atom; and $R^1$ represents any one substituent described in Table A1 or Table A2 (hereinafter referred to as "Compound group SX111").

The Compound (L-2), wherein Q represents the group represented by Q12; $R^{3b}$ represents a chlorine atom; $R^{3c}$ represents a hydrogen atom; and $R^1$ represents any one substituent described in Table A1 or Table A2 (hereinafter referred to as "Compound group SX112").

The Compound (L-2), wherein Q represents the group represented by Q13; $R^{3b}$ represents a chlorine atom; $R^{3c}$ represents a hydrogen atom; and $R^1$ represents any one substituent described in Table A1 or Table A2 (hereinafter referred to as "Compound group SX113").

The Compound (L-2), wherein Q represents the group represented by Q14; $R^{3b}$ represents a chlorine atom; $R^{3c}$ represents a hydrogen atom; and $R^1$ represents any one substituent described in Table A1 or Table A2 (hereinafter referred to as "Compound group SX114").

The Compound (L-2), wherein Q represents the group represented by Q15; $R^{3b}$ represents a chlorine atom; $R^{3c}$ represents a hydrogen atom; and $R^1$ represents any one substituent described in Table A1 or Table A2 (hereinafter referred to as "Compound group SX115").

The Compound (L-2), wherein Q represents the group represented by Q16; $R^{3b}$ represents a chlorine atom; $R^{3c}$ represents a hydrogen atom; and $R^1$ represents any one substituent described in Table A1 or Table A2 (hereinafter referred to as "Compound group SX116").

The Compound (L-2), wherein Q represents the group represented by Q17; $R^{3b}$ represents a chlorine atom; $R^{3c}$ represents a hydrogen atom; and $R^1$ represents any one substituent described in Table A1 or Table A2 (hereinafter referred to as "Compound group SX117").

The Compound (L-2), wherein Q represents the group represented by Q18; $R^{3b}$ represents a chlorine atom; $R^{3c}$ represents a hydrogen atom; and $R^1$ represents any one substituent described in Table A1 or Table A2 (hereinafter referred to as "Compound group SX118").

The Compound (L-2), wherein Q represents the group represented by Q19; $R^{31}$ represents a chlorine atom; $R^{3c}$ represents a hydrogen atom; and $R^1$ represents any one substituent described in Table A1 or Table A2 (hereinafter referred to as "Compound group SX119").

The Compound (L-2), wherein Q represents the group represented by Q20; $R^{3b}$ represents a chlorine atom; $R^{3c}$ represents a hydrogen atom; and $R^1$ represents any one substituent described in Table A1 or Table A2 (hereinafter referred to as "Compound group SX120").

The Compound (L-2), wherein Q represents the group represented by Q21; $R^{3b}$ represents a chlorine atom; $R^{3c}$ represents a hydrogen atom; and $R^1$ represents any one substituent described in Table A1 or Table A2 (hereinafter referred to as "Compound group SX121").

The Compound (L-2), wherein Q represents the group represented by Q11; $R^{3b}$ represents a bromine atom; $R^{3c}$ represents a hydrogen atom; and $R^1$ represents any one substituent described in Table A1 or Table A2 (hereinafter referred to as "Compound group SX122").

The Compound (L-2), wherein Q represents the group represented by Q12; $R^{3b}$ represents a bromine atom; $R^{3c}$ represents a hydrogen atom; and $R^1$ represents any one substituent described in Table A1 or Table A2 (hereinafter referred to as "Compound group SX123").

The Compound (L-2), wherein Q represents the group represented by Q13; $R^{3b}$ represents a bromine atom; $R^{3c}$ represents a hydrogen atom; and $R^1$ represents any one substituent described in Table A1 or Table A2 (hereinafter referred to as "Compound group SX124").

The Compound (L-2), wherein Q represents the group represented by Q14; $R^{3b}$ represents a bromine atom; $R^{3c}$ represents a hydrogen atom; and $R^1$ represents any one substituent described in Table A1 or Table A2 (hereinafter referred to as "Compound group SX125").

The Compound (L-2), wherein Q represents the group represented by Q15; $R^{3b}$ represents a bromine atom; $R^{3c}$ represents a hydrogen atom; and $R^1$ represents any one substituent described in Table A1 or Table A2 (hereinafter referred to as "Compound group SX126").

The Compound (L-2), wherein Q represents the group represented by Q16; $R^{3b}$ represents a bromine atom; $R^{3c}$ represents a hydrogen atom; and $R^1$ represents any one substituent described in Table A1 or Table A2 (hereinafter referred to as "Compound group SX127").

The Compound (L-2), wherein Q represents the group represented by Q17; $R^{3b}$ represents a bromine atom; $R^{3c}$ represents a hydrogen atom; and $R^1$ represents any one substituent described in Table A1 or Table A2 (hereinafter referred to as "Compound group SX128").

The Compound (L-2), wherein Q represents the group represented by Q18; $R^{31}$ represents a bromine atom; $R^{3c}$ represents a hydrogen atom; and $R^1$ represents any one substituent described in Table A1 or Table A2 (hereinafter referred to as "Compound group SX129").

The Compound (L-2), wherein Q represents the group represented by Q19; $R^{3b}$ represents a bromine atom; $R^{3c}$ represents a hydrogen atom; and $R^1$ represents any one substituent described in Table A1 or Table A2 (hereinafter referred to as "Compound group SX130").

The Compound (L-2), wherein Q represents the group represented by Q20; $R^{3b}$ represents a bromine atom; $R^{3c}$ represents a hydrogen atom; and $R^1$ represents any one substituent described in Table A1 or Table A2 (hereinafter referred to as "Compound group SX131").

The Compound (L-2), wherein Q represents the group represented by Q21; $R^{3b}$ represents a bromine atom; $R^{3c}$ represents a hydrogen atom; and $R^1$ represents any one substituent described in Table A1 or Table A2 (hereinafter referred to as "Compound group SX132").

The Compound (L-2), wherein Q represents the group represented by Q11; $R^{3b}$ represents an iodine atom; $R^{3c}$ represents a hydrogen atom; and $R^1$ represents any one substituent described in Table A1 or Table A2 (hereinafter referred to as "Compound group SX133").

The Compound (L-2), wherein Q represents the group represented by Q12; $R^{3b}$ represents an iodine atom; $R^{3c}$ represents a hydrogen atom; and $R^1$ represents any one substituent described in Table A1 or Table A2 (hereinafter referred to as "Compound group SX134").

The Compound (L-2), wherein Q represents the group represented by Q13; $R^{3b}$ represents an iodine atom; $R^{3c}$ represents a hydrogen atom; and $R^1$ represents any one substituent described in Table A1 or Table A2 (hereinafter referred to as "Compound group SX135").

The Compound (L-2), wherein Q represents the group represented by Q14; $R^{3b}$ represents an iodine atom; $R^{3c}$ represents a hydrogen atom; and $R^1$ represents any one substituent described in Table A1 or Table A2 (hereinafter referred to as "Compound group SX136").

The Compound (L-2), wherein Q represents the group represented by Q15; $R^{3b}$ represents an iodine atom; $R^{3c}$ represents a hydrogen atom; and $R^1$ represents any one substituent described in Table A1 or Table A2 (hereinafter referred to as "Compound group SX137").

The Compound (L-2), wherein Q represents the group represented by Q16; $R^{3b}$ represents an iodine atom; $R^{3c}$ represents a hydrogen atom; and $R^1$ represents any one substituent described in Table A1 or Table A2 (hereinafter referred to as "Compound group SX138").

The Compound (L-2), wherein Q represents the group represented by Q17; $R^{3b}$ represents an iodine atom; $R^{3c}$ represents a hydrogen atom; and $R^1$ represents any one substituent described in Table A1 or Table A2 (hereinafter referred to as "Compound group SX139").

The Compound (L-2), wherein Q represents the group represented by Q18; $R^{3b}$ represents an iodine atom; $R^{3c}$ represents a hydrogen atom; and $R^1$ represents any one substituent described in Table A1 or Table A2 (hereinafter referred to as "Compound group SX140").

The Compound (L-2), wherein Q represents the group represented by Q19; $R^{3b}$ represents an iodine atom; $R^{3c}$ represents a hydrogen atom; and $R^1$ represents any one substituent described in Table A1 or Table A2 (hereinafter referred to as "Compound group SX141").

The Compound (L-2), wherein Q represents the group represented by Q20; $R^{3b}$ represents an iodine atom; $R^{3c}$ represents a hydrogen atom; and $R^1$ represents any one substituent described in Table A1 or Table A2 (hereinafter referred to as "Compound group SX142").

The Compound (L-2), wherein Q represents the group represented by Q21; $R^{3b}$ represents an iodine atom; $R^{3c}$ represents a hydrogen atom; and $R^1$ represents any one substituent described in Table A1 or Table A2 (hereinafter referred to as "Compound group SX143").

The Compound (L-2), wherein Q represents the group represented by Q11; $R^{3b}$ represents a trifluoromethyl group; $R^{3c}$ represents a hydrogen atom; and $R^1$ represents any one substituent described in Table A1 or Table A2 (hereinafter referred to as "Compound group SX144").

The Compound (L-2), wherein Q represents the group represented by Q12; $R^{3b}$ represents a trifluoromethyl group; $R^{3c}$ represents a hydrogen atom; and $R^1$ represents any one substituent described in Table A1 or Table A2 (hereinafter referred to as "Compound group SX145").

The Compound (L-2), wherein Q represents the group represented by Q13; $R^{3b}$ represents a trifluoromethyl group; $R^{3c}$ represents a hydrogen atom; and $R^1$ represents any one substituent described in Table A1 or Table A2 (hereinafter referred to as "Compound group SX146").

The Compound (L-2), wherein Q represents the group represented by Q14; $R^{3b}$ represents a trifluoromethyl group; $R^{3c}$ represents a hydrogen atom; and $R^1$ represents any one substituent described in Table A1 or Table A2 (hereinafter referred to as "Compound group SX147").

The Compound (L-2), wherein Q represents the group represented by Q15; $R^{3b}$ represents a trifluoromethyl group; $R^{3c}$ represents a hydrogen atom; and $R^1$ represents any one substituent described in Table A1 or Table A2 (hereinafter referred to as "Compound group SX148").

The Compound (L-2), wherein Q represents the group represented by Q16; $R^{3b}$ represents a trifluoromethyl group; $R^{3c}$ represents a hydrogen atom; and $R^1$ represents any one substituent described in Table A1 or Table A2 (hereinafter referred to as "Compound group SX149").

The Compound (L-2), wherein Q represents the group represented by Q17; $R^{3b}$ represents a trifluoromethyl group; $R^{3c}$ represents a hydrogen atom; and $R^1$ represents any one substituent described in Table A1 or Table A2 (hereinafter referred to as "Compound group SX150").

The Compound (L-2), wherein Q represents the group represented by Q18; $R^{3b}$ represents a trifluoromethyl group; $R^{3c}$ represents a hydrogen atom; and $R^1$ represents any one substituent described in Table A1 or Table A2 (hereinafter referred to as "Compound group SX151").

The Compound (L-2), wherein Q represents the group represented by Q19; $R^{3b}$ represents a trifluoromethyl group; $R^{3c}$ represents a hydrogen atom; and $R^1$ represents any one substituent described in Table A1 or Table A2 (hereinafter referred to as "Compound group SX152").

The Compound (L-2), wherein Q represents the group represented by Q20; $R^{3b}$ represents a trifluoromethyl group; $R^{3c}$ represents a hydrogen atom; and $R^1$ represents any one substituent described in Table A1 or Table A2 (hereinafter referred to as "Compound group SX153").

The Compound (L-2), wherein Q represents the group represented by Q21; $R^{3b}$ represents a trifluoromethyl group; $R^{3c}$ represents a hydrogen atom; and $R^1$ represents any one substituent described in Table A1 or Table A2 (hereinafter referred to as "Compound group SX154").

The Compound (L-2), wherein Q represents the group represented by Q11; $R^{3b}$ represents a hydrogen atom; $R^{3c}$ represents a chlorine atom; and $R^1$ represents any one substituent described in Table A1 or Table A2 (hereinafter referred to as "Compound group SX155").

The Compound (L-2), wherein Q represents the group represented by Q12; $R^{3b}$ represents a hydrogen atom; $R^{3c}$ represents a chlorine atom; and $R^1$ represents any one substituent described in Table A1 or Table A2 (hereinafter referred to as "Compound group SX156").

The Compound (L-2), wherein Q represents the group represented by Q13; $R^{3b}$ represents a hydrogen atom; $R^{3c}$ represents a chlorine atom; and $R^1$ represents any one substituent described in Table A1 or Table A2 (hereinafter referred to as "Compound group SX157").

The Compound (L-2), wherein Q represents the group represented by Q14; $R^{3b}$ represents a hydrogen atom; $R^{3c}$ represents a chlorine atom; and $R^1$ represents any one substituent described in Table A1 or Table A2 (hereinafter referred to as "Compound group SX158").

The Compound (L-2), wherein Q represents the group represented by Q15; $R^{3b}$ represents a hydrogen atom; $R^{3c}$ represents a chlorine atom; and $R^1$ represents any one substituent described in Table A1 or Table A2 (hereinafter referred to as "Compound group SX159").

The Compound (L-2), wherein Q represents the group represented by Q16; $R^{3b}$ represents a hydrogen atom; $R^{3c}$ represents a chlorine atom; and $R^1$ represents any one substituent described in Table A1 or Table A2 (hereinafter referred to as "Compound group SX160").

The Compound (L-2), wherein Q represents the group represented by Q17; $R^{3b}$ represents a hydrogen atom; $R^{3c}$ represents a chlorine atom; and $R^1$ represents any one substituent described in Table A1 or Table A2 (hereinafter referred to as "Compound group SX161").

The Compound (L-2), wherein Q represents the group represented by Q18; $R^{3b}$ represents a hydrogen atom; $R^{3c}$ represents a chlorine atom; and $R^1$ represents any one substituent described in Table A1 or Table A2 (hereinafter referred to as "Compound group SX162").

The Compound (L-2), wherein Q represents the group represented by Q19; $R^{3b}$ represents a hydrogen atom; $R^{3c}$ represents a chlorine atom; and $R^1$ represents any one substituent described in Table A1 or Table A2 (hereinafter referred to as "Compound group SX163").

The Compound (L-2), wherein Q represents the group represented by Q20; $R^{3b}$ represents a hydrogen atom; $R^{3c}$ represents a chlorine atom; and $R^1$ represents any one substituent described in Table A1 or Table A2 (hereinafter referred to as "Compound group SX164").

The Compound (L-2), wherein Q represents the group represented by Q21; $R^{3b}$ represents a hydrogen atom; $R^{3c}$ represents a chlorine atom; and $R^1$ represents any one substituent described in Table A1 or Table A2 (hereinafter referred to as "Compound group SX165").

The Compound (L-2), wherein Q represents the group represented by Q11; $R^{3b}$ represents a hydrogen atom; $R^{3c}$ represents a bromine atom; and $R^1$ represents any one substituent described in Table A1 or Table A2 (hereinafter referred to as "Compound group SX166").

The Compound (L-2), wherein Q represents the group represented by Q12; $R^{3b}$ represents a hydrogen atom; $R^{3c}$ represents a bromine atom; and $R^1$ represents any one substituent described in Table A1 or Table A2 (hereinafter referred to as "Compound group SX167").

The Compound (L-2), wherein Q represents the group represented by Q13; $R^{3b}$ represents a hydrogen atom; $R^{3c}$ represents a bromine atom; and $R^1$ represents any one substituent described in Table A1 or Table A2 (hereinafter referred to as "Compound group SX168").

The Compound (L-2), wherein Q represents the group represented by Q14; $R^{3b}$ represents a hydrogen atom; $R^{3c}$ represents a bromine atom; and $R^1$ represents any one substituent described in Table A1 or Table A2 (hereinafter referred to as "Compound group SX169").

The Compound (L-2), wherein Q represents the group represented by Q15; $R^{3b}$ represents a hydrogen atom; $R^{3c}$ represents a bromine atom; and $R^1$ represents any one substituent described in Table A1 or Table A2 (hereinafter referred to as "Compound group SX170").

The Compound (L-2), wherein Q represents the group represented by Q16; $R^{3b}$ represents a hydrogen atom; $R^{3c}$ represents a bromine atom; and $R^1$ represents any one substituent described in Table A1 or Table A2 (hereinafter referred to as "Compound group SX171").

The Compound (L-2), wherein Q represents the group represented by Q17; $R^{3b}$ represents a hydrogen atom; $R^{3c}$ represents a bromine atom; and $R^1$ represents any one substituent described in Table A1 or Table A2 (hereinafter referred to as "Compound group SX172").

The Compound (L-2), wherein Q represents the group represented by Q18; $R^{3b}$ represents a hydrogen atom; $R^{3c}$ represents a bromine atom; and $R^1$ represents any one substituent described in Table A1 or Table A2 (hereinafter referred to as "Compound group SX173").

The Compound (L-2), wherein Q represents the group represented by Q19; $R^{3b}$ represents a hydrogen atom; $R^{3c}$ represents a bromine atom; and $R^1$ represents any one substituent described in Table A1 or Table A2 (hereinafter referred to as "Compound group SX174").

The Compound (L-2), wherein Q represents the group represented by Q20; $R^{3b}$ represents a hydrogen atom; $R^{3c}$ represents a bromine atom; and $R^1$ represents any one substituent described in Table A1 or Table A2 (hereinafter referred to as "Compound group SX175").

The Compound (L-2), wherein Q represents the group represented by Q21; $R^{3b}$ represents a hydrogen atom; $R^{3c}$ represents a bromine atom; and $R^1$ represents any one substituent described in Table A1 or Table A2 (hereinafter referred to as "Compound group SX176").

The Compound (L-2), wherein Q represents the group represented by Q11; $R^{3b}$ represents a hydrogen atom; $R^{3c}$ represents an iodine atom; and $R^1$ represents any one substituent described in Table A1 or Table A2 (hereinafter referred to as "Compound group SX177").

The Compound (L-2), wherein Q represents the group represented by Q12; $R^{3b}$ represents a hydrogen atom; $R^{3c}$ represents an iodine atom; and $R^1$ represents any one substituent described in Table A1 or Table A2 (hereinafter referred to as "Compound group SX178").

The Compound (L-2), wherein Q represents the group represented by Q13; $R^{3b}$ represents a hydrogen atom; $R^{3c}$ represents an iodine atom; and $R^1$ represents any one substituent described in Table A1 or Table A2 (hereinafter referred to as "Compound group SX179").

The Compound (L-2), wherein Q represents the group represented by Q14; $R^{3b}$ represents a hydrogen atom; $R^{3c}$ represents an iodine atom; and $R^1$ represents any one substituent described in Table A1 or Table A2 (hereinafter referred to as "Compound group SX180").

The Compound (L-2), wherein Q represents the group represented by Q15; $R^{3b}$ represents a hydrogen atom; $R^{3c}$ represents an iodine atom; and $R^1$ represents any one substituent described in Table A1 or Table A2 (hereinafter referred to as "Compound group SX181").

The Compound (L-2), wherein Q represents the group represented by Q16; $R^{3b}$ represents a hydrogen atom; $R^{3c}$ represents an iodine atom; and $R^1$ represents any one substituent described in Table A1 or Table A2 (hereinafter referred to as "Compound group SX182").

The Compound (L-2), wherein Q represents the group represented by Q17; $R^{3b}$ represents a hydrogen atom; $R^{3c}$ represents an iodine atom; and $R^1$ represents any one substituent described in Table A1 or Table A2 (hereinafter referred to as "Compound group SX183").

The Compound (L-2), wherein Q represents the group represented by Q18; $R^{3b}$ represents a hydrogen atom; $R^{3c}$ represents an iodine atom; and $R^1$ represents any one substituent described in Table A1 or Table A2 (hereinafter referred to as "Compound group SX184").

The Compound (L-2), wherein Q represents the group represented by Q19; $R^{3b}$ represents a hydrogen atom; $R^{3c}$ represents an iodine atom; and $R^1$ represents any one substituent described in Table A1 or Table A2 (hereinafter referred to as "Compound group SX185").

The Compound (L-2), wherein Q represents the group represented by Q20; $R^{3b}$ represents a hydrogen atom; $R^{3c}$ represents an iodine atom; and $R^1$ represents any one substituent described in Table A1 or Table A2 (hereinafter referred to as "Compound group SX186").

The Compound (L-2), wherein Q represents the group represented by Q21; $R^{3b}$ represents a hydrogen atom; $R^{3c}$ represents an iodine atom; and $R^1$ represents any one substituent described in Table A1 or Table A2 (hereinafter referred to as "Compound group SX187").

The Compound (L-2), wherein Q represents the group represented by Q11; $R^{3b}$ represents a hydrogen atom; $R^{3c}$ represents a trifluoromethyl group; and $R^1$ represents any one substituent described in Table A1 or Table A2 (hereinafter referred to as "Compound group SX188").

The Compound (L-2), wherein Q represents the group represented by Q12; $R^{3b}$ represents a hydrogen atom; $R^{3c}$ represents a trifluoromethyl group; and $R^1$ represents any one substituent described in Table A1 or Table A2 (hereinafter referred to as "Compound group SX189").

The Compound (L-2), wherein Q represents the group represented by Q13; $R^{3b}$ represents a hydrogen atom; $R^{3c}$ represents a trifluoromethyl group; and $R^1$ represents any one substituent described in Table A1 or Table A2 (hereinafter referred to as "Compound group SX190").

The Compound (L-2), wherein Q represents the group represented by Q14; $R^{3b}$ represents a hydrogen atom; $R^{3c}$ represents a trifluoromethyl group; and $R^1$ represents any one substituent described in Table A1 or Table A2 (hereinafter referred to as "Compound group SX191").

The Compound (L-2), wherein Q represents the group represented by Q15; $R^{3b}$ represents a hydrogen atom; $R^{3c}$ represents a trifluoromethyl group; and $R^1$ represents any one substituent described in Table A1 or Table A2 (hereinafter referred to as "Compound group SX192").

The Compound (L-2), wherein Q represents the group represented by Q16; $R^{3b}$ represents a hydrogen atom; $R^{3c}$ represents a trifluoromethyl group; and $R^1$ represents any one substituent described in Table A1 or Table A2 (hereinafter referred to as "Compound group SX193").

The Compound (L-2), wherein Q represents the group represented by Q17; $R^{3b}$ represents a hydrogen atom; $R^{3c}$ represents a trifluoromethyl group; and $R^1$ represents any one substituent described in Table A1 or Table A2 (hereinafter referred to as "Compound group SX194").

The Compound (L-2), wherein Q represents the group represented by Q18; $R^{3b}$ represents a hydrogen atom; $R^{3c}$ represents a trifluoromethyl group; and $R^1$ represents any one substituent described in Table A1 or Table A2 (hereinafter referred to as "Compound group SX195").

The Compound (L-2), wherein Q represents the group represented by Q19; $R^{3b}$ represents a hydrogen atom; $R^{3c}$ represents a trifluoromethyl group; and $R^1$ represents any one substituent described in Table A1 or Table A2 (hereinafter referred to as "Compound group SX196").

The Compound (L-2), wherein Q represents the group represented by Q20; $R^{3b}$ represents a hydrogen atom; $R^{3c}$ represents a trifluoromethyl group; and $R^1$ represents any one substituent described in Table A1 or Table A2 (hereinafter referred to as "Compound group SX197").

The Compound (L-2), wherein Q represents the group represented by Q21; $R^{3b}$ represents a hydrogen atom; $R^{3c}$ represents a trifluoromethyl group; and $R^1$ represents any one substituent described in Table A1 or Table A2 (hereinafter referred to as "Compound group SX198").

A compound represented by formula (L-3)

(L-3)

(hereinafter referred to as "Compound (L-3)"), wherein Q represents the group represented by Q11; $R^{3b}$ and $R^{3c}$ each represent a hydrogen atom; and $R^1$ represents any one substituent described in Table A1 or Table A2 (hereinafter referred to as "Compound group SX199").

The Compound (L-3), wherein Q represents the group represented by Q12; $R^{3b}$ and $R^{3c}$ each represent a hydrogen atom; and $R^1$ represents any one substituent described in Table A1 or Table A2 (hereinafter referred to as "Compound group SX200").

The Compound (L-3), wherein Q represents the group represented by Q13; $R^{3b}$ and $R^{3c}$ each represent a hydrogen atom; and $R^1$ represents any one substituent described in Table A1 or Table A2 (hereinafter referred to as "Compound group SX201").

The Compound (L-3), wherein Q represents the group represented by Q14; $R^{3b}$ and $R^{3c}$ each represent a hydrogen atom; and $R^1$ represents any one substituent described in Table A1 or Table A2 (hereinafter referred to as "Compound group SX202").

The Compound (L-3), wherein Q represents the group represented by Q15; $R^{3b}$ and $R^{3c}$ each represent a hydrogen atom; and $R^1$ represents any one substituent described in Table A1 or Table A2 (hereinafter referred to as "Compound group SX203").

The Compound (L-3), wherein Q represents the group represented by Q16; $R^{3b}$ and $R^{3c}$ each represent a hydrogen atom; and $R^1$ represents any one substituent described in Table A1 or Table A2 (hereinafter referred to as "Compound group SX204").

The Compound (L-3), wherein Q represents the group represented by Q17; $R^{3b}$ and $R^{3c}$ each represent a hydrogen atom; and $R^1$ represents any one substituent described in Table A1 or Table A2 (hereinafter referred to as "Compound group SX205").

The Compound (L-3), wherein Q represents the group represented by Q18; $R^{3b}$ and $R^{3c}$ each represent a hydrogen atom; and $R^1$ represents any one substituent described in Table A1 or Table A2 (hereinafter referred to as "Compound group SX206").

The Compound (L-3), wherein Q represents the group represented by Q19; $R^{3b}$ and $R^{3c}$ each represent a hydrogen atom; and $R^1$ represents any one substituent described in Table A1 or Table A2 (hereinafter referred to as "Compound group SX207").

The Compound (L-3), wherein Q represents the group represented by Q20; $R^{3b}$ and $R^{3c}$ each represent a hydrogen atom; and $R^1$ represents any one substituent described in Table A1 or Table A2 (hereinafter referred to as "Compound group SX208").

The Compound (L-3), wherein Q represents the group represented by Q21; $R^{3b}$ and $R^{3c}$ each represent a hydrogen atom; and $R^1$ represents any one substituent described in Table A1 or Table A2 (hereinafter referred to as "Compound group SX209").

The Compound (L-3), wherein Q represents the group represented by Q11; $R^{3b}$ represents a chlorine atom; $R^{3c}$ represents a hydrogen atom; and $R^1$ represents any one substituent described in Table A1 or Table A2 (hereinafter referred to as "Compound group SX210").

The Compound (L-3), wherein Q represents the group represented by Q12; $R^{3b}$ represents a chlorine atom; $R^{3c}$ represents a hydrogen atom; and $R^1$ represents any one substituent described in Table A1 or Table A2 (hereinafter referred to as "Compound group SX211").

The Compound (L-3), wherein Q represents the group represented by Q13; $R^{3b}$ represents a chlorine atom; $R^{3c}$ represents a hydrogen atom; and $R^1$ represents any one substituent described in Table A1 or Table A2 (hereinafter referred to as "Compound group SX212").

The Compound (L-3), wherein Q represents the group represented by Q14; $R^{3b}$ represents a chlorine atom; $R^{3c}$ represents a hydrogen atom; and $R^1$ represents any one substituent described in Table A1 or Table A2 (hereinafter referred to as "Compound group SX213").

The Compound (L-3), wherein Q represents the group represented by Q15; $R^{3b}$ represents a chlorine atom; $R^{3c}$ represents a hydrogen atom; and $R^1$ represents any one substituent described in Table A1 or Table A2 (hereinafter referred to as "Compound group SX214").

The Compound (L-3), wherein Q represents the group represented by Q16; $R^{3b}$ represents a chlorine atom; $R^{3c}$ represents a hydrogen atom; and $R^1$ represents any one substituent described in Table A1 or Table A2 (hereinafter referred to as "Compound group SX215").

The Compound (L-3), wherein Q represents the group represented by Q17; $R^{3b}$ represents a chlorine atom; $R^{3c}$ represents a hydrogen atom; and $R^1$ represents any one substituent described in Table A1 or Table A2 (hereinafter referred to as "Compound group SX216").

The Compound (L-3), wherein Q represents the group represented by Q18; $R^{3b}$ represents a chlorine atom; $R^{3c}$ represents a hydrogen atom; and $R^1$ represents any one substituent described in Table A1 or Table A2 (hereinafter referred to as "Compound group SX217").

The Compound (L-3), wherein Q represents the group represented by Q19; $R^{3b}$ represents a chlorine atom; $R^{3c}$ represents a hydrogen atom; and $R^1$ represents any one substituent described in Table A1 or Table A2 (hereinafter referred to as "Compound group SX218").

The Compound (L-3), wherein Q represents the group represented by Q20; $R^{3b}$ represents a chlorine atom; $R^{3c}$ represents a hydrogen atom; and $R^1$ represents any one substituent described in Table A1 or Table A2 (hereinafter referred to as "Compound group SX219").

The Compound (L-3), wherein Q represents the group represented by Q21; $R^{3b}$ represents a chlorine atom; $R^{3c}$ represents a hydrogen atom; and $R^1$ represents any one substituent described in Table A1 or Table A2 (hereinafter referred to as "Compound group SX220").

The Compound (L-3), wherein Q represents the group represented by Q11; $R^{3b}$ represents a bromine atom; $R^{3c}$ represents a hydrogen atom; and $R^1$ represents any one substituent described in Table A1 or Table A2 (hereinafter referred to as "Compound group SX221").

The Compound (L-3), wherein Q represents the group represented by Q12; $R^{3b}$ represents a bromine atom; $R^{3c}$ represents a hydrogen atom; and $R^1$ represents any one substituent described in Table A1 or Table A2 (hereinafter referred to as "Compound group SX222").

The Compound (L-3), wherein Q represents the group represented by Q13; $R^{3b}$ represents a bromine atom; $R^{3c}$ represents a hydrogen atom; and $R^1$ represents any one substituent described in Table A1 or Table A2 (hereinafter referred to as "Compound group SX223").

The Compound (L-3), wherein Q represents the group represented by Q14; $R^{3b}$ represents a bromine atom; $R^{3c}$ represents a hydrogen atom; and $R^1$ represents any one substituent described in Table A1 or Table A2 (hereinafter referred to as "Compound group SX224").

The Compound (L-3), wherein Q represents the group represented by Q15; $R^{3b}$ represents a bromine atom; $R^{3c}$ represents a hydrogen atom; and $R^1$ represents any one substituent described in Table A1 or Table A2 (hereinafter referred to as "Compound group SX225").

The Compound (L-3), wherein Q represents the group represented by Q16; $R^{3b}$ represents a bromine atom; $R^{3c}$ represents a hydrogen atom; and $R^1$ represents any one substituent described in Table A1 or Table A2 (hereinafter referred to as "Compound group SX226").

The Compound (L-3), wherein Q represents the group represented by Q17; $R^{3b}$ represents a bromine atom; $R^{3c}$ represents a hydrogen atom; and $R^1$ represents any one substituent described in Table A1 or Table A2 (hereinafter referred to as "Compound group SX227").

The Compound (L-3), wherein Q represents the group represented by Q18; $R^{3b}$ represents a bromine atom; $R^{3c}$ represents a hydrogen atom; and $R^1$ represents any one substituent described in Table A1 or Table A2 (hereinafter referred to as "Compound group SX228").

The Compound (L-3), wherein Q represents the group represented by Q19; $R^{3b}$ represents a bromine atom; $R^{3c}$ represents a hydrogen atom; and $R^1$ represents any one substituent described in Table A1 or Table A2 (hereinafter referred to as "Compound group SX229").

The Compound (L-3), wherein Q represents the group represented by Q20; $R^{3b}$ represents a bromine atom; $R^{3c}$ represents a hydrogen atom; and $R^1$ represents any one substituent described in Table A1 or Table A2 (hereinafter referred to as "Compound group SX230").

The Compound (L-3), wherein Q represents the group represented by Q21; $R^{3b}$ represents a bromine atom; $R^{3c}$ represents a hydrogen atom; and $R^1$ represents any one substituent described in Table A1 or Table A2 (hereinafter referred to as "Compound group SX231").

The Compound (L-3), wherein Q represents the group represented by Q11; $R^{3b}$ represents an iodine atom; $R^{3c}$ represents a hydrogen atom; and $R^1$ represents any one substituent described in Table A1 or Table A2 (hereinafter referred to as "Compound group SX232").

The Compound (L-3), wherein Q represents the group represented by Q12; $R^{3b}$ represents an iodine atom; $R^{3c}$ represents a hydrogen atom; and $R^1$ represents any one substituent described in Table A1 or Table A2 (hereinafter referred to as "Compound group SX233").

The Compound (L-3), wherein Q represents the group represented by Q13; $R^{3b}$ represents an iodine atom; $R^{3c}$ represents a hydrogen atom; and $R^1$ represents any one substituent described in Table A1 or Table A2 (hereinafter referred to as "Compound group SX234").

The Compound (L-3), wherein Q represents the group represented by Q14; $R^{3b}$ represents an iodine atom; $R^{3c}$ represents a hydrogen atom; and $R^1$ represents any one substituent described in Table A1 or Table A2 (hereinafter referred to as "Compound group SX235").

The Compound (L-3), wherein Q represents the group represented by Q15; $R^{3b}$ represents an iodine atom; $R^{3c}$ represents a hydrogen atom; and $R^1$ represents any one substituent described in Table A1 or Table A2 (hereinafter referred to as "Compound group SX236").

The Compound (L-3), wherein Q represents the group represented by Q16; $R^{3b}$ represents an iodine atom; $R^{3c}$ represents a hydrogen atom; and $R^1$ represents any one substituent described in Table A1 or Table A2 (hereinafter referred to as "Compound group SX237").

The Compound (L-3), wherein Q represents the group represented by Q17; $R^{3b}$ represents an iodine atom; $R^{3c}$ represents a hydrogen atom; and $R^1$ represents any one substituent described in Table A1 or Table A2 (hereinafter referred to as "Compound group SX238").

The Compound (L-3), wherein Q represents the group represented by Q18; $R^{3b}$ represents an iodine atom; $R^{3c}$ represents a hydrogen atom; and $R^1$ represents any one substituent described in Table A1 or Table A2 (hereinafter referred to as "Compound group SX239").

The Compound (L-3), wherein Q represents the group represented by Q19; $R^{3b}$ represents an iodine atom; $R^{3c}$ represents a hydrogen atom; and $R^1$ represents any one substituent described in Table A1 or Table A2 (hereinafter referred to as "Compound group SX240").

The Compound (L-3), wherein Q represents the group represented by Q20; $R^{3b}$ represents an iodine atom; $R^{3c}$ represents a hydrogen atom; and $R^1$ represents any one substituent described in Table A1 or Table A2 (hereinafter referred to as "Compound group SX241").

The Compound (L-3), wherein Q represents the group represented by Q21; $R^{3b}$ represents an iodine atom; $R^{3c}$ represents a hydrogen atom; and $R^1$ represents any one substituent described in Table A1 or Table A2 (hereinafter referred to as "Compound group SX242").

The Compound (L-3), wherein Q represents the group represented by Q11; $R^{3b}$ represents a trifluoromethyl group; $R^{3c}$ represents a hydrogen atom; and $R^1$ represents any one substituent described in Table A1 or Table A2 (hereinafter referred to as "Compound group SX243").

The Compound (L-3), wherein Q represents the group represented by Q12; $R^{3b}$ represents a trifluoromethyl group; $R^{3c}$ represents a hydrogen atom; and $R^1$ represents any one substituent described in Table A1 or Table A2 (hereinafter referred to as "Compound group SX244").

The Compound (L-3), wherein Q represents the group represented by Q13; $R^{3b}$ represents a trifluoromethyl group; $R^{3c}$ represents a hydrogen atom; and $R^1$ represents any one substituent described in Table A1 or Table A2 (hereinafter referred to as "Compound group SX245").

The Compound (L-3), wherein Q represents the group represented by Q14; $R^{3b}$ represents a trifluoromethyl group; $R^{3c}$ represents a hydrogen atom; and $R^1$ represents any one substituent described in Table A1 or Table A2 (hereinafter referred to as "Compound group SX246").

The Compound (L-3), wherein Q represents the group represented by Q15; $R^{3b}$ represents a trifluoromethyl group; $R^{3c}$ represents a hydrogen atom; and $R^1$ represents any one substituent described in Table A1 or Table A2 (hereinafter referred to as "Compound group SX247").

The Compound (L-3), wherein Q represents the group represented by Q16; $R^{3b}$ represents a trifluoromethyl group; $R^{3c}$ represents a hydrogen atom; and $R^1$ represents any one substituent described in Table A1 or Table A2 (hereinafter referred to as "Compound group SX248").

The Compound (L-3), wherein Q represents the group represented by Q17; $R^{3b}$ represents a trifluoromethyl group; $R^{3c}$ represents a hydrogen atom; and $R^1$ represents any one substituent described in Table A1 or Table A2 (hereinafter referred to as "Compound group SX249").

The Compound (L-3), wherein Q represents the group represented by Q18; $R^{3b}$ represents a trifluoromethyl group; $R^{3c}$ represents a hydrogen atom; and $R^1$ represents any one substituent described in Table A1 or Table A2 (hereinafter referred to as "Compound group SX250").

The Compound (L-3), wherein Q represents the group represented by Q19; $R^{3b}$ represents a trifluoromethyl group; $R^{3c}$ represents a hydrogen atom; and $R^1$ represents any one substituent described in Table A1 or Table A2 (hereinafter referred to as "Compound group SX251").

The Compound (L-3), wherein Q represents the group represented by Q20; $R^{3b}$ represents a trifluoromethyl group; $R^{3c}$ represents a hydrogen atom; and $R^1$ represents any one substituent described in Table A1 or Table A2 (hereinafter referred to as "Compound group SX252").

The Compound (L-3), wherein Q represents the group represented by Q21; $R^{3b}$ represents a trifluoromethyl group; $R^{3c}$ represents a hydrogen atom; and $R^1$ represents any one substituent described in Table A1 or Table A2 (hereinafter referred to as "Compound group SX253").

The Compound (L-3), wherein Q represents the group represented by Q11; $R^{3b}$ represents a hydrogen atom; $R^{3c}$ represents a chlorine atom; and $R^1$ represents any one substituent described in Table A1 or Table A2 (hereinafter referred to as "Compound group SX254").

The Compound (L-3), wherein Q represents the group represented by Q12; $R^{3b}$ represents a hydrogen atom; $R^{3c}$ represents a chlorine atom; and $R^1$ represents any one substituent described in Table A1 or Table A2 (hereinafter referred to as "Compound group SX255").

The Compound (L-3), wherein Q represents the group represented by Q13; $R^{3b}$ represents a hydrogen atom; $R^{3c}$ represents a chlorine atom; and $R^1$ represents any one substituent described in Table A1 or Table A2 (hereinafter referred to as "Compound group SX256").

The Compound (L-3), wherein Q represents the group represented by Q14; $R^{3b}$ represents a hydrogen atom; $R^{3c}$ represents a chlorine atom; and $R^1$ represents any one substituent described in Table A1 or Table A2 (hereinafter referred to as "Compound group SX257").

The Compound (L-3), wherein Q represents the group represented by Q15; $R^{3b}$ represents a hydrogen atom; $R^{3c}$ represents a chlorine atom; and $R^1$ represents any one substituent described in Table A1 or Table A2 (hereinafter referred to as "Compound group SX258").

The Compound (L-3), wherein Q represents the group represented by Q16; $R^{3b}$ represents a hydrogen atom; $R^{3c}$ represents a chlorine atom; and $R^1$ represents any one substituent described in Table A1 or Table A2 (hereinafter referred to as "Compound group SX259").

The Compound (L-3), wherein Q represents the group represented by Q17; $R^{3b}$ represents a hydrogen atom; $R^{3c}$ represents a chlorine atom; and $R^1$ represents any one substituent described in Table A1 or Table A2 (hereinafter referred to as "Compound group SX260").

The Compound (L-3), wherein Q represents the group represented by Q18; $R^{3b}$ represents a hydrogen atom; $R^{3c}$ represents a chlorine atom; and $R^1$ represents any one substituent described in Table A1 or Table A2 (hereinafter referred to as "Compound group SX261").

The Compound (L-3), wherein Q represents the group represented by Q19; $R^{3b}$ represents a hydrogen atom; $R^{3c}$ represents a chlorine atom; and $R^1$ represents any one substituent described in Table A1 or Table A2 (hereinafter referred to as "Compound group SX262").

The Compound (L-3), wherein Q represents the group represented by Q20; $R^{3b}$ represents a hydrogen atom; $R^{3c}$ represents a chlorine atom; and $R^1$ represents any one substituent described in Table A1 or Table A2 (hereinafter referred to as "Compound group SX263").

The Compound (L-3), wherein Q represents the group represented by Q21; $R^{3b}$ represents a hydrogen atom; $R^{3c}$ represents a chlorine atom; and $R^1$ represents any one substituent described in Table A1 or Table A2 (hereinafter referred to as "Compound group SX264").

The Compound (L-3), wherein Q represents the group represented by Q11; $R^{3b}$ represents a hydrogen atom; $R^{3c}$ represents a bromine atom; and $R^1$ represents any one substituent described in Table A1 or Table A2 (hereinafter referred to as "Compound group SX265").

The Compound (L-3), wherein Q represents the group represented by Q12; $R^{3b}$ represents a hydrogen atom; $R^{3c}$ represents a bromine atom; and $R^1$ represents any one substituent described in Table A1 or Table A2 (hereinafter referred to as "Compound group SX266").

The Compound (L-3), wherein Q represents the group represented by Q13; $R^{3b}$ represents a hydrogen atom; $R^{3c}$ represents a bromine atom; and $R^1$ represents any one substituent described in Table A1 or Table A2 (hereinafter referred to as "Compound group SX267").

The Compound (L-3), wherein Q represents the group represented by Q14; $R^{3b}$ represents a hydrogen atom; $R^{3c}$ represents a bromine atom; and $R^1$ represents any one substituent described in Table A1 or Table A2 (hereinafter referred to as "Compound group SX268").

The Compound (L-3), wherein Q represents the group represented by Q15; $R^{3b}$ represents a hydrogen atom; $R^{3c}$ represents a bromine atom; and $R^1$ represents any one substituent described in Table A1 or Table A2 (hereinafter referred to as "Compound group SX269").

The Compound (L-3), wherein Q represents the group represented by Q16; $R^{3b}$ represents a hydrogen atom; $R^{3c}$ represents a bromine atom; and $R^1$ represents any one substituent described in Table A1 or Table A2 (hereinafter referred to as "Compound group SX270").

The Compound (L-3), wherein Q represents the group represented by Q17; $R^{3b}$ represents a hydrogen atom; $R^{3c}$ represents a bromine atom; and $R^1$ represents any one substituent described in Table A1 or Table A2 (hereinafter referred to as "Compound group SX271").

The Compound (L-3), wherein Q represents the group represented by Q18; $R^{3b}$ represents a hydrogen atom; $R^{3c}$ represents a bromine atom; and $R^1$ represents any one substituent described in Table A1 or Table A2 (hereinafter referred to as "Compound group SX272").

The Compound (L-3), wherein Q represents the group represented by Q19; $R^{3b}$ represents a hydrogen atom; $R^{3c}$ represents a bromine atom; and $R^1$ represents any one substituent described in Table A1 or Table A2 (hereinafter referred to as "Compound group SX273").

The Compound (L-3), wherein Q represents the group represented by Q20; $R^{3b}$ represents a hydrogen atom; $R^{3c}$ represents a bromine atom; and $R^1$ represents any one substituent described in Table A1 or Table A2 (hereinafter referred to as "Compound group SX274").

The Compound (L-3), wherein Q represents the group represented by Q21; $R^{3b}$ represents a hydrogen atom; $R^{3c}$ represents a bromine atom; and $R^1$ represents any one substituent described in Table A1 or Table A2 (hereinafter referred to as "Compound group SX275").

The Compound (L-3), wherein Q represents the group represented by Q11; $R^{3b}$ represents a hydrogen atom; $R^{3c}$ represents an iodine atom; and $R^1$ represents any one substituent described in Table A1 or Table A2 (hereinafter referred to as "Compound group SX276").

The Compound (L-3), wherein Q represents the group represented by Q12; $R^{3b}$ represents a hydrogen atom; $R^{3c}$ represents an iodine atom; and $R^1$ represents any one substituent described in Table A1 or Table A2 (hereinafter referred to as "Compound group SX277").

The Compound (L-3), wherein Q represents the group represented by Q13; $R^{3b}$ represents a hydrogen atom; $R^{3c}$ represents an iodine atom; and $R^1$ represents any one substituent described in Table A1 or Table A2 (hereinafter referred to as "Compound group SX278").

The Compound (L-3), wherein Q represents the group represented by Q14; $R^{3b}$ represents a hydrogen atom; $R^{3c}$ represents an iodine atom; and $R^1$ represents any one substituent described in Table A1 or Table A2 (hereinafter referred to as "Compound group SX279").

The Compound (L-3), wherein Q represents the group represented by Q15; $R^{3b}$ represents a hydrogen atom; $R^{3c}$ represents an iodine atom; and $R^1$ represents any one substituent described in Table A1 or Table A2 (hereinafter referred to as "Compound group SX280").

The Compound (L-3), wherein Q represents the group represented by Q16; $R^{3b}$ represents a hydrogen atom; $R^{3c}$ represents an iodine atom; and $R^1$ represents any one substituent described in Table A1 or Table A2 (hereinafter referred to as "Compound group SX281").

The Compound (L-3), wherein Q represents the group represented by Q17; $R^{3b}$ represents a hydrogen atom; $R^{3c}$ represents an iodine atom; and $R^1$ represents any one substituent described in Table A1 or Table A2 (hereinafter referred to as "Compound group SX282").

The Compound (L-3), wherein Q represents the group represented by Q18; $R^{3b}$ represents a hydrogen atom; $R^{3c}$ represents an iodine atom; and $R^1$ represents any one substituent described in Table A1 or Table A2 (hereinafter referred to as "Compound group SX283").

The Compound (L-3), wherein Q represents the group represented by Q19; $R^{3b}$ represents a hydrogen atom; $R^{3c}$ represents an iodine atom; and $R^1$ represents any one substituent described in Table A1 or Table A2 (hereinafter referred to as "Compound group SX284").

The Compound (L-3), wherein Q represents the group represented by Q20; $R^{3b}$ represents a hydrogen atom; $R^{3c}$ represents an iodine atom; and $R^1$ represents any one substituent described in Table A1 or Table A2 (hereinafter referred to as "Compound group SX285").

The Compound (L-3), wherein Q represents the group represented by Q21; $R^{3b}$ represents a hydrogen atom; $R^{3c}$ represents an iodine atom; and $R^1$ represents any one substituent described in Table A1 or Table A2 (hereinafter referred to as "Compound group SX286").

The Compound (L-3), wherein Q represents the group represented by Q11; $R^{3b}$ represents a hydrogen atom; $R^{3c}$ represents a trifluoromethyl group; and $R^1$ represents any one substituent described in Table A1 or Table A2 (hereinafter referred to as "Compound group SX287").

The Compound (L-3), wherein Q represents the group represented by Q12; $R^{3b}$ represents a hydrogen atom; $R^{3c}$ represents a trifluoromethyl group; and $R^1$ represents any one substituent described in Table A1 or Table A2 (hereinafter referred to as "Compound group SX288").

The Compound (L-3), wherein Q represents the group represented by Q13; $R^{3b}$ represents a hydrogen atom; $R^{3c}$ represents a trifluoromethyl group; and $R^1$ represents any one substituent described in Table A1 or Table A2 (hereinafter referred to as "Compound group SX289").

The Compound (L-3), wherein Q represents the group represented by Q14; $R^{3b}$ represents a hydrogen atom; $R^{3c}$ represents a trifluoromethyl group; and $R^1$ represents any one substituent described in Table A1 or Table A2 (hereinafter referred to as "Compound group SX290").

The Compound (L-3), wherein Q represents the group represented by Q15; $R^{3b}$ represents a hydrogen atom; $R^{3c}$ represents a trifluoromethyl group; and $R^1$ represents any one substituent described in Table A1 or Table A2 (hereinafter referred to as "Compound group SX291").

The Compound (L-3), wherein Q represents the group represented by Q16; $R^{3b}$ represents a hydrogen atom; $R^{3c}$ represents a trifluoromethyl group; and $R^1$ represents any one substituent described in Table A1 or Table A2 (hereinafter referred to as "Compound group SX292").

The Compound (L-3), wherein Q represents the group represented by Q17; $R^{3b}$ represents a hydrogen atom; $R^{3c}$ represents a trifluoromethyl group; and $R^1$ represents any one substituent described in Table A1 or Table A2 (hereinafter referred to as "Compound group SX293").

The Compound (L-3), wherein Q represents the group represented by Q18; $R^{3b}$ represents a hydrogen atom; $R^{3c}$ represents a trifluoromethyl group; and $R^1$ represents any one substituent described in Table A1 or Table A2 (hereinafter referred to as "Compound group SX294").

The Compound (L-3), wherein Q represents the group represented by Q19; $R^{3b}$ represents a hydrogen atom; $R^{3c}$ represents a trifluoromethyl group; and $R^1$ represents any one substituent described in Table A1 or Table A2 (hereinafter referred to as "Compound group SX295").

The Compound (L-3), wherein Q represents the group represented by Q20; $R^{3b}$ represents a hydrogen atom; $R^{3c}$ represents a trifluoromethyl group; and $R^1$ represents any one substituent described in Table A1 or Table A2 (hereinafter referred to as "Compound group SX296").

The Compound (L-3), wherein Q represents the group represented by Q21; $R^{3b}$ represents a hydrogen atom; $R^{3c}$ represents a trifluoromethyl group; and $R^1$ represents any one substituent described in Table A1 or Table A2 (hereinafter referred to as "Compound group SX297").

A compound represented by formula (L-4)

(L-4)

(hereinafter referred to as "Compound (L-4)"), wherein Q represents the group represented by Q11; $R^{3c}$ represents a hydrogen atom; and $R^1$ represents any one substituent described in Table A1 or Table A2 (hereinafter referred to as "Compound group SX298").

The Compound (L-4), wherein Q represents the group represented by Q12; $R^{3c}$ represents a hydrogen atom; and $R^1$ represents any one substituent described in Table A1 or Table A2 (hereinafter referred to as "Compound group SX299").

The Compound (L-4), wherein Q represents the group represented by Q13; $R^{3c}$ represents a hydrogen atom; and $R^1$ represents any one substituent described in Table A1 or Table A2 (hereinafter referred to as "Compound group SX300").

The Compound (L-4), wherein Q represents the group represented by Q14; $R^{3c}$ represents a hydrogen atom; and $R^1$ represents any one substituent described in Table A1 or Table A2 (hereinafter referred to as "Compound group SX301").

The Compound (L-4), wherein Q represents the group represented by Q15; $R^{3c}$ represents a hydrogen atom; and $R^1$ represents any one substituent described in Table A1 or Table A2 (hereinafter referred to as "Compound group SX302").

The Compound (L-4), wherein Q represents the group represented by Q16; $R^{3c}$ represents a hydrogen atom; and $R^1$ represents any one substituent described in Table A1 or Table A2 (hereinafter referred to as "Compound group SX303").

The Compound (L-4), wherein Q represents the group represented by Q17; $R^{3c}$ represents a hydrogen atom; and $R^1$ represents any one substituent described in Table A1 or Table A2 (hereinafter referred to as "Compound group SX304").

The Compound (L-4), wherein Q represents the group represented by Q18; $R^{3c}$ represents a hydrogen atom; and $R^1$ represents any one substituent described in Table A1 or Table A2 (hereinafter referred to as "Compound group SX305").

The Compound (L-4), wherein Q represents the group represented by Q19; $R^{3c}$ represents a hydrogen atom; and $R^1$ represents any one substituent described in Table A1 or Table A2 (hereinafter referred to as "Compound group SX306").

The Compound (L-4), wherein Q represents the group represented by Q20; $R^{3c}$ represents a hydrogen atom; and $R^1$ represents any one substituent described in Table A1 or Table A2 (hereinafter referred to as "Compound group SX307").

The Compound (L-4), wherein Q represents the group represented by Q21; $R^{3c}$ represents a hydrogen atom; and $R^1$ represents any one substituent described in Table A1 or Table A2 (hereinafter referred to as "Compound group SX308").

The Compound (L-4), wherein Q represents the group represented by Q11; $R^{3c}$ represents a chlorine atom; and $R^1$ represents any one substituent described in Table A1 or Table A2 (hereinafter referred to as "Compound group SX309").

The Compound (L-4), wherein Q represents the group represented by Q12; $R^{3c}$ represents a chlorine atom; and $R^1$ represents any one substituent described in Table A1 or Table A2 (hereinafter referred to as "Compound group SX310").

The Compound (L-4), wherein Q represents the group represented by Q13; $R^{3c}$ represents a chlorine atom; and $R^1$ represents any one substituent described in Table A1 or Table A2 (hereinafter referred to as "Compound group SX311").

The Compound (L-4), wherein Q represents the group represented by Q14; $R^{3c}$ represents a chlorine atom; and $R^1$ represents any one substituent described in Table A1 or Table A2 (hereinafter referred to as "Compound group SX312").

The Compound (L-4), wherein Q represents the group represented by Q15; $R^{3c}$ represents a chlorine atom; and $R^1$ represents any one substituent described in Table A1 or Table A2 (hereinafter referred to as "Compound group SX313").

The Compound (L-4), wherein Q represents the group represented by Q16; $R^{3c}$ represents a chlorine atom; and $R^1$ represents any one substituent described in Table A1 or Table A2 (hereinafter referred to as "Compound group SX314").

The Compound (L-4), wherein Q represents the group represented by Q17; $R^{3c}$ represents a chlorine atom; and $R^1$ represents any one substituent described in Table A1 or Table A2 (hereinafter referred to as "Compound group SX315").

The Compound (L-4), wherein Q represents the group represented by Q18; $R^{3c}$ represents a chlorine atom; and $R^1$ represents any one substituent described in Table A1 or Table A2 (hereinafter referred to as "Compound group SX316").

The Compound (L-4), wherein Q represents the group represented by Q19; $R^{3c}$ represents a chlorine atom; and $R^1$ represents any one substituent described in Table A1 or Table A2 (hereinafter referred to as "Compound group SX317").

The Compound (L-4), wherein Q represents the group represented by Q20; $R^{3c}$ represents a chlorine atom; and $R^1$ represents any one substituent described in Table A1 or Table A2 (hereinafter referred to as "Compound group SX318").

The Compound (L-4), wherein Q represents the group represented by Q21; $R^{3c}$ represents a chlorine atom; and $R^1$ represents any one substituent described in Table A1 or Table A2 (hereinafter referred to as "Compound group SX319").

The Compound (L-4), wherein Q represents the group represented by Q11; $R^{3c}$ represents a bromine atom; and $R^1$ represents any one substituent described in Table A1 or Table A2 (hereinafter referred to as "Compound group SX320").

The Compound (L-4), wherein Q represents the group represented by Q12; $R^{3c}$ represents a bromine atom; and $R^1$ represents any one substituent described in Table A1 or Table A2 (hereinafter referred to as "Compound group SX321").

The Compound (L-4), wherein Q represents the group represented by Q13; $R^{3c}$ represents a bromine atom; and $R^1$ represents any one substituent described in Table A1 or Table A2 (hereinafter referred to as "Compound group SX322").

The Compound (L-4), wherein Q represents the group represented by Q14; $R^{3c}$ represents a bromine atom; and $R^1$ represents any one substituent described in Table A1 or Table A2 (hereinafter referred to as "Compound group SX323").

The Compound (L-4), wherein Q represents the group represented by Q15; $R^{3c}$ represents a bromine atom; and $R^1$ represents any one substituent described in Table A1 or Table A2 (hereinafter referred to as "Compound group SX324").

The Compound (L-4), wherein Q represents the group represented by Q16; $R^{3c}$ represents a bromine atom; and $R^1$ represents any one substituent described in Table A1 or Table A2 (hereinafter referred to as "Compound group SX325").

The Compound (L-4), wherein Q represents the group represented by Q17; $R^{3c}$ represents a bromine atom; and $R^1$ represents any one substituent described in Table A1 or Table A2 (hereinafter referred to as "Compound group SX326").

The Compound (L-4), wherein Q represents the group represented by Q18; $R^{3c}$ represents a bromine atom; and $R^1$ represents any one substituent described in Table A1 or Table A2 (hereinafter referred to as "Compound group SX327").

The Compound (L-4), wherein Q represents the group represented by Q19; $R^{3c}$ represents a bromine atom; and $R^1$ represents any one substituent described in Table A1 or Table A2 (hereinafter referred to as "Compound group SX328").

The Compound (L-4), wherein Q represents the group represented by Q20; $R^{3c}$ represents a bromine atom; and $R^1$ represents any one substituent described in Table A1 or Table A2 (hereinafter referred to as "Compound group SX329").

The Compound (L-4), wherein Q represents the group represented by Q21; $R^{3c}$ represents a bromine atom; and $R^1$ represents any one substituent described in Table A1 or Table A2 (hereinafter referred to as "Compound group SX330").

The Compound (L-4), wherein Q represents the group represented by Q11; $R^{3c}$ represents an iodine atom; and $R^1$ represents any one substituent described in Table A1 or Table A2 (hereinafter referred to as "Compound group SX331").

The Compound (L-4), wherein Q represents the group represented by Q12; $R^{3c}$ represents an iodine atom; and $R^1$ represents any one substituent described in Table A1 or Table A2 (hereinafter referred to as "Compound group SX332").

The Compound (L-4), wherein Q represents the group represented by Q13; $R^{3c}$ represents an iodine atom; and $R^1$ represents any one substituent described in Table A1 or Table A2 (hereinafter referred to as "Compound group SX333").

The Compound (L-4), wherein Q represents the group represented by Q14; $R^{3c}$ represents an iodine atom; and $R^1$ represents any one substituent described in Table A1 or Table A2 (hereinafter referred to as "Compound group SX334").

The Compound (L-4), wherein Q represents the group represented by Q15; $R^{3c}$ represents an iodine atom; and $R^1$ represents any one substituent described in Table A1 or Table A2 (hereinafter referred to as "Compound group SX335").

The Compound (L-4), wherein Q represents the group represented by Q16; $R^{3c}$ represents an iodine atom; and $R^1$ represents any one substituent described in Table A1 or Table A2 (hereinafter referred to as "Compound group SX336").

The Compound (L-4), wherein Q represents the group represented by Q17; $R^{3c}$ represents an iodine atom; and $R^1$ represents any one substituent described in Table A1 or Table A2 (hereinafter referred to as "Compound group SX337").

The Compound (L-4), wherein Q represents the group represented by Q18; $R^{3c}$ represents an iodine atom; and $R^1$ represents any one substituent described in Table A1 or Table A2 (hereinafter referred to as "Compound group SX338").

The Compound (L-4), wherein Q represents the group represented by Q19; $R^{3c}$ represents an iodine atom; and $R^1$ represents any one substituent described in Table A1 or Table A2 (hereinafter referred to as "Compound group SX339").

The Compound (L-4), wherein Q represents the group represented by Q20; $R^{3c}$ represents an iodine atom; and $R^1$ represents any one substituent described in Table A1 or Table A2 (hereinafter referred to as "Compound group SX340").

The Compound (L-4), wherein Q represents the group represented by Q21; $R^{3c}$ represents an iodine atom; and $R^1$ represents any one substituent described in Table A1 or Table A2 (hereinafter referred to as "Compound group SX341").

The Compound (L-4), wherein Q represents the group represented by Q11; $R^{3c}$ represents a trifluoromethyl group; and $R^1$ represents any one substituent described in Table A1 or Table A2 (hereinafter referred to as "Compound group SX342").

The Compound (L-4), wherein Q represents the group represented by Q12; $R^{3c}$ represents a trifluoromethyl group; and $R^1$ represents any one substituent described in Table A1 or Table A2 (hereinafter referred to as "Compound group SX343").

The Compound (L-4), wherein Q represents the group represented by Q13; $R^{3c}$ represents a trifluoromethyl group;

and R¹ represents any one substituent described in Table A1 or Table A2 (hereinafter referred to as "Compound group SX344").

The Compound (L-4), wherein Q represents the group represented by Q14; $R^{3c}$ represents a trifluoromethyl group; and R¹ represents any one substituent described in Table A1 or Table A2 (hereinafter referred to as "Compound group SX345").

The Compound (L-4), wherein Q represents the group represented by Q15; $R^{3c}$ represents a trifluoromethyl group; and R¹ represents any one substituent described in Table A1 or Table A2 (hereinafter referred to as "Compound group SX346").

The Compound (L-4), wherein Q represents the group represented by Q16; $R^{3c}$ represents a trifluoromethyl group; and R¹ represents any one substituent described in Table A1 or Table A2 (hereinafter referred to as "Compound group SX347").

The Compound (L-4), wherein Q represents the group represented by Q17; $R^{3c}$ represents a trifluoromethyl group; and R¹ represents any one substituent described in Table A1 or Table A2 (hereinafter referred to as "Compound group SX348").

The Compound (L-4), wherein Q represents the group represented by Q18; $R^{3c}$ represents a trifluoromethyl group; and R¹ represents any one substituent described in Table A1 or Table A2 (hereinafter referred to as "Compound group SX349").

The Compound (L-4), wherein Q represents the group represented by Q19; $R^{3c}$ represents a trifluoromethyl group; and R¹ represents any one substituent described in Table A1 or Table A2 (hereinafter referred to as "Compound group SX350").

The Compound (L-4), wherein Q represents the group represented by Q20; $R^{3c}$ represents a trifluoromethyl group; and R¹ represents any one substituent described in Table A1 or Table A2 (hereinafter referred to as "Compound group SX351").

The Compound (L-4), wherein Q represents the group represented by Q21; $R^{3c}$ represents a trifluoromethyl group; and R¹ represents any one substituent described in Table A1 or Table A2 (hereinafter referred to as "Compound group SX352").

A compound represented by formula (L-5)

(L-5)

(hereinafter referred to as "Compound (L-5)"), wherein Q represents the group represented by Q11; $R^{3b}$ represents a hydrogen atom; and R¹ represents any one substituent described in Table A1 or Table A2 (hereinafter referred to as "Compound group SX353").

The Compound (L-5), wherein Q represents the group represented by Q12; $R^{3b}$ represents a hydrogen atom; and R¹ represents any one substituent described in Table A1 or Table A2 (hereinafter referred to as "Compound group SX354").

The Compound (L-5), wherein Q represents the group represented by Q13; $R^{3b}$ represents a hydrogen atom; and R¹ represents any one substituent described in Table A1 or Table A2 (hereinafter referred to as "Compound group SX355").

The Compound (L-5), wherein Q represents the group represented by Q14; $R^{3b}$ represents a hydrogen atom; and R¹ represents any one substituent described in Table A1 or Table A2 (hereinafter referred to as "Compound group SX356").

The Compound (L-5), wherein Q represents the group represented by Q15; $R^{3b}$ represents a hydrogen atom; and R¹ represents any one substituent described in Table A1 or Table A2 (hereinafter referred to as "Compound group SX357").

The Compound (L-5), wherein Q represents the group represented by Q16; $R^{3b}$ represents a hydrogen atom; and R¹ represents any one substituent described in Table A1 or Table A2 (hereinafter referred to as "Compound group SX358").

The Compound (L-5), wherein Q represents the group represented by Q17; $R^{3b}$ represents a hydrogen atom; and R¹ represents any one substituent described in Table A1 or Table A2 (hereinafter referred to as "Compound group SX359").

The Compound (L-5), wherein Q represents the group represented by Q18; $R^{3b}$ represents a hydrogen atom; and R¹ represents any one substituent described in Table A1 or Table A2 (hereinafter referred to as "Compound group SX360").

The Compound (L-5), wherein Q represents the group represented by Q19; $R^{3b}$ represents a hydrogen atom; and R¹ represents any one substituent described in Table A1 or Table A2 (hereinafter referred to as "Compound group SX361").

The Compound (L-5), wherein Q represents the group represented by Q20; $R^{3b}$ represents a hydrogen atom; and R¹ represents any one substituent described in Table A1 or Table A2 (hereinafter referred to as "Compound group SX362").

The Compound (L-5), wherein Q represents the group represented by Q21; $R^{3b}$ represents a hydrogen atom; and R¹ represents any one substituent described in Table A1 or Table A2 (hereinafter referred to as "Compound group SX363").

The Compound (L-5), wherein Q represents the group represented by Q11; $R^{3b}$ represents a chlorine atom; and R¹ represents any one substituent described in Table A1 or Table A2 (hereinafter referred to as "Compound group SX364").

The Compound (L-5), wherein Q represents the group represented by Q12; $R^{3b}$ represents a chlorine atom; and R¹ represents any one substituent described in Table A1 or Table A2 (hereinafter referred to as "Compound group SX365").

The Compound (L-5), wherein Q represents the group represented by Q13; $R^{3b}$ represents a chlorine atom; and R¹ represents any one substituent described in Table A1 or Table A2 (hereinafter referred to as "Compound group SX366").

The Compound (L-5), wherein Q represents the group represented by Q14; $R^{3b}$ represents a chlorine atom; and R¹ represents any one substituent described in Table A1 or Table A2 (hereinafter referred to as "Compound group SX367").

The Compound (L-5), wherein Q represents the group represented by Q15; $R^{3b}$ represents a chlorine atom; and R¹ represents any one substituent described in Table A1 or Table A2 (hereinafter referred to as "Compound group SX368").

The Compound (L-5), wherein Q represents the group represented by Q16; $R^{3b}$ represents a chlorine atom; and $R^1$ represents any one substituent described in Table A1 or Table A2 (hereinafter referred to as "Compound group SX369").

The Compound (L-5), wherein Q represents the group represented by Q17; $R^{3b}$ represents a chlorine atom; and $R^1$ represents any one substituent described in Table A1 or Table A2 (hereinafter referred to as "Compound group SX370").

The Compound (L-5), wherein Q represents the group represented by Q18; $R^{3b}$ represents a chlorine atom; and $R^1$ represents any one substituent described in Table A1 or Table A2 (hereinafter referred to as "Compound group SX371").

The Compound (L-5), wherein Q represents the group represented by Q19; $R^{3b}$ represents a chlorine atom; and $R^1$ represents any one substituent described in Table A1 or Table A2 (hereinafter referred to as "Compound group SX372").

The Compound (L-5), wherein Q represents the group represented by Q20; $R^{3b}$ represents a chlorine atom; and $R^1$ represents any one substituent described in Table A1 or Table A2 (hereinafter referred to as "Compound group SX373").

The Compound (L-5), wherein Q represents the group represented by Q21; $R^{3b}$ represents a chlorine atom; and $R^1$ represents any one substituent described in Table A1 or Table A2 (hereinafter referred to as "Compound group SX374").

The Compound (L-5), wherein Q represents the group represented by Q11; $R^{3b}$ represents a bromine atom; and $R^1$ represents any one substituent described in Table A1 or Table A2 (hereinafter referred to as "Compound group SX375").

The Compound (L-5), wherein Q represents the group represented by Q12; $R^{3b}$ represents a bromine atom; and $R^1$ represents any one substituent described in Table A1 or Table A2 (hereinafter referred to as "Compound group SX376").

The Compound (L-5), wherein Q represents the group represented by Q13; $R^{3b}$ represents a bromine atom; and $R^1$ represents any one substituent described in Table A1 or Table A2 (hereinafter referred to as "Compound group SX377").

The Compound (L-5), wherein Q represents the group represented by Q14; $R^{3b}$ represents a bromine atom; and $R^1$ represents any one substituent described in Table A1 or Table A2 (hereinafter referred to as "Compound group SX378").

The Compound (L-5), wherein Q represents the group represented by Q15; $R^{3b}$ represents a bromine atom; and $R^1$ represents any one substituent described in Table A1 or Table A2 (hereinafter referred to as "Compound group SX379").

The Compound (L-5), wherein Q represents the group represented by Q16; $R^{3b}$ represents a bromine atom; and $R^1$ represents any one substituent described in Table A1 or Table A2 (hereinafter referred to as "Compound group SX380").

The Compound (L-5), wherein Q represents the group represented by Q17; $R^{3b}$ represents a bromine atom; and $R^1$ represents any one substituent described in Table A1 or Table A2 (hereinafter referred to as "Compound group SX381").

The Compound (L-5), wherein Q represents the group represented by Q18; $R^{3b}$ represents a bromine atom; and $R^1$ represents any one substituent described in Table A1 or Table A2 (hereinafter referred to as "Compound group SX382").

The Compound (L-5), wherein Q represents the group represented by Q19; $R^{3b}$ represents a bromine atom; and $R^1$ represents any one substituent described in Table A1 or Table A2 (hereinafter referred to as "Compound group SX383").

The Compound (L-5), wherein Q represents the group represented by Q20; $R^{3b}$ represents a bromine atom; and $R^1$ represents any one substituent described in Table A1 or Table A2 (hereinafter referred to as "Compound group SX384").

The Compound (L-5), wherein Q represents the group represented by Q21; $R^{3b}$ represents a bromine atom; and $R^1$ represents any one substituent described in Table A1 or Table A2 (hereinafter referred to as "Compound group SX385").

The Compound (L-5), wherein Q represents the group represented by Q11; $R^{3b}$ represents an iodine atom; and $R^1$ represents any one substituent described in Table A1 or Table A2 (hereinafter referred to as "Compound group SX386").

The Compound (L-5), wherein Q represents the group represented by Q12; $R^{3b}$ represents an iodine atom; and $R^1$ represents any one substituent described in Table A1 or Table A2 (hereinafter referred to as "Compound group SX387").

The Compound (L-5), wherein Q represents the group represented by Q13; $R^{3b}$ represents an iodine atom; and $R^1$ represents any one substituent described in Table A1 or Table A2 (hereinafter referred to as "Compound group SX388").

The Compound (L-5), wherein Q represents the group represented by Q14; $R^{3b}$ represents an iodine atom; and $R^1$ represents any one substituent described in Table A1 or Table A2 (hereinafter referred to as "Compound group SX389").

The Compound (L-5), wherein Q represents the group represented by Q15; $R^{3b}$ represents an iodine atom; and $R^1$ represents any one substituent described in Table A1 or Table A2 (hereinafter referred to as "Compound group SX390").

The Compound (L-5), wherein Q represents the group represented by Q16; $R^{3b}$ represents an iodine atom; and $R^1$ represents any one substituent described in Table A1 or Table A2 (hereinafter referred to as "Compound group SX391").

The Compound (L-5), wherein Q represents the group represented by Q17; $R^{3b}$ represents an iodine atom; and $R^1$ represents any one substituent described in Table A1 or Table A2 (hereinafter referred to as "Compound group SX392").

The Compound (L-5), wherein Q represents the group represented by Q18; $R^{3b}$ represents an iodine atom; and $R^1$ represents any one substituent described in Table A1 or Table A2 (hereinafter referred to as "Compound group SX393").

The Compound (L-5), wherein Q represents the group represented by Q19; $R^{3b}$ represents an iodine atom; and $R^1$ represents any one substituent described in Table A1 or Table A2 (hereinafter referred to as "Compound group SX394").

The Compound (L-5), wherein Q represents the group represented by Q20; $R^{3b}$ represents an iodine atom; and $R^1$ represents any one substituent described in Table A1 or Table A2 (hereinafter referred to as "Compound group SX395").

The Compound (L-5), wherein Q represents the group represented by Q21; $R^{3b}$ represents an iodine atom; and $R^1$ represents any one substituent described in Table A1 or Table A2 (hereinafter referred to as "Compound group SX396").

The Compound (L-5), wherein Q represents the group represented by Q11; $R^{3b}$ represents a trifluoromethyl group; and $R^1$ represents any one substituent described in Table A1 or Table A2 (hereinafter referred to as "Compound group SX397").

The Compound (L-5), wherein Q represents the group represented by Q12; $R^{3b}$ represents a trifluoromethyl group; and $R^1$ represents any one substituent described in Table A1 or Table A2 (hereinafter referred to as "Compound group SX398").

The Compound (L-5), wherein Q represents the group represented by Q13; $R^{3b}$ represents a trifluoromethyl group; and $R^1$ represents any one substituent described in Table A1 or Table A2 (hereinafter referred to as "Compound group SX399").

The Compound (L-5), wherein Q represents the group represented by Q14; $R^{3b}$ represents a trifluoromethyl group; and $R^1$ represents any one substituent described in Table A1 or Table A2 (hereinafter referred to as "Compound group SX400").

The Compound (L-5), wherein Q represents the group represented by Q15; $R^{3b}$ represents a trifluoromethyl group; and $R^1$ represents any one substituent described in Table A1 or Table A2 (hereinafter referred to as "Compound group SX401").

The Compound (L-5), wherein Q represents the group represented by Q16; $R^{3b}$ represents a trifluoromethyl group; and $R^1$ represents any one substituent described in Table A1 or Table A2 (hereinafter referred to as "Compound group SX402").

The Compound (L-5), wherein Q represents the group represented by Q17; $R^{3b}$ represents a trifluoromethyl group; and $R^1$ represents any one substituent described in Table A1 or Table A2 (hereinafter referred to as "Compound group SX403").

The Compound (L-5), wherein Q represents the group represented by Q18; $R^{3b}$ represents a trifluoromethyl group; and $R^1$ represents any one substituent described in Table A1 or Table A2 (hereinafter referred to as "Compound group SX404").

The Compound (L-5), wherein Q represents the group represented by Q19; $R^{3b}$ represents a trifluoromethyl group; and $R^1$ represents any one substituent described in Table A1 or Table A2 (hereinafter referred to as "Compound group SX405").

The Compound (L-5), wherein Q represents the group represented by Q20; $R^{3b}$ represents a trifluoromethyl group; and $R^1$ represents any one substituent described in Table A1 or Table A2 (hereinafter referred to as "Compound group SX406").

The Compound (L-5), wherein Q represents the group represented by Q21; $R^{3b}$ represents a trifluoromethyl group; and $R^1$ represents any one substituent described in Table A1 or Table A2 (hereinafter referred to as "Compound group SX407").

Q31 to Q52 represent the following groups.

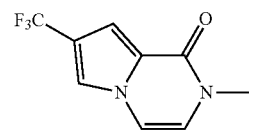

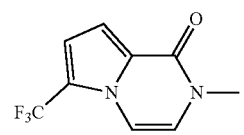

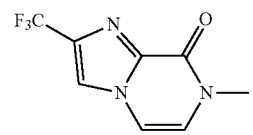

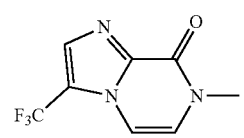

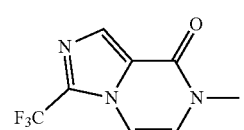

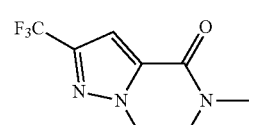

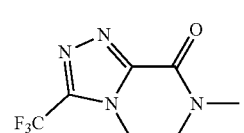

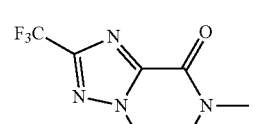

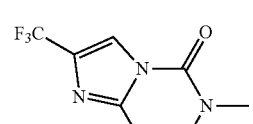

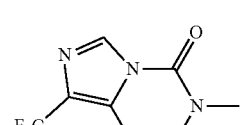

127

-continued

Q41 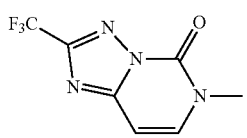

Q42 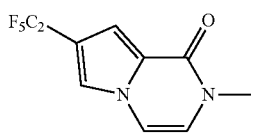

Q43 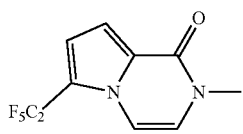

Q44 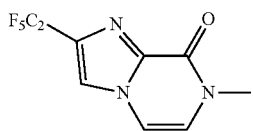

Q45 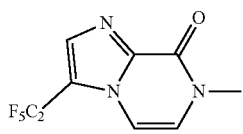

Q46 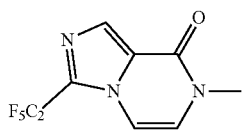

Q47 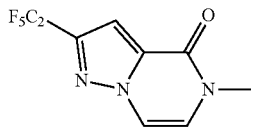

Q48 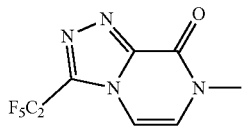

Q49 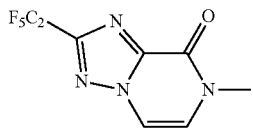

Q50 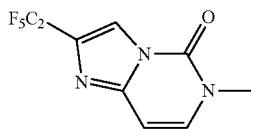

Q51 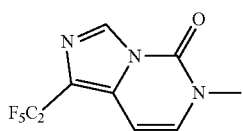

128

-continued

Q52 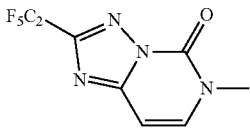

A compound represented by formula (L-6)

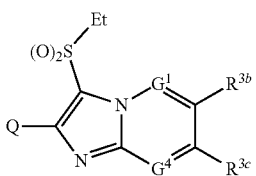

(L-6)

(hereinafter referred to as "Compound (L-6)"), wherein Q represents the group represented by Q31; $G^1$ and $G^4$ each represent CH; $R^{3b}$ represents any one substituent described in Table 8A to Table 11A; and $R^{3c}$ represents a hydrogen atom (hereinafter referred to as "Compound group SX408").

TABLE 3A

F
Me
Et
Pr
i-Pr
$CHF_2$
$CH=CH_2$
$CMe=CH_2$
$CMe_2CN$
$CMeCN_2$
1-F—c-Pr
2,2-$F_2$—c-Pr
c-Bu
c-Pen
c-Hex
1-CN—c-Bu
1-CN—c-Pen
1-CN—c-Hex
C(O)Me
C(O)c-Pr
C(O)OEt
C(O)NHc-Pr
CH=N—OH
CH=N—OMe
CH=N—OEt
CH=N—$OCH_2CF_3$
CMe=N—OH
CMe=N—OMe
CMe=N—OEt
CMe=N—$OCH_2CF_3$
C(NH2)=N—$OCH_2CF_3$
SEt
S(O)Et
S(O)$_2$Et
c-Pr

TABLE 4A

Ph
3-F—Ph
4-F—Ph
3-Cl—Ph
4-Cl—Ph
3-$CF_3$—Ph
4-$CF_3$—Ph
3-$NMe_2$—Ph

TABLE 4A-continued

4-NMe₂—Ph
3-CN—Ph
4-CN—Ph
4-C(O)NMe₂—Ph
4-NHC(O)Me—Ph
3,4-F₂—Ph
3,5-F₂—Ph
2,4-F₂—Ph
3,4,5-F₃—Ph
3,4-Cl₂—Ph
3,5-Cl₂—Ph
3,5-Cl₂-4-F—Ph
OPh
O-2-F—Ph
O-3-CF₃—Ph
O-4-CF₃—Ph
NH₂
NHCH₂CF₃
NHc-Pr
NH(1-CN—c-Pr)
NHOMe
NMe₂
NHC(O)Me
NHC(O)c-Pr
NMeC(O)c-Pr
NO₂
1-CN—c-Pr

TABLE 5A

Py2
4-F—Py2
5-F—Py2
4-Cl—Py2
5-Cl—Py2
4-CF₃—Py2
5-CF₃—Py2
6-CF₃—Py2
3-Me—Py2
4-Me—Py2
5-Me—Py2
6-Me—Py2
4-CN—Py2
5-CN—Py2
5-OCH₂CF₂CF₃—Py2
3,5-F₂—Py2
Py3
6-CF₃—Py3
5-CF₃—Py3
6-F—Py3
6-Cl—Py3
Py4
OPy2
OPy3
OPy4
O-5-CF₃—Py2
O-6-CF₃—Py2
OMe
OEt
OPr
Oi-Pr
Oc-Pr
OCMe₂CN
CN
CHO

TABLE 6A

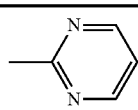

TABLE 6A-continued

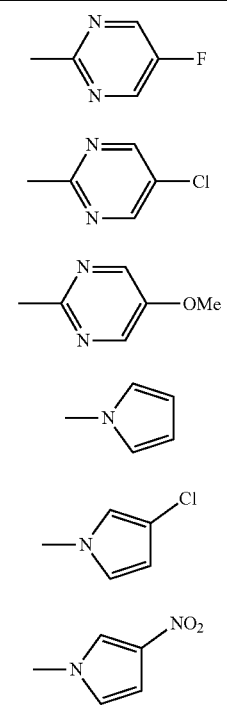

TABLE 7A

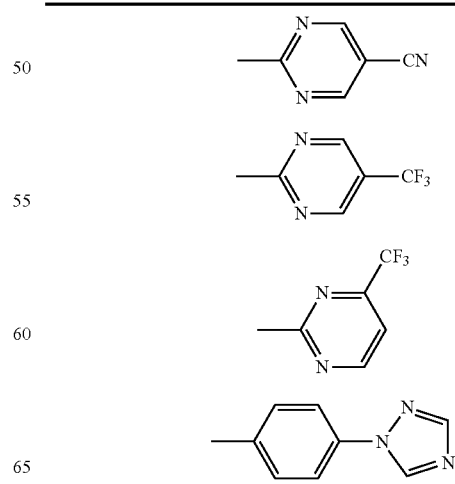

TABLE 7A-continued
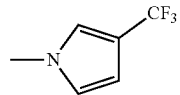
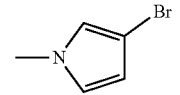
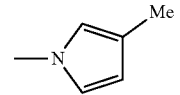
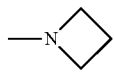
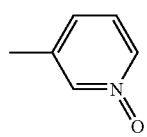
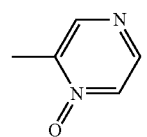
TABLE 8A
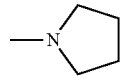
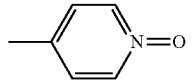
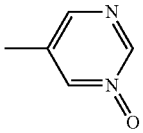
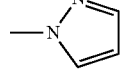
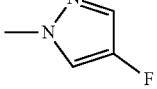
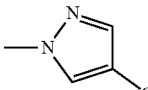
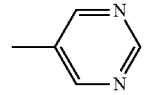
TABLE 8A-continued
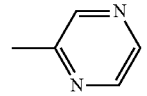
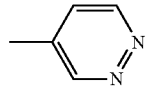
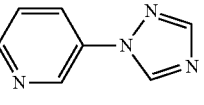
TABLE 9A
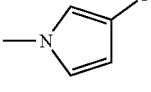
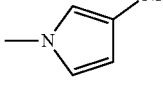
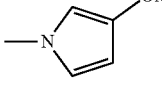

TABLE 10A

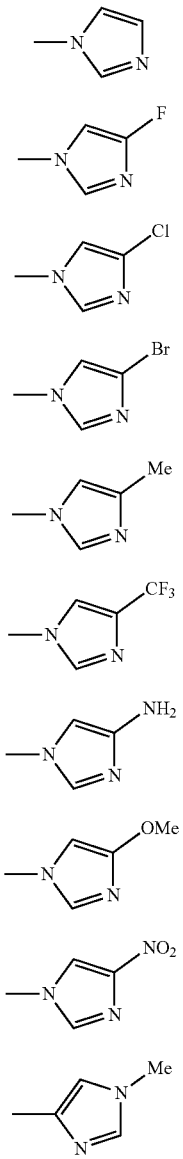

TABLE 11A

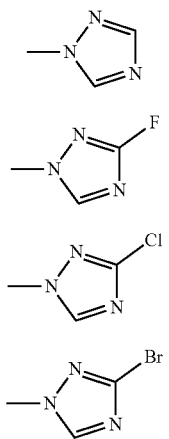

TABLE 11A-continued

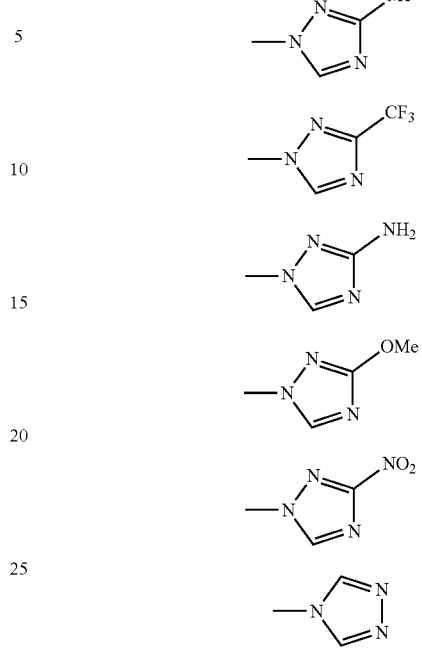

The Compound (L-6), wherein Q represents the group represented by Q32; $G^1$ and $G^4$ each represent CH; $R^{3b}$ represents any one substituent described in Table 3A to Table 11A; and $R^{3c}$ represents a hydrogen atom (hereinafter referred to as "Compound group SX409").

The Compound (L-6), wherein Q represents the group represented by Q33; $G^1$ and $G^4$ each represent CH; $R^{3b}$ represents any one substituent described in Table 3A to Table 11A; and $R^{3c}$ represents a hydrogen atom (hereinafter referred to as "Compound group SX410").

The Compound (L-6), wherein Q represents the group represented by Q34; $G^1$ and $G^4$ each represent CH; $R^{3b}$ represents any one substituent described in Table 3A to Table 11A; and $R^{3c}$ represents a hydrogen atom (hereinafter referred to as "Compound group SX411").

The Compound (L-6), wherein Q represents the group represented by Q35; $G^1$ and $G^4$ each represent CH; $R^{3b}$ represents any one substituent described in Table 3A to Table 11A; and $R^{3c}$ represents a hydrogen atom (hereinafter referred to as "Compound group SX412").

The Compound (L-6), wherein Q represents the group represented by Q36; $G^1$ and $G^4$ each represent CH; $R^{3b}$ represents any one substituent described in Table 3A to Table 11A; and $R^{3c}$ represents a hydrogen atom (hereinafter referred to as "Compound group SX413").

The Compound (L-6), wherein Q represents the group represented by Q37; $G^1$ and $G^4$ each represent CH; $R^{3b}$ represents any one substituent described in Table 3A to Table 11A; and $R^{3c}$ represents a hydrogen atom (hereinafter referred to as "Compound group SX414").

The Compound (L-6), wherein Q represents the group represented by Q38; $G^1$ and $G^4$ each represent CH; $R^{3b}$ represents any one substituent described in Table 3A to Table 11A; and $R^{3c}$ represents a hydrogen atom (hereinafter referred to as "Compound group SX415").

The Compound (L-6), wherein Q represents the group represented by Q39; $G^1$ and $G^4$ each represent CH; $R^{3b}$ represents any one substituent described in Table 3A to Table 11A; and $R^{3c}$ represents a hydrogen atom (hereinafter referred to as "Compound group SX416").

The Compound (L-6), wherein Q represents the group represented by Q40; $G^1$ and $G^4$ each represent CH; $R^{3b}$ represents any one substituent described in Table 3A to Table 11A; and $R^{3c}$ represents a hydrogen atom (hereinafter referred to as "Compound group SX417").

The Compound (L-6), wherein Q represents the group represented by Q41; $G^1$ and $G^4$ each represent CH; $R^{3b}$ represents any one substituent described in Table 3A to Table 11A; and $R^{3c}$ represents a hydrogen atom (hereinafter referred to as "Compound group SX418").

The Compound (L-6), wherein Q represents the group represented by Q42; $G^1$ and $G^4$ each represent CH; $R^{3b}$ represents any one substituent described in Table 3A to Table 11A; and $R^{3c}$ represents a hydrogen atom (hereinafter referred to as "Compound group SX419").

The Compound (L-6), wherein Q represents the group represented by Q43; $G^1$ and $G^4$ each represent CH; $R^{3b}$ represents any one substituent described in Table 3A to Table 11A; and $R^{3c}$ represents a hydrogen atom (hereinafter referred to as "Compound group SX420").

The Compound (L-6), wherein Q represents the group represented by Q44; $G^1$ and $G^4$ each represent CH; $R^{3b}$ represents any one substituent described in Table 3A to Table 11A; and $R^{3c}$ represents a hydrogen atom (hereinafter referred to as "Compound group SX421").

The Compound (L-6), wherein Q represents the group represented by Q45; $G^1$ and $G^4$ each represent CH; $R^{3b}$ represents any one substituent described in Table 3A to Table 11A; and $R^{3c}$ represents a hydrogen atom (hereinafter referred to as "Compound group SX422").

The Compound (L-6), wherein Q represents the group represented by Q46; $G^1$ and $G^4$ each represent CH; $R^{3b}$ represents any one substituent described in Table 3A to Table 11A; and $R^{3c}$ represents a hydrogen atom (hereinafter referred to as "Compound group SX423").

The Compound (L-6), wherein Q represents the group represented by Q47; $G^1$ and $G^4$ each represent CH; $R^{3b}$ represents any one substituent described in Table 3A to Table 11A; and $R^{3c}$ represents a hydrogen atom (hereinafter referred to as "Compound group SX424").

The Compound (L-6), wherein Q represents the group represented by Q48; $G^1$ and $G^4$ each represent CH; $R^{3b}$ represents any one substituent described in Table 3A to Table 11A; and $R^{3c}$ represents a hydrogen atom (hereinafter referred to as "Compound group SX425").

The Compound (L-6), wherein Q represents the group represented by Q49; $G^1$ and $G^4$ each represent CH; $R^{3b}$ represents any one substituent described in Table 3A to Table 11A; and $R^{3c}$ represents a hydrogen atom (hereinafter referred to as "Compound group SX426").

The Compound (L-6), wherein Q represents the group represented by Q50; $G^1$ and $G^4$ each represent CH; $R^{3b}$ represents any one substituent described in Table 3A to Table 11A; and $R^{3c}$ represents a hydrogen atom (hereinafter referred to as "Compound group SX427").

The Compound (L-6), wherein Q represents the group represented by Q51; $G^1$ and $G^4$ each represent CH; $R^{3b}$ represents any one substituent described in Table 3A to Table 11A; and $R^{3c}$ represents a hydrogen atom (hereinafter referred to as "Compound group SX428").

The Compound (L-6), wherein Q represents the group represented by Q52; $G^1$ and $G^4$ each represent CH; $R^{3b}$ represents any one substituent described in Table 3A to Table 11A; and $R^{3c}$ represents a hydrogen atom (hereinafter referred to as "Compound group SX429").

The Compound (L-6), wherein Q represents the group represented by Q31; $G^1$ and $G^4$ each represent CH; $R^{3b}$ represents a hydrogen atom; and $R^{3c}$ represents any one substituent described in Table 3A to Table 11A (hereinafter referred to as "Compound group SX430").

The Compound (L-6), wherein Q represents the group represented by Q32; $G^1$ and $G^4$ each represent CH; $R^{3b}$ represents a hydrogen atom; and $R^{3c}$ represents any one substituent described in Table 3A to Table 11A (hereinafter referred to as "Compound group SX431").

The Compound (L-6), wherein Q represents the group represented by Q33; $G^1$ and $G^4$ each represent CH; $R^{3b}$ represents a hydrogen atom; and $R^{3c}$ represents any one substituent described in Table 3A to Table 11A (hereinafter referred to as "Compound group SX432").

The Compound (L-6), wherein Q represents the group represented by Q34; $G^1$ and $G^4$ each represent CH; $R^{3b}$ represents a hydrogen atom; and $R^{3c}$ represents any one substituent described in Table 3A to Table 11A (hereinafter referred to as "Compound group SX433").

The Compound (L-6), wherein Q represents the group represented by Q35; $G^1$ and $G^4$ each represent CH; $R^{3b}$ represents a hydrogen atom; and $R^{3c}$ represents any one substituent described in Table 3A to Table 11A (hereinafter referred to as "Compound group SX434").

The Compound (L-6), wherein Q represents the group represented by Q36; $G^1$ and $G^4$ each represent CH; $R^{3b}$ represents a hydrogen atom; and $R^{3c}$ represents any one substituent described in Table 3A to Table 11A (hereinafter referred to as "Compound group SX435").

The Compound (L-6), wherein Q represents the group represented by Q37; $G^1$ and $G^4$ each represent CH; $R^{3b}$ represents a hydrogen atom; and $R^{3c}$ represents any one substituent described in Table 3A to Table 11A (hereinafter referred to as "Compound group SX436").

The Compound (L-6), wherein Q represents the group represented by Q38; $G^1$ and $G^4$ each represent CH; $R^{3b}$ represents a hydrogen atom; and $R^{3c}$ represents any one substituent described in Table 3A to Table 11A (hereinafter referred to as "Compound group SX437").

The Compound (L-6), wherein Q represents the group represented by Q39; $G^1$ and $G^4$ each represent CH; $R^{3b}$ represents a hydrogen atom; and $R^{3c}$ represents any one substituent described in Table 3A to Table 11A (hereinafter referred to as "Compound group SX438").

The Compound (L-6), wherein Q represents the group represented by Q40; $G^1$ and $G^4$ each represent CH; $R^{3b}$ represents a hydrogen atom; and $R^{3c}$ represents any one substituent described in Table 3A to Table 11A (hereinafter referred to as "Compound group SX439").

The Compound (L-6), wherein Q represents the group represented by Q41; $G^1$ and $G^4$ each represent CH; $R^{3b}$ represents a hydrogen atom; and $R^{3c}$ represents any one substituent described in Table 3A to Table 11A (hereinafter referred to as "Compound group SX440").

The Compound (L-6), wherein Q represents the group represented by Q42; $G^1$ and $G^4$ each represent CH; $R^{3b}$ represents a hydrogen atom; and $R^{3c}$ represents any one substituent described in Table 3A to Table 11A (hereinafter referred to as "Compound group SX441").

The Compound (L-6), wherein Q represents the group represented by Q43; $G^1$ and $G^4$ each represent CH; $R^{3b}$ represents a hydrogen atom; and $R^{3c}$ represents any one substituent described in Table 3A to Table 11A (hereinafter referred to as "Compound group SX442").

The Compound (L-6), wherein Q represents the group represented by Q44; $G^1$ and $G^4$ each represent CH; $R^{3b}$ represents a hydrogen atom; and $R^{3c}$ represents any one substituent described in Table 3A to Table 11A (hereinafter referred to as "Compound group SX443").

The Compound (L-6), wherein Q represents the group represented by Q45; $G^1$ and $G^4$ each represent CH; $R^{3b}$ represents a hydrogen atom; and $R^{3c}$ represents any one substituent described in Table 3A to Table 11A (hereinafter referred to as "Compound group SX444").

The Compound (L-6), wherein Q represents the group represented by Q46; $G^1$ and $G^4$ each represent CH; $R^{3b}$ represents a hydrogen atom; and $R^{3c}$ represents any one substituent described in Table 3A to Table 11A (hereinafter referred to as "Compound group SX445").

The Compound (L-6), wherein Q represents the group represented by Q47; $G^1$ and $G^4$ each represent CH; $R^{3b}$ represents a hydrogen atom; and $R^{3c}$ represents any one substituent described in Table 3A to Table 11A (hereinafter referred to as "Compound group SX446").

The Compound (L-6), wherein Q represents the group represented by Q48; $G^1$ and $G^4$ each represent CH; $R^{3b}$ represents a hydrogen atom; and $R^{3c}$ represents any one substituent described in Table 3A to Table 11A (hereinafter referred to as "Compound group SX447").

The Compound (L-6), wherein Q represents the group represented by Q49; $G^1$ and $G^4$ each represent CH; $R^{3b}$ represents a hydrogen atom; and $R^{3c}$ represents any one substituent described in Table 3A to Table 11A (hereinafter referred to as "Compound group SX448").

The Compound (L-6), wherein Q represents the group represented by Q50; $G^1$ and $G^4$ each represent CH; $R^{3b}$ represents a hydrogen atom; and $R^{3c}$ represents any one substituent described in Table 3A to Table 11A (hereinafter referred to as "Compound group SX449").

The Compound (L-6), wherein Q represents the group represented by Q51; $G^1$ and $G^4$ each represent CH; $R^{3b}$ represents a hydrogen atom; and $R^{3c}$ represents any one substituent described in Table 3A to Table 11A (hereinafter referred to as "Compound group SX450").

The Compound (L-6), wherein Q represents the group represented by Q52; $G^1$ and $G^4$ each represent CH; $R^{3b}$ represents a hydrogen atom; and $R^{3c}$ represents any one substituent described in Table 3A to Table 11A (hereinafter referred to as "Compound group SX451").

The Compound (L-6), wherein Q represents the group represented by Q31; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX452").

The Compound (L-6), wherein Q represents the group represented by Q32; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX453").

The Compound (L-6), wherein Q represents the group represented by Q33; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX454").

The Compound (L-6), wherein Q represents the group represented by Q34; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX455").

The Compound (L-6), wherein Q represents the group represented by Q35; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX456").

The Compound (L-6), wherein Q represents the group represented by Q36; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX457").

The Compound (L-6), wherein Q represents the group represented by Q37; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX458").

The Compound (L-6), wherein Q represents the group represented by Q38; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX459").

The Compound (L-6), wherein Q represents the group represented by Q39; G represents a nitrogen atom; $G^4$ represents CH; $R^{3b}$ represents any one substituent described in Table 3A to Table 11A; and $R^{3c}$ represents a hydrogen atom (hereinafter referred to as "Compound group SX460").

The Compound (L-6), wherein Q represents the group represented by Q40; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX461").

The Compound (L-6), wherein Q represents the group represented by Q41; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX462").

The Compound (L-6), wherein Q represents the group represented by Q42; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX463").

The Compound (L-6), wherein Q represents the group represented by Q43; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX464").

The Compound (L-6), wherein Q represents the group represented by Q44; G represents a nitrogen atom; $G^4$ represents CH; $R^{3b}$ represents any one substituent described in Table 3A to Table 11A; and $R^{3c}$ represents a hydrogen atom (hereinafter referred to as "Compound group SX465").

The Compound (L-6), wherein Q represents the group represented by Q45; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX466").

The Compound (L-6), wherein Q represents the group represented by Q46; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX467").

The Compound (L-6), wherein Q represents the group represented by Q47; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX468").

The Compound (L-6), wherein Q represents the group represented by Q48; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX469").

The Compound (L-6), wherein Q represents the group represented by Q49; G represents a nitrogen atom; $G^4$ represents CH; $R^{3b}$ represents any one substituent described in Table 3A to Table 11A; and $R^{3c}$ represents a hydrogen atom (hereinafter referred to as "Compound group SX470").

The Compound (L-6), wherein Q represents the group represented by Q50; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX471").

The Compound (L-6), wherein Q represents the group represented by Q51; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX472").

The Compound (L-6), wherein Q represents the group represented by Q52; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX473").

The Compound (L-6), wherein Q represents the group represented by Q31; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX474").

The Compound (L-6), wherein Q represents the group represented by Q32; G represents a nitrogen atom; $G^4$ represents CH; $R^{3b}$ represents a hydrogen atom; and $R^{3c}$ represents any one substituent described in Table 3A to Table 11A (hereinafter referred to as "Compound group SX475").

The Compound (L-6), wherein Q represents the group represented by Q33; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX476").

The Compound (L-6), wherein Q represents the group represented by Q34; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX477").

The Compound (L-6), wherein Q represents the group represented by Q35; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX478").

The Compound (L-6), wherein Q represents the group represented by Q36; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX479").

The Compound (L-6), wherein Q represents the group represented by Q37; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX480").

The Compound (L-6), wherein Q represents the group represented by Q38; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX481").

The Compound (L-6), wherein Q represents the group represented by Q39; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX482").

The Compound (L-6), wherein Q represents the group represented by Q40; G represents a nitrogen atom; $G^4$ represents CH; $R^{3b}$ represents a hydrogen atom; and $R^{3c}$ represents any one substituent described in Table 3A to Table 11A (hereinafter referred to as "Compound group SX483").

The Compound (L-6), wherein Q represents the group represented by Q41; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX484").

The Compound (L-6), wherein Q represents the group represented by Q42; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX485").

The Compound (L-6), wherein Q represents the group represented by Q43; G represents a nitrogen atom; $G^4$ represents CH; $R^{3b}$ represents a hydrogen atom; and $R^{3c}$ represents any one substituent described in Table 3A to Table 11A (hereinafter referred to as "Compound group SX486").

The Compound (L-6), wherein Q represents the group represented by Q44; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX487").

The Compound (L-6), wherein Q represents the group represented by Q45; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX488").

The Compound (L-6), wherein Q represents the group represented by Q46; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX489").

The Compound (L-6), wherein Q represents the group represented by Q47; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX490").

The Compound (L-6), wherein Q represents the group represented by Q48; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX491").

The Compound (L-6), wherein Q represents the group represented by Q49; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX492").

The Compound (L-6), wherein Q represents the group represented by Q50; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX493").

The Compound (L-6), wherein Q represents the group represented by Q51; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX494").

The Compound (L-6), wherein Q represents the group represented by Q52; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX495").

The Compound (L-6), wherein Q represents the group represented by Q31; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX496").

The Compound (L-6), wherein Q represents the group represented by Q32; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX497").

The Compound (L-6), wherein Q represents the group represented by Q33; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX498").

The Compound (L-6), wherein Q represents the group represented by Q34; G represents CH; $G^4$ represents a nitrogen atom; $R^{3b}$ represents any one substituent described in Table 3A to Table 11A; and $R^{3c}$ represents a hydrogen atom (hereinafter referred to as "Compound group SX499").

The Compound (L-6), wherein Q represents the group represented by Q35; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX500").

The Compound (L-6), wherein Q represents the group represented by Q36; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX501").

The Compound (L-6), wherein Q represents the group represented by Q37; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX502").

The Compound (L-6), wherein Q represents the group represented by Q38; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX503").

The Compound (L-6), wherein Q represents the group represented by Q39; G represents CH; $G^4$ represents a nitrogen atom; $R^{3b}$ represents any one substituent described in Table 3A to Table 11A; and $R^{3c}$ represents a hydrogen atom (hereinafter referred to as "Compound group SX504").

The Compound (L-6), wherein Q represents the group represented by Q40; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX505").

The Compound (L-6), wherein Q represents the group represented by Q41; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX506").

The Compound (L-6), wherein Q represents the group represented by Q42; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX507").

The Compound (L-6), wherein Q represents the group represented by Q43; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX508").

The Compound (L-6), wherein Q represents the group represented by Q44; G represents CH; $G^4$ represents a nitrogen atom; $R^{3b}$ represents any one substituent described in Table 3A to Table 11A; and $R^{3c}$ represents a hydrogen atom (hereinafter referred to as "Compound group SX509").

The Compound (L-6), wherein Q represents the group represented by Q45; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX510").

The Compound (L-6), wherein Q represents the group represented by Q46; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX511").

The Compound (L-6), wherein Q represents the group represented by Q47; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX512").

The Compound (L-6), wherein Q represents the group represented by Q48; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX513").

The Compound (L-6), wherein Q represents the group represented by Q49; G represents CH; $G^4$ represents a nitrogen atom; $R^{3b}$ represents any one substituent described in Table 3A to Table 11A; and $R^{3c}$ represents a hydrogen atom (hereinafter referred to as "Compound group SX514").

The Compound (L-6), wherein Q represents the group represented by Q50; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX515").

The Compound (L-6), wherein Q represents the group represented by Q51; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX516").

The Compound (L-6), wherein Q represents the group represented by Q52; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX517").

The Compound (L-6), wherein Q represents the group represented by Q31; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX518").

The Compound (L-6), wherein Q represents the group represented by Q32; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX519").

The Compound (L-6), wherein Q represents the group represented by Q33; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX520").

The Compound (L-6), wherein Q represents the group represented by Q34; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX521").

The Compound (L-6), wherein Q represents the group represented by Q35; G represents CH; $G^4$ represents a nitrogen atom; $R^{3b}$ represents a hydrogen atom; and $R^{3c}$ represents any one substituent described in Table 3A to Table 11A (hereinafter referred to as "Compound group SX522").

The Compound (L-6), wherein Q represents the group represented by Q36; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX523").

The Compound (L-6), wherein Q represents the group represented by Q37; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX524").

The Compound (L-6), wherein Q represents the group represented by Q38; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX525").

The Compound (L-6), wherein Q represents the group represented by Q39; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX526").

The Compound (L-6), wherein Q represents the group represented by Q40; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX527").

The Compound (L-6), wherein Q represents the group represented by Q41; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX528").

The Compound (L-6), wherein Q represents the group represented by Q42; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX529").

The Compound (L-6), wherein Q represents the group represented by Q43; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX530").

The Compound (L-6), wherein Q represents the group represented by Q44; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX531").

The Compound (L-6), wherein Q represents the group represented by Q45; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX532").

The Compound (L-6), wherein Q represents the group represented by Q46; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX533").

The Compound (L-6), wherein Q represents the group represented by Q47; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX534").

The Compound (L-6), wherein Q represents the group represented by Q48; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX535").

The Compound (L-6), wherein Q represents the group represented by Q49; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX536").

The Compound (L-6), wherein Q represents the group represented by Q50; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX537").

The Compound (L-6), wherein Q represents the group represented by Q51; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX538").

The Compound (L-6), wherein Q represents the group represented by Q52; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX539").

A compound represented by formula (L-7)

$$\text{(L-7)}$$

(hereinafter referred to as "Compound (L-7)"), wherein Q represents the group represented by Q31; and $R^{3c}$ represents any one substituent described in Table 3A to Table 11A (hereinafter referred to as "Compound group SX540").

The Compound (L-7), wherein Q represents the group represented by Q32; and $R^{3c}$ represents any one substituent described in Table 3A to Table 11A (hereinafter referred to as "Compound group SX541").

The Compound (L-7), wherein Q represents the group represented by Q33; and $R^{3c}$ represents any one substituent described in Table 3A to Table 11A (hereinafter referred to as "Compound group SX542").

The Compound (L-7), wherein Q represents the group represented by Q34; and $R^{3c}$ represents any one substituent described in Table 3A to Table 11A (hereinafter referred to as "Compound group SX543").

The Compound (L-7), wherein Q represents the group represented by Q35; and $R^{3c}$ represents any one substituent described in Table 3A to Table 11A (hereinafter referred to as "Compound group SX544").

The Compound (L-7), wherein Q represents the group represented by Q36; and $R^{3c}$ represents any one substituent described in Table 3A to Table 11A (hereinafter referred to as "Compound group SX545").

The Compound (L-7), wherein Q represents the group represented by Q37; and $R^{3c}$ represents any one substituent described in Table 3A to Table 11A (hereinafter referred to as "Compound group SX546").

The Compound (L-7), wherein Q represents the group represented by Q38; and $R^{3c}$ represents any one substituent described in Table 3A to Table 11A (hereinafter referred to as "Compound group SX547").

The Compound (L-7), wherein Q represents the group represented by Q39; and $R^{3c}$ represents any one substituent described in Table 3A to Table 11A (hereinafter referred to as "Compound group SX548").

The Compound (L-7), wherein Q represents the group represented by Q40; and $R^{3c}$ represents any one substituent described in Table 3A to Table 11A (hereinafter referred to as "Compound group SX549").

The Compound (L-7), wherein Q represents the group represented by Q41; and $R^{3c}$ represents any one substituent described in Table 3A to Table 11A (hereinafter referred to as "Compound group SX550").

The Compound (L-7), wherein Q represents the group represented by Q42; and $R^{3c}$ represents any one substituent described in Table 3A to Table 11A (hereinafter referred to as "Compound group SX551").

The Compound (L-7), wherein Q represents the group represented by Q43; and $R^{3c}$ represents any one substituent described in Table 3A to Table 11A (hereinafter referred to as "Compound group SX552").

The Compound (L-7), wherein Q represents the group represented by Q44; and $R^{3c}$ represents any one substituent described in Table 3A to Table 11A (hereinafter referred to as "Compound group SX553").

The Compound (L-7), wherein Q represents the group represented by Q45; and $R^{3c}$ represents any one substituent described in Table 3A to Table 11A (hereinafter referred to as "Compound group SX554").

The Compound (L-7), wherein Q represents the group represented by Q46; and $R^{3c}$ represents any one substituent described in Table 3A to Table 11A (hereinafter referred to as "Compound group SX555").

The Compound (L-7), wherein Q represents the group represented by Q47; and $R^{3c}$ represents any one substituent described in Table 3A to Table 11A (hereinafter referred to as "Compound group SX556").

The Compound (L-7), wherein Q represents the group represented by Q48; and $R^{3c}$ represents any one substituent described in Table 3A to Table 11A (hereinafter referred to as "Compound group SX557").

The Compound (L-7), wherein Q represents the group represented by Q49; and $R^{3c}$ represents any one substituent described in Table 3A to Table 11A (hereinafter referred to as "Compound group SX558").

The Compound (L-7), wherein Q represents the group represented by Q50; and $R^{3c}$ represents any one substituent described in Table 3A to Table 11A (hereinafter referred to as "Compound group SX559").

The Compound (L-7), wherein Q represents the group represented by Q51; and $R^{3c}$ represents any one substituent described in Table 3A to Table 11A (hereinafter referred to as "Compound group SX560").

The Compound (L-7), wherein Q represents the group represented by Q52; and $R^{3c}$ represents any one substituent described in Table 3A to Table 11A (hereinafter referred to as "Compound group SX561").

A compound represented by formula (L-8)

(L-8)

(hereinafter referred to as "Compound (L-8)"), wherein Q represents the group represented by Q31; and $R^{3b}$ represents any one substituent described in Table 3A to Table 11A (hereinafter referred to as "Compound group SX562").

The Compound (L-8), wherein Q represents the group represented by Q32; and $R^{3b}$ represents any one substituent described in Table 3A to Table 11A (hereinafter referred to as "Compound group SX563").

The Compound (L-8), wherein Q represents the group represented by Q33; and $R^{3b}$ represents any one substituent described in Table 3A to Table 11A (hereinafter referred to as "Compound group SX564").

The Compound (L-8), wherein Q represents the group represented by Q34; and $R^{3b}$ represents any one substituent described in Table 3A to Table 11A (hereinafter referred to as "Compound group SX565").

The Compound (L-8), wherein Q represents the group represented by Q35; and $R^{3b}$ represents any one substituent described in Table 3A to Table 11A (hereinafter referred to as "Compound group SX566").

The Compound (L-8), wherein Q represents the group represented by Q36; and $R^{3b}$ represents any one substituent described in Table 3A to Table 11A (hereinafter referred to as "Compound group SX567").

The Compound (L-8), wherein Q represents the group represented by Q37; and $R^{3b}$ represents any one substituent described in Table 3A to Table 11A (hereinafter referred to as "Compound group SX568").

The Compound (L-8), wherein Q represents the group represented by Q38; and $R^{3b}$ represents any one substituent described in Table 3A to Table 11A (hereinafter referred to as "Compound group SX569").

The Compound (L-8), wherein Q represents the group represented by Q39; and $R^{3b}$ represents any one substituent described in Table 3A to Table 11A (hereinafter referred to as "Compound group SX570").

The Compound (L-8), wherein Q represents the group represented by Q40; and $R^{3b}$ represents any one substituent described in Table 3A to Table 11A (hereinafter referred to as "Compound group SX571").

The Compound (L-8), wherein Q represents the group represented by Q41; and $R^{3b}$ represents any one substituent described in Table 3A to Table 11A (hereinafter referred to as "Compound group SX572").

The Compound (L-8), wherein Q represents the group represented by Q42; and $R^{3b}$ represents any one substituent described in Table 3A to Table 11A (hereinafter referred to as "Compound group SX573").

The Compound (L-8), wherein Q represents the group represented by Q43; and $R^{3b}$ represents any one substituent described in Table 3A to Table 11A (hereinafter referred to as "Compound group SX574").

The Compound (L-8), wherein Q represents the group represented by Q44; and $R^{3b}$ represents any one substituent described in Table 3A to Table 11A (hereinafter referred to as "Compound group SX575").

The Compound (L-8), wherein Q represents the group represented by Q45; and $R^{3b}$ represents any one substituent described in Table 3A to Table 11A (hereinafter referred to as "Compound group SX576").

The Compound (L-8), wherein Q represents the group represented by Q46; and $R^{3b}$ represents any one substituent described in Table 3A to Table 11A (hereinafter referred to as "Compound group SX577").

The Compound (L-8), wherein Q represents the group represented by Q47; and $R^{3b}$ represents any one substituent described in Table 3A to Table 11A (hereinafter referred to as "Compound group SX578").

The Compound (L-8), wherein Q represents the group represented by Q48; and $R^{3b}$ represents any one substituent described in Table 3A to Table 11A (hereinafter referred to as "Compound group SX579").

The Compound (L-8), wherein Q represents the group represented by Q49; and $R^{3b}$ represents any one substituent described in Table 3A to Table 11A (hereinafter referred to as "Compound group SX580").

The Compound (L-8), wherein Q represents the group represented by Q50; and $R^{3b}$ represents any one substituent described in Table 3A to Table 11A (hereinafter referred to as "Compound group SX581").

The Compound (L-8), wherein Q represents the group represented by Q51; and $R^{3b}$ represents any one substituent described in Table 3A to Table 11A (hereinafter referred to as "Compound group SX582").

The Compound (L-8), wherein Q represents the group represented by Q52; and $R^{3b}$ represents any one substituent described in Table 3A to Table 11A (hereinafter referred to as "Compound group SX583").

A compound represented by formula (L-9)

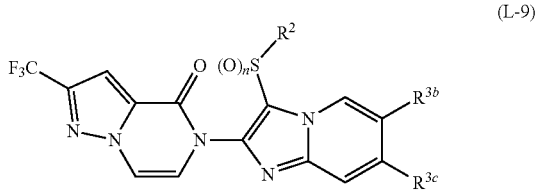

(L-9)

(hereinafter referred to as "Compound (L-9)"), wherein n represents 1; $R^2$ represents an ethyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX584").

The Compound (L-9), wherein n represents 0; $R^2$ represents an ethyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX585").

The Compound (L-9), wherein n represents 2; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX586").

The Compound (L-9), wherein n represents 1; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX587").

The Compound (L-9), wherein n represents 0; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX588").

The Compound (L-9), wherein n represents 1; $R^2$ represents an ethyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX589").

The Compound (L-9), wherein n represents 0; $R^2$ represents an ethyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX590").

The Compound (L-9), wherein n represents 2; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX591").

The Compound (L-9), wherein n represents 1; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX592").

The Compound (L-9), wherein n represents 0; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX593").

A compound represented by formula (L-10)

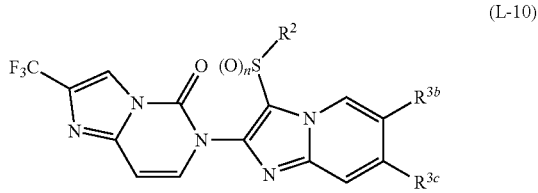

(L-10)

(hereinafter referred to as "Compound (L-10)"), wherein n represents 1; $R^2$ represents an ethyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX594").

The Compound (L-10), wherein n represents 0; $R^2$ represents an ethyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX595").

The Compound (L-10), wherein n represents 2; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX596").

The Compound (L-10), wherein n represents 1; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX597").

The Compound (L-10), wherein n represents 0; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX598").

The Compound (L-10), wherein n represents 1; $R^2$ represents an ethyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX599").

The Compound (L-10), wherein n represents 0; $R^2$ represents an ethyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX600").

The Compound (L-10), wherein n represents 2; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX601").

The Compound (L-10), wherein n represents 1; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX602").

The Compound (L-10), wherein n represents 0; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX603").

A compound represented by formula (L-11)

(hereinafter referred to as "Compound (L-11)"), wherein n represents 1; $R^2$ represents an ethyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX604").

The Compound (L-11), wherein n represents 0; $R^2$ represents an ethyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX605").

The Compound (L-11), wherein n represents 2; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX606").

The Compound (L-11), wherein n represents 1; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX607").

The Compound (L-11), wherein n represents 0; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX608").

The Compound (L-11), wherein n represents 1; $R^2$ represents an ethyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX609").

The Compound (L-11), wherein n represents 0; $R^2$ represents an ethyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX610").

The Compound (L-11), wherein n represents 2; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX611").

The Compound (L-11), wherein n represents 1; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX612").

The Compound (L-11), wherein n represents 0; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX613").

A compound represented by formula (L-12)

(hereinafter referred to as "Compound (L-12)"), wherein n represents 1; $R^2$ represents an ethyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX614").

The Compound (L-12), wherein n represents 0; $R^2$ represents an ethyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX615").

The Compound (L-12), wherein n represents 2; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX616").

The Compound (L-12), wherein n represents 1; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX617").

The Compound (L-12), wherein n represents 0; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX618").

The Compound (L-12), wherein n represents 1; $R^2$ represents an ethyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX619").

The Compound (L-12), wherein n represents 0; $R^2$ represents an ethyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX620").

The Compound (L-12), wherein n represents 2; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX621").

The Compound (L-12), wherein n represents 1; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX622").

The Compound (L-12), wherein n represents 0; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX623").

A compound represented by formula (L-13)

$$(L\text{-}13)$$

(hereinafter referred to as "Compound (L-13)"), wherein n represents 1; $R^2$ represents an ethyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX624").

The Compound (L-13), wherein n represents 0; $R^2$ represents an ethyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX625").

The Compound (L-13), wherein n represents 2; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX626").

The Compound (L-13), wherein n represents 1; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX627").

The Compound (L-13), wherein n represents 0; $R^2$ represents a methyl group; $R^{3c}$ represents a hydrogen atom; and $R^{3b}$ represents any one substituent of a hydrogen atom, a chlorine atom, a bromine atom, an iodine atom, a trifluoromethyl group, and the substituents described in Table 3A to Table 11A (hereinafter referred to as "Compound group SX628").

The Compound (L-13), wherein n represents 1; $R^2$ represents an ethyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX629").

The Compound (L-13), wherein n represents 0; $R^2$ represents an ethyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX630").

The Compound (L-13), wherein n represents 2; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX631").

The Compound (L-13), wherein n represents 1; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX632").

The Compound (L-13), wherein n represents 0; $R^2$ represents a methyl group; $R^{3b}$ represents a hydrogen atom; and $R^{3c}$ represents any one substituent of a chlorine atom, a bromine atom, an iodine atom, a trifluoromethyl group, and the substituents described in Table 3A to Table 11A (hereinafter referred to as "Compound group SX633").

Next, Formulation Examples of the Present compound are shown below. The "part(s)" represents "part(s) by weight". Also, the expression of "Present compound S" represents the compounds described in the Compound groups SX1 to SX633.

Formulation Example 1

Any one of the Present compound S (10 parts) is mixed with a mixture of xylene (35 parts) and DMF (35 parts), then polyoxyethylene styryl phenyl ether (14 parts) and calcium dodecylbenzene sulfonate (6 parts) are added thereto, and the resulting mixture is mixed to obtain each formulation.

Formulation Example 2

Sodium lauryl sulfate (4 parts), calcium lignin sulfonate (2 parts), wet silica (20 parts), and diatomaceous earth (54 parts) are mixed, any one of the Present compound S (20 parts) is added thereto, and the resulting mixture is mixed to obtain each formulation.

Formulation Example 3

To any one of the Present compound S (2 parts) are added wet silica (1 part), calcium lignin sulfonate (2 parts), bentonite (30 parts), and kaolin clay (65 parts), and the resulting mixture is mixed. To the mixture is then added an appropriate amount of water, the resulting mixture is additionally stirred, and subjected to granulation with a granulator and forced-air drying to obtain each formulation.

Formulation Example 4

Any one of the Present compound S (1 part) is mixed with an appropriate amount of acetone, then wet silica (5 parts), acidic isopropyl phosphate (0.3 part), and kaolin clay (93.7 parts) are added thereto, the resulting mixture is mixed with stirring thoroughly, and acetone is removed from the mixture by evaporation to obtain each formulation.

Formulation Example 5

A mixture of polyoxyethylene alkyl ether sulfate ammonium salt and wet silica (weight ratio of 1:1) (35 parts), any one of the Present compound S (20 parts), and water (45 parts) are thoroughly mixed to obtain each formulation.

Formulation Example 6

Any one of the Present compound S (0.1 part) is mixed with a mixture of xylene (5 parts) and trichloroethane (5 parts), and the resulting mixture is then mixed with kerosene (89.9 parts) to obtain each formulation.

Formulation Example 7

Any one of the Present compound S (10 mg) is mixed with acetone (0.5 mL), the resulting solution is added dropwise to a solid feed powder for an animal (solid feed powder for rearing and breeding CE-2, manufactured by CLEA Japan, Inc.) (5 g), the resulting mixture is uniformly mixed, and then acetone is dried by evaporation to obtain each poison bait.

Formulation Example 8

Any one of the Present compound S (0.1 part) and Neothiozole (manufactured by Chuo Kasei Co., Ltd.) (49.9 parts) are placed into an aerosol can. After mounting an aerosol valve, dimethyl ether (25 parts) and LPG (25 parts) are filled, then the aerosol can is shaken, and further an actuator is mounted thereto to obtain each oily aerosol.

Formulation Example 9

A mixture of any one of the Present compound S (0.6 part), 2,6-di-tert-butyl-4-methylphenol (0.01 part), xylene (5 part), kerosene (3.39 parts), and Rheodol (registered trademark) MO-60 (1 part), and distilled water (50 parts) are filled into an aerosol container, and a valve part is attached. Then, LPG (40 parts) is filled therein through the valve to obtain each aqueous aerosol.

Formulation Example 10

Any one of the Present compound S (0.1 g) is mixed with propylene glycol (2 mL), and the resulting solution is impregnated into a ceramic plate having a size of 4.0 cm×4.0 cm and a thickness of 1.2 cm to obtain each thermal smoking agent.

Formulation Example 11

Any one of the Present compound S (5 parts) and ethylene-methyl methacrylate copolymer (the ratio of the methyl methacrylate relative to the total weight of the copolymer: 10% by weight) (95 parts) are melted and kneaded, and the resulting kneaded product is extruded from an extrusion molding machine to obtain each rod-shaped molded product having a length of 15 cm and a diameter of 3 mm.

Formulation Example 12

Any one of the Present compound S (5 parts) and a flexible vinyl chloride resin (95 parts) are melted and kneaded, and the resulting kneaded product is extruded from an extrusion molding machine to obtain each rod-shaped molded product having a length of 15 cm and a diameter of 3 mm.

Formulation Example 13

Any one of the Present compound S (100 mg), lactose (68.75 mg), corn starch (237.5 mg), microcrystalline cellulose (43.75 mg), polyvinylpyrrolidone (18.75 mg), sodium carboxymethyl starch (28.75 mg), and magnesium stearate (2.5 mg) are mixed, and the resulting mixture is compressed to an appropriate size to obtain each tablet.

Formulation Example 14

Any one of the Present compound S (25 mg), lactose (60 mg), corn starch (25 mg), carmellose calcium (6 mg), and an appropriate amount of 5% hydroxypropyl methylcellulose are mixed, and the resulting mixture is filled into a hard shell gelatin capsule or a hydroxypropyl methylcellulose capsule to obtain each capsule.

Formulation Example 15

To any one of the Present compound S (100 mg), fumaric acid (500 mg), sodium chloride (2,000 mg), methylparaben (150 mg), propylparaben (50 mg), granulated sugar (25,000 mg), sorbitol (70% solution) (13,000 mg), Veegum (registered trademark) K (100 mg), perfume (35 mg), and colorant (500 mg) is added distilled water so that the final volume is set to be 100 mL, and the resulting mixture is mixed to obtain each suspension for oral administration.

Formulation Example 16

Any one of the Present compound S (5 parts) is mixed with an emulsifier (5 parts), benzyl alcohol (3 parts), and propylene glycol (30 parts), phosphate buffer is added thereto so that the pH of the solution is set to be 6.0 to 6.5, and then water is added thereto as the rest parts to obtain each solution for oral administration.

Formulation Example 17

Aluminum distearate (5 parts) is added to fractional distilled coconut oil (57 parts) and polysorbate 85 (3 parts), and dispersed by heating. The resulting mixture is cooled to room temperature, and saccharin (25 parts) is dispersed in the oil vehicle. Any one of the Present compound S (10 parts) is distributed thereto to obtain each paste-like formulation for oral administration.

Formulation Example 18

Any one of the Present compound S (5 parts) is mixed with a limestone filler (95 parts), and the resulting mixture is subjected to a wet granulation to obtain each granule for oral administration.

Formulation Example 19

Any one of the Present compound S (5 parts) is mixed with diethylene glycol monoethyl ether (80 parts), propylene carbonate (15 parts) is added thereto, and the resulting mixture is mixed to obtain each spot-on solution.

Formulation Example 20

Any one of the Present compound S (10 parts) is mixed with diethylene glycol monoethyl ether (70 parts), 2-octyldodecanol (20 parts) is added thereto, and the resulting mixture is mixed to obtain each pour-on solution.

Formulation Example 21

Any one of the Present compound S (0.1 part), sodium polyoxyethylene lauryl ether sulfate (25% aqueous solution) (40 parts), lauramidopropyl betaine (5 parts), coconut oil fatty acid ethanolamide (5 parts), carboxyvinyl polymer (0.5 part), and purified water (49.4 parts) are thoroughly mixed to obtain each shampoo formulation.

Formulation Example 22

Any one of the Present compound S (0.15 part), an animal feed (95 parts), and a mixture (4.85 parts) consisting of calcium hydrogen phosphate, diatomaceous earth, Aerosil (registered trademark), and carbonate (or chalk) are mixed with stirring thoroughly to obtain each premix for an animal feed.

Formulation Example 23

Any one of the Present compound S (7.2 g) and Hosco (registered trademark) S-55 (92.8 g) are mixed at 100° C., the resulting mixture is poured into a suppository mold, and subjected to cooling solidification to obtain each suppository.

Next, Test Examples are used to show effects of the Present compounds on harmful arthropods. In the following Test Examples, the tests were carried out at 25° C.

Test Method 1

Each test compound is formulated according to the method described in the Formulation Example 5 to obtain each formulation, and water containing Sindaine (registered trademark) (0.03% by volume) is added thereto to prepare a diluted solution containing a prescribed concentration of each test compound.

Cucumber (*Cucumis sativus*) seedlings (on the developmental stage of the second true leaf) are planted in a container and approximately 30 cotton aphids (*Aphis gossypii*) (all stages of life) are released onto the cucumber seedlings. After 1 day, each of said diluted solutions is sprayed into the seedlings in a ratio of 10 mL/seedling. After additional 5 days, the number of the surviving insects is examined and the controlling value is calculated by the following equation.

$$\text{Controlling value (\%)} = \{1 - (Cb \times Tai)/(Cai \times Tb)\} \times 100$$

wherein the symbols in the equation represent the following meanings.

Cb: Number of the test insects in non-treated area;

Cai: Number of the surviving insects at the time of the investigation in non-treated area; Tb: Number of the test insects in treated area;

Tai: Number of the surviving insects at the time of the investigation in treated area;

Here, the "non-treated area" represents an area where the same treatment procedure as that of the treated area is done except for not using each test compound.

Test Example 1-1

When the prescribed concentration was 500 ppm and the following Present compound was used as a test compound to carry out a test according to the Test method 1, the following Present compound showed 90% or greater as the controlling value.

Present compound: 2

Test Example 1-2

When the prescribed concentration was 50 ppm and each of the following Present compounds was used as a test compound to carry out a test according to the Test method 1, each of the following Present compounds showed 90% or greater as the controlling value.

Present compounds: 2, 4, 5, 6, 7, 8, 9, 10, 11, 12, 14, 15, 16, 18, 19, 20, 21, 22, 23, 24, 25, 27, 28, 29, 30, 31

Test Method 2

Each test compound is formulated according to the method described in the Formulation Example 5 to obtain each formulation, and water is added thereto to prepare a diluted solution containing a prescribed concentration of each test compound.

Cucumber seedlings (on the developmental stage of the second true leaf) are planted in a container, and each of said diluted solutions is irrigated into the plant foot in a ratio of 5 mL/seedlings. After 7 days, approximately 30 cotton aphids (*Aphis gossypii*) (all stages of life) are released onto the surfaces of leaves of the cucumber seedlings. After additional 6 days, the number of the surviving insects is examined and the controlling value is calculated by the following equation.

Controlling value (%)={1−($Cb \times Tai$)/($Cai \times Tb$)}×100 wherein the symbols in the equation represent the following meanings.

Cb: Number of the test insects in non-treated area;
Cai: Number of the surviving insects at the time of the investigation in non-treated area;
Tb: Number of the test insects in treated area;
Tai: Number of the surviving insects at the time of the investigation in treated area;

Here, the "non-treated area" represents an area where the same treatment procedure as that of the treated area is done except for not using each test compound.

Test Example 2-1

When the prescribed concentration was 1000 ppm and the following Present compound was used as a test compound to carry out a test according to the Test method 2, the following Present compound showed 90% or greater as the controlling value.
Present compound: 2

Test Example 2-2

When the prescribed concentration was 250 ppm and each of the following Present compounds was used as a test compound to carry out a test according to the Test method 2, each of the following Present compounds showed 90% or greater as the controlling value.
Present compounds: 6, 7, 10, 21, 26
Test Method 3

Each test compound is formulated according to the method described in the Formulation Example 5 to obtain each formulation, and water containing Sindaine (registered trademark) (0.03% by volume) is added thereto to prepare a diluted solution containing a prescribed concentration of each test compound.

Cabbage (*Brassicae oleracea*) seedlings (on the developmental stage of the second to third true leaf) are planted in a container, and each of said diluted solutions is sprayed into the seedlings in a ratio of 20 mL/seedlings. Thereafter, the stem and leaf of the seedlings are cut out, and placed into a container lined with a filter paper. Five (5) the 3rd instar larvae of cotton worm (*Spodoptera litura*) are released into the container. After 5 days, the number of the surviving insects is counted, and the mortality of insects is calculated by the following equation.

Mortality (%)=(1−Number of surviving insects/5)×100

Test Example 3-1

When the prescribed concentration was 500 ppm and the following Present compound was used as a test compound to carry out a test according to the Test method 3, the following Present compound showed 80% or greater as the mortality.
Present compound: 2

Test Example 3-2

When the prescribed concentration was 50 ppm and each of the following Present compounds was used as a test compound to carry out a test according to the Test method 3, each of the following Present compounds showed 80% or greater as the mortality.
Present compounds: 2, 5, 6, 7, 8, 9, 10, 11, 12, 14, 15, 16, 17, 18, 19, 20, 21, 22, 24, 25, 26, 27, 28, 29, 30, 31
Test Method 4

Each test compound is formulated according to the method described in the Formulation Example 5 to obtain each formulation, and water containing Sindaine (registered trademark) (0.03% by volume) is added thereto to prepare a diluted solution containing a prescribed concentration of each test compound.

Cabbage seedlings (on the developmental stage of the second to third true leaf) are planted in a container, and each of said diluted solutions is sprayed into the seedlings in a ratio of 20 mL/seedlings. Thereafter, the stem and leaf of the seedlings are cut out, and placed into a container lined with a filter paper. Five (5) the 3rd instar larvae of diamondback moth (*Plutella xylostella*) are released into the container. After 5 days, the number of the surviving insects is counted, and the mortality of insects is calculated by the following equation.

Mortality (%)=(1−Number of surviving insects/5)×100

Test Example 4-1

When the prescribed concentration was 500 ppm and the following Present compound was used as a test compound to carry out a test according to the Test method 4, the following Present compound showed 80% or greater as the mortality.
Present compound: 2

Test Example 4-2

When the prescribed concentration was 50 ppm and each of the following Present compounds was used as a test compound to carry out a test according to the Test method 4, each of the following Present compounds showed 80% or greater as the mortality.
Present compounds: 2, 4, 5, 6, 7, 8, 9, 10, 11, 12, 14, 15, 16, 17, 18, 19, 20, 21, 22, 23, 24, 25, 26, 27, 28, 29, 30, 31
Test Method 5

Each test compound is dissolved into a mixed solution (50 μL) of polyoxyethylene sorbitan mono-cocoate and acetone (at a volume ratio of polyoxyethylene sorbitan mono-cocoate:acetone=5:95) per 1 mg of the test compound. Water containing Sindaine (registered trademark) (0.03% by volume) is added thereto to prepare a diluted solution containing a prescribed concentration of each test compound.

Young seedlings of corns (*Zea mays*) are immersed into each of said diluted solutions for 30 seconds. Thereafter, two of said seedlings are placed into a petri dish (diameter: 90 mm), and 10 the 2nd instar larvae of western corn rootworm (*Diabrotica virgifera virgifera*) are released into the dish. After 5 days, the number of the dead insects is counted, and the mortality of insects is calculated by the following equation.

Mortality (%)=(Number of dead insects/10)×100

Test Example 5-1

When the prescribed concentration was 500 ppm and the following Present compound was used as a test compound to carry out a test according to the Test method 5, the following Present compound showed 80% or greater as the mortality.
Present compound: 2

Test Example 5-2

When the prescribed concentration was 50 ppm and each of the following Present compounds was used as a test compound to carry out a test according to the Test method 5, each of the following Present compounds showed 80% or greater as the mortality.
Present compounds: 2, 5, 6, 7, 9, 10, 12, 23, 24, 25, 26, 27, 28, 29, 30, 31
Test Method 6

The Present compound (1 mg) is dissolved into a mixed solution (10 μL) of xylene, DMF, and surfactant (at a volume ratio of xylene:DMF:surfactant=4:4:1), and the resulting solution is diluted with water containing a spreader (0.02% by volume) to prepare a diluted solution A containing a prescribed concentration of the Present compound.

The Present ingredient (1 mg) is dissolved into a mixed solution (10 μL) of xylene, DMF, and surfactant (at a volume ratio of xylene:DMF: surfactant=4:4:1), and the resulting solution is diluted with water containing a spreader (0.02% by volume) to prepare a diluted solution B containing a prescribed concentration of the Present ingredient.

The diluted solution A and the diluted solution B are mixed to prepare a diluted solution C.

A lamina (length: 1.5 cm) of cucumber cotyledon is placed into each well of a 24 well microplate, then two (2) wingless adults and eight (8) larvae of cotton aphids (*Aphis gossypii*) are released into each well, and 20 μL of the diluted solution C is sprayed into each well. Said well is defined as "treated area".

A well into which 20 μL of water containing a spreader (0.02% by volume) instead of the diluted solution C is sprayed is defined as "non-treated area".

After the diluted solution C is dried, the upper part of the microplate is covered by a film sheet. After 5 days, the number of the surviving insects in each well is examined.

The controlling value is calculated by the following equation.

Controlling value (%)={1−(*Tai*)/(*Cai*)}×100 wherein the symbols in the equation represent the following meanings.
Cai: Number of the surviving insects at the time of the investigation in non-treated area;
Tai: Number of the surviving insects at the time of the investigation in treated area.

Specific examples of the diluted solution C of which the effects can be confirmed in the Test method 6 include the following 1) to 5).
1) A diluted solution C of any one combination described in the List A, wherein the concentration of the Present compound is 200 ppm and the concentration of the Present ingredient is 2,000 ppm. In the List A, Comp X represents any one compound selected from the Present compounds 1 to 31.
List A:
Comp X+clothianidin; Comp X+thiamethoxam; Comp X+imidacloprid; Comp X+thiacloprid; Comp X+flupyradifurone; Comp X+sulfoxaflor; Comp X+triflumezopyrim; Comp X+dicloromezotiaz; Comp X+beta-cyfluthrin; Comp X+tefluthrin; Comp X+fipronil; Comp X+chlorantraniliprole; Comp X+cyantraniliprole; Comp X+tetraniliprole; Comp X+thiodicarb; Comp X+carbofuran; Comp X+fluxametamide; Comp X+afoxolaner; Comp X+fluralaner; Comp X+broflanilide; Comp X+abamectin; Comp X+fluopyram; Comp X+fluensulfone; Comp X+fluazaindolizine; Comp X+tioxazafen; Comp X+flupyrimin; Comp X+mycorrhizal fungi; Comp X+*Bradyrhizobium japonicum* TA-11; Comp X+*Bacillus firmus*; Comp X+*Bacillus firmus* 1-1582; Comp X+*Bacillus amyloliquefaciens*; Coamp X+*Bacillus amyloliquefaciens* FZB42; Comp X+*Pasteuria nishizawae*; Comp X+*Pasteuria nishizawae* Pn1; Comp X+*Pasteuria penetrans*; Comp X+tebuconazole; Coamp X+prothioconazole; Comp X+metconazole; Comp X+ipconazole; Comp X+triticonazole; Comp X+difenoconazole; Comp X+imazalil; Comp X+triadimenol; Comp X+tetraconazole; Comp X+flutriafol; Comp X+mandestrobin; Comp X+azoxystrobin; Comp X+pyraclostrobin; Comp X+trifloxystrobin; Comp X+fluoxastrobin; Comp X+picoxystrobin; Comp X+fenamidone; Comp X+metalaxyl; Comp X+metalaxyl-M; Comp X+fludioxonil; Comp X+sedaxane; Comp X+penflufen; Comp X+fluxapyroxad; Comp X+benzovindiflupyr; Comp X+boscalid; Comp X+carboxin; Comp X+penthiopyrad; Comp X+flutolanil; Comp X+captan; Comp X+thiram; Comp X+tolclofos-methyl; Comp X+thiabendazole; Comp X+ethaboxam; Comp X+mancozeb; Comp X+picarbutrazox; Comp X+oxathiapiprolin; Comp X+silthiofam; Comp X+inpyrfluxam.
2) A diluted solution C of any one combination described in the List A, wherein the concentration of the Present compound is 200 ppm and the concentration of the Present ingredient is 200 ppm.
3) A diluted solution C of any one combination described in the List A, wherein the concentration of the Present compound is 500 ppm and the concentration of the Present ingredient is 50 ppm.
4) A diluted solution C of any one combination described in the List A, wherein the concentration of the Present compound is 500 ppm and the concentration of the Present ingredient is 5 ppm.
5) A diluted solution C of any one combination described in the List A, wherein the concentration of the Present compound is 500 ppm and the concentration of the Present ingredient is 0.5 ppm.

INDUSTRIAL APPLICABILITY

The Present compounds have excellent control effects on harmful arthropods.

The invention claimed is:
1. A compound represented by formula (I)

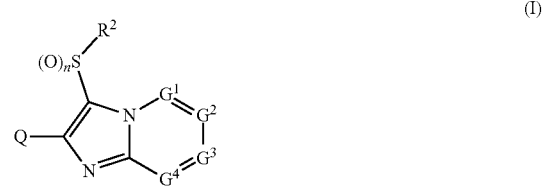

wherein:
R² represents a C1-C6 alkyl group optionally substituted with one or more halogen atom(s), a cyclopropyl group, or a cyclopropylmethyl group;

n represents 0, 1, or 2;

$G^1$ represents a nitrogen atom or $CR^{3a}$;

$G^2$ represents a nitrogen atom or $CR^{3b}$;

$G^3$ represents a nitrogen atom or $CR^{3c}$;

$G^4$ represents a nitrogen atom or $CR^{3d}$;

$R^{3a}$, $R^{3b}$, $R^{3c}$, and $R^{3d}$ are identical to or different from each other, and each represent a C1-C6 chain hydrocarbon group optionally substituted with one or more substituent(s) selected from Group B, a C3-C7 cycloalkyl group optionally substituted with one or more substituent(s) selected from Group E, a phenyl group optionally substituted with one or more substituent(s) selected from Group H, a 5 or 6 membered aromatic heterocyclic group optionally substituted with one or more substituent(s) selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{31}R^{32}$, $NR^{24}NR^{11}C(O)NR^{31}R^{32}$, $N=CHNR^{31}R^{32}$, $N=S(O)_p R^{15}R^{16}$, $C(O)R^{13}$, $C(O)OR^{17}$, $C(O)NR^{31}R^{32}$, $C(O)NR^{11}S(O)_2R^{23}$, $CR^{30}=NOR^{17}$, $NR^{11}CR^{24}=NOR^{17}$, $S(O)_m R^{23}$, a cyano group, a nitro group, a hydrogen atom, or a halogen atom;

p represents 0 or 1;

m represents 0, 1, or 2;

$R^{30}$ represents a C1-C6 chain hydrocarbon group optionally substituted with one or more halogen atom(s), a halogen atom, $OR^{35}$, $NR^{36}R^{37}$, or a hydrogen atom;

$R^{35}$ represents a C1-C6 chain hydrocarbon group optionally substituted with one or more halogen atom(s);

$R^{17}$ represents a C1-C6 chain hydrocarbon group optionally substituted with one or more halogen atom(s), a phenyl group optionally substituted with one or more substituent(s) selected from Group D, or a hydrogen atom;

$R^{11}$, $R^{24}$, $R^{36}$, and $R^{37}$ are identical to or different from each other, and each represent a C1-C6 chain hydrocarbon group optionally substituted with one or more halogen atom(s), or a hydrogen atom;

$R^{12}$ represents a C1-C6 chain hydrocarbon group optionally substituted with one or more substituent(s) selected from Group F, a C3-C7 cycloalkyl group optionally substituted with one or more substituent(s) selected from Group J, a C3-C7 cycloalkenyl group optionally substituted with one or more substituent(s) selected from Group J, a phenyl group optionally substituted with one or more substituent(s) selected from Group D, a 6 membered aromatic heterocyclic group optionally substituted with one or more substituent(s) selected from Group D, a hydrogen atom, or $S(O)_2R^{23}$;

$R^{23}$ represents a C1-C6 chain hydrocarbon group optionally substituted with one or more halogen atom(s), or a phenyl group optionally substituted with one or more substituent(s) selected from Group D;

$R^{11a}$ and $R^{12a}$ are combined with the nitrogen atom to which they are attached to form a 3-7 membered nonaromatic heterocyclic group optionally substituted with one or more substituent(s) selected from Group E;

$R^{13}$ represents a C1-C6 chain hydrocarbon group optionally substituted with one or more halogen atom(s), a C3-C7 cycloalkyl group optionally substituted with one or more halogen atom(s), a (C3-C6 cycloalkyl) C1-C3 alkyl group optionally substituted with one or more halogen atom(s), a phenyl group optionally substituted with one or more substituent(s) selected from Group D, a 5 or 6 membered aromatic heterocyclic group optionally substituted with one or more substituent(s) selected from Group D, or a hydrogen atom;

$R^{14}$ represents a C1-C6 chain hydrocarbon group optionally substituted with one or more halogen atom(s), a C3-C7 cycloalkyl group optionally substituted with one or more halogen atom(s), a (C3-C6 cycloalkyl) C1-C3 alkyl group optionally substituted with one or more halogen atom(s), or a phenyl C1-C3 alkyl group, wherein the phenyl moiety in said phenyl C1-C3 alkyl group is optionally substituted with one or more substituent(s) selected from Group D;

$R^{15}$ and $R^{16}$ are identical to or different from each other, and each represent a C1-C6 alkyl group optionally substituted with one or more halogen atom(s);

$R^{31}$ represents a C1-C6 alkyl group optionally substituted with one or more halogen atom(s), or a hydrogen atom;

$R^{32}$ represents a C1-C6 chain hydrocarbon group optionally substituted with one or more substituent(s) selected from Group F, a C3-C7 cycloalkyl group optionally substituted with one or more substituent(s) selected from Group J, $S(O)_2R^{23}$, or a hydrogen atom;

Q represents a group represented by Q1 or a group represented by Q2;

Q1

Q2

Z represents an oxygen atom or a sulfur atom;

the combination of $A^2$ and $A^3$ represents:

a combination wherein $A^2$ represents $CR^{4a}$, and $A^3$ represents a nitrogen atom or $CR^{4b}$; or a combination wherein $A^2$ represents a nitrogen atom, and $A^3$ represents $CR^{4b}$;

the combination of $B^1$, $B^2$, and $B^3$ represents:

a combination wherein $B^1$ represents $CR^1$, $B^2$ represents a nitrogen atom or $CR^{6b}$, and $B^3$ represents a nitrogen atom or $CR^{6c}$;

a combination wherein $B^1$ represents a nitrogen atom or $CR^{6a}$, $B^2$ represents $CR^1$, and $B^3$ represents a nitrogen atom or $CR^{6c}$; or a combination wherein $B^1$ represents a nitrogen atom or $CR^{6a}$, $B^2$ represents a nitrogen atom or $CR^{6b}$, and $B^3$ represents $CR^1$;

$R^1$ represents a C1-C6 chain hydrocarbon group substituted with one or more substituent(s) selected from the group consisting of a cyano group and a halogen atom, a C3-C4 cycloalkyl group optionally substituted with one or more substituent(s) selected from the group consisting of a cyano group and a halogen atom, $SR^8$, $S(O)R^8$, $S(O)_2R^8$, $OR^8$, or $OS(O)_2R^8$;

$R^8$ represents a C1-C6 chain hydrocarbon group substituted with one or more substituent(s) selected from the group consisting of a cyano group and a halogen atom, or a C3-C4 cycloalkyl group optionally substituted with one or more substituent(s) selected from the group consisting of a cyano group and a halogen atom;

$R^{4a}$, $R^{4b}$, $R^{6a}$, $R^{6b}$, and $R^{6c}$ are identical to or different from each other, and each represent a C1-C6 chain hydrocarbon group optionally substituted with one or more halogen atom(s), a C3-C7 cycloalkyl group optionally substituted with one or more halogen atom(s), a C1-C6 alkoxy group optionally substituted with one or more halogen atom(s), $NR^{25}R^{26}$, $C(O)R^7$, $C(O)OR^7$, $C(O)NR^{19}R^{20}$, $NR^{25}C(O)R^{18}$, $NR^{25}C(O)OR^{18}$, $NR^{25}C(O)NR^{19}R^{20}$, a cyano group, a halogen atom, or a hydrogen atom;

$R^{19}$ and $R^{25}$ are identical to or different from each other, and each represent a C1-C6 chain hydrocarbon group optionally substituted with one or more halogen atom(s), or a hydrogen atom;

$R^{26}$ represents a C1-C6 chain hydrocarbon group optionally substituted with one or more substituent(s) selected from Group L, a C3-C7 cycloalkyl group optionally substituted with one or more substituent(s) selected from Group M, a C3-C7 cycloalkenyl group optionally substituted with one or more substituent(s) selected from Group M, a phenyl group optionally substituted with one or more substituent(s) selected from Group K, a 6 membered aromatic heterocyclic group optionally substituted with one or more substituent(s) selected from Group K, a hydrogen atom, or $S(O)_2R^{27}$;

$R^{27}$ represents a C1-C6 chain hydrocarbon group optionally substituted with one or more halogen atom(s), a C3-C7 cycloalkyl group optionally substituted with one or more halogen atom(s), or a phenyl group optionally substituted with one or more substituent(s) selected from Group K; and $R^7$, $R^{18}$, and $R^{20}$ are identical to or different from each other, and each represent a C1-C6 chain hydrocarbon group optionally substituted with one or more substituent(s) selected from Group L, a C3-C7 cycloalkyl group optionally substituted with one or more substituent(s) selected from Group M, or a hydrogen atom;

Group B: a group consisting of a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C3-C6 cycloalkyl group optionally substituted with one or more halogen atom(s), a cyano group, a hydroxy group, and a halogen atom;

Group C: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), and a halogen atom;

Group D: a group consisting of a C1-C6 chain hydrocarbon group optionally substituted with one or more halogen atom(s), a hydroxy group, a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a sulfanyl group, a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), an amino group, $NHR^{21}$, $NR^{21}R^{22}$, $C(O)R^{21}$, $OC(O)R^{21}$, $C(O)OR^{21}$, a cyano group, a nitro group, and a halogen atom;

$R^{21}$ and $R^{22}$ are identical to or different from each other, and each represent a C1-C6 alkyl group optionally substituted with one or more halogen atom(s);

Group E: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a halogen atom, an oxo group, a hydroxy group, a cyano group, and a nitro group;

Group F: a group consisting of a C1-C6 alkoxy group optionally substituted with one or more halogen atom(s), a phenyl group optionally substituted with one or more substituent(s) selected from Group D, a 5 or 6 membered aromatic heterocyclic group optionally substituted with one or more substituent(s) selected from Group D, a C3-C7 cycloalkyl group optionally substituted with one or more halogen atom(s), a 3-7 membered nonaromatic heterocyclic group optionally substituted with one or more substituent(s) selected from Group C, an amino group, $NHR^{21}$, $NR^{21}R^{22}$, a halogen atom, and a cyano group;

Group H: a group consisting of a C1-C6 alkyl group optionally substituted with one or more halogen atom(s), a 5 or 6 membered aromatic heterocyclic group optionally substituted with one or more substituent(s) selected from Group D, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a halogen atom, a nitro group, a cyano group, and an amino group;

$R^9$ represents a C1-C6 alkyl group optionally substituted with one or more halogen atom(s), or a C3-C6 cycloalkyl group optionally substituted with one or more halogen atom(s);

$R^{10}$ represents a C1-C6 alkyl group optionally substituted with one or more halogen atom(s), a C3-C6 cycloalkyl group optionally substituted with one or more halogen atom(s), or a hydrogen atom:

Group J: a group consisting of a C1-C6 alkyl group optionally substituted with one or more halogen atom(s), a halogen atom, and a cyano group;

Group K: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C3-C6 cycloalkyl group optionally substituted with one or more halogen atom(s), a (C1-C6 alkyl optionally substituted with one or more halogen atom(s))amino group, a di(C1-C4 alkyl)amino group optionally substituted with one or more halogen atom(s), a C2-C6 alkylcarbonyl group optionally substituted with one or more halogen atom(s), a C2-C6 alkoxycarbonyl group optionally substituted with one or more halogen atom(s), a C2-C6 alkoxycarbonyloxy group optionally substituted with one or more halogen atom(s), an aminocarbonyl group, a (C1-C6 alkyl optionally substituted with one or more halogen atom(s))aminocarbonyl group, a [di(C1-C4 alkyl)amino optionally substituted with one or more halogen atom(s)]carbonyl group, a (C2-C6 alkoxycarbonyl optionally substituted with one or more halogen atom(s))amino group, a (C2-C6 alkoxycarbonyl)(C1-C6 alkyl)amino group optionally substituted with one or more halogen atom(s), a cyano group, an amino group, a nitro group, a hydroxy group, and a halogen atom;

Group L: a group consisting of a C3-C6 cycloalkyl group optionally substituted with one or more halogen atom(s), a phenyl group optionally substituted with one or more substituent(s) selected from Group K, a 5 or 6 membered aromatic heterocyclic group optionally substituted with one or more substituent(s) selected from Group K, a C1-C6 alkoxy group optionally substituted with one or more halogen atom(s), a (C1-C6 alkyl optionally substituted with one or more halogen atom(s))amino group, a di(C1-C4 alkyl)amino group optionally substituted with one or more halogen atom(s), a cyano group, an amino group, a nitro group, a hydroxy group, and a halogen atom;

Group M: a group consisting of a C1-C6 alkyl group optionally substituted with one or more halogen atom(s), a C1-C6 alkoxy group optionally substituted with one or more halogen atom(s), a C2-C6 alkoxycarbonyl group optionally substituted with one or more halogen atom(s), an amino group, a cyano group, and a halogen atom, or an N-oxide thereof.

2. The compound or an N-oxide thereof according to claim 1, wherein Q represents the group represented by Q1.

3. The compound or an N-oxide thereof according to claim 1, wherein Q represents the group represented by Q2.

4. The compound or an N-oxide thereof according to claim 1, wherein $R^{3a}$, $R^{3b}$, $R^{3c}$, and $R^{3d}$ are identical to or different from each other, and each represent a C1-C6 alkyl group, a C2-C6 alkenyl group, a C3-C7 cycloalkyl group, wherein said C1-C6 alkyl group, said C2-C6 alkenyl group, and said C3-C7 cycloalkyl group are optionally substituted with one or more substituent(s) selected from the group consisting of a halogen atom and a cyano group, a phenyl group, a pyridyl group, a pyrimidinyl group wherein said phenyl group, said pyridyl group, and said pyrimidinyl group are optionally substituted with one or more substituent(s) from Group J, $OR^{12}$, $CR^{30}=NOR^{17}$, a hydrogen atom, or a halogen atom.

5. The compound or an N-oxide thereof according to claim 1, wherein $G^1$ represents a nitrogen atom or CH;
$G^2$ represents $CR^{3b}$;
$G^3$ represents $CR^{3c}$;
$G^4$ represents a nitrogen atom or CH; and
$R^{3b}$ and $R^{3c}$ are identical to or different from each other, and each represent a C1-C6 alkyl group, a C2-C6 alkenyl group, a C3-C7 cycloalkyl group wherein said C1-C6 alkyl group, said C2-C6 alkenyl group, and said C3-C7 cycloalkyl group are optionally substituted with one or more substituent(s) selected from the group consisting of a halogen atom and a cyano group, $OR^{12}$, a hydrogen atom, or a halogen atom.

6. The compound or an N-oxide thereof according to claim 1, wherein
$G^1$ represents CH;
$G^2$ represents $CR^{3b}$;
$G^3$ represents $CR^{3c}$;
$G^4$ represents CH; and
$R^{3b}$ and $R^{3c}$ are identical to or different from each other, and each represent a C1-C6 alkyl group optionally substituted with one or more halogen atom(s), or a hydrogen atom.

7. The compound or an N-oxide thereof according to claim 1, wherein
$R^1$ represents a C1-C6 alkyl group substituted with one or more substituent(s) selected from the group consisting of a halogen atom and a cyano group; or a cyclopropyl group optionally substituted with one or more substituent(s) selected from the group consisting of a cyano group and a halogen atom.

8. The compound or an N-oxide thereof according to claim 1, wherein $R^2$ represents an ethyl group.

9. The compound or an N-oxide thereof according to claim 1, wherein Z represents an oxygen atom.

10. A composition for controlling a harmful arthropod comprising the compound or an N-oxide thereof according to claim 1.

11. A composition comprising one or more ingredient(s) selected from the group consisting of Group (a), Group (b), Group (c), and Group (d), and the compound or an N-oxide thereof according to claim 1:

Group (a): a group consisting of insecticidal active ingredients, miticidal active ingredients, and nematicidal active ingredients;
Group (b): fungicidal active ingredients;
Group (c): plant growth regulatory ingredients;
Group (d): repellent ingredients.

12. A method for controlling a harmful arthropod which comprises applying an effective amount of the compound or an N-oxide thereof according to claim 1 to a harmful arthropod or a habitat where a harmful arthropod lives.

13. A seed or a vegetative reproduction organ holding an effective amount of the compound or an N-oxide thereof according to claim 1.

14. A method for controlling a harmful arthropod which comprises applying an effective amount of the composition according to claim 11 to a harmful arthropod or a habitat where a harmful arthropod lives.

15. A seed or a vegetative reproduction organ holding an effective amount of the composition according to claim 11.

* * * * *